United States Patent
Ali et al.

(10) Patent No.: US 10,682,400 B2
(45) Date of Patent: Jun. 16, 2020

(54) COMBINATION VACCINE DEVICES AND METHODS OF KILLING CANCER CELLS

(71) Applicants: President and Fellows of Harvard College, Cambridge, MA (US); Dana-Farber Cancer Institute, Inc., Boston, MA (US)

(72) Inventors: Omar Abdel-Rahman Ali, Cambridge, MA (US); David J. Mooney, Sudbury, MA (US); Glenn Dranoff, Lexington, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 4 days.

(21) Appl. No.: 15/303,985

(22) PCT Filed: Apr. 30, 2015

(86) PCT No.: PCT/US2015/028468
§ 371 (c)(1),
(2) Date: Oct. 13, 2016

(87) PCT Pub. No.: WO2015/168379
PCT Pub. Date: Nov. 5, 2015

(65) Prior Publication Data
US 2017/0042995 A1 Feb. 16, 2017

Related U.S. Application Data

(60) Provisional application No. 61/986,600, filed on Apr. 30, 2014.

(51) Int. Cl.
| | | |
|---|---|---|
| A61K 39/00 | (2006.01) | |
| C07K 16/28 | (2006.01) | |
| C07K 16/30 | (2006.01) | |
| A61K 39/12 | (2006.01) | |
| A61K 39/39 | (2006.01) | |
| A61K 39/395 | (2006.01) | |
| A61K 47/34 | (2017.01) | |
| A61K 47/36 | (2006.01) | |
| A61K 39/02 | (2006.01) | |
| C12N 7/00 | (2006.01) | |

(52) U.S. Cl.
CPC ......... *A61K 39/0011* (2013.01); *A61K 39/02* (2013.01); *A61K 39/12* (2013.01); *A61K 39/39* (2013.01); *A61K 39/3955* (2013.01); *A61K 47/34* (2013.01); *A61K 47/36* (2013.01); *C07K 16/2803* (2013.01); *C07K 16/2818* (2013.01); *C07K 16/30* (2013.01); *C07K 16/3053* (2013.01); *C12N 7/00* (2013.01); *A61K 2039/507* (2013.01); *A61K 2039/5152* (2013.01); *A61K 2039/54* (2013.01); *A61K 2039/55516* (2013.01); *A61K 2039/55522* (2013.01); *A61K 2039/55561* (2013.01); *C07K 2317/21* (2013.01); *C07K 2317/24* (2013.01)

(58) Field of Classification Search
CPC ........................... A61K 39/39; A61K 39/0011
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 5,951,976 A | 9/1999 | Segal |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,352,694 B1 | 3/2002 | June et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |

(Continued)

FOREIGN PATENT DOCUMENTS

| | | |
|---|---|---|
| AU | 2018201930 A1 | 4/2018 |
| CN | 1757662 A | 4/2006 |

(Continued)

OTHER PUBLICATIONS

Hodi et al. (N England J Med 2010; 363:711-723) (Year: 2010).*
Quintana and Cohen (J. Autoimmunity 2001 17: 191-197) (Year: 2001).*
Duraiswanny et al. (Cancer Research Jun. 2013 73(12): 3591-3603) (Year: 2013).*

(Continued)

*Primary Examiner* — Peter J Reddig
(74) *Attorney, Agent, or Firm* — McCarter & English, LLP; Maria Laccotripe Zacharakis; Maneesh Gulati

(57) ABSTRACT

The present invention comprises compositions, methods, and devices for enhancing an endogenous immune response against a cancer. Devices and methods provide therapeutic immunity to subjects against cancer.

26 Claims, 13 Drawing Sheets

Specification includes a Sequence Listing.

(56) References Cited

U.S. PATENT DOCUMENTS

| | | |
|---|---|---|
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 6,858,222 B2 | 2/2005 | Nelson et al. |
| 6,974,698 B1 | 12/2005 | Miller et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,244,714 B1 | 7/2007 | Gonda et al. |
| 7,410,953 B2 | 8/2008 | Kawasaki |
| 7,427,602 B1 | 9/2008 | Shea et al. |
| 7,569,850 B2 | 8/2009 | Noy et al. |
| 7,575,759 B2 | 8/2009 | Murphy et al. |
| 7,592,326 B2 | 9/2009 | Karaolis |
| 7,687,241 B2 | 3/2010 | Chen |
| 7,709,458 B2 | 5/2010 | Karaolis et al. |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,354,119 B2 | 1/2013 | Geistlich et al. |
| 8,367,628 B2 | 2/2013 | Goodwin et al. |
| 8,535,719 B2 | 9/2013 | Badylak et al. |
| 8,709,464 B2 | 4/2014 | Ma et al. |
| 8,728,456 B2 | 5/2014 | Sands et al. |
| 8,883,308 B2 | 11/2014 | Polshettiwar et al. |
| 8,932,583 B2 | 1/2015 | Mooney et al. |
| 9,012,399 B2 | 4/2015 | Cao et al. |
| 9,132,210 B2 | 9/2015 | Mooney et al. |
| 9,139,809 B2 | 9/2015 | Porcelli et al. |
| 9,150,631 B2 | 10/2015 | Super et al. |
| 9,370,558 B2 | 6/2016 | Ali et al. |
| 9,381,235 B2 | 7/2016 | Sands et al. |
| 9,446,107 B2 | 9/2016 | Mooney et al. |
| 9,486,512 B2 | 11/2016 | Kim et al. |
| 9,591,360 B2 | 3/2017 | Jennings et al. |
| 9,675,561 B2 | 6/2017 | Bencherif et al. |
| 9,770,535 B2 | 9/2017 | Mooney et al. |
| 9,821,045 B2 | 11/2017 | Ali et al. |
| 9,937,249 B2 | 4/2018 | Kim et al. |
| 10,045,947 B2 | 8/2018 | Bencherif et al. |
| 10,080,789 B2 | 9/2018 | Sands et al. |
| 10,137,184 B2 | 11/2018 | Mooney et al. |
| 10,149,897 B2 | 12/2018 | Mooney et al. |
| 2002/0045672 A1 | 4/2002 | Harris et al. |
| 2002/0131853 A1 | 9/2002 | Nagasawa |
| 2002/0131953 A1 | 9/2002 | Takashima et al. |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0194397 A1 | 10/2003 | Mishra |
| 2003/0232895 A1 | 12/2003 | Omidian et al. |
| 2004/0043034 A1 | 3/2004 | Jensenius et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0213795 A1* | 10/2004 | Collins .............. C07K 16/2803 424/155.1 |
| 2004/0220111 A1 | 11/2004 | Kleinman et al. |
| 2004/0228858 A1* | 11/2004 | Hanson .............. C07K 16/2818 424/143.1 |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0113929 A1 | 5/2008 | Lipford et al. |
| 2008/0138416 A1 | 6/2008 | Rauh et al. |
| 2008/0152624 A1 | 6/2008 | Paludan et al. |
| 2008/0206308 A1 | 8/2008 | Jabbari et al. |
| 2008/0233181 A1 | 9/2008 | Nagy et al. |
| 2008/0268019 A1 | 10/2008 | Badylak et al. |
| 2008/0268052 A1 | 10/2008 | Voytik-Harbin et al. |
| 2009/0017096 A1 | 1/2009 | Lowman et al. |
| 2009/0061014 A1 | 3/2009 | Messersmith et al. |
| 2009/0192079 A1 | 7/2009 | Santos et al. |
| 2009/0238853 A1 | 9/2009 | Liu et al. |
| 2009/0252752 A1 | 10/2009 | Tahara et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055102 A1 | 3/2010 | Langermann |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0008443 A1 | 1/2011 | Alsberg et al. |
| 2011/0020216 A1 | 1/2011 | Mooney et al. |
| 2011/0117170 A1 | 5/2011 | Cao et al. |
| 2011/0207166 A1 | 8/2011 | Vaiselbuh |
| 2011/0223255 A1 | 9/2011 | Thiesen et al. |
| 2011/0253643 A1 | 10/2011 | Polshettiwar et al. |
| 2011/0256184 A1 | 10/2011 | Lei et al. |
| 2011/0300186 A1 | 12/2011 | Hellstrom et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0294888 A1 | 11/2012 | Kishimoto et al. |
| 2012/0329791 A1 | 12/2012 | Ashwell et al. |
| 2013/0029030 A1 | 1/2013 | Larsen |
| 2013/0035283 A1 | 2/2013 | Super et al. |
| 2013/0045246 A1 | 2/2013 | Edwards et al. |
| 2013/0052117 A1 | 2/2013 | Imai et al. |
| 2013/0072547 A1 | 3/2013 | Hackam et al. |
| 2013/0145488 A1 | 6/2013 | Wang et al. |
| 2013/0177536 A1 | 7/2013 | Mooney et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0072510 A1 | 3/2014 | Shea et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0205653 A1 | 7/2014 | Dubensky, Jr. et al. |
| 2014/0227327 A1 | 8/2014 | Bencherif et al. |
| 2014/0227723 A1 | 8/2014 | Ingber et al. |
| 2014/0234423 A1 | 8/2014 | Sands et al. |
| 2015/0024026 A1 | 1/2015 | Mooney et al. |
| 2015/0072009 A1 | 3/2015 | Kim et al. |
| 2015/0359928 A1 | 12/2015 | Gu et al. |
| 2015/0366956 A1 | 12/2015 | Mooney et al. |

(56) References Cited

U.S. PATENT DOCUMENTS

| | | | |
|---|---|---|---|
| 2016/0220667 A1 | 8/2016 | Mooney et al. |
| 2016/0220668 A1 | 8/2016 | Mooney et al. |
| 2016/0228543 A1 | 8/2016 | Mooney et al. |
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0182138 A1 | 6/2017 | Kim et al. |
| 2017/0246281 A1 | 8/2017 | Super et al. |
| 2017/0362307 A1 | 12/2017 | Ingber et al. |
| 2018/0021253 A1 | 1/2018 | Sandeep et al. |
| 2018/0117171 A1 | 5/2018 | Mooney et al. |
| 2018/0164298 A1 | 6/2018 | Ali et al. |
| 2018/0243231 A1 | 8/2018 | Bencherif et al. |
| 2018/0289789 A1 | 10/2018 | Ali et al. |
| 2018/0320157 A1 | 11/2018 | Super et al. |
| 2018/0344821 A1 | 12/2018 | Kim et al. |
| 2018/0371058 A1 | 12/2018 | Watters et al. |
| 2019/0060525 A1 | 2/2019 | Shah et al. |
| 2019/0076373 A1 | 3/2019 | Bencherif et al. |
| 2019/0125849 A1 | 5/2019 | Mooney et al. |
| 2019/0183992 A1 | 6/2019 | Sands et al. |
| 2019/0216910 A1 | 7/2019 | Mooney et al. |

FOREIGN PATENT DOCUMENTS

| | | | |
|---|---|---|---|
| CN | 101655611 A | 2/2010 |
| EP | 0562862 A1 | 9/1993 |
| EP | 1452191 A2 | 9/2004 |
| EP | 1561481 A2 | 8/2005 |
| EP | 1712238 A1 | 10/2006 |
| EP | 1975230 A1 | 10/2008 |
| JP | 2000-503884 A | 4/2000 |
| JP | 2001-524136 A | 11/2001 |
| JP | 2003-506401 A | 2/2003 |
| JP | 2003-180815 A | 7/2003 |
| JP | 2004-159849 A | 6/2004 |
| JP | 2004-520043 A | 7/2004 |
| JP | 2005-160669 A | 6/2005 |
| JP | 2005-170816 A | 6/2005 |
| JP | 2005-528401 A | 9/2005 |
| JP | 2007-500673 A | 1/2007 |
| JP | 2007-503881 A | 3/2007 |
| JP | 2007-505827 A | 3/2007 |
| JP | 2007-528848 A | 10/2007 |
| JP | 2008-515503 A | 5/2008 |
| JP | 2008-528114 A | 7/2008 |
| JP | 2009-519042 A | 5/2009 |
| JP | 2009-521406 A | 6/2009 |
| JP | 2009-540921 A | 11/2009 |
| JP | 2010-502824 A | 1/2010 |
| JP | 2010-508976 A | 3/2010 |
| JP | 2010-227012 A | 10/2010 |
| JP | 2011-511684 A | 4/2011 |
| JP | 2011-511834 A | 4/2011 |
| JP | 2013-531043 A | 8/2013 |
| WO | WO-1996/02555 A1 | 2/1996 |
| WO | WO-1996/16086 A1 | 5/1996 |
| WO | WO-1998/12228 A1 | 3/1998 |
| WO | WO-1998/16266 A1 | 4/1998 |
| WO | WO-1999/44583 A2 | 9/1999 |
| WO | WO-1999/51259 A2 | 10/1999 |
| WO | WO-2000/50006 A2 | 8/2000 |
| WO | WO-2001/10421 A1 | 2/2001 |
| WO | WO-2001/35932 A2 | 5/2001 |
| WO | WO-2001/37810 A2 | 5/2001 |
| WO | WO-2002/16557 A2 | 2/2002 |
| WO | WO-2002/40071 A1 | 5/2002 |
| WO | WO-2002/058723 A2 | 8/2002 |
| WO | WO-2002/092054 A2 | 11/2002 |
| WO | WO-2003/020161 A2 | 3/2003 |
| WO | WO-2003/020884 A2 | 3/2003 |
| WO | WO-2003/088905 A2 | 10/2003 |
| WO | WO-2004/006990 A2 | 1/2004 |
| WO | WO-2004/029230 A2 | 4/2004 |
| WO | WO-2004/030706 A2 | 4/2004 |
| WO | WO-2004/031371 A2 | 4/2004 |
| WO | WO-2004/089413 A1 | 10/2004 |
| WO | WO-2005/013896 A2 | 2/2005 |
| WO | WO-2005/013933 A1 | 2/2005 |
| WO | WO-2005/020849 A2 | 3/2005 |
| WO | WO-2005/025614 A2 | 3/2005 |
| WO | WO-2005/026318 A2 | 3/2005 |
| WO | WO-2005/037190 A2 | 4/2005 |
| WO | WO-2005/037293 A1 | 4/2005 |
| WO | WO-2005/046748 A1 | 5/2005 |
| WO | WO-2005/072088 A2 | 8/2005 |
| WO | WO-2005/104755 A2 | 11/2005 |
| WO | WO-2006/039045 A2 | 4/2006 |
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | WO-2007/030901 A1 | 3/2007 |
| WO | WO-2007/039150 A2 | 4/2007 |
| WO | WO-2007/042554 A2 | 4/2007 |
| WO | WO-2007/063075 A1 | 6/2007 |
| WO | WO-2007/064152 A1 | 6/2007 |
| WO | WO-2007/070660 A2 | 6/2007 |
| WO | WO-2007/078196 A1 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |
| WO | WO-2007/150020 A1 | 12/2007 |
| WO | WO-2008/008266 A2 | 1/2008 |
| WO | WO-2008/018707 A1 | 2/2008 |
| WO | WO-2008/031525 A1 | 3/2008 |
| WO | WO-2008/043157 A1 | 4/2008 |
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A2 | 12/2008 |
| WO | WO-2008/157394 A2 | 12/2008 |
| WO | WO-2009/002401 A2 | 12/2008 |
| WO | WO-2009/005769 A2 | 1/2009 |
| WO | WO-2009/018500 A1 | 2/2009 |
| WO | WO-2009/024775 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009102465 A2 * | 8/2009 | ............ A61K 39/39 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | WO-2011/043834 A1 | 4/2011 |
| WO | WO-2011/043835 A1 | 4/2011 |
| WO | WO-11063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A1 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | WO-2013/012924 A2 | 1/2013 |
| WO | WO-2013/106852 A1 | 7/2013 |
| WO | WO-2013/158673 A1 | 10/2013 |
| WO | WO-2013/172967 A1 | 11/2013 |
| WO | WO-2013/190555 A2 | 12/2013 |
| WO | WO-2014/063128 A1 | 4/2014 |
| WO | WO-2014/189805 A1 | 11/2014 |
| WO | WO-2015/066535 A1 | 5/2015 |
| WO | WO-2015/077354 A1 | 5/2015 |
| WO | WO-2015/154078 A1 | 10/2015 |
| WO | WO-15168379 A2 | 11/2015 |

(56) References Cited

FOREIGN PATENT DOCUMENTS

| WO | WO-2016/004068 A1 | 1/2016 |
|---|---|---|
| WO | WO-16123573 A1 | 8/2016 |
| WO | WO-16161372 A1 | 10/2016 |
| WO | WO-2017/143024 A2 | 8/2017 |
| WO | WO-2018/013797 A1 | 1/2018 |
| WO | WO-2018/026884 A1 | 2/2018 |

OTHER PUBLICATIONS

Zhang et al. (Am. J. Pathology Dec. 2002 161(6): 2295-2309) (Year: 2002).*
MGI—Mouse Facts (http://www.informatics.jax.org/mgihome/other/mouse_facts1.shtml, Aug. 9, 2018). (Year: 2018).*
Callahan and Wolchok (J. Leukocyte Biology Jul. 2013 94: 41-53) (Year: 2013).*
AMP-224, https://www.cancer.gov/publications/dictionaries/cancer-drug/def/anti-pd-1-fusion-protein-amp-224, retrieved Apr. 24, 2019 (Year: 2019).*
Hodi et al. (New England J. Med. Aug. 19, 2010 363(8): 711-723) (Year: 2010).*
Ali et al., Biomaterial-based vaccine induces regression of established; intracranial glioma in rats. Pharm Res. May 2011;28(5):1074-80.
Ali et al., In situ regulation of DC subsets and T cells mediates tumor regression in mice. Sci Transl Med. Nov. 25, 2009;1(8):8ra19.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Bristol-Myers Squibb. "Investigational Anti-PD-1 Immunotherapy BMS-936558 Showed Clinical Activity in Phase 1 Trial of Patients with Previously-Treated Non-Small-Cell Lung Cancer, Metastatic Melanoma and Renal Cell Cancer," bms.com Jun. 2, 2012. <news.bms.com/press-release/financial-news/investigational-anti-pd-1-immunotherapy-bms-936558-showed-clinical-acti>.
Bristol-Myers Squibb. A Phase 1 Study of Nivolumab (BMS-936558) in Subjects With Advanced or Recurrent Malignancies (MDX1106-03). In: ClinicalTrials.gov [Internet]. Bethesda (MD): National Library of Medicine (US). 2000—[cited Oct. 25, 2016]. Available from: https://clinicaltrials.gov/ct2/show/NCT00730639 NLM Identifier: NCT00730639.
Bristol-Myers Squibb. Multiple Ascending Dose (MDX1105-01) (Anti-PDL1). In: ClinicalTrials.gov [Internet]. Bethesda (MD): National Library of Medicine (US). 2000—[cited Oct. 25, 2016]. Available from: https://clinicaltrials.gov/ct2/show/NCT00729664 NLM Identifier: NCT00729664.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
Duraiswamy et al., Dual blockade of PD-1 and CTLA-4 combined with tumor vaccine effectively restores T-cell rejection function in tumors—response. Cancer Res. Jan. 15, 2014;74(2):633-4.
Fransen et al., Local immunomodulation for cancer therapy: Providing treatment where needed. Oncoimmunology. Nov. 1, 2013;2(11):e26493.
Furqan et al., STAT inhibitors for cancer therapy. J Hematol Oncol. Dec. 5, 2013;6:90.
Ichida et al., A small-molecule inhibitor of tgf-Beta signaling replaces sox2 in reprogramming by inducing nanog. Cell Stem Cell. Nov. 6, 2009;5(5):491-503.
Jiang et al., Click hydrogels, microgels and nanogels: emerging platforms for drug delivery and tissue engineering. Biomaterials. Jun. 2014;35(18):4969-85.
Kyi et al., Checkpoint blocking antibodies in cancer immunotherapy. FEBS; Lett. Jan. 21, 2014;588(2):368-76.
Li et al., pH sensitive Laponite/alginate hybrid hydrogels: swelling behaviour and release mechanism. Soft Matter. Jun. 2, 2011;7(13):6231-6238.
Liu et al., Selective inhibition of IDO1 effectively regulates mediators of antitumor immunity. Blood. Apr. 29, 2010;115(17):3520-30.
MacroGenics. Safety Study of MGA271 in Refractory Cancer. In: ClinicalTrials.gov [Internet]. Bethesda (MD): National Library of Medicine (US). 2000—[cited Oct. 25, 2016]. Available from: clinicaltrials.gov/ct2/show/NCT01391143 NLM Identifier: NCT01391143.
MedImmune LLC. Study to Assess the Safety, Tolerability, and Pharmacokinetics of AMP-224 in Patients With Advanced Cancer. In: ClinicalTrials.gov [Internet]. Bethesda (MD): National Library of Medicine (US). 2000—[cited Oct. 25, 2016]. Available from: clinicaltrials.gov/ct2/show/NCT01352884 NLM Identifier: NCT01352884.
Merck. "Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer," merck.com Oct. 29, 2013. <www.mercknewsroom.com/news-release/research-and-development-news/merck-announces-presentation-interim-data-phase-1b-study->.
Pardoll. The blockade of immune checkpoints in cancer immunotherapy. Nat; Rev Cancer. Mar. 22, 2012;12(4):252-64.
Platten et al., Cancer Immunotherapy by Targeting IDO1/TDO and Their Downstream Effectors. Front Immunol. Jan. 12, 2015;5:673.
PRNewswire. "GlaxoSmithKline and Amplimmune Form Global Strategic Collaboration," prnewswire.com Aug. 4, 2010. <http://www.prnewswire.com/news-releases/glaxosmithkline-and-amplimmune-form-global-strategic-collaboration-99938599.html>.
Ribas et al., Phase III randomized clinical trial comparing tremelimumab with standard-of-care chemotherapy in patients with advanced melanoma. J Clin Oncol. Feb. 10, 2013;31(5):616-22.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Tang et al., Combining radiation and immunotherapy: a new systemic therapy for solid tumors? Cancer Immunol Res. Sep. 2014;2(9):831-8.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Wang-Gillam et al., A phase I study of IMP321 and gemcitabine as the front-line therapy in patients with advanced pancreatic adenocarcinoma. Invest New Drugs. Jun. 2013;31(3):707-13.
Xiong et al., Transcription Factor Stats as a Novel Molecular Target for Cancer Prevention. Cancers (Basel). Apr. 16, 2014;6(2):926-57.
Zhao et al., a cell-permeable Stat3 SH2 domain mimetic inhibits Stat3 activation and induces antitumor cell effects in vitro. J Biol Chem. Nov. 12, 2010;285(46):35855-65.
Aharoni et al., New findings and old controversies in the research of multiple sclerosis and its model experimental autoimmune encephalomyelitis. Expert Rev Clin Immunol. May 2013;9(5):423-40.
Bartholomew et al., Mesenchymal stem cells suppress lymphocyte proliferation in vitro and prolong skin graft survival in vivo. Exp Hematol. Jan. 2002;30(1):42-8.
Chapman, Endosomal proteases in antigen presentation. Curr Opin Immunol. Feb. 2006;18(1):78-84.
Gutsmiedl et al., Copper-free "click" modification of DNA via nitrile oxide-norbornene 1,3-dipolar cycloaddition. Org Lett. Jun. 4, 2009;11(11):2405-8.
Howard et al., Polymer micelles with hydrazone-ester dual linkers for tunable release of dexamethasone. Pharm Res. Oct. 2011;28(10):2435-46.

(56) References Cited

OTHER PUBLICATIONS

Jones et al., Preparation of 6 alpha- and 6 beta-carboxymethyl steroid conjugates and their use in radioimmunoassay for progesterone. Steroids. Mar. 1974;23(3):323-36.
Khomyakova et al., DNA or RNA oligonucleotide 2'-hydrazides for chemoselective click-type ligation with carbonyl compounds. Nucleosides Nucleotides Nucleic Acids. Jul.-Aug. 2011;30(7-8):577-84.
Kim et al., Synthesis and characterization of dexamethasone-conjugated linear polyethylenimine as a gene carrier. Journal of Cellular Biochemistry. Jun. 1, 2010;110(3):743-751.
Knight et al., Synthesis and evaluation of an 18F-labelled norbornene derivative for copper-free click chemistry reactions. Org Biomol Chem. Jun. 21, 2013;11(23):3817-25.
Liederer et al., Enzymes involved in the bioconversion of ester-based prodrugs. J Pharm Sci. Jun. 2006;95(6):1177-95.
Rossin et al., In vivo chemistry for pretargeted tumor imaging in live mice. Angew Chem Int Ed Engl. Apr. 26, 2010;49(19):3375-8.
Santini et al., A controlled-release microchip. Nature. Jan. 28, 1999;397(6717):335-8.
Saxon et al., Cell surface engineering by a modified Staudinger reaction. Science. Mar. 17, 2000;287(5460):2007-10.
Simmons et al., GM-CSF as a systemic adjuvant in a phase II prostate cancer vaccine trial. Prostate. Jun. 1, 1999;39(4):291-7.
Stockmann et al., Exploring isonitrile-based click chemistry for ligation with biomolecules. Organic & Biomolecular Chemistry. 2011;9:7300-7302.
UniProtKB/Swiss-Prot Accession No. Q61885.1, Feb. 13, 2019.
Van Berkel et al., Metal-free triazole formation as a tool for bioconjugation. Chembiochem. Sep. 3, 2007;8(13):1504-8.
Abrahams et al., Expression and secretion of antiviral factors by trophoblast cells following stimulation by the TLR-3 agonist, Poly(I : C). Hum Reprod. Sep. 2006;21(9):2432-9.
Agache et al., Mechanical properties and Young's modulus of human skin in vivo. Arch Dermatol Res. 1980;269(3):221-32.
Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.
Aguado et al., Improving viability of stem cells during syringe needle flow through the design of hydrogel cell carriers. Tissue Eng Part A. Apr. 2012;18(7-8):806-15.
Akira et al., Pathogen recognition and innate immunity. Cell. Feb. 24, 2006;124(4):783-801.
Akira et al., Toll-like receptors: critical proteins linking innate and acquired immunity. Nat Immunol. Aug. 2001;2(8):675-80.
Akpalo et al., Fibrin-polyethylene oxide interpenetrating polymer networks: new self-supported biomaterials combining the properties of both protein gel and synthetic polymer. Acta Biomater. Jun. 2011;7(6):2418-27.
Aldhous, Print Me a Heart and a Set of Arteries. New Scientist. 2006;2547:19.
Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.
Ali et al., Converging Cell Therapy with Biomaterials. Cell Transplantation from Laboratory to Clinic. 2006:591-609.
Ali et al., Identification of immune factors regulating antitumor immunity using polymeric vaccines with multiple adjuvants. Cancer Res. Mar. 15, 2014;74(6):1670-81.
Ali et al., In situ regulation of DC subsets and T cells mediates tumor regression in mice. Sci Transl Med. Nov. 25, 2009;1(8):8ra19, 1-10.
Ali et al., Infection-mimicking materials to program dendritic cells in situ. Nat Mater. Feb. 2009;8(2):151-8.
Ali et al., Inflammatory cytokines presented from polymer matrices differentially generate and activate DCs in situ.. Adv Funct Mater. Aug. 1, 2013;23(36):4621-4628.
Ali et al., Sustained GM-CSF and PEI condensed pDNA presentation increases the level and duration of gene expression in dendritic cells. J Control Release. Dec. 18, 2008;132(3):273-8.
Ali et al., The efficacy of intracranial PLG-based vaccines is dependent on direct implantation into brain tissue. J Control Release. Sep. 25, 2011;154(3):249-57.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineering growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
Ambrosini et al., Astrocytes produce dendritic cell-attracting chemokines in vitro and in multiple sclerosis lesions. J Neuropathol Exp Neurol. Aug. 2005;64(8):706-15.
American Diabetes Association, Standards of Medical Care in Diabetes—2013. Diabetes Care. 2013;36(S1):S11-S66.
Anderson et al., Biomaterial microarrays: rapid, microscale screening of polymer-cell interaction. Biomaterials. Aug. 2005;26(23):4892-7.
Anderson et al., Nanoliter-scale synthesis of arrayed biomaterials and application to human embryonic stem cells. Nat Biotechnol. Jul. 2004;22(7):863-6.
Anderson et al., The NOD mouse: a model of immune dysregulation. Annu Rev Immunol. 2005;23:447-85.
Anderson, A role for nitric oxide in muscle repair: nitric oxide-mediated activation of muscle satellite cells. Mol Biol Cell. May 2000;11(5):1859-74.
Annabi et al., Controlling the porosity and microarchitecture of hydrogels for tissue engineering. Tissue Eng Part B Rev. Aug. 2010;16(4):371-83.
Annual Review. 2008:122-131.
Arany et al., At the edge of translation—materials to program cells for directed differentiation. Oral Dis. Apr. 2011;17(3):241-51.
Aschner et al., Metabolic memory for vascular disease in diabetes. Diabetes Technol Ther. Jun. 2012;14 Suppl 1:S68-74.
Atala et al., Endoscopic treatment of vesicoureteral reflux with a chondrocyte-alginate suspension. J Urol. Aug. 1994;152(2 Pt 2):641-3.
Aubin et al., Directed 3D cell alignment and elongation in microengineered hydrogels. Biomaterials. Sep. 2010;31(27):6941-6951.
Augst et al., Alginate hydrogels as biomaterials. Macromol Biosci. Aug. 7, 2006;6(8):623-33.
Babensee et al., Host response to tissue engineered devices. Advanced Drug Delivery Reviews. Aug. 3, 1998;33(1-2):111-139.
Bachelder et al., Acid-degradable polyurethane particles for protein-based vaccines: biological evaluation and in vitro analysis of particle degradation products. Mol Pharm. Sep.-Oct. 2008;5(5):876-84.
Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007;11 4(5):855-9.
Balakrishna et al., Structural correlates of antibacterial and membrane-permeabilizing activities in acylpolyamines. Antimicrob Agents Chemother. Mar. 2006;50(3):852-61.
Banchereau et al., Dendritic cells and the control of immunity. Nature. Mar. 19, 1998;392(6673):245-52.

(56) References Cited

OTHER PUBLICATIONS

Bar-Cohen et al., Electroactive Polymer Actuators and Sensors. MRS Bullet. 2008;33(3):173-181.

Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.

Barbero et al., Growth factor supplemented matrigel improves ectopic skeletal muscle formation—a cell therapy approach. J Cell Physiol. Feb. 2001;186(2):183-92.

Barbucci et al., Hyaluronic acid hydrogel in the treatment of osteoarthritis. Biomaterials. Dec. 2002;23(23):4503-13.

Barrio et al., A two-dimensional numerical study of spatial pattern formation in interacting Turing systems. Bull Math Biol. May 1999;61(3):483-505.

Baskin et al., Copper-free click chemistry for dynamic in vivo imaging. Proc Natl Acad Sci U S A. Oct. 23, 2007;104(43):16793-7.

Bates, Improved muscle regeneration by combining VEGF with IGF1. Regen Med. Nov. 2010;5(6):853-4.

Beaucage et al., The Functionalization of Oligonucleotides via Phosphoramidite Derivatives. Tetrahedron. Mar. 5, 1993;49(10):1925-1963.

Beauchamp et al., Dynamics of myoblast transplantation reveal a discrete minority of precursors with stem cell-like properties as the myogenic source. J Cell Biol. Mar. 22, 1999;144(6):1113-22.

Becker et al., Cytological demonstration of the clonal nature of spleen colonies derived from transplanted mouse marrow cells. Nature. Feb. 2, 1963;197:452-4.

Beebe et al., Functional hydrogel structures for autonomous flow control inside microfluidic channels. Nature. Apr. 6, 2000;404(6778):588-90.

Bekiari et al., Study of poly(N,N-dimethylacrylamide)/CdS nanocomposite organic/inorganic gels. Langmuir. Sep. 14, 2004;20(19):7972-5.

Bell, Models for the specific adhesion of cells to cells. Science. May 12, 1978;200(4342):618-27.

Bencherif et al., End-group effects on the properties of PEG-co-PGA hydrogels. Acta Biomater. Jul. 2009;5(6):1872-83.

Bencherif et al., Influence of cross-linker chemistry on release kinetics of PEG-co-PGA hydrogels. J Biomed Mater Res A. Jul. 2009;90(1):142-53.

Bencherif et al., Influence of the degree of methacrylation on hyaluronic acid hydrogels properties. Biomaterials. Apr. 2008;29(12):1739-49.

Bencherif et al., Injectable preformed scaffolds with shape-memory properties. Proc Natl Acad Sci U S A. Nov. 27, 2012;109(48):19590-5.

Bencherif et al., Nanostructured hybrid hydrogels prepared by a combination of atom transfer radical polymerization and free radical polymerization. Biomaterials. Oct. 2009;30(29):5270-8.

Bencherif et al., Synthesis by AGET ATRP of degradable nanogel precursors for in situ formation of nanostructured hyaluronic acid hydrogel. Biomacromolecules. Sep. 14, 2009;10(9):2499-507.

Benton et al., Photocrosslinking of gelatin macromers to synthesize porous hydrogels that promote valvular interstitial cell function. Tissue Eng Part A. Nov. 2009;15(11):3221-30.

Berg et al., Il-10 is a central regulator of cyclooxygenase-2 expression and prostaglandin production. J Immunol. Feb. 15, 2001;166(4):2674-80.

Bergstraesser et al., Stimulation and inhibition of human mammary epithelial cell duct morphogenesis in vitro. Proc Assoc Am Physicians. Mar. 1996;108(2):140-54.

Bianco et al., The meaning, the sense and the significance: translating the science of mesenchymal stem cells into medicine. Nat Med. Jan. 2013;19(1):35-42.

Bilodeau et al., Regular Pyramid Punch Problem. J Appl Mech. 1992;59(3):519-523.

Bischoff, Proliferation of muscle satellite cells on intact myofibers in culture. Dev Biol. May 1986;115(1):129-39.

Blanas et al., Induction of autoimmune diabetes by oral administration of autoantigen. Science. Dec. 6, 1996;274(5293):1707-9.

Blumenthal et al., Polyurethane scaffolds seeded with genetically engineered skeletal myoblasts: a promising tool to regenerate myocardial function. Artif Organs. Feb. 2010;34(2):E46-54.

Boateng et al., Wound healing dressings and drug delivery systems: a review. J Pharm Sci. Aug. 2008;97(8):2892-923.

Boerckel et al., Mechanical regulation of vascular growth and tissue regeneration in vivo. Proc Natl Acad Sci U S A. Sep. 13, 2011;108(37):E674-80.

Bohl et al., Role of synthetic extracellular matrix in development of engineered dental pulp. J Biomater Sci Polym Ed. 1998;9(7):749-64.

Bonauer et al., MicroRNA-92a controls angiogenesis and functional recovery of ischemic tissues in mice. Science. Jun. 26, 2009;324(5935):1710-3.

Boontheekul et al., Controlling alginate gel degradation utilizing partial oxidation and bimodal molecular weight distribution. Biomaterials. May 2005;26(15):2455-65.

Boontheekul et al., Regulating myoblast phenotype through controlled gel stiffness and degradation. Tissue Eng. Jul. 2007;13(7):1431-42.

Borselli et al., Functional muscle regeneration with combined delivery of angiogenesis and myogenesis factors. Proc Natl Acad Sci U S A. Feb. 23, 2010;107(8):3287-92.

Bouhadir et al., Degradation of partially oxidized alginate and its potential application for tissue engineering. Biotechnol Prog. Sep.-Oct. 2001;17(5):945-50.

Bouhadir et al., Synthesis of Cross-Linked Poly(aldehyde guluronate) Hydrogels. Polymer. Jun. 1999;40(12):3575-3584.

Bowne et al., Injection of DNA encoding granulocyte-macrophage colony-stimulating factor recruits dendritic cells for immune adjuvant effects. Cytokines Cell Mol Ther. Dec. 1999;5(4):217-25.

Brinkman et al., Photo-cross-linking of type I collagen gels in the presence of smooth muscle cells: mechanical properties, cell viability, and function. Biomacromolecules. Jul.-Aug. 2003; 4(4):890-5.

Brinkmann et al., Neutrophil extracellular traps kill bacteria. Science. Mar. 5, 2004;303(5663):1532-5.

Brouwers et al., Can the growth factors PTHrP, Ihh and VEGF, together regulate the development of a long bone? J Biomech. 2006;39(15):2774-82.

Broxmeyer, Insights into the biology of cord blood stem/progenitor cells. Cell Prolif. Apr. 2011;44 Suppl 1:55-9.

Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.

Bryant et al., Photo-patterning of porous hydrogels for tissue engineering. Biomaterials. Jul. 2007;28(19):2978-86.

Bucki et al., Combined antibacterial and anti-inflammatory activity of a cationic disubstituted dexamethasone-spermine conjugate. Antimicrob Agents Chemother. Jun. 2010;54(6):2525-33.

Buckwalter et al., Form of Antigen Dictates Immunity: Irradiated Cell vs. Whole Cell Lysate Vaccination. J Immunol. Apr. 1, 2007;178(1 Suppl):S77.

Bullard et al., Fetal wound healing: current biology. World J Surg. Jan. 2003;27(1):54-61.

Buonaguro et al., Translating tumor antigens into cancer vaccines. Clin Vaccine Immunol. Jan. 2011;18(1):23-34.

Burdick et al., Controlled degradation and mechanical behavior of photopolymerized hyaluronic acid networks. Biomacromolecules. Jan.-Feb. 2005;6(1):386-91.

Burdick et al., Photoencapsulation of osteoblasts in injectable RGD-modified PEG hydrogels for bone tissue engineering. Biomaterials. Nov. 2002;23(22):4315-23.

Burdick et al., Stimulation of neurite outgrowth by neurotrophins delivered from degradable hydrogels. Biomaterials. Jan. 2006;27(3):452-9.

Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.

(56) References Cited

OTHER PUBLICATIONS

Bégué et al., Vaccination against human papillomavirus. Implementation and efficacy against cervical cancer control. Bull Acad Natl Med. Dec. 2007;191(9):1805-16.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009;30(25):4085-93.
care.diabetesjournals.org, Standards of Medical Care in Diabetes. Diabetes Care. Jan. 2013;36(Suppl 1):S1-S2.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6):133-8.
Champion et al., Shape induced inhibition of phagocytosis of polymer particles. Pharm Res. Jan. 2009;26(1):244-9.
Chan et al., Antifibrotic effects of suramin in injured skeletal muscle after laceration. J Appl Physiol. Sep. 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.
Chang, Mouse models for studies of retinal degeneration and diseases. Methods Mol Biol. 2013;935:27-39.
Chen et al., Adipogenic differentiation of adipose tissue-derived human mesenchymal stem cells: effect of gastric bypass surgery. Surg Endosc. Dec. 2012;26(12):3449-56.
Chen et al., Functional Human Vascular Network Generated in Photocrosslinkable Gelatin Methacrylate Hydrogels. Adv Funct Mater. May 23, 2012;22(10):2027-2039.
Chen et al., Integrated approach to designing growth factor delivery systems. FASEB J. Dec. 2007;21(14):3896-903.
Chen et al., Polymeric growth factor delivery strategies for tissue engineering. Pharm Res. Aug. 2003;20(8):1103-12.
Chen et al., Programmed cell death of dendritic cells in immune regulation. Immunol Rev. Jul. 2010;236:11-27.
Chen et al., Skeletal muscle stem cells. Reprod Biol Endocrinol. Nov. 13, 2003;1:101. 7 pages.
Chen et al., Spatio-temporal VEGF and PDGF delivery patterns blood vessel formation and maturation. Pharm Res. Feb. 2007;24(2):258-64.
Chiang et al., Whole tumor antigen vaccines. Semin Immunol. Jun. 2010;22(3):132-43.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001-6.
Choi, Replacement Organs, Hot Off the Press. New Scientist. 2003;177(2379):16.

Chou et al., Characterization of Photocross Linked Alginate Hydrogels for Nucleus Pulposus Cell Encapsulation. J Biomed Mater Res A. 2009;91A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al., Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990;50(12):3487-92.
Cohen et al., Controlled delivery systems for proteins based on poly(lactic/glycolic acid) microspheres. Pharm Res. Jun. 1991;8(6):713-20.
Comisar et al., Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.
Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering, vol. 2. Third Edition. Pergamon Press. Chapter 4, pp. 125-171, (1978).
Coutinho et al., The anti-inflammatory and immunosuppressive effects of glucocorticoids, recent developments and mechanistic insights. Mol Cell Endocrinol. Mar. 15, 2011;335(1):2-13.
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inching toward the finish line. J Clin Invest. Feb. 2002;109(3):311-2.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dainiak et al., Gelatin-fibrinogen cryogel dermal matrices for wound repair: preparation, optimisation and in vitro study. Biomaterials. Jan. 2010;31(1):67-76.
Dar et al., Optimization of cardiac cell seeding and distribution in 3D porous alginate scaffolds. Biotechnol Bioeng. Nov. 5, 2002;80(3):305-12.

(56) References Cited

OTHER PUBLICATIONS

Daro et al., Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts. Biophys J. Apr. 1999;76(4):2307-16.
Den Haan et al., CD8(+) but not CD8(-) dendritic cells cross-prime cytotoxic T cells in vivo. J Exp Med. Dec. 18, 2000;192(12):1685-96.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian skeletal muscle constructs engineered in vitro. In Vitro Cell Dev Biot Anim. May 2000;36(5):327-35.
Deshmane et al., Monocyte chemoattractant protein-1 (MCP-1): an overview. J Interferon Cytokine Res. Jun. 2009;29(6):313-26.
Dexter et al., Conditions controlling the proliferation of haemopoietic stem cells in vitro. J Cell Physiol. Jun. 1977;91(3):335-44.
Di Nicola et al., Human bone marrow stromal cells suppress T-lymphocyte proliferation induced by cellular or nonspecific mitogenic stimuli. Blood. May 15, 2002;99(10):3838-43.
Diduch et al., Two cell lines from bone marrow that differ in terms of collagen synthesis, osteogenic characteristics, and matrix mineralization. J Bone Joint Surg Am. Jan. 1993;75(1):92-105.
Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al., Antigens and Receptors. Lippincott's Illustrated Reviews: Immunology. Wolters Kluwer/Lippincott Williams & Wilsons, Philadelphia. Chapter 12, pp. 11-23, (2008).
Doan et al., Subcellular localization of a sporulation membrane protein is achieved through a network of interactions along and across the septum. Mol Microbiol. Mar. 2005;55(6):1767-81.
Donati et al., New hypothesis on the role of alternating sequences in calcium-alginate gels. Biomacromolecules. Mar.-Apr. 2005;6(2):1031-40.
Dong et al., Antitumor effect of secreted Flt3-ligand can act at distant tumor sites in a murine model of head and neck cancer. Cancer Gene Ther. Feb. 2003;10(2):96-104.
Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Dranoff, Cytokines in cancer pathogenesis and cancer therapy. Nat Rev Cancer. Jan. 2004;4(1):11-22.
Dranoff, GM-CSF-based cancer vaccines. Immunol Rev. Oct. 2002;188:147-54.
Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.
Dufort et al., Balancing forces: architectural control of mechanotransduction. Nat Rev Mol Cell Biol. May 2011;12(5):308-19.
Dupont et al., Role of YAP/TAZ in mechanotransduction. Nature. Jun. 8, 2011;474(7350):179-83.
Edwards et al., Evaluation of biomechanical properties of human skin. Clin Dermatol. Jul.-Aug. 1995;13(4):375-80.
Egholm et al., Peptide Nucleic Acids (PNA). Oligonucleotide Analogues with an Achiral Peptide Backbone. J Am Chem Soc. 1992;114(5):1895-1897.
Egholm et al., PNA hybridizes to complementary oligonucleotides obeying the Watson-Crick hydrogen-bonding rules. Nature. Oct. 7, 1993;365(6446):566-8.
Ehrbar et al., Endothelial cell proliferation and progenitor maturation by fibrin-bound VEGF variants with differential susceptibilities to local cellular activity. J Control Release. Jan. 3, 2005;101(1-3):93-109.
Eiselt et al., Porous carriers for biomedical applications based on alginate hydrogels. Biomaterials. Oct. 2000;21(19):1921-7.
El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.
El-Behi et al., The encephalitogenicity of T(H)17 cells is dependent on IL-1- and IL-23-induced production of the cytokine GM-CSF. Nat Immunol. Jun. 2011;12(6):568-75.
Eldar et al., Elucidating mechanisms underlying robustness of morphogen gradients. Curr Opin Genet Dev. Aug. 2004;14(4):435-9.
Eldar et al., Robustness of the BMP morphogen gradient in *Drosophila* embryonic patterning. Nature. Sep. 19, 2002;419(6904):304-8.
Eldar et al., Self-enhanced ligand degradation underlies robustness of morphogen gradients. Dev Cell. Oct. 2003;5(4):635-46.
Eming et al., Inflammation in wound repair: molecular and cellular mechanisms. J Invest Dermatol. Mar. 2007;127(3):514-25.
Engler et al., Matrix elasticity directs stem cell lineage specification. Cell. Aug. 25, 2006;126(4):677-89.
Engler et al., Microtissue elasticity: measurements by atomic force microscopy and its influence on cell differentiation. Methods Cell Biol. 2007;83:521-45.
Engler et al., Substrate compliance versus ligand density in cell on gel responses. Biophys J. Jan. 2004;86(1 Pt 1):617-28.
Ennett et al., Temporally regulated delivery of VEGF in vitro and in vivo. J Biomed Mater Res A. Oct. 2006;79(1):176-84.
Exposito et al., The fibrillar collagen family. Int J Mol Sci. Jan. 28, 2010;11(2):407-26.
Faissner et al., Boundaries and inhibitory molecules in developing neural tissues. Glia. Apr. 1995;13(4):233-54.
Falanga, Wound healing and its impairment in the diabetic foot. Lancet. Nov. 12, 2005;366(9498):1736-43.
Falsey et al., Peptide and small molecule microarray for high throughput cell adhesion and functional assays. Bioconjug Chem. May-Jun. 2001;12(3):346-53.
Farrar et al., T helper subset development: roles of instruction, selection, and transcription. J Clin Invest. Feb. 2002;109(4):431-5.
Fauquemberque et al., HLA-A*0201-restricted CEA-derived peptide CAP1 is not a suitable target for T-cell-based immunotherapy. J Immunother. May 2010;33(4):402-13.
Ferrara et al., Angiogenesis as a therapeutic target. Nature. Dec. 15, 2005;438(7070):967-74.
Ferrara et al., Discovery and development of bevacizumab, an anti-VEGF antibody for treating cancer. Nat Rev Drug Discov. May 2004;3(5):391-400.
Fischbach et al., Polymeric Systems for Bioinspired Delivery of Angiogenic Molecules. Adv Polym Sci. 2006;203:191-221.
Fischer et al., A brilliant monomeric red fluorescent protein to visualize cytoskeleton dynamics in Dictyostelium. FEBS Lett. Nov. 5, 2004;577(1-2):227-32.

(56) References Cited

OTHER PUBLICATIONS

Fischer et al., Visualizing cytoskeleton dynamics in mammalian cells using a humanized variant of monomeric red fluorescent protein. FEBS Lett. May 1, 2006;580(10):2495-502.
Fisher et al., The study of protein mechanics with the atomic force microscope. Trends Biochem Sci. Oct. 1999;24(10):379-84.
Folkman, Angiogenesis. Annu Rev Med. 2006;57:1-18.
Fonseca et al., Capitalizing on the immunogenicity of dying tumor cells. Clin Cancer Res. Mar. 15, 2008;14(6):1603-8.
Fontaine et al., Surgical treatment of peripheral circulation disorders. Helv Chir Acta. Dec. 1954;21(5-6):499-533.
Ford et al., Specificity, magnitude, and kinetics of MOG-specific CD8+ T cell responses during experimental autoimmune encephalomyelitis. Eur J Immunol. Jan. 2005;35(1):76-85.
Fox, Management of worsening multiple sclerosis with mitoxantrone: a review. Clin Ther. Apr. 2006;28(4):461-74.
Friedenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Gamvrellis et al., Vaccines that facilitate antigen entry into dendritic cells. Immunol Cell Biol. Oct. 2004;82(5):506-16.
Ganguly et al., The role of dendritic cells in autoimmunity. Nat Rev Immunol. Aug. 2013;13(8):566-77.
Gardel et al., Traction stress in focal adhesions correlates biphasically with actin retrograde flow speed. J Cell Biol. Dec. 15, 2008;183(6):999-1005.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3. May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AA144040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.

(56) References Cited

OTHER PUBLICATIONS

GenBank Accession No. CB171013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_001025081.1, Jan. 19, 2019.
GenBank Accession No. NP_001020252.1, Jan. 19, 2019.
GenBank Accession No. P49771.1, Jan. 9, 2013.
GenBank Accession No. Q61552.1, dated Jan. 16, 2016.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Getts et al., Current landscape for T-cell targeting in autoimmunity and transplantation. Immunotherapy. Jul. 2011;3(7):853-70.
Gilboa, DC-based cancer vaccines. J Clin Invest. May 2007;117(5):1195-203.
Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.
Godbey et al. Tracking the intracellular path of poly(ethylenimine)/DNA complexes for gene delivery. Proc Natl Acad Sci U S A. Apr. 27, 1999;96(9):5177-81.
Godbey et al., Size matters: molecular weight affects theefficiency of poly(ethylenimine) as a gene delivery vehicle. J Biomed Mater Res. Jun. 5, 1999;45(3):268-75.
Goddard et al., Polymer surface modification for the attachment of bioactive compounds. Progress in Polymer Science. Jul. 2007;32(7):698-725.
Gomez-Cambronero, Rapamycin inhibits GM-CSF-induced neutrophil migration. FEBS Lett. Aug. 28, 2003;550(1-3):94-100.
Gospodarowicz et al., Effect of fibroblast growth factor on the division and fusion of bovine myoblasts. J Cell Biol. Aug. 1976;70(2 pt 1):395-405.
Graessley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Haase et al., CD40 is necessary for activation of naïve T cells by a dendritic cell line in vivo but not in vitro. Scand J Immunol. Mar. 2004;59(3):237-45.
Halim et al., Biologic and synthetic skin substitutes: An overview. Indian J Plast Surg. Sep. 2010;43(Suppl):S23-8.

Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Hanada, Efficacy of rehabilitative therapy in regional musculoskeletal conditions. Best Pract Res Clin Rheumatol. Feb. 2003;17(1):151-66.
Hansell et al., Additive-free clicking for polymer functionalization and coupling by tetrazine-norbornene chemistry. J Am Chem Soc. Sep. 7, 2011;133(35):13828-31.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harris et al., Open pore biodegradable matrices formed with gas foaming. J Biomed Mater Res. Dec. 5, 1998;42(3):396-402.
Harris, Classification, Diagnostic Criteria, and Screening for Diabetes. Diabetes in America. NIH Publication No. 95/1468. Chapter 2. (1995):15-36.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hashimoto et al., Development of alginate wound dressings linked with hybrid peptides derived from laminin and elastin. Biomaterials. Mar.-Apr. 2004;25(7-8):1407-14.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.
Helm et al., Synergy between interstitial flow and VEGF directs capillary morphogenesis in vitro through a gradient amplification mechanism. Proc Natl Acad Sci U S A. Nov. 1, 2005;102(44):15779-84.
Henry et al., VIVA Investigators. The VIVA trial: Vascular endothelial growth factor in Ischemia for Vascular Angiogenesis. Circulation. Mar. 18, 2003;107(10):1359-65.
Hermanson, Bioconjugate Techniques. Academic Press, New York. pp. 152-186, (1996).
Heslop et al., Transplanted primary neonatal myoblasts can give rise to functional satellite cells as identified using the Myf5nlacZl+ mouse. Gene Ther. May 2001;8(10):778-83.
Hildner et al., Batf3 deficiency reveals a critical role for CD8alpha+ dendritic cells in cytotoxic T cell immunity. Science. Nov. 14, 2008;322(5904):1097-100.
Hill et al., Designing scaffolds to enhance transplanted myoblast survival and migration. Tissue Eng. May 2006;12(5):1295-304.
Hill et al., Muscle satellite (stem) cell activation during local tissue injury and repair. J Anat. Jul. 2003;203(1):89-99.
Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.
Hirano et al., Peptide and Protein Presenting Materials for Tissue Engineering. Adv Mat. Jan. 16, 2004;16(1):17-25.
Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.

(56) References Cited

OTHER PUBLICATIONS

Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.
Holland et al., Dual growth factor delivery from degradable oligo(poly(ethylene glycol) fumarate) hydrogel scaffolds for cartilage tissue engineering. Journal of Controlled Release. 2005;101:111-125.
Holland et al., Transforming growth factor-beta 1 release from oligo(poly(ethylene glycol) fumarate) hydrogels in conditions that model the cartilage wound healing environment. J Control Release. Jan. 8, 2004;94(1):101-14.
Horsley et al., IL-4 acts as a myoblast recruitment factor during mammalian muscle growth. Cell. May 16, 2003;113(4):483-94.
Hsiong et al., Differentiation stage alters matrix control of stem cells. J Biomed Mater Res A. Apr. 2008;85A(1):145-56.
Hu et al., Tolerogenic dendritic cells and their potential applications. Immunology. Mar. 2011;132(3):307-14.
Huang et al., Fabrication and in vitro Testing of Polymeric Delivery Systems for Condensed DNA. J Biomed Mater Res. 2003;67:1384-1392.
Huang et al., Long-Term In Vivo Gene Expression via Delivery of PEI-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands ata glance. J Cell Sci. Oct. 1, 2006;119(Pt 19):3901-3.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al., Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003. 12 pages.
Iellem et al., Unique chemotactic response profile and specific expression of chemokine receptors CCR4 and CCR8 by CD4(+)CD25(+) regulatory T cells. J Exp Med. Sep. 17, 2001;194(6):847-53.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Isern et al., Self-renewing human bone marrow mesenspheres promote hematopoietic stem cell expansion. Cell Rep. May 30, 2013;3(5):1714-24.
Ishihara et al., Roles of bradykinin in vascular permeability and angiogenesis in solid tumor. Int Immunopharmacol. Mar. 2002;2(4):499-509.
Iwamoto et al., Preparation of an Ionic Polymer Gel Microactuator and Measurement of its Periodic Motions. Nippon Kagaku Kaishi. 1997;9:609-614.

Jager et al., Effector and regulatory T-cell subsets in autoimmunity and tissue inflammation. Scand J Immunol. Sep. 2010;72(3):173-84.
Jain, Molecular Regeneration of Vessel Maturation. Nat Med. Jun. 1, 2003;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(−/−) setting. Immunity. Mar. 2002;16(3):429-39.
Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jewett et al., Rapid Cu-free click chemistry with readily synthesized biarylazacyclooctynones. J Am Chem Soc. Mar. 24, 2010;132(11):3688-90.
Jiang et al. Two-piconewton slip bond between fibronectin and the cytoskeleton depends on talin. Nature. Jul. 17, 2003;424(6946):334-7.
Jiang et al., Self-organization of periodic patterns by dissociated feather mesenchymal cells and the regulation of size, number and spacing of primordia. Development. Nov. 1999;126(22):4997-5009.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;117(7):1902-13.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jorgensen et al., Treatment of an immortalized APC cell line with both cytokines and LPS ensures effective T-cell activation in vitro. Scand J Immunol. Nov. 2002;56(5):492-503.
Jugdutt et al., Aging and defective healing, adverse remodeling, and blunted post-conditioning in the reperfused wounded heart. J Am Coll Cardiol. Apr. 8, 2008;51(14):1399-403.
Juntanen et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels. J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.
Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Katayama et al., Integrated analysis of the genome and the transcriptome by FANTOM. Brief Bioinform. Sep. 2004;5(3):249-58.
Kathuria et al., Synthesis and characterization of elastic and macroporous chitosan-gelatin cryogels for tissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.
Kennedy et al., Rapid and extensive collapse from electrically responsive macroporous hydrogels. Adv Healthc Mater. Apr. 2014;3(4):500-7.

(56) References Cited

OTHER PUBLICATIONS

Khetan et al., Degradation-mediated cellular traction directs stem cell fate in covalently crosslinked three-dimensional hydrogels. Nat Mater. May 2013;12(5):458-65.

Khownium et al., Novel endotoxin-sequestering compounds with terephthalaldehyde-bis-guanylhydrazone scaffolds. Bioorg Med Chem Lett. Mar. 1, 2006;16(5):1305-8.

Kim et al., An overview of cartilage tissue engineering. Yonsei Med J. Dec. 2000;41(6):766-73.

Kim et al., Injectable, spontaneously assembling, inorganic scaffolds modulate immune cells in vivo and increase vaccine efficacy. Nat Biotechnol. Jan. 2015;33(1):64-72.

Kim et al., Multifunctional capsule-in-capsules for immunoprotection and trimodal imaging. Angew Chem Int Ed Engl. Mar. 1, 2011;50(10):2317-21.

Kim et al., The effect of VEGF on the myogenic differentiation of adipose tissue derived stem cells within thermosensitive hydrogel matrices. Biomaterials. Feb. 2010;31(6):1213-8.

Kinoshita et al., Successive injections in mdx mice of myoblasts grown with bFGF. Neuromuscul Disord. May 1996;6(3):187-93.

Kisak et al. The vesosome—a multicompartment drug delivery vehicle. Curr Med Chem. Jan. 2004;11(2):199-219.

Klebanoff et al., CD8+ T-cell memory in tumor immunology and immunotherapy. Immunol Rev. Jun. 2006;211:214-24.

Klein et al., Cell-Cycle Control by Physiological Matrix Elasticity and In Viivo Tissue Stiffening. Curr Biol. Sep. 29, 2009;19:1511-1518.

Klinman, Immunotherapeutic uses of CpG oligodeoxynucleotides. Nat Rev Immunol. Apr. 2004;4(4):249-58.

Koehler et al., A Diels-Alder modulated approach to control and sustain the release of dexamethasone and induce osteogenic differentiation of human mesenchymal stem cells. Biomaterials. May 2013;34(16):4150-4158.

Kohane, Microparticles and nanoparticles for drug delivery. Biotechnol Bioeng. Feb. 1, 2007;96(2):203-9.

Kondo et al., A reaction-diffusion wave on the skin of the marine angelfish Pomacanthus. Nature. Aug. 31, 1995;376(6543):765-8.

Kong et al., Controlling Degradation of Hydrogels via the Size of Cross-Linked Junctions. Adv Mater. Nov. 30, 2004;16(21):1917-1921.

Kong et al., Controlling rigidity and degradation of alginate hydrogels via molecular weight distribution. Biomacromolecules. Sep.-Oct. 2004;5(5):1720-7.

Kong et al., Decoupling the Dependence of Rheological/Mechanical Properties of Hydrogels from Solids Concentration. Polymer. 2002;43(23):6239-6246.

Kong et al., Design of biodegradable hydrogel for the local and sustained delivery of angiogenic plasmid DNA. Pharm Res. May 2008;25(5):1230-8.

Kong et al., Designing alginate hydrogels to maintain viability of immobilized cells. Biomaterials. Oct. 2003;24(22):4023-9.

Kong et al., FRET measurements of cell-traction forces and nanoscale clustering of adhesion ligands varied by substrate stiffness. Proc Natl Acad Sci U S A. Mar. 22, 2005;102(12):4300-5.

Kong et al., Non-viral gene delivery regulated by stiffness of cell adhesion substrates. Nat Mater. Jun. 2005;4(6):460-4.

Koo et al., Bioorthogonal copper-free click chemistry in vivo for tumor-targeted delivery of nanoparticles. Angew Chem Int Ed Engl. Nov. 19, 2012;51(47):11836-40.

Kratky et al., Direct activation of antigen-presenting cells is required for CD8+ T-cell priming and tumor vaccination. Proc Natl Acad Sci U S A. Oct. 18, 2011;108(42):17414-9.

Krieg, Development of TLR9 agonists for cancer therapy. J Clin Invest. May 2007;117(5):1184-94.

Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.

Kruisbeek et al., Proliferative assays for T cell function. Curr Protoc Immunol. May 2004;Chapter 3:Unit 3.12. 20 pages.

Kumamoto et al., Induction of tumor-specific protective immunity by in situ Langerhans cell vaccine. Nat Biotechnol. Jan. 2002;20(1):64-9.

Kumar et al., Toll-like receptors and innate immunity. Biochem Biophys Res Commun. Oct. 30, 2009;388(4):621-5.

Kurts et al., CD8 T cell ignorance or tolerance to islet antigens depends on antigen dose. Proc Natl Acad Sci U S A. Oct. 26, 1999;96(22):12703-7.

Kuwahara et al., Cell delivery using an injectable and adhesive transglutaminase-gelatin gel. Tissue Eng Part C Methods. Aug. 2010;16(4):609-18.

Kwon et al., Electrically erodible polymer gel for controlled release of drugs. Nature. Nov. 28, 1991;354(6351):291-3.

Kwon et al., In vivo targeting of dendritic cells for activation of cellular immunity using vaccine carriers based on pH-responsive microparticles. Proc Natl Acad Sci U S A. Dec. 20, 2005;102(51):18264-8.

Langenkamp et al., Kinetics of dendritic cell activation: impact on priming of TH1, TH2 and nonpolarized T cells. Nat Immunol. Oct. 2000;1(4):311-6.

Langer et al., Tissue engineering. Science. May 14, 1993;260(5110):920-6.

Lanzavecchia et al., Regulation of T cell immunity by dendritic cells. Cell. Aug. 10, 2001;106(3):263-6.

Lao et al., Magnetic and hydrogel composite materials for hyperthermia applications. J Mater Sci Mater Med. Oct. 2004;15(10):1061-4.

Latorre et al., Applications of magnetic nanoparticles in medicine: magnetic fluid hyperthermia. P R Health Sci J. Sep. 2009;28(3):227-38.

Latz et al., TLR9 signals after translocating from the ER to CpG DNA in the lysosome. Nat Immunol. Feb. 2004;5(2):190-8.

Lauterbach et al., Mouse CD8alpha+ DCs and human BDCA3+ DCs are major producers of IFN-lambda in response to poly IC. J Exp Med. Nov. 22, 2010;207(12):2703-17.

Leach et al., Coating of VEGF-releasing scaffolds with bioactive glass for angiogenesis and bone regeneration. Biomaterials. Jun. 2006;27(17):3249-55.

Lee et al., Controlling Mechanical and Swelling Properties of Alginate Hydrogels Independently by Cross-Linker Type and Cross-Linking Density. Macromolecules. Apr. 2000;33(11):4291-4294.

Lee et al., Engineering liver tissue spheroids with inverted colloidal crystal scaffolds. Biomaterials. Sep. 2009;30(27):4687-94.

Lee et al., Hydrogel Formation via Vell Crosslinking. Advanced Materials. Nov. 2003;15(21):1828-1832.

Lee et al., Hydrogels for tissue engineering. Chem Rev. Jul. 2001;101(7):1869-79.

Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.

Lefaucheur et al., The cellular events of injured muscle regeneration depend on the nature of the injury. Neuromuscul Disord. Nov. 1995;5(6):501-9.

Lele et al., Investigating complexity of protein-protein interactions in focal adhesions. Biochem Biophys Res Commun. May 9, 2008;369(3):929-34.

Lensch et al., Scientific and clinical opportunities for modeling blood disorders with embryonic stem cells. Blood. Apr. 1, 2006;107(7):2605-12.

Leor et al., Cells, scaffolds, and molecules for myocardial tissue engineering. Pharmacol Ther. Feb. 2005;105(2):151-63.

Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.

Letsinger et al., Phosphoramidate analogs of oligonucleotides. J Org Chem. Nov. 1970;35(11):3800-3.

Levental et al., Soft biological materials and their impact on cell function. Soft Matter. 2007;3:299-306.

Li et al., Effect of growth factors and extracellular matrix materials on the proliferation and differentiation of microencapsulated myoblasts. J Biomater Sci Polym Ed. 2003;14(6):533-49.

(56) References Cited

OTHER PUBLICATIONS

Li et al., Effects of Three-Dimensional Scaffolds on Cell Organization and Tissue Development. Biotechnology and Bioprocess Engineering. Oct. 2001;6(5):311-325.
Li et al., Purified hybrid cells from dendritic cell and tumor cell fusions are superior activators of antitumor immunity. Cancer Immunol Immunother. Nov. 2001;50(9):456-62.
Li, TNF-alpha is a mitogen in skeletal muscle. Am J Physiol Cell Physiol. Aug. 2003;285(2):C370-6.
Lin et al., Transdermal regulation of vascular network bioengineering using a photopolymerizable methacrylated gelatin hydrogel. Biomaterials. Sep. 2013;34(28):6785-96.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu et al., Preparation of uniform calcium alginate gel beads by membrane emulsification coupled with internal gelation. Journal of Applied Polymer Science. Nov. 22, 2002;87(5):848-852.
Liu et al., Syntheses of click PEG-dexamethasone conjugates for the treatment of rheumatoid arthritis. Biomacromolecules. Oct. 11, 2010;11(10):2621-8.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Urology. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Lutterotti et al., Antigen-specific tolerance by autologous myelin peptide-coupled cells: a phase 1 trial in multiple sclerosis. Sci Transl Med. Jun. 5, 2013;5(188):188ra75.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Maini, Spatial and spatio-temporal patterns in a cell-haptotaxis model. J Math Biol. 1989;27(5):507-22.

Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.
Mammoto et al., Mechanical control of tissue and organ development. Development. May 2010;137(9):1407-20.
Manavski et al., Vascular niche controls organ regeneration. Circ Res. Mar. 28, 2014;114(7):1077-9.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci U S A. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKinney-Freeman et al., Muscle-derived hematopoietic stem cells are hematopoietic in origin. Proc Natl Acad Sci U S A. Feb. 5, 2002;99(3):1341-6.
McKinnon et al., Biophysically defined and cytocompatible covalently adaptable networks as viscoelastic 3D cell culture systems. Adv Mater. Feb. 12, 2014;26(6):865-72.
McPherron et al., Regulation of skeletal muscle mass in mice by a new TGF-beta superfamily member. Nature. May 1, 1997;387(6628):83-90.
McQualter et al., Granulocyte macrophage colony-stimulating factor: a new putative therapeutic target in multiple sclerosis. J Exp Med. Oct. 1, 2001;194(7):873-82.
McWhorter et al., Modulation of macrophage phenotype by cell shape. Proc Natl Acad Sci U S A. Oct. 22, 2013;110(43):17253-8.
Meier et al., Peptide Nucleic Acids(PNAs)—Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008;103(2):194-202. Includes supplementary materials.
Melief et al., Immunotherapy of established (pre)malignant disease by synthetic long peptide vaccines. Nat Rev Cancer. May 2008;8(5):351-60.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.

(56) References Cited

OTHER PUBLICATIONS

Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient. 3 pages.
Metters et al., Fundamental studies of biodegradable hydrogels as cartilage replacement materials. Biomed Sci Instrum. 1999;35:33-8.
Meyer et al., Clinical investigations of Toll-like receptor agonists. Expert Opin Investig Drugs. Jul. 2008;17(7):1051-65.
Meylan et al., Intracellular pattern recognition receptors in the host response. Nature. Jul. 6, 2006;442(7098):39-44.
Miljkovic et al., Chondrogenesis, bone morphogenetic protein-4 and mesenchymal stem cells. Osteoarthritis Cartilage. Oct. 2008;16(10):1121-30.
Miller et al., Hepatocyte growth factor affects satellite cell activation and differentiation in regenerating skeletal muscle. Am J Physiol Cell Physiol. Jan. 2000;278(1):C174-81.
Miller et al., Lipopolysaccharide sequestrants: structural correlates of activity and toxicity in novel acylhomospermines. J Med Chem. Apr. 7, 2005;48(7):2589-99.
Miller et al., Melanoma. N Engl J Med. Jul. 6, 2006;355(1):51-65.
Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005;18(2):219-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.
Mooney et al., Cytoskeletal filament assembly and the control of cell spreading and function by extracellular matrix. J Cell Sci. Jun. 1995;108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell regulation of TH1-TH2 development. Nat Immunol. Sep. 2000;1(3):199-205.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.
Nair et al., Polymers as biomaterials for tissue engineering and controlled drug delivery. Adv Biochem Eng Biotechnol. 2006;102:47-90.
NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic cells. Nature Medicine. Mar. 1, 1998;4(3):328-32.
Neves et al., Imaging cell surface glycosylation in vivo using "double click" chemistry. Bioconjug Chem. Jun. 19, 2013;24(6):934-41.
Niamlang et al., Electrically controlled release of salicylic acid from poly(p-phenylene vinylene)/polyacrylamide hydrogels. Int J Pharm. Apr. 17, 2009;371(1-2):126-33.
Nichol et al., Cell-laden microengineered gelatin methacrylate hydrogels. Biomaterials. Jul. 2010;31(21):5536-44.
Nicodemus et al., Cell encapsulation in biodegradable hydrogels for tissue engineering applications. Tissue Eng Part B Rev. Jun. 2008;14(2):149-65.
Niessen et al., The alpha 6 beta 4 integrin is a receptor for both laminin and kalinin. Exp Cell Res. Apr. 1994;211(2):360-7.
Ning et al., Protein modification by strain-promoted alkyne-nitrone cycloaddition. Angew Chem Int Ed Engl. Apr. 12, 2010;49(17):3065-8.
Nogueira De Francischi et al., Inhibition by rapamycin of leukocyte migration and bronchial hyperreactivity induced by injection of Sephadex beads to guinea-pigs. Br J Pharmacol. Dec. 1993;110(4):1381-6.
Noguera-Troise et al., Blockade of Dll4 inhibits tumour growth by promoting non-productive angiogenesis. Nature. Dec. 21, 2006;444(7122):1032-7.
Nuttelman et al., Dexamethasone-functionalized gels induce osteogenic differentiation of encapsulated hMSCs. J Biomed Mater Res A. Jan. 2006;76(1):183-95.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000;1(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistance-forming modification. Science. Aug. 31, 2012;337(6098):1111-5.

(56) References Cited

OTHER PUBLICATIONS

Oldenhove et al., Decrease of Foxp3+ Treg cell number and acquisition of effector cell phenotype during lethal infection. Immunity. Nov. 20, 2009;31(5):772-86.

Oneto et al., Implantable biomaterial based on click chemistry for targeting small molecules. Acta Biomaterialia. 2014;10:5099-5105.

Orner et al., Arrays for the combinatorial exploration of cell adhesion. J Am Chem Soc. Sep. 8, 2004;126(35):10808-9.

Osunkoya et al., Synthesis and fate of immunological surface receptors on cultured Burkitt lymphoma cells. Int J Cancer. Mar. 15, 1969;4(2):159-65.

Ota et al., Percutaneous subxiphoid access to the epicardium using a miniature crawling robotic device. Innovations (Phila). 2006 Fall;1(5):227-31.

Overwijk et al., Tumor regression and autoimmunity after reversal of a functionally tolerant state of self-reactive CD8+ T cells. J Exp Med. Aug. 18, 2003;198(4):569-80.

Ozawa et al., Microenvironmental VEGF concentration, not total dose, determines a threshold between normal and aberrant angiogenesis. J Clin Invest. Feb. 2004;113(4):516-27.

Padilla et al., Insufficient TLR activation contributes to the slow development of CD8+ T cell responses in Trypanosoma cruzi infection. J Immunol. Jul. 15, 2009;183(2):1245-52.

Page-McCaw et al., Matrix metalloproteinases and the regulation of tissue remodelling. Nat Rev Mol Cell Biol. Mar. 2007;8(3):221-33.

Pailler-Mattei et al., In vivo measurements of the elastic mechanical properties of human skin by indentation tests. Med Eng Phys. Jun. 2008;30(5):599-606.

Pajonk et al., From sol-gel to aerogels and cryogels. J Non Cryst Solids. May 1990;121(1-3):66-67.

Palacio et al., Interleukin 10 and tumor necrosis factor alpha gene expression in respiratory and peripheral muscles. Relation to sarcolemmal damage. Arch Bronconeumol. Jul. 2002;38(7):311-6.

Paradee et al., Effects of crosslinking ratio, model drugs, and electric field strength on electrically controlled release for alginate-based hydrogel. J Mater Sci Mater Med. Apr. 2012;23(4):999-1010.

Parekh et al., Modulus-driven differentiation of marrow stromal cells in 3D scaffolds that is independent of myosin-based cytoskeletal tension. Biomaterials. Mar. 2011;32(9):2256-64.

Parekkadan et al., Mesenchymal stem cell-derived molecules reverse fulminant hepatic failure. PLoS One. Sep. 26, 2007;2(9):e941.

Park et al., Photopolymerized hyaluronic acid-based hydrogels and interpenetrating networks. Biomaterials. Mar. 2003;24(6):893-900.

Parker et al., Effect of mitoxantrone on outcome of children with first relapse of acute lymphoblastic leukaemia (ALL R3): an open-label randomised trial. Lancet. Dec. 11, 2010;376(9757):2009-17.

Partridge et al., Conversion of mdx myofibres from dystrophin-negative to -positive by injection of normal myoblasts. Nature. Jan. 12, 1989;337(6203):176-9.

Patterson et al., Differential binding of chemokines to macrophages and neutrophils in the human inflamed synovium. Arthritis Res. 2002;4(3):209-14.

Pawlaczyk et al., Age-dependent biomechanical properties of the skin. Postepy Dermatol Alergol. Oct. 2013;30(5):302-6.

Pedersen et al., Induction of regulatory dendritic cells by dexamethasone and 1alpha,25-Dihydroxyvitamin D(3). Immunol Lett. Jan. 30, 2004;91(1):63-9.

Pek et al., The effect of matrix stiffness on mesenchymal stem cell differentiation in a 3D thixotropic gel. Biomaterials. Jan. 2010;31(3):385-91.

Pelinkovic et al., Tissue engineering and gene therapy of the musculoskeletal system with muscle cells. Z Orthop Ihre Grenzgeb. Sep.-Oct. 2000;138(5):402-6.

Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.

Peters et al., Engineering vascular networks in porous polymer matrices. J Biomed Mater Res. Jun. 15, 2002;60(4):668-78.

Peyton et al., The use of poly(ethylene glycol) hydrogels to investigate the impact of ECM chemistry and mechanics on smooth muscle cells. Biomaterials. Oct. 2006;27(28):4881-93.

Phillippi, Patterning of Multiple Cell Lineages from a Single Stem Cell Population. Annual Meeting of the American Society for Cell Biology. Dec. 10, 2006.

Pinho et al., PDGFRa and CD51 mark human nestin+ sphere-forming mesenchymal stem cells capable of hematopoietic progenitor cell expansion. J Exp Med. Jul. 1, 2013;210(7):1351-67.

Pluen et al., Role of tumor-host interactions in interstitial diffusion of macromolecules: cranial vs. subcutaneous tumors. Proc Natl Acad Sci U S A. Apr. 10, 2001;98(8):4628-33.

Pooyan et al., Conjugates bearing multiple formyl-methionyl peptides display enhanced binding to but not activation of phagocytic cells. Bioconjug Chem. Mar.-Apr. 2002;13(2):216-23.

Pope et al., Organ-specific regulation of the CD8 T cell response to Listeria monocytogenes infection. J Immunol. Mar. 1, 2001;166(5):3402-9.

Porter et al., Separation of Natural Populations of Coliform Bacteria from Freshwater and Sewage by Magnetic-Bead Cell Sorting. J Microbiol Meth. 1998;33(3):221-226.

Pouzet et al., Factors affecting functional outcome after autologous skeletal myoblast transplantation. Ann Thorac Surg. Mar. 2001;71(3):844-50; discussion 850-1.

Pulendran et al., Flt3-ligand and granulocyte colony-stimulating factor mobilize distinct human dendritic cell subsets in vivo. J Immunol. Jul. 1, 2000;165(1):566-72.

Qi et al., Patterned differentiation of individual embryoid bodies in spatially organized 3D hybrid microgels. Adv Mater. Dec. 7, 2010;22(46):5276-81.

Qin et al., Soft lithography for micro- and nanoscale patterning. Nat Protoc. Mar. 2010;5(3):491-502.

Qiu et al., Environment-sensitive hydrogels for drug delivery. Adv Drug Deliv Rev. Dec. 31, 2001;53(3):321-39.

Qu et al., Development of approaches to improve cell survival in myoblast transfer therapy. J Cell Biol. Sep. 7, 1998;142(5):1257-67.

Qu-Petersen et al., Identification of a novel population of muscle stem cells in mice: potential for muscle regeneration. J Cell Biol. May 27, 2002;157(5):851-64.

Quezada et al., CTLA4 blockade and GM-CSF combination immunotherapy alters the intratumor balance of effector and regulatory T cells. J Clin Invest. Jul. 2006;116(7):1935-45.

Raeber et al., Molecularly engineered PEG hydrogels: a novel model system for proteolytically mediated cell migration. Biophys J. Aug. 2005;89(2):1374-88.

Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.

Ramón-Azcón et al., Gelatin methacrylate as a promising hydrogel for 3D microscale organization and proliferation of dielectrophoretically patterned cells. Lab on a Chip. Aug. 21, 2012;12(16):2959-69.

Randolph et al., Migration of dendritic cell subsets and their precursors. Annu Rev Immunol. 2008;26:293-316.

Ranganath et al., Harnessing the mesenchymal stem cell secretome for the treatment of cardiovascular disease. Cell Stem Cell. Mar. 2, 2012;10(3):244-58.

Raposo et al., Extracellular vesicles: exosomes, microvesicles, and friends. J Cell Biol. Feb. 18, 2013;200(4):373-83.

Rappolee et al., Macrophage-derived growth factors. Curr Top Microbiol Immunol. 1992;181:87-140.

Rapraeger, Syndecan-regulated receptor signaling. J Cell Biol. May 29, 2000;149(5):995-8.

Rautio et al., Prodrugs: design and clinical applications. Nat Rev Drug Discov. Mar. 2008;7(3):255-70.

Reddy et al., Exploiting lymphatic transport and complement activation in nanoparticle vaccines. Nat Biotechnol. Oct. 2007;25(10):1159-64.

Reimann et al., Satellite Cells in Normal and Regenerated Soleus Muscles of mdx and Control Mice. Eur J Neurosci. 1998;10:366, Abstract No. 153.07.

(56) References Cited

OTHER PUBLICATIONS

Reis E Sousa., Activation of dendritic cells: translating innate into adaptive immunity. Curr Opin Immunol. Feb. 2004;16(1):21-5.
Research Results of National Institute of Advanced Industrial Science and Technology, retrieved online at: http://www.aist.go.jp/aist_j/press_release/pr2006/pr20060719.html. 4 pages, (2006).
Rhoads et al., Satellite cell-mediated angiogenesis in vitro coincides with a functional hypoxia-inducible factor pathway. Am J Physiol Cell Physiol. Jun. 2009;296(6):C1321-8.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Cancer immunotherapy: moving beyond current vaccines. Nat Med. Sep. 2004;10(9):909-15.
Rosenberg et al., Impact of cytokine administration on the generation of antitumor reactivity in patients with metastatic melanoma receiving a peptide vaccine. J Immunol. Aug. 1, 1999;163(3):1690-5.
Rossin et al., Diels-Alder reaction for tumor pretargeting: in vivo chemistry can boost tumor radiation dose compared with directly labeled antibody. J Nucl Med. Nov. 2013;54(11):1989-95.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-9.
Sansonetti, The innate signaling of dangers and the dangers of innate signaling. Nat Immunol. Dec. 2006;7(12):1237-42.
Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.
Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Serafini et al., High-dose granulocyte-macrophage colony-stimulating factor-producing vaccines impair the immune response through the recruitment of myeloid suppressor cells. Cancer Res. Sep. 1, 2004;64(17):6337-43.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shin et al., Contractile forces sustain and polarize hematopoiesis from stem and progenitor cells. Cell Stem Cell. Jan. 2, 2014;14(1):81-93.

(56) References Cited

OTHER PUBLICATIONS

Shin et al., Lamins regulate cell trafficking and lineage maturation of adult human hematopoietic cells. Proc Natl Acad Sci U S A. Nov. 19, 2013;110(47):18892-7.

Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.

Shoichet et al., Stability of hydrogels used in cell encapsulation: An in vitro comparison of alginate and agarose. Biotechnol Bioeng. May 20, 1996;50(4):374-81.

Shortman et al., Steady-state and inflammatory dendritic-cell development. Nat Rev Immunol. Jan. 2007;7(1):19-30.

Sick et al., WNT and DKK determine hair follicle spacing through a reaction-diffusion mechanism. Science. Dec. 1, 2006;314(5804):1447-50.

Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.

Silva et al., Effects of VEGF temporal and spatial presentation on angiogenesis. Biomaterials. Feb. 2010;31(6):1235-41.

Silva et al., Material-based deployment enhances efficacy of endothelial progenitor cells. Proc Natl Acad Sci U S A. Sep. 23, 2008;105(38):14347-52.

Silva et al., Spatiotemporal control of vascular endothelial growth factor delivery from injectable hydrogels enhances angiogenesis. J Thromb Haemost. Mar. 2007;5(3):590-8.

Singer et al., Cutaneous wound healing. N Engl J Med. Sep. 2, 1999;341(10):738-46.

Skokos et al., CD8-DCs induce IL-12-independent Th1 differentiation through Delta 4 Notch-like ligand in response to bacterial LPS. J Exp Med. Jul. 9, 2007;204(7):1525-31.

Skuk et al., Efficacy of myoblast transplantation in nonhuman primates following simple intramuscular cell injections: toward defining strategies applicable to humans. Exp Neurol. May 2002;175(1):112-26.

Skuk et al., Myoblast transplantation: the current status of a potential therapeutic tool for myopathies. J Muscle Res Cell Motil. 2003;24(4-6):285-300.

Sletten et al., A bioorthogonal quadricyclane ligation. J Am Chem Soc. Nov. 9, 2011;133(44):17570-3.

Sletten et al., A hydrophilic azacyclooctyne for Cu-free click chemistry. Org Lett. Jul. 17, 2008;10(14):3097-9.

Smidsrød et al., Alginate as immobilization matrix for cells. Trends Biotechnol. Mar. 1990;8(3):71-8.

Sohier et al., Critical factors in the design of growth factor releasing scaffolds for cartilage tissue engineering. Expert Opin Drug Deliv. May 2008;5(5):543-66.

Solon et al., Fibroblast adaptation and stiffness matching to soft elastic substrates. Biophys J. Dec. 15, 2007;93(12):4453-61.

Sonawane et al., Chloride accumulation and swelling in endosomes enhances DNA transfer by polyamine-DNA polyplexes. J Biol Chem. Nov. 7, 2003;278(45):44826-31.

Stachowiak et al., Inverse opal hydrogel-collagen composite scaffolds as a supportive microenvironment for immune cell migration. J Biomed Mater Res A. Jun. 1, 2008;85(3):815-28.

Steinman et al., Taking dendritic cells into medicine. Nature. Sep. 27, 2007;449(7161):419-26.

Storrie et al., Sustained delivery of plasmid DNA from polymeric scaffolds for tissue engineering. Adv Drug Deliv Rev. Jul. 7, 2006;58(4):500-14.

Straub et al., Animal models for muscular dystrophy show different patterns of sarcolemmal disruption. J Cell Biol. Oct. 20, 1997;139(2):375-85.

Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.

Sun et al., Highly stretchable and tough hydrogels. Nature. Sep. 6, 2012;489(7414):133-6.

Sun et al., Sustained vascular endothelial growth factor delivery enhances angiogenesis and perfusion in ischemic hind limb. Pharm Res. Jul. 2005;22(7):1110-6.

Suri et al., Photopatterned collagen-hyaluronic acid interpenetrating polymer network hydrogels. Acta Biomater. Sep. 2009;5(7):2385-97.

Swift et al., Nuclear lamin-A scales with tissue stiffness and enhances matrix-directed differentiation. Science. Aug. 30, 2013;341(6149):1240104. 17 pages.

Syed et al., Stem cell therapy market. Nat Rev Drug Discov. Mar. 2013;12(3):185-6.

Tabata et al., Enhanced Vascularization and Tissue Granulation by Basic Fibroblast Growth Factor Impregnated in Gelatin Hydrogels. Journal of Controlled Release. Sep. 1994;31(2):189-199.

Takahashi et al., Induction of pluripotent stem cells from adult human fibroblasts by defined factors. Cell. Nov. 30, 2007;131(5):861-72.

Takeshita et al., Therapeutic angiogenesis. A single intraarterial bolus of vascular endothelial growth factor augments revascularization in a rabbit ischemic hind limb model. J Clin Invest. Feb. 1994;93(2):662-70.

Tamura et al., Immunotherapy of tumors with autologous tumor-derived heat shock protein preparations. Science. Oct. 3, 1997;278(5335):117-20.

Tanaka et al., Collapse of gels in an electric field. Science. Oct. 29, 1982;218(4571):467-9.

Tannous, Gaussia luciferase reporter assay for monitoring biological processes in culture and in vivo. Nat Protoc. 2009;4(4):582-91.

Tatsumi et al., HGF/SF is present in normal adult skeletal muscle and is capable of activating satellite cells. Dev Biol. Feb. 1, 1998;194(1):114-28.

Ten Dijke et al., Growth Factors for Wound Healing. Nat Biotechnol. 1989;7:793-798.

Thelin et al., In Vivo Enrichment of Diabetogenic T Cells. Diabetes. Aug. 2017;66(8):2220-2229.

Thomas et al., Intravenous infusion of bone marrow in patients receiving radiation and chemotherapy. N Engl J Med. Sep. 12, 1957;257(11):491-6.

Thornton et al., Shape retaining injectable hydrogels for minimally invasive bulking. J Urol. Aug. 2004;172(2):763-8.

Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.

Thurston et al., The Delta paradox: DLL4 blockade leads to more tumour vessels but less tumour growth. Nat Rev Cancer. May 2007;7(5):327-31.

Tidball, Inflammatory cell response to acute muscle injury. Med Sci Sports Exerc. Jul. 1995;27(7):1022-32.

Tomer et al., Electrically Controlled Release of Macromolecules from Cross-Linked Hyaluronic Acid Hydrogels. Journal of Controlled Release. Mar. 1995;33(3):405-413.

Tong et al., Engineering interpenetrating network hydrogels as biomimetic cell niche with independently tunable biochemical and mechanical properties. Biomaterials. Feb. 2014;35(6):1807-15.

Tourniaire et al., Polymer microarrays for cellular adhesion. Chem Commun (Camb). May 28, 2006;(20):2118-20.

Trappmann et al., Extracellular-matrix tethering regulates stem-cell fate. Nat Mater. May 27, 2012;11(7):642-9.

Trappmann et al., How cells sense extracellular matrix stiffness: a material's perspective. Curr Opin Biotechnol. Oct. 2013;24(5):948-53.

Tripathi et al., Elastic and macroporous agarose-gelatin cryogels with isotropic and anisotropic porosity for tissue engineering. J Biomed Mater Res A. Sep. 1, 2009;90(3):680-94.

Tsien, The green fluorescent protein. Annu Rev Biochem. 1998;67:509-44.

Turing, Discussion: Turing's Theory of Morphogenesis—Its Influence on Modelling Biological Pattern and Form. Bull Math Biol. 1990;52(1-2):119-159.

(56) References Cited

OTHER PUBLICATIONS

Turing, The Chemical Basis of Morphogenesis. Philosophical Transactions of the Royal Society of London. Series B. 1952;237(641):37-72.
Uchida et al., Immunization by particle bombardment of antigen-loaded poly-(DL-lactide-co-glycolide) microspheres in mice. Vaccine. Mar. 15, 2006;24(12):2120-30.
Udono, Cancer immunotherapy with blocking of immune checkpoint. Journal of Okayama Medical Association. Apr. 2013;125:13-18.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Vandenburgh et al., Tissue-engineered skeletal muscle organoids for reversible gene therapy. Hum Gene Ther. Nov. 10, 1996;7(17):2195-200.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.
Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.

Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
Von Mehren et al., The influence of granulocyte macrophage colony-stimulating factor and prior chemotherapy on the immunological response to a vaccine (ALVAC-CEA B7.1) in patients with metastatic carcinoma. Clin Cancer Res. May 2001;7(5):1181-91.
W.H.O., World Health Organization, Global Burden of Musculoskeletal Disease Revealed in new WHO Report. Bull World Health Organ. 2003;81(11):853-854.
W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Waldron-Lynch et al., Advances in Type 1 diabetes therapeutics: immunomodulation and beta-cell salvage. Endocrinol Metab Clin North Am. Jun. 2009;38(2):303-17.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.
Wang et al., Photothermal effects of supramolecularly assembled gold nanoparticles for the targeted treatment of cancer cells. Angew Chem Int Ed Engl. May 17, 2010;49(22):3777-81.
Warner et al., Cyclooxygenases: new forms, new inhibitors, and lessons from the clinic. FASEB J. May 2004;18(7):790-804.
Webber et al., Controlled release of dexamethasone from peptide nanofiber gels to modulate inflammatory response. Biomaterials. Oct. 2012;33(28):6823-32.
Weeks et al., The effects of chemokine, adhesion and extracellular matrix molecules on binding of mesenchymal stromal cells to poly(l-lactic acid). Cytotherapy. Oct. 2012;14(9):1080-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.

(56) References Cited

OTHER PUBLICATIONS

Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.
Xie et al., Preparation and Application of Surface-Coated Superparamagnetic Nanobeads in the Isolation of Genomic DNA. J Magn Magnetic Mater. Jun. 2004;277(1-2):16-23.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.
Yang et al., The effect of incorporating RGD adhesive peptide in polyethylene glycol diacrylate hydrogel on osteogenesis of bone marrow stromal cells. Biomaterials. Oct. 2005;26(30):5991-8.
Yeung et al., Effects of substrate stiffness on cell morphology, cytoskeletal structure, and adhesion. Cell Motil Cytoskeleton. Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Sequence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science. Dec. 21, 2007;318(5858):1917-20.
Yuen et al., Mimicking nature by codelivery of stimulant and inhibitor to create temporally stable and spatially restricted angiogenic zones. Proc Natl Acad Sci U S A. Oct. 19, 2010;107(42):17933-8.
Yuk et al., Electric current-sensitive drug delivery systems using sodium alginate/polyacrylic acid composites. Pharm Res. Jul. 1992;9(7):955-7.
Zammit et al., Kinetics of myoblast proliferation show that resident satellite cells are competent to fully regenerate skeletal muscle fibers. Exp Cell Res. Nov. 15, 2002;281(1):39-49.
Zammit et al., Muscle satellite cells adopt divergent fates: a mechanism for self-renewal? J Cell Biol. Aug. 2, 2004;166(3):347-57.
Zeltinger et al., Effect of pore size and void fraction on cellular adhesion, proliferation, and matrix deposition. Tissue Eng. Oct. 2001;7(5):557-72.
Zemel et al., Optimal matrix rigidity for stress fiber polarization in stem cells. Nat Phys. Jun. 1, 2010;6(6):468-473.
Zhang et al., A comparative study of the antigen-specific immune response induced by co-delivery of CpG ODN and antigen using fusion molecules or biodegradable microparticles. J Pharm Sci. Dec. 2007;96(12):3283-92.
Zhang et al., A tension-induced mechanotransduction pathway promotes epithelial morphogenesis. Nature. Mar. 3, 2011;471(7336):99-103.
Zhang et al., Talin depletion reveals independence of initial cell spreading from integrin activation and traction. Nat Cell Biol. Sep. 2008;10(9):1062-8.
Zhao et al., Active scaffolds for on-demand drug and cell delivery. Proc Natl Acad Sci U S A. Jan. 4, 2011;108(1):67-72.
Zhao et al., Directed cell migration via chemoattractants released from degradable microspheres. Biomaterials. Aug. 2005;26(24):5048-63.
Zhao et al., Stress-relaxation behavior in gels with ionic and covalent crosslinks. J Appl Phys. Mar. 15, 2010;107(6):63509.
Zhou et al., Instability of the transcription factor Foxp3 leads to the generation of pathogenic memory T cells in vivo. Nat Immunol. Sep. 2009;10(9):1000-7.
Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.
Zhou et al., Peptide-labeled quantum dots for imaging GPCRs in whole cells and as single molecules. Bioconjug Chem. Mar.-Apr. 2007;18(2):323-32.
Zizzari et al., The Macrophage Galactose-Type C-Type Lectin (MGL) Modulates Regulatory T Cell Functions. PLoS One. Jul. 6, 2015;10(7):e0132617. 12 pages.
Japanese Office Action for Application No. 2016-565339, dated Jan. 8, 2019. 9 pages.
U.S. Appl. No. 15/434,781, filed Feb. 16, 2017, 2017-0246281, Published.
U.S. Appl. No. 13/386,950, filed Jan. 25, 2012, U.S. Pat. No. 8,728,456, Issued.
U.S. Appl. No. 14/185,494, filed Feb. 20, 2014, U.S. Pat. No. 9,381,235, Issued.
U.S. Appl. No. 15/147,442, filed May 5, 2016, U.S. Pat. No. 10,080,789, Issued.
U.S. Appl. No. 16/121,988, filed Sep. 5, 2018, 2019-0183992, Published.
U.S. Appl. No. 15/564,905, filed Oct. 6, 2017, 2018-0164298, Published.
U.S. Appl. No. 16/316,778, filed Jan. 10, 2019, Pending.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, 2019-0125849, Published.
U.S. Appl. No. 13/877,572, filed Nov. 19, 2013, 2014-0079752, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Published.
U.S. Appl. No. 16/033,025, filed Jul. 11, 2018, 2019-0076373, Published.
U.S. Appl. No. 14/394,552, filed Oct. 15, 2014, U.S. Pat. No. 9,937,249, Issued.
U.S. Appl. No. 15/935,392, filed Mar. 26, 2018, 2018-0344821, Published.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.

(56) References Cited

OTHER PUBLICATIONS

U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, 2018-0289789, Published.
U.S. Appl. No. 15/563,878, filed Oct. 2, 2017, 2018-0117171, Published.
U.S. Appl. No. 15/546,852, filed Jul. 27, 2017, 2018-0021253, Published.
U.S. Appl. No. 16/075,937, filed Aug. 6, 2018, 2019-0060525, Published.
Ali et al., Relationship of vaccine efficacy to the kinetics of DC and T-cell responses induced by PLG-based cancer vaccines. Biomater. 2011;1(1):66-75.
Anderson et al., Crosslinking CD3 with CD2 using sepharose-immobilized antibodies enhances T lymphocyte proliferation. Cell Immunol. Sep. 1988;115(2):246-56.
Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120(1):205-17.
Bierer et al., T cell receptors: adhesion and signaling. Adv Cancer Res. 1991;56:49-76.
Bjork et al., Tuning the shape of mesoporous silica particles by alterations in parameter space: from rods to platelets. Langmuir. Nov. 5, 2013;29(44):13551-61.
Bojarova et al., Sugared biomaterial binding lectins: achievements and perspectives. Biomater Sci. Jul. 19, 2016;4(8):1142-60.
Brodie et al., In vivo migration and function of transferred HIV-1-specific cytotoxic T cells. Nat Med. Jan. 1999;5(1):34-41.
Damle et al., Stimulation via the CD3 and CD28 molecules induces responsiveness to IL-4 in CD4+CD29+CD45R-memory T lymphocytes. J Immunol. Sep. 15, 1989;143(6):1761-7.
Drury et al., Hydrogels for tissue engineering: scaffold design variables and applications. Biomaterials. Nov. 2003;24(24):4337-51.
Dudley et al., CD8+ enriched "young" tumor infiltrating lymphocytes can mediate regression of metastatic melanoma. Clin Cancer Res. Dec. 15, 2010;16(24):6122-31.
Fadel et al., A carbon nanotube-polymer composite for T-cell therapy. Nat Nanotechnol. Aug. 2014;9(8):639-47.
Fadel et al., Enhanced cellular activation with single walled carbon nanotube bundles presenting antibody stimuli. Nano Lett. Jul. 2008;8(7):2070-6.
Fesnak et al., Engineered T cells: the promise and challenges of cancer immunotherapy. Nat Rev Cancer. Aug. 23, 2016;16(9):566-81.
Garlie et al., T cells coactivated with immobilized anti-CD3 and anti-CD28 as potential immunotherapy for cancer. J Immunother. Jul. 1999;22(4):336-45.
Gimmi et al., B-cell surface antigen B7 provides a costimulatory signal that induces T cells to proliferate and secrete interleukin 2. Proc Natl Acad Sci U S A. Aug. 1, 1991;88(15):6575-9.
Harding et al., CD28-mediated signalling co-stimulates murine T cells and prevents induction of anergy in T-cell clones. Nature. Apr. 16, 1992;356(6370):607-9.
Hasan et al., Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.
Haso et al., Anti-CD22-chimeric antigen receptors targeting B-cell precursor acute lymphoblastic leukemia. Blood. Feb. 14, 2013;121(7):1165-74.
Hollyman et al., Manufacturing validation of biologically functional T cells targeted to CD19 antigen for autologous adoptive cell therapy. J Immunother. Feb.-Mar. 2009;32(2):169-80.
Huppa et al., T-cell-antigen recognition and the immunological synapse. Nat Rev Immunol. Dec. 2003;3(12):973-83.
June et al., Adoptive cellular therapy: a race to the finish line. Sci Transl Med. Mar. 25, 2015;7(280):280ps7.
June et al., The B7 and CD28 receptor families. Immunol Today. Jul. 1994;15(7):321-31.
Kratz, Albumin as a drug carrier: design of prodrugs, drug conjugates and nanoparticles. J Control Release. Dec. 18, 2008;132(3):171-83.
Kupferschmidt et al., Mesoporous silica particles potentiate antigen-specific T-cell responses. Nanomedicine (Lond). 2014;9(12):1835-46.
Lee et al., The immunological synapse balances T cell receptor signaling and degradation. Science. Nov. 14, 2003;302(5648):1218-22.
Levine et al., Effects of CD28 costimulation on long-term proliferation of CD4+ T cells in the absence of exogenous feeder cells. J Immunol. Dec. 15, 1997;159(12):5921-30.
Li et al., Mesoporous silica nanoparticles in biomedical applications. Chem Soc Rev. Apr. 7, 2012;41(7):2590-605.
Li et al., Recent advances of biomaterials in biotherapy. Regen Biomater. Jun. 2016;3(2):99-105.
Li et al., The effect of surface modification of mesoporous silica micro-rod scaffold on immune cell activation and infiltration. Biomaterials. Mar. 2016;83:249-56.
Liao et al., Synthesis of mesoporous silica nanoparticle-encapsulated alginate microparticles for sustained release and targeting therapy. J Biomed Mater Res B Appl Biomater. Feb. 2014;102(2):293-302.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Mahony et al., Mesoporous silica nanoparticles act as a self-adjuvant for ovalbumin model antigen in mice. Small. Sep. 23, 2013;9(18):3138-46.
Mandal et al., Polymer-based synthetic dendritic cells for tailoring robust and multifunctional T cell responses. ACS Chem Biol. Feb. 20, 2015;10(2):485-92.
Mangsbo et al., Enhanced tumor eradication by combining CTLA-4 or PD-1 blockade with CpG therapy. J Immunother. Apr. 2010;33(3):225-35.
Maus et al., Ex vivo expansion of polyclonal and antigen-specific cytotoxic T lymphocytes by artificial APCs expressing ligands for the T-cell receptor, CD28 and 4-1 BB. Nat Biotechnol. Feb. 2002;20(2):143-8.
McKay et al., Click chemistry in complex mixtures: bioorthogonal bioconjugation. Chem Biol. Sep. 18, 2014;21(9):1075-101.
Mehta et al., Engineering New Approaches to Cancer Vaccines. Cancer Immunol Res. Aug. 2015;3(8):836-43.
Melief et al., T-cell immunotherapy of tumors by adoptive transfer of cytotoxic T lymphocytes and by vaccination with minimal essential epitopes. Immunol Rev. Jun. 1995;145:167-77.
Meng et al., Use of a lipid-coated mesoporous silica nanoparticle platform for synergistic gemcitabine and paclitaxel delivery to human pancreatic cancer in mice. ACS Nano. 2015;9(4):3540-57.
Meyer et al., Biodegradable nanoellipsoidal artificial antigen presenting cells for antigen specific T-cell activation. Small. Apr. 2015;11(13):1519-25.
NCBI, MeSH. Nivolumab. Retrieved online at: https://www.ncbi.nlm.nih/gov/mesh/?term=nivolumab. 3 pages, (2010).
Perica et al., Enrichment and Expansion with Nanoscale Artificial Antigen Presenting Cells for Adoptive Immunotherapy. ACS Nano. Jul. 28, 2015;9(7):6861-71.
Qin et al., CD22-Targeted Chimeric Antigen Receptor (CAR) T Cells Containing The 4-1 BB Costimulatory Domain Demonstrate Enhanced Persistence and Superior Efficacy Against B-Cell Precursor Acute Lymphoblastic Leukemia (ALL) Compared to Those Containing CD28. Blood. 2013;122:1431.

(56) References Cited

OTHER PUBLICATIONS

Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.

Riddell et al., Principles for adoptive T cell therapy of human viral diseases. Annu Rev Immunol. 1995;13:545-86.

Riddell et al., Restoration of viral immunity in immunodeficient humans by the adoptive transfer of T cell clones. Science. Jul. 10, 1992;257(5067):238-41.

Riddell et al., The use of anti-CD3 and anti-CD28 monoclonal antibodies to clone and expand human antigen-specific T cells. J Immunol Methods. Apr. 17, 1990;128(2):189-201.

Rosenberg et al., Adoptive cell transfer as personalized immunotherapy for human cancer. Science. Apr. 3, 2015;348(6230):62-8.

Rosenberg et al., Durable complete responses in heavily pretreated patients with metastatic melanoma using T-cell transfer immunotherapy. Clin Cancer Res. Jul. 1, 2011;17(13):4550-7.

Rubbi et al., Evidence of surface antigen detachment during incubation of cells with immunomagnetic beads. J Immunol Methods. Dec. 3, 1993;166(2):233-41.

Schwartz, A cell culture model for T lymphocyte clonal anergy. Science. Jun. 15, 1990;248(4961):1349-56.

Sheppard et al., Polyethyleneimine is a potent systemic adjuvant for glycoprotein antigens. Int Immunol. Oct. 2014;26(10):531-8.

Shibuya et al., Anti-CD3/anti-CD28 bead stimulation overcomes CD3 unresponsiveness in patients with head and neck squamous cell carcinoma. Arch Otolaryngol Head Neck Surg. Apr. 2000;126(4):473-9.

Singh et al., Hydrogels and scaffolds for immunomodulation. Adv Mater. Oct. 2014;26(38):6530-41.

Springer et al., The lymphocyte function-associated LFA-1, CD2, and LFA-3 molecules: cell adhesion receptors of the immune system. Annu Rev Immunol. 1987;5:223-52.

Steenblock et al., A comprehensive platform for ex vivo T-cell expansion based on biodegradable polymeric artificial antigen-presenting cells. Mol Ther. Apr. 2008;16(4):765-72.

Steenblock et al., An artificial antigen-presenting cell with paracrine delivery of IL-2 impacts the magnitude and direction of the T cell response. J Biol Chem. Oct. 7, 2011;286(40):34883-92.

Sunshine et al., Particle shape dependence of CD8+ T cell activation by artificial antigen presenting cells. Biomaterials. Jan. 2014;35(1):269-277.

Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.

Turtle et al., CD19 CAR-T cells of defined CD4+:CD8+ composition in adult B cell ALL patients. J Clin Invest. Jun. 1, 2016;126(6):2123-38.

Wang et al., Mouse CD229 Ligation Co-stimulates T Cell Activation. The Journal of Immunology. May 2012;188(suppl 1):176.7.

Wegmann et al., Polyethyleneimine is a potent mucosal adjuvant for viral glycoprotein antigens. Nat Biotechnol. Sep. 2012;30(9):883-8.

Yee et al., Melanocyte destruction after antigen-specific immunotherapy of melanoma: direct evidence of t cell-mediated vitiligo. J Exp Med. Dec. 4, 2000;192(11):1637-44.

Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.

\* cited by examiner

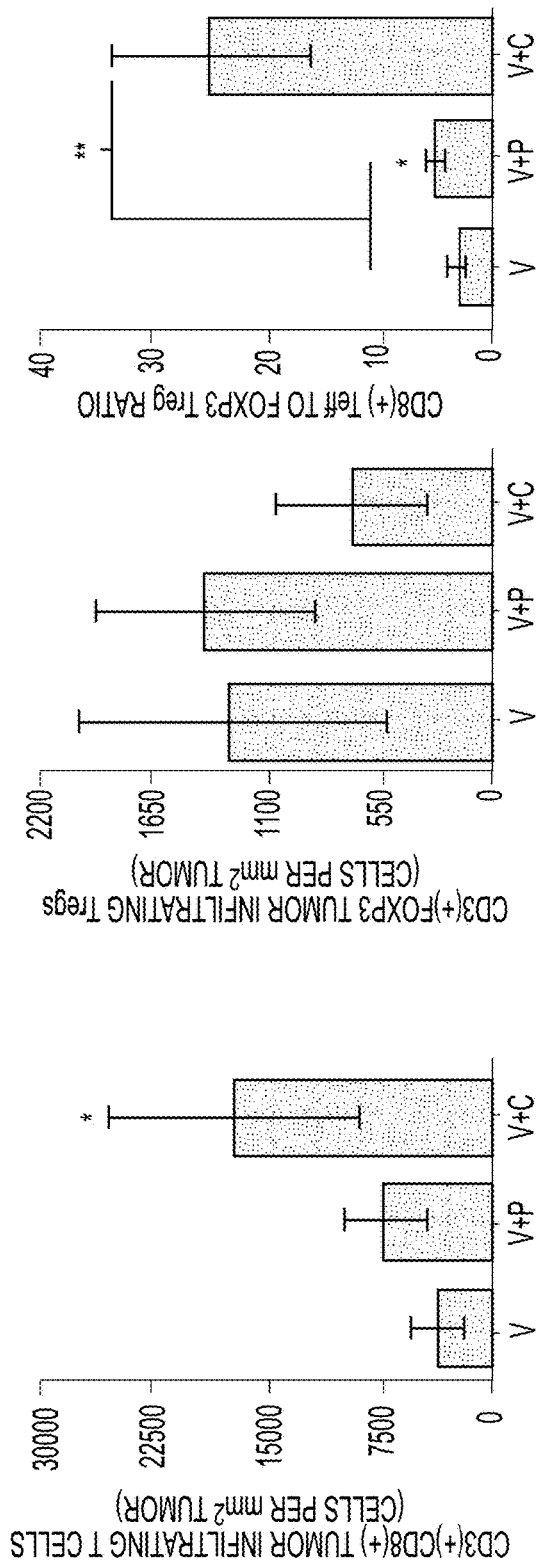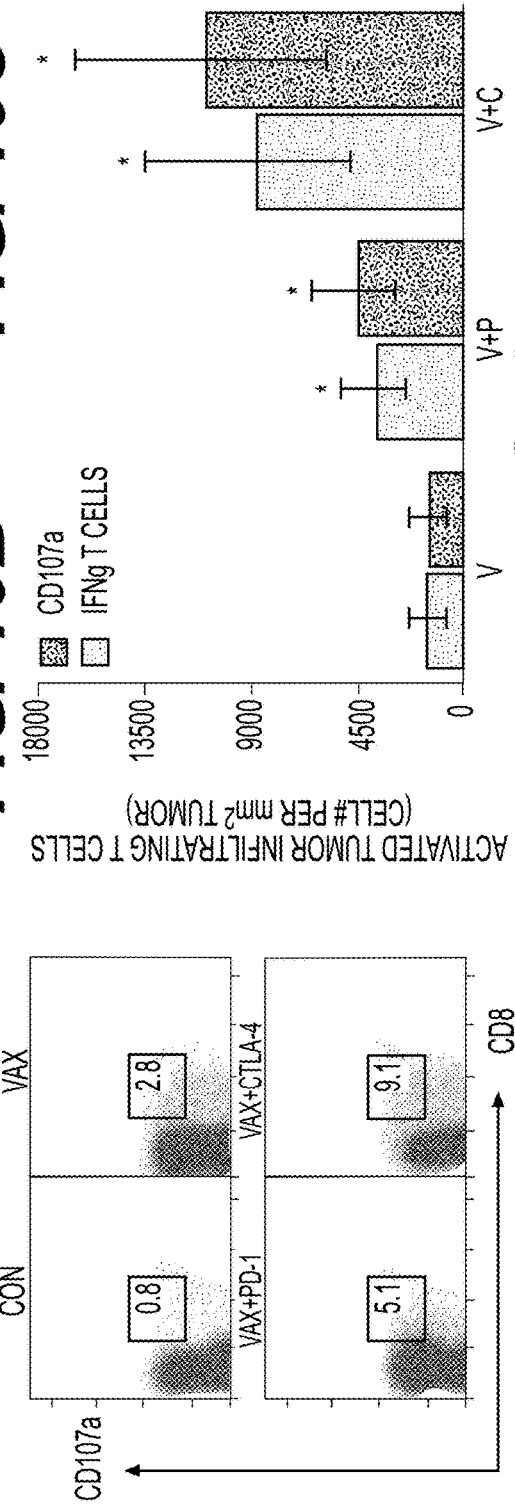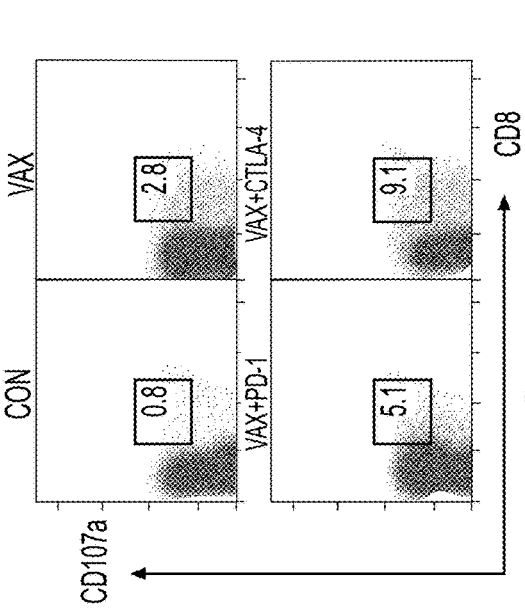

SEQUENCE LISTING

```
<160> NUMBER OF SEQ ID NOS: 440

<210> SEQ ID NO 1
<211> LENGTH: 309
<212> TYPE: PRT
<213> ORGANISM: Mus musculus

<400> SEQUENCE: 1

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
            100                 105                 110

Pro Gln Lys His Gly Leu Glu Leu Ala Ser Asp His His Gly Asn Phe
        115                 120                 125

Ser Ile Thr Leu Arg Asn Val Thr Pro Arg Asp Ser Gly Leu Tyr Cys
    130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
```

```
                180                 185                 190
Leu Ala Thr Gly Ala Cys Ile Val Gly Ile Leu Cys Leu Pro Leu Ile
            195                 200                 205

Leu Leu Leu Val Tyr Lys Gln Arg Gln Val Ala Ser His Arg Arg Ala
        210                 215                 220

Gln Glu Leu Val Arg Met Asp Ser Ser Asn Thr Gln Gly Ile Glu Asn
225                 230                 235                 240

Pro Gly Phe Glu Thr Thr Pro Pro Phe Gln Gly Met Pro Glu Ala Lys
            245                 250                 255

Thr Arg Pro Pro Leu Ser Tyr Val Ala Gln Arg Gln Pro Ser Glu Ser
        260                 265                 270

Gly Arg Tyr Leu Leu Ser Asp Pro Ser Thr Pro Leu Ser Pro Pro Gly
    275                 280                 285

Pro Gly Asp Val Phe Phe Pro Ser Leu Asp Pro Val Pro Asp Ser Pro
        290                 295                 300

Asn Ser Glu Ala Ile
305

<210> SEQ ID NO 2
<211> LENGTH: 930
<212> TYPE: DNA
<213> ORGANISM: Mus musculus

<400> SEQUENCE: 2
atgggtgtcc ccgcggtccc agaggccagc agcccgcgct ggggaaccct gctccttgct    60
attttcctgg ctgcatccag aggtctggta gcagccttca aggtcaccac tccatattct   120
ctctatgtgt gtcccgaggg acagaatgcc accctcacct gcaggattct gggccccgtg   180
tccaaagggc acgatgtgac catctacaag acgtggtacc tcagctcacg aggcgaggtc   240
cagatgtgca agaacaccg gcccatacgc aacttcacat tgcagcacct tcagcaccac   300
ggaagccacc tgaaagccaa cgccagccat gaccagcccc agaagcatgg gctagagcta   360
gcttctgacc accacggtaa cttctctatc accctgcgca atgtgacccc aagggacagc   420
ggcctctact gctgtctagt gatagaatta aaaaaccacc acccagaaca acggttctac   480
gggtccatgg agctacaggt acaggcaggc aaaggctcgg ggtccacatg catggcgtct   540
aatgagcagg acagtgacag catcacggct gcggccctgg ccaccggcgc ctgcatcgtg   600
ggaatcctct gcctccccct tatcctgctg ctggtctata gcagagaca ggtggcctct    660 caccgccgtg cccaggagtt ggtgaggatg acagcagca acacccaagg aatcgaaaac   720
ccaggcttcg agaccactcc acccttccag gggatgcctg aggccaagac caggccgcca   780
ctgtcctatg tggcccagcg gcaaccttcg gagtcaggac ggtacctgct ctctgacccc   840
agcacacctc tgtcgcctcc aggccctggg gacgtcttt tcccatccct agatccagtc   900
cctgactccc ctaactctga agccatctaa                                    930

<210> SEQ ID NO 3
<211> LENGTH: 277
<212> TYPE: PRT
<213> ORGANISM: Homo sapiens

<400> SEQUENCE: 3

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30
```

Gly Asp Thr Tyr Pro Ser Asn Asp Arg Cys Cys His Glu Cys Arg Pro
            35                  40                  45
Gly Asn Gly Met Val Ser Arg Cys Ser Arg Ser Gln Asn Thr Val Cys
        50                  55                  60
Arg Pro Cys Gly Pro Gly Phe Tyr Asn Asp Val Val Ser Ser Lys Pro
65                  70                  75                  80
Cys Lys Pro Cys Thr Trp Cys Asn Leu Arg Ser Gly Ser Glu Arg Lys
                85                  90                  95
Gln Leu Cys Thr Ala Thr Gln Asp Thr Val Cys Arg Cys Arg Ala Gly
            100                 105                 110
Thr Gln Pro Leu Asp Ser Tyr Lys Pro Gly Val Asp Cys Ala Pro Cys
        115                 120                 125
Pro Pro Gly His Phe Ser Pro Gly Asp Asn Gln Ala Cys Lys Pro Trp
    130                 135                 140
Thr Asn Cys Thr Leu Ala Gly Lys His Thr Leu Gln Pro Ala Ser Asn
145                 150                 155                 160
Ser Ser Asp Ala Ile Cys Glu Asp Arg Asp Pro Pro Ala Thr Gln Pro
                165                 170                 175
Gln Glu Thr Gln Gly Pro Pro Ala Arg Pro Ile Thr Val Gln Pro Thr
            180                 185                 190
Glu Ala Trp Pro Arg Thr Ser Gln Gly Pro Ser Thr Arg Pro Val Glu
        195                 200                 205
Val Pro Gly Gly Arg Ala Val Ala Ala Ile Leu Gly Leu Gly Leu Val
    210                 215                 220
Leu Gly Leu Leu Gly Pro Leu Ala Ile Leu Leu Ala Leu Tyr Leu Leu
225                 230                 235                 240
Arg Arg Asp Gln Arg Leu Pro Pro Asp Ala His Lys Pro Pro Gly Gly
                245                 250                 255
Gly Ser Phe Arg Thr Pro Ile Gln Glu Glu Gln Ala Asp Ala His Ser
            260                 265                 270
Thr Leu Ala Lys Ile
        275

<210> SEQ ID NO 4
<211> LENGTH: 1120
<212> TYPE: DNA
<213> ORGANISM: Homo sapiens

<400> SEQUENCE: 4
ccgcaaggaa aacccagact ctggcgacag cagagacgag gatgtgcgtg ggggctcggc      60
ggctgggccg cgggccgtgt gcggctctgc tcctcctggg cctggggctg agcaccgtga     120
cggggctcca ctgtgtcggg gacacctacc ccagcaacga ccgtgctgc cacgagtgca     180
ggccaggcaa cgggatggtg agccgctgca gccgctccca gaacacggtg tgccgtccgt     240
gcgggccggg cttctacaac gacgtggtca gctccaagcc gtgcaagccc tgcacgtggt     300
gtaacctcag aagtgggagt gagcggaagc agctgtgcac ggccacacag gacacagtct     360
gccgctgccg ggcgggcacc cagcccctgg acagctacaa gcctggagtt gactgtgccc     420
cctgccctcc agggcacttc tccccaggcg acaaccaggc ctgcaagccc tggaccaact     480
gcaccttggc tgggaagcac accctgcagc cggccagcaa tagctcggac gcaatctgtg     540
aggacaggga cccccagcc acgcagcccc aggagaccca gggccccccg gccaggccca     600
tcactgtcca gcccactgaa gcctggccca gaacctcaca gggaccctcc acccggcccg     660

-continued

```
tggaggtccc cggggccgt gcggttgccg ccatcctggg cctgggcctg gtgctggggc    720
tgctgggccc cctggccatc ctgctggccc tgtacctgct ccggagggac cagaggctgc    780
cccccgatgc ccacaagccc cctggggag gcagtttccg gaccccatc caagaggagc     840 aggccgacgc ccactccacc ctggccaaga tctgacctgg gcccaccaag gtggacgctg    900
ggccccgcca ggctggagcc cggagggtct gctgggcgag cagggcaggt gcaggccgcc    960
tgccccgcca cgctcctggg ccaactctgc accgttctag gtgccgatgg ctgcctccgg   1020
ctctctgctt acgtatgcca tgcataccctc ctgccccgcg ggaccacaat aaaaaccttg  1080
gcagacggga gtctccgacc ggcaaaaaaa aaaaaaaaa                          1120
```

<210> SEQ ID NO 5
<211> LENGTH: 255
<212> TYPE: PRT
<213> ORGANISM: Homo sapiens

<400> SEQUENCE: 5

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255
```

<210> SEQ ID NO 6
<211> LENGTH: 6001
<212> TYPE: DNA
<213> ORGANISM: Homo sapiens

<400> SEQUENCE: 6

```
caaggaggga tcccacagat gtcacagggc tgtcacagag ctgtggtggg aatttcccat    60
gagaccccgc ccctggctga gtcaccgcac tcctgtgttt gacctgaagt cctctcgagc   120
tgcagaagcc tgaagaccaa ggagtggaaa gttctccggc agccctgaga tctcaagagt   180
gacatttgtg agaccagcta atttgattaa aattctcttg gaatcagctt tgctagtatc   240
atacctgtgc cagatttcat catgggaaac agctgttaca acatagtagc cactctgttg   300
ctggtcctca actttgagag gacaagatca ttgcaggatc cttgtagtaa ctgcccagct   360
ggtacattct gtgataataa caggaatcag atttgcagtc cctgtcctcc aaatagtttc   420
tccagcgcag gtgacaaag gacctgtgac atatgcaggc agtgtaaagg tgttttcagg   480
accaggaagg agtgttcctc caccagcaat gcagagtgtg actgcactcc agggtttcac   540
tgcctggggg caggatgcag catgtgtgaa caggattgta acaaggtca agaactgaca   600 aaaaaaggtt gtaaagactg ttgctttggg acatttaacg atcagaaacg tggcatctgt   660
cgaccctgga caaactgttc tttgatgga aagtctgtgc ttgtgaatgg gacgaaggag   720
agggacgtgg tctgtggacc atctccagcc gacctctctc cgggagcatc ctctgtgacc   780
ccgcctgccc ctgcgagaga gccaggacac tctccgcaga tcatctcctt ctttcttgcg   840
ctgacgtcga ctgcgttgct cttcctgctg ttcttcctca cgctccgttt ctctgttgtt   900
aaacggggca gaaagaaact cctgtatata ttcaaacaac catttatgag accagtacaa   960
actactcaag aggaagatgg ctgtagctgc cgatttccag aagaagaaga aggaggatgt  1020
gaactgtgaa atggaagtca atagggctgt tgggactttc ttgaaaagaa gcaaggaaat  1080
atgagtcatc cgctatcaca gctttcaaaa gcaagaacac catcctacat aatacccagg  1140
attcccccaa cacacgttct tttctaaatg ccaatgagtt ggcctttaaa aatgcaccac  1200
tttttttttt tttttgacag ggtctcactc tgtcacccag gctggagtgc agtggcacca  1260
ccatggctct ctgcagcctt gacctctggg agctcaagtg atcctcctgc ctcagtctcc  1320
tgagtagctg gaactacaag gaagggccac cacacctgac taacttttt gttttttgtt  1380 tggtaaagat ggcatttcac catgttgtac aggctggtct caaactccta ggttcacttt  1440
ggcctcccaa agtgctggga ttacagacat gaactgccag gcccggccaa ataatgcac   1500 cacttttaac agaacagaca gatgaggaca gagctggtga taaaaaaaaa aaaaaaaag   1560 cattttctag ataccactta acaggtttga gctagttttt ttgaaatcca agaaaatta    1620 tagtttaaat tcaattacat agtccagtgg tccaactata attataatca aaatcaatgc   1680
aggtttgttt tttggtgcta atatgacata tgacaataag ccacgaggtg cagtaagtac   1740
ccgactaaag tttccgtggg ttctgtcatg taacacgaca tgctccaccg tcagggggga   1800
gtatgagcag agtgcctgag tttagggtca aggacaaaaa acctcaggcc tggaggaagt   1860
tttggaaaga gttcaagtgt ctgtatatcc tatggtcttc tccatcctca cacttctgc    1920 ctttgtcctg ctccctttta agccaggtta cattctaaaa attcttaact tttaacataa   1980
tattttatac caaagccaat aaatgaactg catatgatag gtatgaagta cagtgagaaa   2040
attaacacct gtgagctcat tgtcctacca cagcactaga gtgggggccg ccaaactccc   2100
atggccaaac ctggtgcacc atttgccttt gtttgtctgt tggtttgctt gagacagtct   2160
tgctctgttg cccaggctgg aatggagtgg ctattcacag gcacaatcat agcacacttt   2220
agccttaaac tcctgggctc aagtgatcca cccgcctcag tctcccaagt agctgggatt   2280
acaggtgcaa acctggcatg cctgccattg tttggcttat gatctaagga tagcttttta   2340
```

```
aattttattc attttattttt tttttgagac agtgtctcac tctgtctccc aggctggagt    2400
acagtggtac aatcttggat caccgcctcc cagtttcaag tgatctccct gcctcagcct    2460
cctaagtagc tgggactaca ggtatgtgcc accacgcctg gctaatttt atattttag      2520
tagagacggg gtttcaccat gttgtccagg ctggtctcaa actcctgacc tcaggtgatc    2580
tgcccacctc tgcctcccaa agtgctggga ttacaggcat gagccaccat gcctggccat    2640
ttcttacact tttgtatgac atgcctattg caagcttgcg tgcctctgtc ccatgttatt    2700
ttactctggg atttaggtgg agggagcagc ttctatttgg aacattggcc atcgcatggc    2760
aaatgggtat ctgtcacttc tgctcctatt tagttggttc tactataacc tttagagcaa    2820
atcctgcagc caagccaggc atcaataggg cagaaaagta tattctgtaa ataggggtga    2880
ggagaagata tttctgaaca atagtctact gcagtaccaa attgctttc aaagtggctg     2940
ttctaatgta ctcccgtcag tcatataagt gtcatgtaag tatcccattg atccacatcc    3000
ttgctaccct ctggtactat caggtgccct aattttgcc aagccagtgg gtatagaatg     3060
agatctcact gtggtcttag tttgcatttg cttggttact gatgagcacc ttgtcaaata    3120
tttatatacc atttgtgttt attttttta ataaaatgct tgctcatgct tttttgccca    3180
tttgcaaaaa aacttgggc cggtgcagt ggctcatgcc tgtagtccca gctctttggg     3240
aggccaaggt gggcagatcg cttgagccca ggagttcgag accagccttg caacatggc    3300
gaaaccctgt ctttacaaaa aatacaaaaa ttagccgggt gtggtggtgt gcacctgaag    3360
tcccagctac tcagtaggtt cgctttgagc ctgggaggca gaggttgcag tgagctggga    3420
ccgcatcact acacttcagc ctgggcaaca gagaaaaacc ttttctcaga acaaacaaa     3480
cccaaatgtg gttgtttgtc ctgattccta aaaggtcttt atgtattcta gataataatc    3540
tttggtcagt tatatgtgtt aaaaaatatc ttctttgtgg ccaggcacgg tagctcacac    3600
ctgtaatccc agcactttgc ggggctgagg tgggtggatc atctgaggtc aagagttcaa    3660
gatcagcctg gccaacacag tgaaacccca tctctactaa acatgtacaa aacttagctg    3720
ggtatggtgg cgggtgcctg taaccccagc tgctccagag gctgtggcag aagaatcgct    3780
tgaacccagg aggcagaggt tgcagcgagc caagattgtg ccattgcact ccagactggg    3840
tgacaagagt gaaattctgc ctatctatct atctatctat ctatatctat atatatatat    3900
atatatatcc tttgtaattt atttttccct ttttaaaatt ttttataaaa ttcttttta    3960
tttttatttt tagcagaggt gaggtttctg aggtttcatt atgttgccca ggctggtctt    4020
gaactcctga gctcaagtga tcctcccacc tcagccttcc aaagtgctgg aattgcagac    4080
atgagccacc gcgcccctcc tgtttttctc taattaatgg tgtctttctt tgtctttctg    4140
gtaataagca aaaagttctt catttgattt ggttaaattt ataactgttt tctcatatgg    4200
ttaacatttt ttcttgcctg gctaaagaaa tccttttctg cccaatacta taagagagtt    4260
tgcccacatt ttattccaaa agttttaagt tttgtctttc atcttgaagt ctaatgtatc    4320
aggaactggc ttttgtgcct gttgggaggt agtgatccaa ttccatgtct tgcatgtagg    4380
taaccactgg tccctgcgcc atgtattcaa tacgtcgtct ttctcctgcg ggtctgcaat    4440
ctcacctacc atccatcaag tttccatagg gccatgggtc tgcttctggg ctccctgttc    4500
tgttccattg tcaatttgtc tatcctgtgc cagtatcaca ctgtgtttat tacaatagct    4560
ttgtaacagc tctcgatatc cggtaggaca tctccctcca ccttcttttt ctacttcaga    4620
agtgtcttag ctaggtcagg cacggtggct cacgcctgta atcccagcac tttgggaggc    4680
cgacgcggat ggatcacctg aggtcaggag ttttgagaca gcctggccaa catggtgaaa    4740
```

```
cccatctct actaaaaaat acaaaaatta gtcaggcatg gtggcatgtg cctgtaatcc   4800
cagctatttg ggaggctgag gccggagaat tgcttgaacc cggggggcgg aggttgcagt   4860
gagccgagat cgtaccattg cactccagcc tgggtgacag agcgaaactc tgtctcagga   4920
aaaaaagaa aagagatgtc ttggttattc ttggttcttt attattcaat ataaatttta   4980
gaagctgaat ttgaaaagat ttggattgga atttcattaa atctacaggt caatttaggg   5040
agagttgata attttacaga attgagtcat ctggtgttcc aataagaata agagaacaat   5100
tattggctgt acaattcttg ccaaatagta ggcaaagcaa agcttaggaa gtatactggt   5160
gccatttcag gaacaaagct aggtgcgaat attttttgtct ttctgaatca tgatgctgta   5220
agttctaaag tgatttctcc tcttggcttt ggacacatgg tgtttaatta cctactgctg   5280
actatccaca aacagaaaga gactggtcat gccccacagg gttggggtat ccaagataat   5340
ggagcgaggc tctcatgtgt cctaggttac acaccgaaaa tccacagttt attctgtgaa   5400
gaaaggaggc tatgtttatg atacagactg tgatatttttt atcatagcct attctggtat   5460
catgtgcaaa agctataaat gaaaaacaca ggaacttggc atgtgagtca ttgctccccc   5520
taaatgacaa ttaataagga aggaacattg agacagaata aaatgatccc cttctgggtt   5580
taatttagaa agttccataa ttaggtttaa tagaaataaa tgtaaatttc tatgattaaa   5640
aataaattag cacatttagg gatacacaaa ttataaatca tttctaaat gctaaaaaca   5700
agctcaggtt ttttttcagaa gaaagtttta attttttttc tttagtggaa gatatcactc   5760
tgacggaaag ttttgatgtg aggggcggat gactataaag tgggcatctt cccccacagg   5820
aagatgtttc catctgtggg tgagaggtgc ccaccgcagc tagggcaggt tacatgtgcc   5880
ctgtgtgtgg taggacttgg agagtgatct ttatcaacgt ttttatttaa aagactatct   5940
aataaaacac aaaactatga tgttcacagg aaaaaaagaa taagaaaaaa agaaaaaaaa   6000
a                                                                  6001
```

<210> SEQ ID NO 7
<211> LENGTH: 223
<212> TYPE: PRT
<213> ORGANISM: Homo sapiens

<400> SEQUENCE: 7

Met Ala Cys Leu Gly Phe Gln Arg His Lys Ala Gln Leu Asn Leu Ala
1               5                   10                  15

Thr Arg Thr Trp Pro Cys Thr Leu Leu Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

```
Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 8
<211> LENGTH: 2025
<212> TYPE: DNA
<213> ORGANISM: Homo sapiens

<400> SEQUENCE: 8
cttctgtgtg tgcacatgtg taatacatat ctgggatcaa agctatctat ataaagtcct      60
tgattctgtg tgggttcaaa cacatttcaa agcttcagga tcctgaaagg ttttgctcta    120
cttcctgaag acctgaacac cgctcccata agccatggc ttgccttgga tttcagcggc    180
acaaggctca gctgaacctg gctaccagga cctggccctg cactctcctg ttttttcttc    240
tcttcatccc tgtcttctgc aaagcaatgc acgtggccca gctgctgtg gtactggcca    300 gcagccgagg catcgccagc tttgtgtgtg agtatgcatc tccaggcaaa gccactgagg    360
tccgggtgac agtgcttcgg caggctgaca gccaggtgac tgaagtctgt gcggcaacct    420
acatgatggg gaatgagttg accttcctag atgattccat ctgcacgggc acctccagtg    480
gaaatcaagt gaacctcact atccaaggac tgagggccat ggacacggga ctctacatct    540
gcaaggtgga gctcatgtac ccaccgccat actacctggg cataggcaac ggaacccaga    600
tttatgtaat tgatccagaa ccgtgcccag attctgactt cctcctctgg atccttgcag    660
cagttagttc ggggttgttt tttatagct ttctcctcac agctgtttct tgagcaaaa    720 tgctaaagaa aagaagccct cttacaacag gggtctatgt gaaaatgccc ccaacagagc    780
cagaatgtga aaagcaattt cagccttatt ttattcccat caattgagaa accattatga    840
agaagagagt ccatatttca atttccaaga gctgaggcaa ttctaacttt tttgctatcc    900
agctattttt atttgtttgt gcatttgggg ggaattcatc tctctttaat ataaagttgg    960
atgcggaacc caaattacgt gtactacaat ttaaagcaaa ggagtagaaa dacagagctg   1020
ggatgtttct gtcacatcag ctccactttc agtgaaagca tcacttggga ttaatatggg   1080
gatgcagcat tatgatgtgg gtcaaggaat taagttaggg aatggcacag cccaaagaag   1140
gaaaaggcag ggagcgaggg agaagactat attgtacaca ccttatattt acgtatgaga   1200
cgtttatagc cgaaatgatc ttttcaagtt aaatttttatg ccttttattt cttaaacaaa   1260
tgtatgatta catcaaggct tcaaaaatac tcacatggct atgttttagc cagtgatgct   1320
aaaggttgta ttgcatatat acatatatat atatatatat atatatatat atatatatat   1380
atatatatat tttaatttga tagtattgtg catagagcca cgtatgtttt tgtgtatttg   1440
ttaatggttt gaatataaac actatatggc agtgtctttc caccttgggt cccagggaag   1500
ttttgtggag gagctcagga cactaataca ccaggtagaa cacaaggtca tttgctaact   1560
agcttggaaa ctggatgagg tcatagcagt gcttgattgc gtggaattgt gctgagttgg   1620
tgttgacatg tgctttgggg cttttacacc agttcctttc aatggtttgc aaggaagcca   1680
```

```
cagctggtgg tatctgagtt gacttgacag aacactgtct tgaagacaat ggcttactcc    1740
aggagaccca caggtatgac cttctaggaa gctccagttc gatgggccca attcttacaa    1800
acatgtggtt aatgccatgg acagaagaag gcagcaggtg cagaatgggg gtgcatgaag    1860
gtttctgaaa attaacactg cttgtgtttt taactcaata ttttccatga aaatgcaaca    1920
acatgtataa tattttttaat taaataaaaa tctgtggtgg tcgttttaaa aaaaaaaaa    1980 aaaaaaaaa aaaaaaaaaa aaaaaaaaaa aaaaaaaaaa aaaaa                     2025
```

<210> SEQ ID NO 9
<211> LENGTH: 2115
<212> TYPE: DNA
<213> ORGANISM: Homo sapiens

<400> SEQUENCE: 9

```
agtttccctt ccgctcacct ccgcctgagc agtggagaag gcggcactct ggtgggctg      60 ctccaggcat gcagatccca caggcgccct ggccagtcgt ctgggcggtg ctacaactgg    120
gctggcggcc aggatggttc ttagactccc cagacaggcc ctggaacccc ccaccttct    180 ccccagccct gctcgtggtg accgaagggg acaacgccac cttcacctgc agcttctcca    240
acacatcgga gagcttcgtg ctaaactggt accgcatgag ccccagcaac cagacggaca    300
agctggccgc cttccccgag gaccgcagcc agcccggcca ggactgccgc ttccgtgtca    360
cacaactgcc caacgggcgt gacttccaca tgagcgtggt cagggcccgg cgcaatgaca    420
gcggcaccta cctctgtggg gccatctccc tggcccccaa ggcgcagatc aaagagagcc    480
tgcgggcaga gctcagggtg acagagagaa gggcagaagt gcccacagcc caccccagcc    540
cctcacccag gccagccggc cagttccaaa ccctggtggt tggtgtcgtg ggcggcctgc    600
tgggcagcct ggtgctgcta gtctgggtcc tggccgtcat ctgctcccgg gccgcacgag    660
ggacaatagg agccaggcgc accggccagc ccctgaagga ggacccctca gccgtgcctg    720
tgttctctgt ggactatggg gagctggatt ccagtggcg agagaagacc ccggagcccc    780
ccgtgccctg tgtccctgag cagacggagt atgccaccat tgtctttcct agcggaatgg    840
gcacctcatc ccccgcccgc aggggctcag ctgacgg ccc tcggagtgcc cagccactga    900
ggcctgagga tggacactgc tcttggcccc tctgaccggc ttccttggcc accagtgttc    960
tgcagaccct ccaccatgag cccgggtcag cgcatttcct caggagaagc aggcagggtg   1020
caggccattg caggccgtcc aggggctgag ctgcctgggg gcgaccgggg ctccagcctg   1080
cacctgcacc aggcacagcc ccaccacagg actcatgtct caatgcccac agtgagccca   1140
ggcagcaggt gtcaccgtcc cctacaggga gggccagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc gccgtggccc tgcctgacgc cccggagcct   1320
cctgcctgaa cttgggggct ggttggagat ggcttggag cagccaaggt gcccctggca    1380
gtggcatccc gaaacgccct ggacgcaggg cccaagactg ggcacaggag tgggaggtac   1440
atggggctgg ggactcccca ggagttatct gctccctgca ggcctagaga agtttcaggg   1500
aaggtcagaa gagctcctgg ctgtggtggg cagggcagga aacccctcca cctttacaca   1560
tgcccaggca gcacctcagg ccctttgtgg ggcaggaag ctgaggcagt aagcgggcag    1620
gcagagctgg aggcctttca ggcccagcca gcactctggc ctcctgccgc cgcattccac   1680
cccagcccct cacaccactc gggagaggga catcctacgg tcccaaggtc aggagggcag   1740
```

```
ggctggggtt gactcaggcc cctcccagct gtggccacct gggtgttggg agggcagaag   1800
tgcaggcacc tagggccccc catgtgccca ccctgggagc tctccttgga acccattcct   1860
gaaattattt aaaggggttg gccgggctcc caccagggcc tgggtgggaa ggtacaggcg   1920
ttccccgggg gcctagtacc cccgccgtgg cctatccact cctcacatcc acacactgca   1980
cccccactcc tggggcaggg ccaccagcat ccaggcggcc agcaggcacc tgagtggctg   2040
ggacaaggga tcccccttcc ctgtggttct attatattat aattataatt aaatatgaga   2100
gcatgctaag gaaaa                                                   2115

<210> SEQ ID NO 10
<211> LENGTH: 288
<212> TYPE: PRT
<213> ORGANISM: Homo sapiens

<400> SEQUENCE: 10

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 11
<211> LENGTH: 290
```

```
<212> TYPE: PRT
<213> ORGANISM: Homo sapiens

<400> SEQUENCE: 11

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 12
<211> LENGTH: 531
<212> TYPE: DNA
<213> ORGANISM: Homo sapiens

<400> SEQUENCE: 12
atgaggatat tgctgtctt tatattcatg acctactggc atttgctgaa cgccccatac      60
aacaaaatca accaaagaat tttggttgtg gatccagtca cctctgaaca tgaactgaca     120
tgtcaggctg agggctaccc caaggccgaa gtcatctgga caagcagtga ccatcaagtc     180
ctgagtggta agaccaccac caccaattcc aagagagagg agaagctttt caatgtgacc     240
agcacactga gaatcaacac aacaactaat gagattttct actgcacttt taggagatta     300
```

```
gatcctgagg aaaaccatac agctgaattg gtcatcccag aactacctct ggcacatcct    360
ccaaatgaaa ggactcactt ggtaattctg ggagccatct tattatgcct tggtgtagca    420
ctgacattca tcttccgttt aagaaaaggg agaatgatgg atgtgaaaaa atgtggcatc    480
caagatacaa actcaaagaa gcaaagtgat acacatttgg aggagacgta a             531
```

<210> SEQ ID NO 13
<211> LENGTH: 273
<212> TYPE: PRT
<213> ORGANISM: Homo sapiens

<400> SEQUENCE: 13

```
Met Ile Phe Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

<210> SEQ ID NO 14
<211> LENGTH: 1223
<212> TYPE: DNA
<213> ORGANISM: Homo sapiens

<400> SEQUENCE: 14

```
gcaaaccttaa agctgaatga acaactttc ttctcttgaa tatatcttaa cgccaaattt    60
```

```
tgagtgctttt tttgttaccc atcctcatat gtcccagctg aaagaatcc tgggttggag    120 ctactgcatg ttgattgttt tgttttcct tttggctgtt cattttggtg gctactataa    180
ggaaatctaa cacaaacagc aactgttttt tgttgtttac ttttgcatct ttacttgtgg    240
agctgtggca agtcctcata tcaaatacag aacatgatct tcctcctgct aatgttgagc    300
ctggaattgc agcttcacca gatagcagct ttattcacag tgacagtccc taaggaactg    360
tacataatag agcatggcag caatgtgacc ctggaatgca actttgacac tggaagtcat    420
gtgaaccttg gagcaataac agccagtttg caaaaggtgg aaaatgatac atccccacac    480
cgtgaaagag ccactttgct ggaggagcag ctgcccctag ggaaggcctc gttccacata    540
cctcaagtcc aagtgaggga cgaaggacag taccaatgca taatcatcta tggggtcgcc    600
tgggactaca agtacctgac tctgaaagtc aaagcttcct acaggaaaat aaacactcac    660
atcctaaagg ttccagaaac agatgaggta gagctcacct gccaggctac aggttatcct    720
ctggcagaag tatcctggcc aaacgtcagc gttcctgcca acaccagcca ctccaggacc    780
cctgaaggcc tctaccaggt caccagtgtt ctgcgcctaa agccaccccc tggcagaaac    840
ttcagctgtg tgttctggaa tactcacgtg agggaactta cttttggccag cattgacctt    900 caaagtcaga tggaacccag gacccatcca acttggctgc ttcacatttt catcccctcc    960
tgcatcattg ctttcatttt catagccaca gtgatagccc taagaaaaca actctgtcaa   1020
aagctgtatt cttcaaaaga cacaacaaaa agacctgtca ccacaacaaa gagggaagtg   1080
aacagtgcta tctgaacctg tggtcttggg agccagggtg acctgatatg acatctaaag   1140
aagcttctgg actctgaaca agaattcggt ggcctgcaga gcttgccatt tgcacttttc   1200
aaatgccttt ggatgaccca gca                                           1223
```

<210> SEQ ID NO 15
<211> LENGTH: 289
<212> TYPE: PRT
<213> ORGANISM: Homo sapiens

<400> SEQUENCE: 15

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Ser Leu Leu Pro
145                 150                 155                 160
```

```
Leu Gly Gly Leu Pro Leu Leu Ile Thr Thr Cys Phe Cys Leu Phe Cys
            165                 170                 175

Cys Leu Arg Arg His Gln Gly Lys Gln Asn Glu Leu Ser Asp Thr Ala
        180                 185                 190

Gly Arg Glu Ile Asn Leu Val Asp Ala His Leu Lys Ser Glu Gln Thr
            195                 200                 205

Glu Ala Ser Thr Arg Gln Asn Ser Gln Val Leu Leu Ser Glu Thr Gly
        210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
            245                 250                 255

Tyr Ala Ser Leu Asn His Ser Val Ile Gly Pro Asn Ser Arg Leu Ala
        260                 265                 270

Arg Asn Val Lys Glu Ala Pro Thr Glu Tyr Ala Ser Ile Cys Val Arg
        275                 280                 285

Ser

<210> SEQ ID NO 16
<211> LENGTH: 3216
<212> TYPE: DNA
<213> ORGANISM: Homo sapiens

<400> SEQUENCE: 16
```

| | | |
|---|---|---|
| gtctttctgt tcacttttt tcacaaaatc atccaggctc ttcctactct cctctcttac | 60 |
| cacctctctc ttcttttttt ttttttttta gttatttcac agatgccact ggggtaggta | 120 |
| aactgaccca actctgcagc actcagaaga cgaagcaaag ccttctactt gagcagtttt | 180 |
| tccatcactg atatgtgcag gaaatgaaga cattgcctgc catgcttgga actgggaaat | 240 |
| tattttgggt cttcttctta atcccatatc tggacatctg aacatccat gggaaagaat | 300 |
| catgtgatgt acagctttat ataaagagac aatctgaaca ctccatctta gcaggagatc | 360 |
| cctttgaact agaatgccct gtgaaatact gtgctaacag gcctcatgtg acttggtgca | 420 |
| agctcaatgg aacaacatgt gtaaaacttg aagatagaca aacaagttgg aaggaagaga | 480 |
| agaacatttc attttcatt ctacattttg aaccagtgct tcctaatgac aatgggtcat | 540 |
| accgctgttc tgcaaattt cagtctaatc tcattgaaag ccactcaaca actctttatg | 600 |
| tgacagatgt aaaaagtgcc tcagaacgac cctccaagga cgaaatggca agcagaccct | 660 |
| ggctcctgta gttactt cctttgggg gattgcctct actcatcact acctgtttct | 720 |
| gcctgttctg ctgcctgaga aggcaccaag gaaagcaaaa tgaactctct gacacagcag | 780 |
| gaagggaaat taacctggtt gatgctcacc ttaagagtga gcaaacagaa gcaagcacca | 840 |
| ggcaaaattc ccaagtactg ctatcagaaa ctggaattta tgataatgac cctgaccttt | 900 |
| gtttcaggat gcaggaaggg tctgaagttt attctaatcc atgcctggaa gaaaacaaac | 960 |
| caggcattgt ttatgcttcc ctgaaccatt ctgtcattgg accgaactca agactggcaa | 1020 |
| gaaatgtaaa agaagcacca acagaatatg catccatatg tgtgaggagt aagtctgtt | 1080 |
| tctgactcca acagggacca ttgaatgatc agcatgttga catcattgtc tgggctcaac | 1140 |
| aggatgtcaa ataatatttc tcaatttgag aattttact ttagaaatgt tcatgttagt | 1200 |
| gcttgggtct aagggtccta taggataaat gattaaaatt tctctcagaa acttatttgg | 1260 |
| gagcttttta tattatagcc ttgaataaca aaatctctcc aaaactggtt gacatcatga | 1320 |
| gtagcagaat agtagaacgt ttaaacttag ctacatttta cccaatatac aaactcgatc | 1380 |

```
ttgcctttga agctattgga aagacttgta gggaaaagag gtttgtgtta cctgcatcag    1440
ttcactacac actcttgaaa acaaaatgtc ccaatttgac taaccaacca taaatacagt    1500
aatgattgta tatttcaagt cagtcttcca aaataagaaa ttttgctgt gtcagtctaa     1560 gaatggtgtt tcttaaatgc aaaggagaaa tcattttagg cttgatgtaa gaaaatgaaa    1620
ataataaatg gtgcaataaa aatatagaat ataccaattg gatatagggt agatgttcca    1680
catacctggc aaacaaatgc ttatatctac tctgttagat tgataagcaa atataggtat    1740
taatggagca gtcaacgtat agcacattta tgaggaaagt agagactcac tgggtcacat    1800
agactaatgg ataggaatgt gacataatgc tgctgaatta atatacttat gggcatctga    1860
atagtttaaa agttagtcag aataggtatc actgggcaag tgaagatagc ttaaactgct    1920
tcatgcttga cttgatagca agttaaagtg caattaatgg aatggaggaa aacccagaat    1980
atttaattgg tctgtagggg tcaatttgct ttcattcacc acatctgcat cttgctgttc    2040
ttcttactaa ggaatcaggg caaatcatct gtagtgacat attttagttt gctaatcatt    2100
tattttaaaa tactgaggtt gcagccactt aagagtatag caaagatgg attcagattt     2160 ttggactttc caaagtactt gagttaaact atttcaaaaa tagcctataa ttttattcaa    2220
cagtttgagg ctattcgaat tctcaggtgc tgctactgaa taatgtaata gtcttcatac    2280
aaagtggata gcaaaggtta aaatccattt caacaaatat gtgagctgag ctgctgcaca    2340
aaggaatgtg atgtgtgtgt gtgtgtgtgt gtgtgtgtgt gttaggtggg gtgggtgaca    2400
acagaaatgg tgcacgagaa actgatcaaa ttgacattat attttcagtt tgcttatgaa    2460
gctcaaaata ctagagtaaa tgggtcatta agaaaataa tatgtgaaat tatggagttt     2520
agaatacaag tggggtatat atacaaaaag acaaaactga ggttttgtgg tggagagatt    2580
ttcttaagta acactggcat taagttttag ctccttagat ttgggggtgc aaatattctt    2640
ttgagtcact gttattttgc caattacacc tagaatttca agcaaccaat tcgagatagg    2700
ctgttttagc caggctgcat ttgtggacaa cttatgtaag aaagacatgt tagaatagct    2760
gcttgtggta ttcttaaaaa tagaaacagg aaatatgggg aggatacatt tagctgtcct    2820
cttatcagat gaacacacga aattgaacag ttccttcatg attctctcaa acttaaaagc    2880
aaaatatttc tgtcttattt aaaatatcct tagtatgtct tatagtaaag ataatgctga    2940
taatgatttc atctctaaga tgtattaata tatttgtact gtttgccaaa atcacaaatc    3000
atttatgttt ttattccttt tcaaaatggt gtcagagaca tacatgcatt tcccaaatg     3060 actctacttc actattattt acatggctta tttcattagt ttatagaggg tttgagaaaa    3120
agaatatgta gataatttaa tggtttttca caaatttaa gcttgtgatt gtgctcaatg     3180
agaaggtaaa gttattaaaa cttatttgaa atcaaa                              3216
```

<210> SEQ ID NO 17
<211> LENGTH: 301
<212> TYPE: PRT
<213> ORGANISM: Homo sapiens

<400> SEQUENCE: 17

```
Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45
```

Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
            195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Gly Asn Val Tyr
            260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
            290                 295                 300

<210> SEQ ID NO 18
<211> LENGTH: 1116
<212> TYPE: DNA
<213> ORGANISM: Homo sapiens

<400> SEQUENCE: 18
ggagagttaa aactgtgcct aacagaggtg tcctctgact tttcttctgc aagctccatg      60
ttttcacatc ttcccttga ctgtgtcctg ctgctgctgc tgctactact tacaaggtcc     120
tcagaagtgg aatacagagc ggaggtcggt cagaatgcct atctgccctg cttctacacc     180
ccagccgccc cagggaacct cgtgcccgtc tgctgggca aggagcctg tcctgtgttt       240 gaatgtggca acgtggtgct caggactgat gaaagggatg tgaattattg gacatccaga     300
tactggctaa atggggattt ccgcaaagga gatgtgtccc tgaccataga gaatgtgact     360
ctagcagaca gtgggatcta ctgctgccgg atccaaatcc caggcataat gaatgatgaa     420
aaatttaacc tgaagttggt catcaaacca gccaaggtca cccctgcacc gactctgcag     480
agagacttca ctgcagcctt ccaaggatg cttaccacca ggggacatgg cccagcagag     540
acacagacac tggggagcct ccctgatata aatctaacac aaatatccac attggccaat     600
gagttacggg actctagatt ggccaatgac ttacgggact ctggagcaac catcagaata     660

| | |
|---|---|
| ggcatctaca tcggagcagg gatctgtgct gggctggctc tggctcttat cttcggcgct | 720 |
| ttaattttca aatggtattc tcatagcaaa gagaagatac agaatttaag cctcatctct | 780 |
| ttggccaacc tccctccctc aggattggca aatgcagtag cagagggaat tcgctcagaa | 840 |
| gaaaacatct ataccattga agagaacgta tatgaagtgg aggagcccaa tgagtattat | 900 |
| tgctatgtca gcagcaggca gcaaccctca caaccttggg gttgtcgctt tgcaatgcca | 960 |
| tagatccaac caccttattt ttgagcttgg tgttttgtct ttttcagaaa ctatgagctg | 1020 |
| tgtcacctga ctggttttgg aggttctgtc cactgctatg gagcagagtt ttcccatttt | 1080 |
| cagaagataa tgactcacat gggaattgaa ctggga | 1116 |

<210> SEQ ID NO 19
<211> LENGTH: 3868
<212> TYPE: DNA
<213> ORGANISM: Homo sapiens

<400> SEQUENCE: 19

| | |
|---|---|
| ggaggtcttg tttccggaag atgttgcaag gctgtggtga aggcaggtgc agcctagcct | 60 |
| cctgctcaag ctacaccctg gccctccacg catgaggccc tgcagaactc tggagatggt | 120 |
| gcctacaagg gcagaaaagg acaagtcggc agccgctgtc ctgagggcac cagctgtggt | 180 |
| gcaggagcca agacctgagg gtggaagtgt cctcttagaa tggggagtgc ccagcaaggt | 240 |
| gtacccgcta ctggtgctat ccagaattcc catctctccc tgctctctgc ctgagctctg | 300 |
| ggccttagct cctccctggg cttggtagag acaggtgtg aggccctcat gggatgtagg | 360 |
| ctgtctgaga ggggagtgga aagaggaagg ggtgaaggag ctgtctgcca tttgactatg | 420 |
| caaatggcct ttgactcatg ggaccctgtc ctcctcactg ggggcagggt ggagtggagg | 480 |
| gggagctact aggctggtat aaaaatctta cttcctctat tctctgagcc gctgctgccc | 540 |
| ctgtgggaag ggacctcgag tgtgaagcat ccttccctgt agctgctgtc cagtctgccc | 600 |
| gccagaccct ctggagaagc ccctgccccc cagcatgggt ttctgccgca gcgccctgca | 660 |
| cccgctgtct ctcctggtgc aggccatcat gctggccatg accctggccc tgggtacctt | 720 |
| gcctgccttc ctaccctgtg agctccagcc ccacggcctg gtgaactgca actggctgtt | 780 |
| cctgaagtct gtgccccact tctccatggc agcacccgt ggcaatgtca ccagcctttc | 840 |
| cttgtcctcc aaccgcatcc accacctcca tgattctgac tttgcccacc tgcccagcct | 900 |
| gcggcatctc aacctcaagt ggaactgccc gccggttggc ctcagcccca tgcacttccc | 960 |
| ctgccacatg accatcgagc ccagcacctt cttggctgtg cccaccctgg aagagctaaa | 1020 |
| cctgagctac aacaacatca tgactgtgcc tgcgctgccc aaatccctca tatccctgtc | 1080 |
| cctcagccat accaacatcc tgatgctaga ctctgccagc ctcgccggcc tgcatgccct | 1140 |
| gcgcttccta ttcatggacg gcaactgtta ttacaagaac cctgcaggc aggcactgga | 1200 |
| ggtggcccg ggtgccctcc ttggcctggg caacctcacc cacctgtcac tcaagtacaa | 1260 |
| caacctcact gtggtgcccc gcaacctgcc ttccagcctg gagtatctgc tgttgtccta | 1320 |
| caaccgcatc gtcaaactgg cgcctgagga cctggccaat ctgaccgccc tgcgtgtgct | 1380 |
| cgatgtgggc ggaaattgcc gccgctgcga ccacgctccc aaccctgca tggagtgccc | 1440 |
| tcgtcacttc ccccagctac atcccgatac cttcagccac ctgagccgtc ttgaaggcct | 1500 |
| ggtgttgaag gacagttctc tctcctggct gaatgccagt tggttccgtg ggctgggaaa | 1560 |
| cctccgagtg ctggacctga gtgagaactt cctctacaaa tgcatcacta aaaccaaggc | 1620 |
| cttccagggc ctaacacagc tgcgcaagct taacctgtcc ttcaattacc aaaagagggt | 1680 |

```
gtcctttgcc cacctgtctc tggcccttc cttcgggagc ctggtcgccc tgaaggagct    1740
ggacatgcac ggcatcttct tccgctcact cgatgagacc acgctccggc cactggcccg   1800
cctgcccatg ctccagactc tgcgtctgca gatgaacttc atcaaccagg cccagctcgg   1860
catcttcagg gccttccctg gcctgcgcta cgtggacctg tcggacaacc gcatcagcgg   1920
agcttcggag ctgacagcca ccatggggga ggcagatgga ggggagaagg tctggctgca   1980
gcctggggac cttgctccgg ccccagtgga cactcccagc tctgaagact tcaggcccaa   2040
ctgcagcacc ctcaacttca ccttggatct gtcacggaac aacctggtga ccgtgcagcc   2100
ggagatgttt gcccagctct cgcacctgca gtgcctgcgc ctgagccaca actgcatctc   2160
gcaggcagtc aatggctccc agttcctgcc gctgaccggt ctgcaggtgc tagacctgtc   2220
ccacaataag ctgacctct accacgagca ctcattcacg gagctaccac gactggaggc   2280
cctggacctc agctacaaca gccagccctt tggcatgcag ggcgtgggcc acaacttcag   2340
cttcgtggct cacctgcgca ccctgcgcca cctcagcctg gcccacaaca acatccacag   2400
ccaagtgtcc cagcagctct gcagtacgtc gctgcgggcc ctggacttca gcggcaatgc   2460
actgggccat atgtgggccg agggagacct ctatctgcac ttcttccaag gcctgagcgg   2520
tttgatctgg ctggacttgt cccagaaccg cctgcacacc ctcctgcccc aaaccctgcg   2580
caacctcccc aagagcctac aggtgctgcg tctccgtgac aattacctgg ccttctttaa   2640
gtggtggagc ctccacttcc tgcccaaact ggaagtcctc gacctggcag gaaaccagct   2700
gaaggccctg accaatggca gcctgcctgc tggcacccgg ctccggaggc tggatgtcag   2760
ctgcaacagc atcagcttcg tggcccccgg cttcttttcc aaggccaagg agctgcgaga   2820
gctcaaccct agcgccaacg ccctcaagac agtggaccac tcctggtttg ggccctggc   2880
gagtgccctg caaatactag atgtaagcgc caaccctctg cactgcgcct gtggggcggc   2940
ctttatggac ttcctgctgg aggtgcaggc tgccgtgccc ggtctgccca gccgggtgaa   3000
gtgtggcagt ccgggccagc tccagggcct cagcatcttt gcacaggacc tgcgcctctg   3060
cctggatgag gccctctcct gggactgttt cgccctctcg ctgctggctg tggctctggg   3120
cctgggtgtg cccatgctgc atcacctctg tggctggac ctctggtact gcttccacct   3180
gtgcctggcc tggcttccct ggcgggggcg gcaaagtggg cgagatgagg atgccctgcc   3240
ctacgatgcc ttcgtggtct tcgacaaaac gcagagcgca gtggcagact gggtgtacaa   3300
cgagcttcgg gggcagctgg aggagtgccg tgggcgctgg gcactccgcc tgtgcctgga   3360
ggaacgcgac tggctgcctg gcaaaaccct ctttgagaac ctgtgggcct cggtctatgg   3420
cagccgcaag acgctgtttg tgctggccca cacggaccgg gtcagtggtc tcttgcgcgc   3480
cagcttcctg ctgcccagc agcgcctgct ggaggaccgc aaggacgtcg tggtgctggt   3540
gatcctgagc cctgacggcc gccgctcccg ctatgtgcgg ctgcgccagc gcctctgccg   3600
ccagagtgtc ctcctctggc cccaccagcc cagtggtcag cgcagcttct gggcccagct   3660
gggcatggcc ctgaccaggg acaaccacca cttctataac cggaacttct gccagggacc   3720
cacggccgaa tagccgtgag ccggaatcct gcacggtgcc acctccacac tcacctcacc   3780
tctgcctgcc tggtctgacc ctcccctgct cgcctccctc accccacacc tgacacagag   3840
caggcactca ataaatgcta ccgaaggc                                      3868
```

<210> SEQ ID NO 20
<211> LENGTH: 1032
<212> TYPE: PRT

<213> ORGANISM: Homo sapiens

<400> SEQUENCE: 20

```
Met Gly Phe Cys Arg Ser Ala Leu His Pro Leu Ser Leu Leu Val Gln
1               5                   10                  15
Ala Ile Met Leu Ala Met Thr Leu Ala Leu Gly Thr Leu Pro Ala Phe
                20                  25                  30
Leu Pro Cys Glu Leu Gln Pro His Gly Leu Val Asn Cys Asn Trp Leu
            35                  40                  45
Phe Leu Lys Ser Val Pro His Phe Ser Met Ala Ala Pro Arg Gly Asn
        50                  55                  60
Val Thr Ser Leu Ser Leu Ser Ser Asn Arg Ile His His Leu His Asp
65                  70                  75                  80
Ser Asp Phe Ala His Leu Pro Ser Leu Arg His Leu Asn Leu Lys Trp
                85                  90                  95
Asn Cys Pro Pro Val Gly Leu Ser Pro Met His Phe Pro Cys His Met
            100                 105                 110
Thr Ile Glu Pro Ser Thr Phe Leu Ala Val Pro Thr Leu Glu Glu Leu
        115                 120                 125
Asn Leu Ser Tyr Asn Asn Ile Met Thr Val Pro Ala Leu Pro Lys Ser
    130                 135                 140
Leu Ile Ser Leu Ser Leu Ser His Thr Asn Ile Leu Met Leu Asp Ser
145                 150                 155                 160
Ala Ser Leu Ala Gly Leu His Ala Leu Arg Phe Leu Phe Met Asp Gly
                165                 170                 175
Asn Cys Tyr Tyr Lys Asn Pro Cys Arg Gln Ala Leu Glu Val Ala Pro
            180                 185                 190
Gly Ala Leu Leu Gly Leu Gly Asn Leu Thr His Leu Ser Leu Lys Tyr
        195                 200                 205
Asn Asn Leu Thr Val Val Pro Arg Asn Leu Pro Ser Ser Leu Glu Tyr
    210                 215                 220
Leu Leu Leu Ser Tyr Asn Arg Ile Val Lys Leu Ala Pro Glu Asp Leu
225                 230                 235                 240
Ala Asn Leu Thr Ala Leu Arg Val Leu Asp Val Gly Gly Asn Cys Arg
                245                 250                 255
Arg Cys Asp His Ala Pro Asn Pro Cys Met Glu Cys Pro Arg His Phe
            260                 265                 270
Pro Gln Leu His Pro Asp Thr Phe Ser His Leu Ser Arg Leu Glu Gly
        275                 280                 285
Leu Val Leu Lys Asp Ser Ser Leu Ser Trp Leu Asn Ala Ser Trp Phe
    290                 295                 300
Arg Gly Leu Gly Asn Leu Arg Val Leu Asp Leu Ser Glu Asn Phe Leu
305                 310                 315                 320
Tyr Lys Cys Ile Thr Lys Thr Lys Ala Phe Gln Gly Leu Thr Gln Leu
                325                 330                 335
Arg Lys Leu Asn Leu Ser Phe Asn Tyr Gln Lys Arg Val Ser Phe Ala
            340                 345                 350
His Leu Ser Leu Ala Pro Ser Phe Gly Ser Leu Val Ala Leu Lys Glu
        355                 360                 365
Leu Asp Met His Gly Ile Phe Phe Arg Ser Leu Asp Glu Thr Thr Leu
    370                 375                 380
Arg Pro Leu Ala Arg Leu Pro Met Leu Gln Thr Leu Arg Leu Gln Met
385                 390                 395                 400
```

```
Asn Phe Ile Asn Gln Ala Gln Leu Gly Ile Phe Arg Ala Phe Pro Gly
                405                 410                 415
Leu Arg Tyr Val Asp Leu Ser Asp Asn Arg Ile Ser Gly Ala Ser Glu
            420                 425                 430
Leu Thr Ala Thr Met Gly Glu Ala Asp Gly Gly Glu Lys Val Trp Leu
        435                 440                 445
Gln Pro Gly Asp Leu Ala Pro Ala Pro Val Asp Thr Pro Ser Ser Glu
450                 455                 460
Asp Phe Arg Pro Asn Cys Ser Thr Leu Asn Phe Thr Leu Asp Leu Ser
465                 470                 475                 480
Arg Asn Asn Leu Val Thr Val Gln Pro Glu Met Phe Ala Gln Leu Ser
                485                 490                 495
His Leu Gln Cys Leu Arg Leu Ser His Asn Cys Ile Ser Gln Ala Val
            500                 505                 510
Asn Gly Ser Gln Phe Leu Pro Leu Thr Gly Leu Gln Val Leu Asp Leu
        515                 520                 525
Ser His Asn Lys Leu Asp Leu Tyr His Glu His Ser Phe Thr Glu Leu
        530                 535                 540
Pro Arg Leu Glu Ala Leu Asp Leu Ser Tyr Asn Ser Gln Pro Phe Gly
545                 550                 555                 560
Met Gln Gly Val Gly His Asn Phe Ser Phe Val Ala His Leu Arg Thr
                565                 570                 575
Leu Arg His Leu Ser Leu Ala His Asn Asn Ile His Ser Gln Val Ser
            580                 585                 590
Gln Gln Leu Cys Ser Thr Ser Leu Arg Ala Leu Asp Phe Ser Gly Asn
        595                 600                 605
Ala Leu Gly His Met Trp Ala Glu Gly Asp Leu Tyr Leu His Phe Phe
        610                 615                 620
Gln Gly Leu Ser Gly Leu Ile Trp Leu Asp Leu Ser Gln Asn Arg Leu
625                 630                 635                 640
His Thr Leu Leu Pro Gln Thr Leu Arg Asn Leu Pro Lys Ser Leu Gln
                645                 650                 655
Val Leu Arg Leu Arg Asp Asn Tyr Leu Ala Phe Phe Lys Trp Trp Ser
            660                 665                 670
Leu His Phe Leu Pro Lys Leu Glu Val Leu Asp Leu Ala Gly Asn Gln
        675                 680                 685
Leu Lys Ala Leu Thr Asn Gly Ser Leu Pro Ala Gly Thr Arg Leu Arg
        690                 695                 700
Arg Leu Asp Val Ser Cys Asn Ser Ile Ser Phe Val Ala Pro Gly Phe
705                 710                 715                 720
Phe Ser Lys Ala Lys Glu Leu Arg Glu Leu Asn Leu Ser Ala Asn Ala
                725                 730                 735
Leu Lys Thr Val Asp His Ser Trp Phe Gly Pro Leu Ala Ser Ala Leu
            740                 745                 750
Gln Ile Leu Asp Val Ser Ala Asn Pro Leu His Cys Ala Cys Gly Ala
        755                 760                 765
Ala Phe Met Asp Phe Leu Leu Glu Val Gln Ala Ala Val Pro Gly Leu
        770                 775                 780
Pro Ser Arg Val Lys Cys Gly Ser Pro Gly Gln Leu Gln Gly Leu Ser
785                 790                 795                 800
Ile Phe Ala Gln Asp Leu Arg Leu Cys Leu Asp Glu Ala Leu Ser Trp
                805                 810                 815
Asp Cys Phe Ala Leu Ser Leu Leu Ala Val Ala Leu Gly Leu Gly Val
```

|     |     |     |     |     | 820 |     |     |     | 825 |     |     |     |     | 830 |
| --- | --- | --- | --- | --- | --- | --- | --- | --- | --- | --- | --- | --- | --- | --- |
| Pro | Met | Leu | His | His | Leu | Cys | Gly | Trp | Asp | Leu | Trp | Tyr | Cys | Phe | His |
|     |     |     | 835 |     |     |     |     | 840 |     |     |     |     | 845 |

Leu Cys Leu Ala Trp Leu Pro Trp Arg Gly Arg Gln Ser Gly Arg Asp
        850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
                900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
        930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg
                965                 970                 975

Arg Ser Arg Tyr Val Arg Leu Arg Gln Arg Leu Cys Arg Gln Ser Val
                980                 985                 990

Leu Leu Trp Pro His Gln Pro Ser  Gly Gln Arg Ser Phe  Trp Ala Gln
        995                 1000                1005

Leu Gly  Met Ala Leu Thr Arg  Asp Asn His His Phe  Tyr Asn Arg
   1010              1015                  1020

Asn Phe Cys Gln Gly Pro Thr  Ala Glu
   1025                1030

<210> SEQ ID NO 21
<211> LENGTH: 3057
<212> TYPE: DNA
<213> ORGANISM: Homo sapiens

<400> SEQUENCE: 21
cactttcgag agtgccgtct atttgccaca cacttccctg atgaaatgtc tggatttgga    60
ctaaagaaaa aaggaaaggc tagcagtcat ccaacagaat catgagacag actttgcctt   120
gtatctactt ttgggggggc cttttgccct ttgggatgct gtgtgcatcc tccaccacca   180
agtgcactgt tagccatgaa gttgctgact gcagccacct gaagttgact caggtacccg   240
atgatctacc cacaaacata acagtgttga accttaccca taatcaactc agaagattac   300
cagccgccaa cttcacaagg tatagccagc taactagctt ggatgtagga tttaacacca   360
tctcaaaact ggagccagaa ttgtgccaga aacttcccat gttaaaagtt ttgaacctcc   420
agcacaatga gctatctcaa ctttctgata aaacctttgc cttctgcacg aatttgactg   480
aactccatct catgtccaac tcaatccaga aaattaaaaa taatcccttt gtcaagcaga   540
agaatttaat cacattagat ctgtctcata atggcttgtc atctacaaaa ttaggaactc   600
aggttcagct ggaaaatctc caagagcttc tattatcaaa caataaaatt caagcgctaa   660
aaagtgaaga actggatatc tttgccaatt catctttaaa aaaattagag ttgtcatcga   720
atcaaattaa agagttttct ccagggtgtt tcacgcaat tggaagatta tttggcctct   780
ttctgaacaa tgtccagctg ggtcccagcc ttacagagaa gctatgtttg gaattagcaa   840
acacaagcat tcggaatctg tctctgagta acagccagct gtccaccacc agcaatacaa   900

```
ctttcttggg actaaagtgg acaaatctca ctatgctcga tctttcctac aacaacttaa    960
atgtggttgg taacgattcc tttgcttggc ttccacaact agaatatttc ttcctagagt   1020
ataataatat acagcatttg ttttctcact ctttgcacgg gcttttcaat gtgaggtacc   1080
tgaatttgaa acggtctttt actaaacaaa gtatttccct tgcctcactc cccaagattg   1140
atgattttc ttttcagtgg ctaaaatgtt tggagcacct taacatggaa gataatgata   1200
ttccaggcat aaaaagcaat atgttcacag gattgataaa cctgaaatac ttaagtctat   1260
ccaactcctt tacaagtttg cgaactttga caaatgaaac atttgtatca cttgctcatt   1320
ctcccttaca catactcaac ctaaccaaga ataaaatctc aaaaatagag agtgatgctt   1380
tctcttggtt gggccaccta gaagtacttg acctgggcct taatgaaatt gggcaagaac   1440
tcacaggcca ggaatggaga ggtctagaaa atattttcga atctatctt tcctacaaca    1500
agtacctgca gctgactagg aactcctttg ccttggtccc aagccttcaa cgactgatgc   1560
tccgaagggt ggcccttaaa aatgtggata gctctccttc accattccag cctcttcgta   1620
acttgaccat tctggatcta agcaacaaca acatagccaa cataaatgat gacatgttgg   1680
agggtcttga gaaactagaa attctcgatt tgcagcataa caacttagca cggctctgga   1740
aacacgcaaa ccctggtggt cccatttatt tcctaaaggg tctgtctcac ctccacatcc   1800
ttaacttgga gtccaacggc tttgacgaga tcccagttga ggtcttcaag gatttatttg   1860
aactaaagat catcgattta ggattgaata atttaaacac acttccagca tctgtcttta   1920
ataatcaggt gtctctaaag tcattgaacc ttcagaagaa tctcataaca tccgttgaga   1980
agaaggtttt cgggccagct ttcaggaacc tgactgagtt agatatgcgc tttaatccct   2040
ttgattgcac gtgtgaaagt attgcctggt ttgttaattg gattaacgag acccatacca   2100
acatccctga gctgtcaagc cactaccttt gcaacactcc acctcactat catgggttcc   2160
cagtgagact ttttgataca tcatcttgca aagacagtgc ccccttttga ctctttttca   2220
tgatcaatac cagtatcctg ttgatttta tctttattgt acttctcatc cactttgagg   2280
gctggaggat atcttttat tggaatgttt cagtacatcg agttcttggt ttcaaagaaa    2340
tagacagaca gacagaacag tttgaatatg cagcatatat aattcatgcc tataaagata   2400
aggattgggt ctgggaacat ttctcttcaa tggaaaagga agaccaatct ctcaaatttt   2460
gtctggaaga aagggacttt gaggcgggtg ttttttgaact agaagcaatt gttaacagca   2520
tcaaaagaag cagaaaaatt attttttgtta taacacacca tctattaaaa gacccattat   2580
gcaaaagatt caaggtacat catgcagttc aacaagctat tgaacaaaat ctggattcca   2640
ttatattggt tttccttgag gagattccag attataaact gaaccatgca ctctgtttgc   2700
gaagaggaat gtttaaatct cactgcatct tgaactggcc agttcagaaa gaacggatag   2760
gtgcctttcg tcataaattg caagtagcac ttggatccaa aaactctgta cattaaattt   2820
atttaaatat tcaattagca aaggagaaac tttctcaatt taaaaagttc tatggcaaat   2880
ttaagttttc cataaaggtg ttataatttg tttattcata tttgtaaatg attatattct   2940
atcacaatta catctcttct aggaaaatgt gtctccttat ttcaggccta tttttgacaa   3000
ttgacttaat tttacccaaa ataaaacata taagcacgta aaaaaaaaaa aaaaaaa      3057
```

<210> SEQ ID NO 22
<211> LENGTH: 904
<212> TYPE: PRT
<213> ORGANISM: Homo sapiens

<400> SEQUENCE: 22

-continued

```
Met Arg Gln Thr Leu Pro Cys Ile Tyr Phe Trp Gly Gly Leu Leu Pro
 1               5                  10                 15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
 50                  55                  60

Arg Leu Pro Ala Ala Asn Phe Thr Arg Tyr Ser Gln Leu Thr Ser Leu
 65               70                  75                  80

Asp Val Gly Phe Asn Thr Ile Ser Lys Leu Glu Pro Glu Leu Cys Gln
                 85                  90                  95

Lys Leu Pro Met Leu Lys Val Leu Asn Leu Gln His Asn Glu Leu Ser
                100                 105                 110

Gln Leu Ser Asp Lys Thr Phe Ala Phe Cys Thr Asn Leu Thr Glu Leu
            115                 120                 125

His Leu Met Ser Asn Ser Ile Gln Lys Ile Lys Asn Asn Pro Phe Val
            130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
            195                 200                 205

Ile Lys Glu Phe Ser Pro Gly Cys Phe His Ala Ile Gly Arg Leu Phe
            210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
            275                 280                 285

Val Gly Asn Asp Ser Phe Ala Trp Leu Pro Gln Leu Glu Tyr Phe Phe
            290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
            355                 360                 365

Gly Ile Lys Ser Asn Met Phe Thr Gly Leu Ile Asn Leu Lys Tyr Leu
            370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415
```

```
Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
            435                 440                 445

Gly Gln Glu Trp Arg Gly Leu Glu Asn Ile Phe Glu Ile Tyr Leu Ser
450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
            485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
            530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
            565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
            595                 600                 605

Gln Val Ser Leu Lys Ser Leu Asn Leu Gln Lys Asn Leu Ile Thr Ser
610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
            645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
            675                 680                 685

Arg Leu Phe Asp Thr Ser Ser Cys Lys Asp Ser Ala Pro Phe Glu Leu
            690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
            725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
            755                 760                 765

Trp Val Trp Glu His Phe Ser Ser Met Glu Lys Glu Asp Gln Ser Leu
            770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
            805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
```

```
                    835                 840                 845
Leu Val Phe Leu Glu Glu Ile Pro Asp Tyr Lys Leu Asn His Ala Leu
        850                 855                 860
Cys Leu Arg Arg Gly Met Phe Lys Ser His Cys Ile Leu Asn Trp Pro
865                 870                 875                 880
Val Gln Lys Glu Arg Ile Gly Ala Phe Arg His Lys Leu Gln Val Ala
                885                 890                 895
Leu Gly Ser Lys Asn Ser Val His
            900
```

<210> SEQ ID NO 23
<211> LENGTH: 10
<212> TYPE: DNA
<213> ORGANISM: Unknown
<220> FEATURE:
<223> OTHER INFORMATION: Description of Unknown:
    Bacterial ribosomal RNA sequence

<400> SEQUENCE: 23
cggaaagacc                                                                10

<210> SEQ ID NO 24
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

```
Met Ala Pro Ala Arg Ser Pro Ser Pro Ser Thr Gln Pro Trp Glu His
1               5                   10                  15
Val Asn Ala Ile Gln Glu Ala Arg Arg Leu Leu Asn Leu Ser Arg Asp
            20                  25                  30
Thr Ala Ala Glu Met Asn Glu Thr Val Glu Val Ile Ser Glu Met Phe
        35                  40                  45
Asp Leu Gln Glu Pro Thr Cys Leu Gln Thr Arg Leu Glu Leu Tyr Lys
    50                  55                  60
Gln Gly Leu Arg Gly Ser Leu Thr Lys Leu Lys Gly Pro Leu Thr Met
65                  70                  75                  80
Met Ala Ser His Tyr Lys Gln His Cys Pro Pro Thr Pro Glu Thr Ser
                85                  90                  95
Cys Ala Thr Gln Ile Ile Thr Phe Glu Ser Phe Lys Glu Asn Leu Lys
            100                 105                 110
Asp Phe Leu Leu Val Ile Pro Phe Asp Cys Trp Glu Pro Val Gln Glu
        115                 120                 125
```

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 25

```
Met Ala Pro Thr Arg Ser Pro Ile Thr Val Thr Arg Pro Trp Lys His
1               5                   10                  15
Val Glu Ala Ile Lys Glu Ala Leu Asn Leu Leu Asp Asp Met Pro Val
            20                  25                  30
```

```
Thr Leu Asn Glu Glu Val Glu Val Ser Asn Glu Phe Ser Phe Lys
         35                  40                  45

Lys Leu Thr Cys Val Gln Thr Arg Leu Lys Ile Phe Glu Gln Gly Leu
 50                  55                  60

Arg Gly Asn Phe Thr Lys Leu Lys Gly Ala Leu Asn Met Thr Ala Ser
 65                  70                  75                  80

Tyr Tyr Gln Thr Tyr Cys Pro Pro Thr Pro Glu Thr Asp Cys Glu Thr
                 85                  90                  95

Gln Val Thr Thr Tyr Ala Asp Phe Ile Asp Ser Leu Lys Thr Phe Leu
            100                 105                 110

Thr Asp Ile Pro Phe Glu Cys Lys Lys Pro Val Gln Lys
            115                 120                 125

<210> SEQ ID NO 26
<211> LENGTH: 781
<212> TYPE: DNA
<213> ORGANISM: Homo sapiens

<400> SEQUENCE: 26
acacagagag aaaggctaaa gttctctgga ggatgtggct gcagagcctg ctgctcttgg      60
gcactgtggc ctgcagcatc tctgcacccg cccgctcgcc cagccccagc acgcagccct    120
gggagcatgt gaatgccatc caggaggccc ggcgtctcct gaacctgagt agagacactg    180
ctgctgagat gaatgaaaca gtagaagtca tctcagaaat gtttgacctc caggagccga    240
cctgcctaca gacccgcctg gagctgtaca agcagggcct gcggggcagc ctcaccaagc    300
tcaagggccc cttgaccatg atggccagcc actacaagca gcactgccct ccaacccgg     360 aaacttcctg tgcaacccag attatcacct ttgaaagttt caaagagaac ctgaaggact    420
ttctgcttgt catccccttt gactgctggg agccagtcca ggagtgagac cggccagatg    480
aggctggcca gccggggag ctgctctctc atgaaacaag agctagaaac tcaggatggt     540
catcttggag ggaccaaggg gtgggccaca gccatggtgg gagtggcctg gacctgccct    600
gggccacact gaccctgata caggcatggc agaagaatgg gaatatttta tactgacaga    660
aatcagtaat atttatatat ttatattttt aaaatattta tttatttatt tatttaagtt    720
catattccat atttattcaa gatgttttac cgtaataatt attattaaaa atatgcttct    780
a                                                                    781

<210> SEQ ID NO 27
<211> LENGTH: 144
<212> TYPE: PRT
<213> ORGANISM: Homo sapiens

<400> SEQUENCE: 27

Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
             20                  25                  30

Val Asn Ala Ile Gln Glu Ala Arg Arg Leu Leu Asn Leu Ser Arg Asp
         35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95
```

```
Met Ala Ser His Tyr Lys Gln His Cys Pro Pro Thr Pro Glu Thr Ser
            100                 105                 110
Cys Ala Thr Gln Ile Ile Thr Phe Glu Ser Phe Lys Glu Asn Leu Lys
            115                 120                 125
Asp Phe Leu Leu Val Ile Pro Phe Asp Cys Trp Glu Pro Val Gln Glu
            130                 135                 140

<210> SEQ ID NO 28
<211> LENGTH: 235
<212> TYPE: PRT
<213> ORGANISM: Homo sapiens

<400> SEQUENCE: 28

Met Thr Val Leu Ala Pro Ala Trp Ser Pro Thr Thr Tyr Leu Leu Leu
1               5                   10                  15
Leu Leu Leu Leu Ser Ser Gly Leu Ser Gly Thr Gln Asp Cys Ser Phe
                20                  25                  30
Gln His Ser Pro Ile Ser Ser Asp Phe Ala Val Lys Ile Arg Glu Leu
            35                  40                  45
Ser Asp Tyr Leu Leu Gln Asp Tyr Pro Val Thr Val Ala Ser Asn Leu
        50                  55                  60
Gln Asp Glu Glu Leu Cys Gly Gly Leu Trp Arg Leu Val Leu Ala Gln
65                  70                  75                  80
Arg Trp Met Glu Arg Leu Lys Thr Val Ala Gly Ser Lys Met Gln Gly
                85                  90                  95
Leu Leu Glu Arg Val Asn Thr Glu Ile His Phe Val Thr Lys Cys Ala
            100                 105                 110
Phe Gln Pro Pro Pro Ser Cys Leu Arg Phe Val Gln Thr Asn Ile Ser
            115                 120                 125
Arg Leu Leu Gln Glu Thr Ser Glu Gln Leu Val Ala Leu Lys Pro Trp
        130                 135                 140
Ile Thr Arg Gln Asn Phe Ser Arg Cys Leu Glu Leu Gln Cys Gln Pro
145                 150                 155                 160
Asp Ser Ser Thr Leu Pro Pro Pro Trp Ser Pro Arg Pro Leu Glu Ala
                165                 170                 175
Thr Ala Pro Thr Ala Pro Gln Pro Pro Leu Leu Leu Leu Leu Leu Leu
            180                 185                 190
Pro Val Gly Leu Leu Leu Leu Ala Ala Ala Trp Cys Leu His Trp Gln
        195                 200                 205
Arg Thr Arg Arg Arg Thr Pro Arg Pro Gly Glu Gln Val Pro Pro Val
        210                 215                 220
Pro Ser Pro Gln Asp Leu Leu Leu Val Glu His
225                 230                 235

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tccatgacgt tcctgacgtt                                                    20

<210> SEQ ID NO 30
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttagggttag ggttagggtt aggg                                             24

<210> SEQ ID NO 31
<211> LENGTH: 386
<212> TYPE: PRT
<213> ORGANISM: Homo sapiens

<400> SEQUENCE: 31
```

| Met | Arg | Ala | Ala | Pro | Leu | Leu | Ala | Arg | Ala | Ala | Ser | Leu | Ala | Leu |
|---|---|---|---|---|---|---|---|---|---|---|---|---|---|---|
| 1 | | | | 5 | | | | | 10 | | | | | 15 |

| Ala | Ser | Cys | Phe | Cys | Phe | Phe | Cys | Trp | Leu | Asp | Arg | Ser | Val | Leu | Ala |
|---|---|---|---|---|---|---|---|---|---|---|---|---|---|---|---|
| | | | 20 | | | | | 25 | | | | 30 | | | |

Lys Glu Leu Lys Phe Val Thr Leu Val Phe Arg His Gly Asp Arg Ser
             35                  40                  45

Pro Ile Asp Thr Phe Pro Thr Asp Pro Ile Lys Glu Ser Ser Trp Pro
 50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Asp Ser
                 85                  90                  95

Tyr Lys His Glu Gln Val Tyr Ile Arg Ser Thr Asp Val Asp Arg Thr
            100                 105                 110

Leu Met Ser Arg Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Ser Glu Ser Val His Asn Phe Thr Leu Pro
210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Thr Gly Leu Gln Met Ala Leu Asp Val Tyr Asn
290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln

|  |  |  | 325 |  |  |  | 330 |  |  |  | 335 |  |
|---|---|---|---|---|---|---|---|---|---|---|---|---|

His Glu Pro Tyr Pro Leu Met Leu Pro Gly Cys Ser Pro Ser Cys Pro
        340              345              350

Leu Glu Arg Phe Ala Glu Leu Val Gly Pro Val Ile Pro Gln Asp Trp
        355              360              365

Ser Thr Glu Val Met Thr Thr Asn Ser His Gln Gly Thr Glu Asp Ser
        370              375              380

Thr Asp
385

<210> SEQ ID NO 32
<211> LENGTH: 3097
<212> TYPE: DNA
<213> ORGANISM: Homo sapiens

<400> SEQUENCE: 32

| ggccagaaac agctctcctc aacatgagag ctgcacccct cctcctggcc agggcagcaa | 60 |
|---|---|
| gcttagcctt ggcttcttgt ttctgctttt tttgctggct agaccgaagt gtactagcca | 120 |
| aggagttgaa gtttgtgact ttggtgtttc ggcatggaga ccgaagtccc attgacacct | 180 |
| ttcccactga ccccataaag gaatcctcat ggccacaagg atttggccaa ctcacccagc | 240 |
| tgggcatgga gcagcattat gaacttggag agtatataag aaagagatat agaaaattct | 300 |
| tgaatgactc ctataaacat gaacaggttt atattcgaag cacagacgtt gaccggactt | 360 |
| tgatgagtcg tatgacaaac ctggcagccc tgttttcccc agaaggtgtc agcatctgga | 420 |
| atcctatcct actctggcag cccatcccgg tgcacacagt tcctctttct gaagatcagt | 480 |
| tgctatacct gcctttcagg aactgccctc gttttcaaga acttgagagt gagctttga | 540 |
| aatcagagga attccagaag aggctgcacc cttataagga ttttatagct accttgggaa | 600 |
| aactttcagg attacatggc caggaccttt ttggaatttg agtaaagtc tacgaccctt | 660 |
| tatattctga gagtgttcac aatttcactt taccctcctg ggccactgag acaccatga | 720 |
| ctaagttgag agaattgtca gaattgtccc tcctgtccct ctatggaatt cacaagcaga | 780 |
| aagagaaatc taggctccaa gggggtgtcc tggtcaatga aatcctcaat cacatgaaga | 840 |
| gagcaactca gataccaagc tacaaaaaac ttatcatgta ttctgcgcat gacactactg | 900 |
| tgactggcct acagatggcg ctagatgttt acaacggact ccttcctccc tatgcttctt | 960 |
| gccacttgac ggaattgtac tttgagaagg gggagtactt tgtggagatg tactaccgga | 1020 |
| atgagacgca gcacgagccg tatccctca tgctacctgg ctgcagcccc agctgtcctc | 1080 |
| tggagaggtt tgctgagctg gttggccctg tgatccctca agactggtcc acggaggtta | 1140 |
| tgaccacaaa cagccatcaa ggtactgagg acagtacaga ttagtgtgca cagagatctc | 1200 |
| tgtagaaaga gtagctgccc tttctcaggg cagatgatgc tttgagaaca tactttggcc | 1260 |
| attaccccc agctttgagg aaaatgggct ttggatgatt attttatgtt ttaggggacc | 1320 |
| cccaacctca ggcaattcca tcctcttcac ccgaccctgc ccccacttgc cataaaactt | 1380 |
| agctaagttt tgttttgttt ttcagcgtta atgtaaaggg gcagcagtgc caaatataa | 1440 |
| cagagataaa gcttaggtca aagttcatag agttcccatg aactatatga ctggccacac | 1500 |
| aggatctttt gtatttaagg attctgagat tttgcttgag caggattaga taaggctgtt | 1560 |
| ctttaaatgt ctgaaatgga acagatttca aaaaaaccc cacaatctag ggtgggaaca | 1620 |
| aggaaggaaa gatgtgaata ggctgatggg caaaaaacca atttacccat cagttccagc | 1680 |
| cttctctcaa ggagaggcaa agaaaggaga tacagtggag acatctggaa agttttctcc | 1740 |

-continued

```
actggaaaac tgctactatc tgtttttata tttctgttaa aatatatgag gctacagaac     1800
taaaaattaa aacctctttg tgtcccttgg tcctggaaca tttatgttcc ttttaaagaa     1860
acaaaaatca aactttacag aaagatttga tgtatgtaat acatatagca gctcttgaag     1920
tatatatatc atagcaaata agtcatctga tgagaacaag ctatttgggc acaacacatc     1980
aggaaagaga gcaccacgtg atggagtttc tccagaagct ccagtgataa agatgttga      2040 ctctaaagtt gatttaaggc caggcatggt ggtttacgcc tataatccca gcattttggg     2100
agtccgaggt gggcagatca cttgagctca ggaggtcaag atcagcctgg caacatggt      2160 gaaaccttgt ctctacataa aatacaaaaa cttagatggg catggtggtg tgtgcctata     2220
gtccactact tgtggggcta aggcaggagg atcacttgag ccccggaggt cgaggctaca     2280
gtgagccaag agtgcactac tgtactccag ccagggcaag agagcgagac cctgtctcaa     2340
taaataaata aataaataaa taaataaata aataaataaa taaataaaaa caaagttgat     2400
taagaaagga agtataggct aggcacagtg gctcacacct gtaatccttg cattttggaa     2460
ggctgaggca ggaggatcac tttaggcctg gtgtgttcaa gaccagcctg gtcaacatag     2520
tgagacactg tctctaccaa aaaaggaag gaagggacac atatcaaact gaaacaaaat      2580
tagaaatgta attatgttat gttctaagtg cctccaagtt caaaacttat tggaatgttg     2640
agagtgtggt tacgaaatac gttaggagga caaaaggaat gtgtaagtct ttaatgcccg     2700
atatcttcag aaaacctaag caaacttaca ggtcctgctg aaactgccca ctctgcaaga     2760
agaaatcatg atatagcttt gccatgtggc agatctacat gtctagagaa cactgtgctc     2820
tattaccatt atggataaag atgagatggt ttctagagat ggtttctact ggctgccaga     2880
atctagagca aagccatccc cgctcctggt tggtcacaga atgactgaca aagacatcga     2940
ttgatatgct tctttgtgtt atttccctcc caagtaaatg tttgtccttg ggtccatttt     3000
ctatgcttgt aactgtcttc tagcagtgag ccaaatgtaa aatagtgaat aaagtcatta     3060
ttaggaagtt caaaagcatt gcttttataa tgaactt                              3097
```

<210> SEQ ID NO 33
<211> LENGTH: 1255
<212> TYPE: PRT
<213> ORGANISM: Homo sapiens

<400> SEQUENCE: 33

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125
```

```
Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
                180                 185                 190

His Pro Cys Ser Pro Met Cys Lys Gly Ser Arg Cys Trp Gly Glu Ser
                195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
    275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
```

-continued

```
         545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
                580                 585                 590
Pro Pro Phe Cys Val Ala Arg Cys Pro Ser Gly Val Lys Pro Asp Leu
                595                 600                 605
Ser Tyr Met Pro Ile Trp Lys Phe Pro Asp Glu Gly Ala Cys Gln
                610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Leu Gly Val Val Phe Gly
                660                 665                 670
Ile Leu Ile Lys Arg Arg Gln Gln Lys Ile Arg Lys Tyr Thr Met Arg
                675                 680                 685
Arg Leu Leu Gln Glu Thr Glu Leu Val Glu Pro Leu Thr Pro Ser Gly
                690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
                740                 745                 750
Lys Val Leu Arg Glu Asn Thr Ser Pro Lys Ala Asn Lys Glu Ile Leu
                755                 760                 765
Asp Glu Ala Tyr Val Met Ala Gly Val Gly Ser Pro Tyr Val Ser Arg
                770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
                835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
                915                 920                 925
Arg Glu Ile Pro Asp Leu Leu Glu Lys Gly Glu Arg Leu Pro Gln Pro
                930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
```

-continued

Ser Arg Met Ala Arg Asp Pro Gln Arg Phe Val Val Ile Gln Asn Glu
             980                 985                 990

Asp Leu Gly Pro Ala Ser Pro Leu Asp Ser Thr Phe Tyr Arg Ser Leu
         995                1000                1005

Leu Glu Asp Asp Met Gly Asp Leu Val Asp Ala Glu Glu Tyr
    1010            1015            1020

Leu Val Pro Gln Gln Gly Phe Phe Cys Pro Asp Pro Ala Pro Gly
    1025            1030            1035

Ala Gly Gly Met Val His His Arg His Arg Ser Ser Thr Arg
    1040            1045            1050

Ser Gly Gly Gly Asp Leu Thr Leu Gly Leu Glu Pro Ser Glu Glu
    1055            1060            1065

Glu Ala Pro Arg Ser Pro Leu Ala Pro Ser Glu Gly Ala Gly Ser
    1070            1075            1080

Asp Val Phe Asp Gly Asp Leu Gly Met Gly Ala Ala Lys Gly Leu
    1085            1090            1095

Gln Ser Leu Pro Thr His Asp Pro Ser Pro Leu Gln Arg Tyr Ser
    1100            1105            1110

Glu Asp Pro Thr Val Pro Leu Pro Ser Glu Thr Asp Gly Tyr Val
    1115            1120            1125

Ala Pro Leu Thr Cys Ser Pro Gln Pro Glu Tyr Val Asn Gln Pro
    1130            1135            1140

Asp Val Arg Pro Gln Pro Pro Ser Pro Arg Glu Gly Pro Leu Pro
    1145            1150            1155

Ala Ala Arg Pro Ala Gly Ala Thr Leu Glu Arg Pro Lys Thr Leu
    1160            1165            1170

Ser Pro Gly Lys Asn Gly Val Val Lys Asp Val Phe Ala Phe Gly
    1175            1180            1185

Gly Ala Val Glu Asn Pro Glu Tyr Leu Thr Pro Gln Gly Gly Ala
    1190            1195            1200

Ala Pro Gln Pro His Pro Pro Ala Phe Ser Pro Ala Phe Asp
    1205            1210            1215

Asn Leu Tyr Tyr Trp Asp Gln Asp Pro Pro Glu Arg Gly Ala Pro
    1220            1225            1230

Pro Ser Thr Phe Lys Gly Thr Pro Thr Ala Glu Asn Pro Glu Tyr
    1235            1240            1245

Leu Gly Leu Asp Val Pro Val
    1250            1255

<210> SEQ ID NO 34
<211> LENGTH: 4664
<212> TYPE: DNA
<213> ORGANISM: Homo sapiens

<400> SEQUENCE: 34
gcttgctccc aatcacagga gaaggaggag gtggaggagg agggctgctt gaggaagtat      60
aagaatgaag ttgtgaagct gagattcccc tccattggga ccggagaaac caggggagcc    120
ccccgggcag ccgcgcgccc cttcccacgg ggccctttac tgcgccgcgc gcccggcccc    180 caccccctcgc agcacccccgc gccccgcgcc ctcccagccg ggtccagccg gagccatggg   240
gccggagccg cagtgagcac catggagctg gcggccttgt gccgctgggg gctcctcctc    300
gccctcttgc ccccggagc cgcgagcacc caagtgtgca ccggcacaga catgaagctg    360 cggctcccctg ccagtcccga gacccacctg gacatgctcc gccacctcta ccagggctgc    420

```
caggtggtgc agggaaacct ggaactcacc tacctgccca ccaatgccag cctgtccttc      480
ctgcaggata tccaggaggt gcagggctac gtgctcatcg ctcacaacca agtgaggcag      540
gtcccactgc agaggctgcg gattgtgcga ggcacccagc tctttgagga caactatgcc      600
ctggccgtgc tagacaatgg agacccgctg aacaatacca ccctgtcac aggggcctcc      660 ccaggaggcc tgcgggagct gcagcttcga agcctcacag agatcttgaa aggaggggtc      720
ttgatccagc ggaaccccca gctctgctac caggacacga ttttgtggaa ggacatcttc      780
cacaagaaca accagctggc tctcacactg atagacacca accgctctcg ggcctgccac      840
ccctgttctc cgatgtgtaa gggctcccgc tgctggggag agagttctga ggattgtcag      900
agcctgacgc gcactgtctg tgccggtggc tgtgcccgct gcaaggggcc actgcccact      960
gactgctgcc atgagcagtg tgctgccggc tgcacgggcc ccaagcactc tgactgcctg     1020
gcctgcctcc acttcaacca cagtggcatc tgtgagctgc actgcccagc cctggtcacc     1080
tacaacacag acacgtttga gtccatgccc aatcccgagg gccggtatac attcggcgcc     1140
agctgtgtga ctgcctgtcc ctacaactac cttttctacgg acgtgggatc ctgcacccte     1200 gtctgccccc tgcacaacca agaggtgaca gcagaggatg aaacacgcg gtgtgagaag     1260 tgcagcaagc cctgtgcccg agtgtgctat ggtctgggca tggagcactt gcgagaggtg     1320
agggcagtta ccagtgccaa tatccaggag tttgctggct gcaagaagat ctttgggagc     1380
ctggcatttc tgccggagag cttttgatggg gacccagcct ccaacactgc ccgctccag     1440 ccagagcagc tccaagtgtt tgagactctg gaagagatca caggttacct atacatctca     1500
gcatggccgg acagcctgcc tgacctcagc gtcttccaga acctgcaagt aatccgggga     1560
cgaattctgc acaatggcgc ctactcgctg accctgcaag ggctgggcat cagctggctg     1620
gggctgcgct cactgaggga actgggcagt ggactggccc tcatccacca taacacccac     1680
ctctgcttcg tgcacacggt gccctgggac cagctctttc ggaacccgca ccaagctctg     1740
ctccacactg ccaaccggcc agaggacgag tgtgtgggcg agggcctggc ctgccaccag     1800
ctgtgcgccc gagggcactg ctggggtcca gggcccaccc agtgtgtcaa ctgcagccag     1860
ttccttcggg gccaggagtg cgtggaggaa tgccgagtac tgcaggggct ccccaggggag     1920 tatgtgaatg ccaggcactg tttgccgtgc caccctgagt gtcagcccca gaatggctca     1980
gtgacctgtt ttggaccgga ggctgaccag tgtgtggcct gtgccactac taaggaccct     2040
cccttctgcg tggcccgctg ccccagcggt gtgaaacctg acctctccta catgcccatc     2100
tggaagtttc cagatgagga gggcgcatgc cagccttgcc ccatcaactg cacccactcc     2160
tgtgtggacc tggatgacaa gggctgcccc gccgagcaga gagccagccc tctgacgtcc     2220
atcatctctg cggtggttgg cattctgctg gtcgtggtct tgggggtggt ctttgggatc     2280
ctcatcaagc gacggcagca gaagatccgg aagtacacga tgcggagact gctgcaggaa     2340
acggagctgg tggagccgct gacacctagc ggagcgatgc caaccaggc gcagatgcgg     2400 atcctgaaag agacggagct gaggaaggtg aaggtgcttg atctggcgc ttttggcaca     2460 gtctacaagg gcatctggat ccctgatggg gagaatgtga aaattccagt ggccatcaaa     2520
gtgttgaggg aaaacacatc ccccaaagcc aacaaagaaa tcttagacga agcatacgtg     2580
atggctggtg tgggctcccc atatgtctcc cgccttctgg gcatctgcct gacatccacg     2640
gtgcagctgg tgacacagct tatgccctat ggctgcctct tagaccatgt ccgggaaaac     2700
cgcggacgcc tgggctccca ggacctgctg aactggtgta tgcagattgc caaggggatg     2760
```

```
agctacctgg aggatgtgcg gctcgtacac agggacttgg ccgctcggaa cgtgctggtc   2820
aagagtccca accatgtcaa aattacagac ttcgggctgg ctcggctgct ggacattgac   2880
gagacagagt accatgcaga tgggggcaag gtgcccatca agtggatggc gctggagtcc   2940
attctccgcc ggcggttcac ccaccagagt gatgtgtgga gttatggtgt gactgtgtgg   3000
gagctgatga cttttggggc caaaccttac gatgggatcc cagcccggga gatccctgac   3060
ctgctggaaa aggggagcg gctgcccag ccccccatct gcaccattga tgtctacatg   3120
atcatggtca aatgttggat gattgactct gaatgtcggc caagattccg ggagttggtg   3180
tctgaattct cccgcatggc cagggacccc cagcgctttg tggtcatcca aatgaggac   3240 ttgggcccag ccagtccctt ggacagcacc ttctaccgct cactgctgga ggacgatgac   3300 atggggacc tggtgatgc tgaggagtat ctggtacccc agcagggctt cttctgtcca   3360
gaccctgccc cgggcgctgg gggcatggtc caccacaggc accgcagctc atctaccagg   3420
agtggcggtg gggacctgac actagggctg gagccctctg aagaggaggc ccccaggtct   3480
ccactggcac cctccgaagg ggctggctcc gatgtatttg atggtgaccct gggaatgggg   3540 gcagccaagg ggctgcaaag cctccccaca catgaccca gccctctaca gcggtacagt   3600
gaggacccca cagtacccct gccctctgag actgatggct acgttgcccc cctgacctgc   3660 agccccagc ctgaatatgt gaaccagcca gatgttcggc cccagccccc ttcgccccga   3720
gagggccctc tgcctgctgc ccgacctgct ggtgccactc tggaaaggcc caagactctc   3780
tccccaggga agaatggggt cgtcaaagac gttttgcct ttgggggtgc cgtggagaac   3840
cccgagtact tgacacccca gggaggagct gccctcagc ccaccctcc tcctgccttc   3900 agcccagcct tcgacaacct ctattactgg gaccaggacc caccagagcg ggggctcca   3960 cccagcacct tcaaagggac acctacggca gagaacccag agtacctggg tctggacgtg   4020
ccagtgtgaa ccagaaggcc aagtccgcag aagccctgat gtgtcctcag ggagcaggga   4080
aggcctgact tctgctggca tcaagaggtg ggagggcccc ccgaccactt ccaggggaac   4140
ctgccatgcc aggaacctgt cctaaggaac cttccttcct gcttgagttc ccagatggct   4200
ggaaggggtc cagcctcgtt ggaagaggaa cagcactggg gagtctttgt ggattctgag   4260
gccctgccca atgagactct agggtccagt ggatgccaca gcccagcttg ccccttcct   4320 tccagatcct gggtactgaa agccttaggg aagctggcct gagaggggaa gcggccctaa   4380
gggagtgtct aagaacaaaa gcgacccatt cagagactgt ccctgaaacc tagtactgcc   4440
ccccatgagg aaggaacagc aatggtgtca gtatccaggc tttgtacaga gtgcttttct   4500
gtttagtttt tactttttt gttttgtttt tttaaagatg aaataaagac ccaggggag   4560 aatgggtgtt gtatggggag gcaagtgtgg ggggtccttc tccacaccca ctttgtccat   4620
ttgcaaatat atttttggaaa acagctaaaa aaaaaaaaa aaaa              4664
```

<210> SEQ ID NO 35
<211> LENGTH: 10
<212> TYPE: PRT
<213> ORGANISM: Homo sapiens

<400> SEQUENCE: 35

Phe Ile Ala Ser Asn Gly Val Lys Leu Val
1               5                   10

<210> SEQ ID NO 36
<211> LENGTH: 15
<212> TYPE: PRT

-continued

```
<213> ORGANISM: Homo sapiens

<400> SEQUENCE: 36

Tyr Ser Val Tyr Phe Asn Leu Pro Ala Asp Thr Ile Tyr Thr Asn
1               5                   10                  15

<210> SEQ ID NO 37
<211> LENGTH: 9
<212> TYPE: PRT
<213> ORGANISM: Homo sapiens

<400> SEQUENCE: 37

Ser Ser Lys Ala Leu Gln Arg Pro Val
1               5

<210> SEQ ID NO 38
<211> LENGTH: 9
<212> TYPE: PRT
<213> ORGANISM: Homo sapiens

<400> SEQUENCE: 38

Gly Phe Lys Gln Ser Ser Lys Ala Leu
1               5

<210> SEQ ID NO 39
<211> LENGTH: 17
<212> TYPE: PRT
<213> ORGANISM: Homo sapiens

<400> SEQUENCE: 39

Ala Thr Gly Phe Lys Gln Ser Ser Lys Ala Leu Gln Arg Pro Val Ala
1               5                   10                  15

Ser

<210> SEQ ID NO 40
<211> LENGTH: 17
<212> TYPE: PRT
<213> ORGANISM: Homo sapiens

<400> SEQUENCE: 40

Ala Thr Gly Phe Lys Gln Ser Ser Lys Ala Leu Gln Arg Pro Val Ala
1               5                   10                  15

Ser

<210> SEQ ID NO 41
<211> LENGTH: 29
<212> TYPE: PRT
<213> ORGANISM: Homo sapiens

<400> SEQUENCE: 41

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu Ser
            20                  25

<210> SEQ ID NO 42
<211> LENGTH: 9
<212> TYPE: PRT
<213> ORGANISM: Homo sapiens

<400> SEQUENCE: 42

Phe Leu Ile Ile Trp Gln Asn Thr Met
1               5
```

```
<210> SEQ ID NO 43
<211> LENGTH: 9
<212> TYPE: PRT
<213> ORGANISM: Homo sapiens

<400> SEQUENCE: 43

Phe Pro Ser Asp Ser Trp Cys Tyr Phe
1               5

<210> SEQ ID NO 44
<211> LENGTH: 9
<212> TYPE: PRT
<213> ORGANISM: Homo sapiens

<400> SEQUENCE: 44

Ser Tyr Leu Asp Ser Gly Ile His Phe
1               5

<210> SEQ ID NO 45
<211> LENGTH: 12
<212> TYPE: PRT
<213> ORGANISM: Homo sapiens

<400> SEQUENCE: 45

Phe Ser Trp Ala Met Asp Leu Asp Pro Lys Gly Ala
1               5                   10

<210> SEQ ID NO 46
<211> LENGTH: 10
<212> TYPE: PRT
<213> ORGANISM: Homo sapiens

<400> SEQUENCE: 46

Ala Cys Asp Pro His Ser Gly His Phe Val
1               5                   10

<210> SEQ ID NO 47
<211> LENGTH: 9
<212> TYPE: PRT
<213> ORGANISM: Homo sapiens

<400> SEQUENCE: 47

Ala Val Cys Pro Trp Thr Trp Leu Arg
1               5

<210> SEQ ID NO 48
<211> LENGTH: 9
<212> TYPE: PRT
<213> ORGANISM: Homo sapiens

<400> SEQUENCE: 48

Ile Leu Asp Lys Val Leu Val His Leu
1               5

<210> SEQ ID NO 49
<211> LENGTH: 14
<212> TYPE: PRT
<213> ORGANISM: Homo sapiens

<400> SEQUENCE: 49

Thr Leu Tyr Gln Asp Asp Thr Leu Thr Leu Gln Ala Ala Gly
1               5                   10
```

```
<210> SEQ ID NO 50
<211> LENGTH: 14
<212> TYPE: PRT
<213> ORGANISM: Homo sapiens

<400> SEQUENCE: 50

Thr Leu Tyr Gln Asp Asp Thr Leu Thr Leu Gln Ala Ala Gly
1               5                   10

<210> SEQ ID NO 51
<211> LENGTH: 16
<212> TYPE: PRT
<213> ORGANISM: Homo sapiens

<400> SEQUENCE: 51

Thr Met Lys Gln Ile Cys Lys Lys Glu Ile Arg Arg Leu His Gln Tyr
1               5                   10                  15

<210> SEQ ID NO 52
<211> LENGTH: 10
<212> TYPE: PRT
<213> ORGANISM: Homo sapiens

<400> SEQUENCE: 52

Lys Ile Leu Asp Ala Val Val Ala Gln Lys
1               5                   10

<210> SEQ ID NO 53
<211> LENGTH: 9
<212> TYPE: PRT
<213> ORGANISM: Homo sapiens

<400> SEQUENCE: 53

Glu Thr Val Ser Glu Gln Ser Asn Val
1               5

<210> SEQ ID NO 54
<211> LENGTH: 9
<212> TYPE: PRT
<213> ORGANISM: Homo sapiens

<400> SEQUENCE: 54

Arg Ile Ala Glu Cys Ile Leu Gly Met
1               5

<210> SEQ ID NO 55
<211> LENGTH: 15
<212> TYPE: PRT
<213> ORGANISM: Homo sapiens

<400> SEQUENCE: 55

Ile Gly Arg Ile Ala Glu Cys Ile Leu Gly Met Asn Pro Ser Arg
1               5                   10                  15

<210> SEQ ID NO 56
<211> LENGTH: 15
<212> TYPE: PRT
<213> ORGANISM: Homo sapiens

<400> SEQUENCE: 56

Ile Gly Arg Ile Ala Glu Cys Ile Leu Gly Met Asn Pro Ser Arg
1               5                   10                  15

<210> SEQ ID NO 57
<211> LENGTH: 10
```

-continued

<212> TYPE: PRT
<213> ORGANISM: Homo sapiens

<400> SEQUENCE: 57

Tyr Val Asp Phe Arg Glu Tyr Glu Tyr Tyr
1               5                   10

<210> SEQ ID NO 58
<211> LENGTH: 14
<212> TYPE: PRT
<213> ORGANISM: Homo sapiens

<400> SEQUENCE: 58

Met Ile Phe Glu Lys His Gly Phe Arg Arg Thr Thr Pro Pro
1               5                   10

<210> SEQ ID NO 59
<211> LENGTH: 10
<212> TYPE: PRT
<213> ORGANISM: Homo sapiens

<400> SEQUENCE: 59

Thr Leu Asp Trp Leu Leu Gln Thr Pro Lys
1               5                   10

<210> SEQ ID NO 60
<211> LENGTH: 9
<212> TYPE: PRT
<213> ORGANISM: Homo sapiens

<400> SEQUENCE: 60

Trp Arg Arg Ala Pro Ala Pro Gly Ala
1               5

<210> SEQ ID NO 61
<211> LENGTH: 9
<212> TYPE: PRT
<213> ORGANISM: Homo sapiens

<400> SEQUENCE: 61

Pro Val Thr Trp Arg Arg Ala Pro Ala
1               5

<210> SEQ ID NO 62
<211> LENGTH: 10
<212> TYPE: PRT
<213> ORGANISM: Homo sapiens

<400> SEQUENCE: 62

Ser Leu Phe Glu Gly Ile Asp Ile Tyr Thr
1               5                   10

<210> SEQ ID NO 63
<211> LENGTH: 9
<212> TYPE: PRT
<213> ORGANISM: Homo sapiens

<400> SEQUENCE: 63

Ala Glu Pro Ile Asn Ile Gln Thr Trp
1               5

<210> SEQ ID NO 64
<211> LENGTH: 11
<212> TYPE: PRT
<213> ORGANISM: Homo sapiens

<400> SEQUENCE: 64

Phe Leu Glu Gly Asn Glu Val Gly Lys Thr Tyr
1               5                   10

<210> SEQ ID NO 65
<211> LENGTH: 9
<212> TYPE: PRT
<213> ORGANISM: Homo sapiens

<400> SEQUENCE: 65

Phe Leu Asp Glu Phe Met Glu Gly Val
1               5

<210> SEQ ID NO 66
<211> LENGTH: 9
<212> TYPE: PRT
<213> ORGANISM: Homo sapiens

<400> SEQUENCE: 66

Glu Glu Lys Leu Ile Val Val Leu Phe
1               5

<210> SEQ ID NO 67
<211> LENGTH: 11
<212> TYPE: PRT
<213> ORGANISM: Homo sapiens

<400> SEQUENCE: 67

Ser Glu Leu Phe Arg Ser Gly Leu Asp Ser Tyr
1               5                   10

<210> SEQ ID NO 68
<211> LENGTH: 9
<212> TYPE: PRT
<213> ORGANISM: Homo sapiens

<400> SEQUENCE: 68

Phe Arg Ser Gly Leu Asp Ser Tyr Val
1               5

<210> SEQ ID NO 69
<211> LENGTH: 9
<212> TYPE: PRT
<213> ORGANISM: Homo sapiens

<400> SEQUENCE: 69

Glu Ala Phe Ile Gln Pro Ile Thr Arg
1               5

<210> SEQ ID NO 70
<211> LENGTH: 11
<212> TYPE: PRT
<213> ORGANISM: Homo sapiens

<400> SEQUENCE: 70

Arg Val Ile Lys Asn Ser Ile Arg Leu Thr Leu
1               5                   10

<210> SEQ ID NO 71
<211> LENGTH: 9
<212> TYPE: PRT
<213> ORGANISM: Homo sapiens

<400> SEQUENCE: 71

```
Lys Ile Asn Lys Asn Pro Lys Tyr Lys
1               5

<210> SEQ ID NO 72
<211> LENGTH: 8
<212> TYPE: PRT
<213> ORGANISM: Homo sapiens

<400> SEQUENCE: 72

Gln Gln Ile Thr Lys Thr Glu Val
1               5

<210> SEQ ID NO 73
<211> LENGTH: 10
<212> TYPE: PRT
<213> ORGANISM: Homo sapiens

<400> SEQUENCE: 73

Ser Leu Tyr Lys Phe Ser Pro Phe Pro Leu
1               5                   10

<210> SEQ ID NO 74
<211> LENGTH: 9
<212> TYPE: PRT
<213> ORGANISM: Homo sapiens

<400> SEQUENCE: 74

Lys Glu Leu Glu Gly Ile Leu Leu Leu
1               5

<210> SEQ ID NO 75
<211> LENGTH: 9
<212> TYPE: PRT
<213> ORGANISM: Homo sapiens

<400> SEQUENCE: 75

Val Val Pro Cys Glu Pro Pro Glu Val
1               5

<210> SEQ ID NO 76
<211> LENGTH: 25
<212> TYPE: PRT
<213> ORGANISM: Homo sapiens

<400> SEQUENCE: 76

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 77
<211> LENGTH: 10
<212> TYPE: PRT
<213> ORGANISM: Homo sapiens

<400> SEQUENCE: 77

Leu Leu Leu Asp Asp Leu Leu Val Ser Ile
1               5                   10

<210> SEQ ID NO 78
<211> LENGTH: 16
<212> TYPE: PRT
<213> ORGANISM: Homo sapiens
```

<400> SEQUENCE: 78

Pro Tyr Tyr Phe Ala Ala Glu Leu Pro Pro Arg Asn Leu Pro Glu Pro
1               5                   10                  15

<210> SEQ ID NO 79
<211> LENGTH: 9
<212> TYPE: PRT
<213> ORGANISM: Homo sapiens

<400> SEQUENCE: 79

Val Val Val Gly Ala Val Gly Val Gly
1               5

<210> SEQ ID NO 80
<211> LENGTH: 10
<212> TYPE: PRT
<213> ORGANISM: Homo sapiens

<400> SEQUENCE: 80

Ile Leu Asp Thr Ala Gly Arg Glu Glu Tyr
1               5                   10

<210> SEQ ID NO 81
<211> LENGTH: 9
<212> TYPE: PRT
<213> ORGANISM: Homo sapiens

<400> SEQUENCE: 81

Arg Pro His Val Pro Glu Ser Ala Phe
1               5

<210> SEQ ID NO 82
<211> LENGTH: 9
<212> TYPE: PRT
<213> ORGANISM: Homo sapiens

<400> SEQUENCE: 82

Lys Ile Phe Ser Glu Val Thr Leu Lys
1               5

<210> SEQ ID NO 83
<211> LENGTH: 9
<212> TYPE: PRT
<213> ORGANISM: Homo sapiens

<400> SEQUENCE: 83

Ser His Glu Thr Val Ile Ile Glu Leu
1               5

<210> SEQ ID NO 84
<211> LENGTH: 10
<212> TYPE: PRT
<213> ORGANISM: Homo sapiens

<400> SEQUENCE: 84

Gln Arg Pro Tyr Gly Tyr Asp Gln Ile Met
1               5                   10

<210> SEQ ID NO 85
<211> LENGTH: 9
<212> TYPE: PRT
<213> ORGANISM: Homo sapiens

<400> SEQUENCE: 85

Arg Leu Ser Ser Cys Val Pro Val Ala
1               5

<210> SEQ ID NO 86
<211> LENGTH: 15
<212> TYPE: PRT
<213> ORGANISM: Homo sapiens

<400> SEQUENCE: 86

Gly Glu Leu Ile Gly Ile Leu Asn Ala Ala Lys Val Pro Ala Asp
1               5                   10                  15

<210> SEQ ID NO 87
<211> LENGTH: 9
<212> TYPE: PRT
<213> ORGANISM: Homo sapiens

<400> SEQUENCE: 87

Ala Ala Arg Ala Val Phe Leu Ala Leu
1               5

<210> SEQ ID NO 88
<211> LENGTH: 9
<212> TYPE: PRT
<213> ORGANISM: Homo sapiens

<400> SEQUENCE: 88

Phe Leu Asp Arg Phe Leu Ser Cys Met
1               5

<210> SEQ ID NO 89
<211> LENGTH: 11
<212> TYPE: PRT
<213> ORGANISM: Homo sapiens

<400> SEQUENCE: 89

Ser Leu Ile Ala Ala Ala Ala Phe Cys Leu Ala
1               5                   10

<210> SEQ ID NO 90
<211> LENGTH: 8
<212> TYPE: PRT
<213> ORGANISM: Homo sapiens

<400> SEQUENCE: 90

Tyr Arg Pro Arg Pro Arg Arg Tyr
1               5

<210> SEQ ID NO 91
<211> LENGTH: 9
<212> TYPE: PRT
<213> ORGANISM: Homo sapiens

<400> SEQUENCE: 91

Tyr Tyr Trp Pro Arg Pro Arg Arg Tyr
1               5

<210> SEQ ID NO 92
<211> LENGTH: 10
<212> TYPE: PRT
<213> ORGANISM: Homo sapiens
<220> FEATURE:
<221> NAME/KEY: misc_feature
<222> LOCATION: (10)..(10)
<223> OTHER INFORMATION: May or may not be present

```
<400> SEQUENCE: 92

Val Leu Pro Asp Val Phe Ile Arg Cys Val
1               5                   10

<210> SEQ ID NO 93
<211> LENGTH: 9
<212> TYPE: PRT
<213> ORGANISM: Homo sapiens

<400> SEQUENCE: 93

Met Leu Ala Val Ile Ser Cys Ala Val
1               5

<210> SEQ ID NO 94
<211> LENGTH: 9
<212> TYPE: PRT
<213> ORGANISM: Homo sapiens

<400> SEQUENCE: 94

Arg Gln Lys Arg Ile Leu Val Asn Leu
1               5

<210> SEQ ID NO 95
<211> LENGTH: 9
<212> TYPE: PRT
<213> ORGANISM: Homo sapiens

<400> SEQUENCE: 95

Asn Tyr Asn Asn Phe Tyr Arg Phe Leu
1               5

<210> SEQ ID NO 96
<211> LENGTH: 10
<212> TYPE: PRT
<213> ORGANISM: Homo sapiens

<400> SEQUENCE: 96

Glu Tyr Ser Lys Glu Cys Leu Lys Glu Phe
1               5                   10

<210> SEQ ID NO 97
<211> LENGTH: 9
<212> TYPE: PRT
<213> ORGANISM: Homo sapiens

<400> SEQUENCE: 97

Glu Tyr Leu Ser Leu Ser Asp Lys Ile
1               5

<210> SEQ ID NO 98
<211> LENGTH: 11
<212> TYPE: PRT
<213> ORGANISM: Homo sapiens

<400> SEQUENCE: 98

Met Leu Met Ala Gln Glu Ala Leu Ala Phe Leu
1               5                   10

<210> SEQ ID NO 99
<211> LENGTH: 9
<212> TYPE: PRT
<213> ORGANISM: Homo sapiens

<400> SEQUENCE: 99
```

```
Ser Leu Leu Met Trp Ile Thr Gln Cys
1               5

<210> SEQ ID NO 100
<211> LENGTH: 10
<212> TYPE: PRT
<213> ORGANISM: Homo sapiens

<400> SEQUENCE: 100

Leu Ala Ala Gln Glu Arg Arg Val Pro Arg
1               5                   10

<210> SEQ ID NO 101
<211> LENGTH: 9
<212> TYPE: PRT
<213> ORGANISM: Homo sapiens

<400> SEQUENCE: 101

Glu Leu Val Arg Arg Ile Leu Ser Arg
1               5

<210> SEQ ID NO 102
<211> LENGTH: 9
<212> TYPE: PRT
<213> ORGANISM: Homo sapiens

<400> SEQUENCE: 102

Ala Pro Arg Gly Val Arg Met Ala Val
1               5

<210> SEQ ID NO 103
<211> LENGTH: 14
<212> TYPE: PRT
<213> ORGANISM: Homo sapiens

<400> SEQUENCE: 103

Ser Leu Leu Met Trp Ile Thr Gln Cys Phe Leu Pro Val Phe
1               5                   10

<210> SEQ ID NO 104
<211> LENGTH: 20
<212> TYPE: PRT
<213> ORGANISM: Homo sapiens

<400> SEQUENCE: 104

Gln Gly Ala Met Leu Ala Ala Gln Glu Arg Arg Val Pro Arg Ala Ala
1               5                   10                  15

Glu Val Pro Arg
            20

<210> SEQ ID NO 105
<211> LENGTH: 18
<212> TYPE: PRT
<213> ORGANISM: Homo sapiens

<400> SEQUENCE: 105

Ala Ala Asp His Arg Gln Leu Gln Leu Ser Ile Ser Ser Cys Leu Gln
1               5                   10                  15

Gln Leu

<210> SEQ ID NO 106
<211> LENGTH: 22
<212> TYPE: PRT
<213> ORGANISM: Homo sapiens
```

```
<400> SEQUENCE: 106

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 107
<211> LENGTH: 22
<212> TYPE: PRT
<213> ORGANISM: Homo sapiens

<400> SEQUENCE: 107

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 108
<211> LENGTH: 13
<212> TYPE: PRT
<213> ORGANISM: Homo sapiens

<400> SEQUENCE: 108

Ile Leu Ser Arg Asp Ala Ala Pro Leu Pro Arg Pro Gly
1               5                   10

<210> SEQ ID NO 109
<211> LENGTH: 14
<212> TYPE: PRT
<213> ORGANISM: Homo sapiens

<400> SEQUENCE: 109

Ala Gly Ala Thr Gly Gly Arg Gly Pro Arg Gly Ala Gly Ala
1               5                   10

<210> SEQ ID NO 110
<211> LENGTH: 9
<212> TYPE: PRT
<213> ORGANISM: Homo sapiens

<400> SEQUENCE: 110

Glu Ala Asp Pro Thr Gly His Ser Tyr
1               5

<210> SEQ ID NO 111
<211> LENGTH: 9
<212> TYPE: PRT
<213> ORGANISM: Homo sapiens

<400> SEQUENCE: 111

Lys Val Leu Glu Tyr Val Ile Lys Val
1               5

<210> SEQ ID NO 112
<211> LENGTH: 9
<212> TYPE: PRT
<213> ORGANISM: Homo sapiens

<400> SEQUENCE: 112

Ser Leu Phe Arg Ala Val Ile Thr Lys
1               5
```

```
<210> SEQ ID NO 113
<211> LENGTH: 10
<212> TYPE: PRT
<213> ORGANISM: Homo sapiens

<400> SEQUENCE: 113

Glu Val Tyr Asp Gly Arg Glu His Ser Ala
1               5                   10

<210> SEQ ID NO 114
<211> LENGTH: 9
<212> TYPE: PRT
<213> ORGANISM: Homo sapiens

<400> SEQUENCE: 114

Arg Val Arg Phe Phe Phe Pro Ser Leu
1               5

<210> SEQ ID NO 115
<211> LENGTH: 9
<212> TYPE: PRT
<213> ORGANISM: Homo sapiens

<400> SEQUENCE: 115

Glu Ala Asp Pro Thr Gly His Ser Tyr
1               5

<210> SEQ ID NO 116
<211> LENGTH: 10
<212> TYPE: PRT
<213> ORGANISM: Homo sapiens

<400> SEQUENCE: 116

Arg Glu Pro Val Thr Lys Ala Glu Met Leu
1               5                   10

<210> SEQ ID NO 117
<211> LENGTH: 10
<212> TYPE: PRT
<213> ORGANISM: Homo sapiens

<400> SEQUENCE: 117

Lys Glu Ala Asp Pro Thr Gly His Ser Tyr
1               5                   10

<210> SEQ ID NO 118
<211> LENGTH: 9
<212> TYPE: PRT
<213> ORGANISM: Homo sapiens

<400> SEQUENCE: 118

Asp Pro Ala Arg Tyr Glu Phe Leu Trp
1               5

<210> SEQ ID NO 119
<211> LENGTH: 11
<212> TYPE: PRT
<213> ORGANISM: Homo sapiens

<400> SEQUENCE: 119

Ile Thr Lys Lys Val Ala Asp Leu Val Gly Phe
1               5                   10

<210> SEQ ID NO 120
<211> LENGTH: 9
```

```
<212> TYPE: PRT
<213> ORGANISM: Homo sapiens

<400> SEQUENCE: 120

Ser Ala Phe Pro Thr Thr Ile Asn Phe
1               5

<210> SEQ ID NO 121
<211> LENGTH: 9
<212> TYPE: PRT
<213> ORGANISM: Homo sapiens

<400> SEQUENCE: 121

Ser Ala Tyr Gly Glu Pro Arg Lys Leu
1               5

<210> SEQ ID NO 122
<211> LENGTH: 9
<212> TYPE: PRT
<213> ORGANISM: Homo sapiens

<400> SEQUENCE: 122

Arg Val Arg Phe Phe Phe Pro Ser Leu
1               5

<210> SEQ ID NO 123
<211> LENGTH: 9
<212> TYPE: PRT
<213> ORGANISM: Homo sapiens

<400> SEQUENCE: 123

Ser Ala Tyr Gly Glu Pro Arg Lys Leu
1               5

<210> SEQ ID NO 124
<211> LENGTH: 15
<212> TYPE: PRT
<213> ORGANISM: Homo sapiens

<400> SEQUENCE: 124

Thr Ser Cys Ile Leu Glu Ser Leu Phe Arg Ala Val Ile Thr Lys
1               5                   10                  15

<210> SEQ ID NO 125
<211> LENGTH: 15
<212> TYPE: PRT
<213> ORGANISM: Homo sapiens

<400> SEQUENCE: 125

Pro Arg Ala Leu Ala Glu Thr Ser Tyr Val Lys Val Leu Glu Tyr
1               5                   10                  15

<210> SEQ ID NO 126
<211> LENGTH: 16
<212> TYPE: PRT
<213> ORGANISM: Homo sapiens

<400> SEQUENCE: 126

Phe Leu Leu Leu Lys Tyr Arg Ala Arg Glu Pro Val Thr Lys Ala Glu
1               5                   10                  15

<210> SEQ ID NO 127
<211> LENGTH: 12
<212> TYPE: PRT
<213> ORGANISM: Homo sapiens
```

<400> SEQUENCE: 127

Glu Tyr Val Ile Lys Val Ser Ala Arg Val Arg Phe
1               5                   10

<210> SEQ ID NO 128
<211> LENGTH: 10
<212> TYPE: PRT
<213> ORGANISM: Homo sapiens

<400> SEQUENCE: 128

Tyr Leu Gln Leu Val Phe Gly Ile Glu Val
1               5                   10

<210> SEQ ID NO 129
<211> LENGTH: 9
<212> TYPE: PRT
<213> ORGANISM: Homo sapiens

<400> SEQUENCE: 129

Glu Tyr Leu Gln Leu Val Phe Gly Ile
1               5

<210> SEQ ID NO 130
<211> LENGTH: 10
<212> TYPE: PRT
<213> ORGANISM: Homo sapiens

<400> SEQUENCE: 130

Arg Glu Pro Val Thr Lys Ala Glu Met Leu
1               5                   10

<210> SEQ ID NO 131
<211> LENGTH: 9
<212> TYPE: PRT
<213> ORGANISM: Homo sapiens

<400> SEQUENCE: 131

Glu Gly Asp Cys Ala Pro Glu Glu Lys
1               5

<210> SEQ ID NO 132
<211> LENGTH: 14
<212> TYPE: PRT
<213> ORGANISM: Homo sapiens

<400> SEQUENCE: 132

Leu Leu Lys Tyr Arg Ala Arg Glu Pro Val Thr Lys Ala Glu
1               5                   10

<210> SEQ ID NO 133
<211> LENGTH: 9
<212> TYPE: PRT
<213> ORGANISM: Homo sapiens

<400> SEQUENCE: 133

Glu Val Asp Pro Ile Gly His Leu Tyr
1               5

<210> SEQ ID NO 134
<211> LENGTH: 9
<212> TYPE: PRT
<213> ORGANISM: Homo sapiens

<400> SEQUENCE: 134

```
Phe Leu Trp Gly Pro Arg Ala Leu Val
1               5
```

<210> SEQ ID NO 135
<211> LENGTH: 9
<212> TYPE: PRT
<213> ORGANISM: Homo sapiens

<400> SEQUENCE: 135

```
Lys Val Ala Glu Leu Val His Phe Leu
1               5
```

<210> SEQ ID NO 136
<211> LENGTH: 9
<212> TYPE: PRT
<213> ORGANISM: Homo sapiens

<400> SEQUENCE: 136

```
Thr Phe Pro Asp Leu Glu Ser Glu Phe
1               5
```

<210> SEQ ID NO 137
<211> LENGTH: 9
<212> TYPE: PRT
<213> ORGANISM: Homo sapiens

<400> SEQUENCE: 137

```
Val Ala Glu Leu Val His Phe Leu Leu
1               5
```

<210> SEQ ID NO 138
<211> LENGTH: 10
<212> TYPE: PRT
<213> ORGANISM: Homo sapiens

<400> SEQUENCE: 138

```
Met Glu Val Asp Pro Ile Gly His Leu Tyr
1               5                   10
```

<210> SEQ ID NO 139
<211> LENGTH: 9
<212> TYPE: PRT
<213> ORGANISM: Homo sapiens

<400> SEQUENCE: 139

```
Glu Val Asp Pro Ile Gly His Leu Tyr
1               5
```

<210> SEQ ID NO 140
<211> LENGTH: 10
<212> TYPE: PRT
<213> ORGANISM: Homo sapiens

<400> SEQUENCE: 140

```
Arg Glu Pro Val Thr Lys Ala Glu Met Leu
1               5                   10
```

<210> SEQ ID NO 141
<211> LENGTH: 9
<212> TYPE: PRT
<213> ORGANISM: Homo sapiens

<400> SEQUENCE: 141

```
Ala Glu Leu Val His Phe Leu Leu Leu
```

```
1               5

<210> SEQ ID NO 142
<211> LENGTH: 10
<212> TYPE: PRT
<213> ORGANISM: Homo sapiens

<400> SEQUENCE: 142

Met Glu Val Asp Pro Ile Gly His Leu Tyr
1               5                   10

<210> SEQ ID NO 143
<211> LENGTH: 9
<212> TYPE: PRT
<213> ORGANISM: Homo sapiens

<400> SEQUENCE: 143

Trp Gln Tyr Phe Phe Pro Val Ile Phe
1               5

<210> SEQ ID NO 144
<211> LENGTH: 9
<212> TYPE: PRT
<213> ORGANISM: Homo sapiens

<400> SEQUENCE: 144

Glu Gly Asp Cys Ala Pro Glu Glu Lys
1               5

<210> SEQ ID NO 145
<211> LENGTH: 16
<212> TYPE: PRT
<213> ORGANISM: Homo sapiens

<400> SEQUENCE: 145

Lys Lys Leu Leu Thr Gln His Phe Val Gln Glu Asn Tyr Leu Glu Tyr
1               5                   10                  15

<210> SEQ ID NO 146
<211> LENGTH: 15
<212> TYPE: PRT
<213> ORGANISM: Homo sapiens

<400> SEQUENCE: 146

Arg Lys Val Ala Glu Leu Val His Phe Leu Leu Leu Lys Tyr Arg
1               5                   10                  15

<210> SEQ ID NO 147
<211> LENGTH: 16
<212> TYPE: PRT
<213> ORGANISM: Homo sapiens

<400> SEQUENCE: 147

Lys Lys Leu Leu Thr Gln His Phe Val Gln Glu Asn Tyr Leu Glu Tyr
1               5                   10                  15

<210> SEQ ID NO 148
<211> LENGTH: 16
<212> TYPE: PRT
<213> ORGANISM: Homo sapiens

<400> SEQUENCE: 148

Ala Cys Tyr Glu Phe Leu Trp Gly Pro Arg Ala Leu Val Glu Thr Ser
1               5                   10                  15
```

<210> SEQ ID NO 149
<211> LENGTH: 15
<212> TYPE: PRT
<213> ORGANISM: Homo sapiens

<400> SEQUENCE: 149

Arg Lys Val Ala Glu Leu Val His Phe Leu Leu Leu Lys Tyr Arg
1               5                   10                  15

<210> SEQ ID NO 150
<211> LENGTH: 12
<212> TYPE: PRT
<213> ORGANISM: Homo sapiens

<400> SEQUENCE: 150

Val Ile Phe Ser Lys Ala Ser Ser Ser Leu Gln Leu
1               5                   10

<210> SEQ ID NO 151
<211> LENGTH: 12
<212> TYPE: PRT
<213> ORGANISM: Homo sapiens

<400> SEQUENCE: 151

Val Ile Phe Ser Lys Ala Ser Ser Ser Leu Gln Leu
1               5                   10

<210> SEQ ID NO 152
<211> LENGTH: 15
<212> TYPE: PRT
<213> ORGANISM: Homo sapiens

<400> SEQUENCE: 152

Val Phe Gly Ile Glu Leu Met Glu Val Asp Pro Ile Gly His Leu
1               5                   10                  15

<210> SEQ ID NO 153
<211> LENGTH: 15
<212> TYPE: PRT
<213> ORGANISM: Homo sapiens

<400> SEQUENCE: 153

Gly Asp Asn Gln Ile Met Pro Lys Ala Gly Leu Leu Ile Ile Val
1               5                   10                  15

<210> SEQ ID NO 154
<211> LENGTH: 15
<212> TYPE: PRT
<213> ORGANISM: Homo sapiens

<400> SEQUENCE: 154

Thr Ser Tyr Val Lys Val Leu His His Met Val Lys Ile Ser Gly
1               5                   10                  15

<210> SEQ ID NO 155
<211> LENGTH: 16
<212> TYPE: PRT
<213> ORGANISM: Homo sapiens

<400> SEQUENCE: 155

Arg Lys Val Ala Glu Leu Val His Phe Leu Leu Leu Lys Tyr Arg Ala
1               5                   10                  15

<210> SEQ ID NO 156

```
<211> LENGTH: 16
<212> TYPE: PRT
<213> ORGANISM: Homo sapiens

<400> SEQUENCE: 156

Phe Leu Leu Leu Lys Tyr Arg Ala Arg Glu Pro Val Thr Lys Ala Glu
1               5                   10                  15

<210> SEQ ID NO 157
<211> LENGTH: 9
<212> TYPE: PRT
<213> ORGANISM: Homo sapiens

<400> SEQUENCE: 157

Glu Val Asp Pro Ala Ser Asn Thr Tyr
1               5

<210> SEQ ID NO 158
<211> LENGTH: 10
<212> TYPE: PRT
<213> ORGANISM: Homo sapiens

<400> SEQUENCE: 158

Gly Val Tyr Asp Gly Arg Glu His Thr Val
1               5                   10

<210> SEQ ID NO 159
<211> LENGTH: 9
<212> TYPE: PRT
<213> ORGANISM: Homo sapiens

<400> SEQUENCE: 159

Asn Tyr Lys Arg Cys Phe Pro Val Ile
1               5

<210> SEQ ID NO 160
<211> LENGTH: 8
<212> TYPE: PRT
<213> ORGANISM: Homo sapiens

<400> SEQUENCE: 160

Ser Glu Ser Leu Lys Met Ile Phe
1               5

<210> SEQ ID NO 161
<211> LENGTH: 9
<212> TYPE: PRT
<213> ORGANISM: Homo sapiens

<400> SEQUENCE: 161

Met Val Lys Ile Ser Gly Gly Pro Arg
1               5

<210> SEQ ID NO 162
<211> LENGTH: 9
<212> TYPE: PRT
<213> ORGANISM: Homo sapiens

<400> SEQUENCE: 162

Glu Val Asp Pro Ile Gly His Val Tyr
1               5

<210> SEQ ID NO 163
<211> LENGTH: 10
<212> TYPE: PRT
```

<213> ORGANISM: Homo sapiens

<400> SEQUENCE: 163

Arg Glu Pro Val Thr Lys Ala Glu Met Leu
1               5                   10

<210> SEQ ID NO 164
<211> LENGTH: 9
<212> TYPE: PRT
<213> ORGANISM: Homo sapiens

<400> SEQUENCE: 164

Glu Gly Asp Cys Ala Pro Glu Glu Lys
1               5

<210> SEQ ID NO 165
<211> LENGTH: 9
<212> TYPE: PRT
<213> ORGANISM: Homo sapiens

<400> SEQUENCE: 165

Ile Ser Gly Gly Pro Arg Ile Ser Tyr
1               5

<210> SEQ ID NO 166
<211> LENGTH: 14
<212> TYPE: PRT
<213> ORGANISM: Homo sapiens

<400> SEQUENCE: 166

Leu Leu Lys Tyr Arg Ala Arg Glu Pro Val Thr Lys Ala Glu
1               5                   10

<210> SEQ ID NO 167
<211> LENGTH: 9
<212> TYPE: PRT
<213> ORGANISM: Homo sapiens

<400> SEQUENCE: 167

Ala Leu Ser Val Met Gly Val Tyr Val
1               5

<210> SEQ ID NO 168
<211> LENGTH: 9
<212> TYPE: PRT
<213> ORGANISM: Homo sapiens

<400> SEQUENCE: 168

Gly Leu Tyr Asp Gly Met Glu His Leu
1               5

<210> SEQ ID NO 169
<211> LENGTH: 9
<212> TYPE: PRT
<213> ORGANISM: Homo sapiens

<400> SEQUENCE: 169

Asp Pro Ala Arg Tyr Glu Phe Leu Trp
1               5

<210> SEQ ID NO 170
<211> LENGTH: 9
<212> TYPE: PRT
<213> ORGANISM: Homo sapiens

```
<400> SEQUENCE: 170

Phe Leu Trp Gly Pro Arg Ala Leu Val
1               5

<210> SEQ ID NO 171
<211> LENGTH: 9
<212> TYPE: PRT
<213> ORGANISM: Homo sapiens

<400> SEQUENCE: 171

Val Arg Ile Gly His Leu Tyr Ile Leu
1               5

<210> SEQ ID NO 172
<211> LENGTH: 9
<212> TYPE: PRT
<213> ORGANISM: Homo sapiens

<400> SEQUENCE: 172

Glu Gly Asp Cys Ala Pro Glu Glu Lys
1               5

<210> SEQ ID NO 173
<211> LENGTH: 15
<212> TYPE: PRT
<213> ORGANISM: Homo sapiens

<400> SEQUENCE: 173

Arg Glu Pro Phe Thr Lys Ala Glu Met Leu Gly Ser Val Ile Arg
1               5                   10                  15

<210> SEQ ID NO 174
<211> LENGTH: 14
<212> TYPE: PRT
<213> ORGANISM: Homo sapiens

<400> SEQUENCE: 174

Ala Glu Leu Val His Phe Leu Leu Leu Lys Tyr Arg Ala Arg
1               5                   10

<210> SEQ ID NO 175
<211> LENGTH: 10
<212> TYPE: PRT
<213> ORGANISM: Homo sapiens

<400> SEQUENCE: 175

Ile Leu Phe Gly Ile Ser Leu Arg Glu Val
1               5                   10

<210> SEQ ID NO 176
<211> LENGTH: 9
<212> TYPE: PRT
<213> ORGANISM: Homo sapiens

<400> SEQUENCE: 176

Lys Val Val Glu Phe Leu Ala Met Leu
1               5

<210> SEQ ID NO 177
<211> LENGTH: 13
<212> TYPE: PRT
<213> ORGANISM: Homo sapiens

<400> SEQUENCE: 177
```

```
Ser Ser Ala Leu Leu Ser Ile Phe Gln Ser Ser Pro Glu
1               5                   10
```

<210> SEQ ID NO 178
<211> LENGTH: 9
<212> TYPE: PRT
<213> ORGANISM: Homo sapiens

<400> SEQUENCE: 178

```
Ser Phe Ser Tyr Thr Leu Leu Ser Leu
1               5
```

<210> SEQ ID NO 179
<211> LENGTH: 9
<212> TYPE: PRT
<213> ORGANISM: Homo sapiens

<400> SEQUENCE: 179

```
Val Ser Ser Phe Phe Ser Tyr Thr Leu
1               5
```

<210> SEQ ID NO 180
<211> LENGTH: 10
<212> TYPE: PRT
<213> ORGANISM: Homo sapiens

<400> SEQUENCE: 180

```
Leu Leu Phe Gly Leu Ala Leu Ile Glu Val
1               5                   10
```

<210> SEQ ID NO 181
<211> LENGTH: 9
<212> TYPE: PRT
<213> ORGANISM: Homo sapiens

<400> SEQUENCE: 181

```
Ala Leu Lys Asp Val Glu Glu Arg Val
1               5
```

<210> SEQ ID NO 182
<211> LENGTH: 9
<212> TYPE: PRT
<213> ORGANISM: Homo sapiens

<400> SEQUENCE: 182

```
Ser Glu Ser Ile Lys Lys Lys Val Leu
1               5
```

<210> SEQ ID NO 183
<211> LENGTH: 9
<212> TYPE: PRT
<213> ORGANISM: Homo sapiens

<400> SEQUENCE: 183

```
Ala Ser Ser Thr Leu Tyr Leu Val Phe
1               5
```

<210> SEQ ID NO 184
<211> LENGTH: 15
<212> TYPE: PRT
<213> ORGANISM: Homo sapiens

<400> SEQUENCE: 184

```
Ser Ser Thr Leu Tyr Leu Val Phe Ser Pro Ser Phe Ser Thr
1               5                   10                  15
```

<210> SEQ ID NO 185
<211> LENGTH: 20
<212> TYPE: PRT
<213> ORGANISM: Homo sapiens

<400> SEQUENCE: 185

Pro Asp Thr Arg Pro Ala Pro Gly Ser Thr Ala Pro Pro Ala His Gly
1               5                   10                  15

Val Thr Ser Ala
            20

<210> SEQ ID NO 186
<211> LENGTH: 9
<212> TYPE: PRT
<213> ORGANISM: Homo sapiens

<400> SEQUENCE: 186

Gln Gly Gln His Phe Leu Gln Lys Val
1               5

<210> SEQ ID NO 187
<211> LENGTH: 9
<212> TYPE: PRT
<213> ORGANISM: Homo sapiens

<400> SEQUENCE: 187

Ser Leu Leu Met Trp Ile Thr Gln Cys
1               5

<210> SEQ ID NO 188
<211> LENGTH: 11
<212> TYPE: PRT
<213> ORGANISM: Homo sapiens

<400> SEQUENCE: 188

Met Leu Met Ala Gln Glu Ala Leu Ala Phe Leu
1               5                   10

<210> SEQ ID NO 189
<211> LENGTH: 10
<212> TYPE: PRT
<213> ORGANISM: Homo sapiens

<400> SEQUENCE: 189

Leu Ala Ala Gln Glu Arg Arg Val Pro Arg
1               5                   10

<210> SEQ ID NO 190
<211> LENGTH: 10
<212> TYPE: PRT
<213> ORGANISM: Homo sapiens

<400> SEQUENCE: 190

Leu Ala Ala Gln Glu Arg Arg Val Pro Arg
1               5                   10

<210> SEQ ID NO 191
<211> LENGTH: 13
<212> TYPE: PRT
<213> ORGANISM: Homo sapiens

<400> SEQUENCE: 191

Ala Pro Arg Gly Pro His Gly Gly Ala Ala Ser Gly Leu

```
1               5              10
```

<210> SEQ ID NO 192
<211> LENGTH: 9
<212> TYPE: PRT
<213> ORGANISM: Homo sapiens

<400> SEQUENCE: 192

```
Met Pro Phe Ala Thr Pro Met Glu Ala
1               5
```

<210> SEQ ID NO 193
<211> LENGTH: 12
<212> TYPE: PRT
<213> ORGANISM: Homo sapiens

<400> SEQUENCE: 193

```
Lys Glu Phe Thr Val Ser Gly Asn Ile Leu Thr Ile
1               5                  10
```

<210> SEQ ID NO 194
<211> LENGTH: 9
<212> TYPE: PRT
<213> ORGANISM: Homo sapiens

<400> SEQUENCE: 194

```
Met Pro Phe Ala Thr Pro Met Glu Ala
1               5
```

<210> SEQ ID NO 195
<211> LENGTH: 9
<212> TYPE: PRT
<213> ORGANISM: Homo sapiens

<400> SEQUENCE: 195

```
Leu Ala Met Pro Phe Ala Thr Pro Met
1               5
```

<210> SEQ ID NO 196
<211> LENGTH: 9
<212> TYPE: PRT
<213> ORGANISM: Homo sapiens

<400> SEQUENCE: 196

```
Ala Arg Gly Pro Glu Ser Arg Leu Leu
1               5
```

<210> SEQ ID NO 197
<211> LENGTH: 14
<212> TYPE: PRT
<213> ORGANISM: Homo sapiens

<400> SEQUENCE: 197

```
Ser Leu Leu Met Trp Ile Thr Gln Cys Phe Leu Pro Val Phe
1               5                  10
```

<210> SEQ ID NO 198
<211> LENGTH: 25
<212> TYPE: PRT
<213> ORGANISM: Homo sapiens

<400> SEQUENCE: 198

```
Leu Leu Glu Phe Tyr Leu Ala Met Pro Phe Ala Thr Pro Met Glu Ala
1               5                  10                  15
```

Glu Leu Ala Arg Arg Ser Leu Ala Gln
            20                  25

<210> SEQ ID NO 199
<211> LENGTH: 25
<212> TYPE: PRT
<213> ORGANISM: Homo sapiens

<400> SEQUENCE: 199

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 200
<211> LENGTH: 12
<212> TYPE: PRT
<213> ORGANISM: Homo sapiens

<400> SEQUENCE: 200

Glu Phe Tyr Leu Ala Met Pro Phe Ala Thr Pro Met
1               5                   10

<210> SEQ ID NO 201
<211> LENGTH: 25
<212> TYPE: PRT
<213> ORGANISM: Homo sapiens

<400> SEQUENCE: 201

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 202
<211> LENGTH: 12
<212> TYPE: PRT
<213> ORGANISM: Homo sapiens

<400> SEQUENCE: 202

Arg Leu Leu Glu Phe Tyr Leu Ala Met Pro Phe Ala
1               5                   10

<210> SEQ ID NO 203
<211> LENGTH: 20
<212> TYPE: PRT
<213> ORGANISM: Homo sapiens

<400> SEQUENCE: 203

Gln Gly Ala Met Leu Ala Ala Gln Glu Arg Arg Val Pro Arg Ala Ala
1               5                   10                  15

Glu Val Pro Arg
            20

<210> SEQ ID NO 204
<211> LENGTH: 20
<212> TYPE: PRT
<213> ORGANISM: Homo sapiens

<400> SEQUENCE: 204

Gln Gly Ala Met Leu Ala Ala Gln Glu Arg Arg Val Pro Arg Ala Ala
1               5                   10                  15

Glu Val Pro Arg

<210> SEQ ID NO 205
<211> LENGTH: 20
<212> TYPE: PRT
<213> ORGANISM: Homo sapiens

<400> SEQUENCE: 205

Pro Gly Val Leu Leu Lys Glu Phe Thr Val Ser Gly Asn Ile Leu Thr
1               5                   10                  15

Ile Arg Leu Thr
            20

<210> SEQ ID NO 206
<211> LENGTH: 20
<212> TYPE: PRT
<213> ORGANISM: Homo sapiens

<400> SEQUENCE: 206

Pro Gly Val Leu Leu Lys Glu Phe Thr Val Ser Gly Asn Ile Leu Thr
1               5                   10                  15

Ile Arg Leu Thr
            20

<210> SEQ ID NO 207
<211> LENGTH: 18
<212> TYPE: PRT
<213> ORGANISM: Homo sapiens

<400> SEQUENCE: 207

Ala Ala Asp His Arg Gln Leu Gln Leu Ser Ile Ser Ser Cys Leu Gln
1               5                   10                  15

Gln Leu

<210> SEQ ID NO 208
<211> LENGTH: 25
<212> TYPE: PRT
<213> ORGANISM: Homo sapiens

<400> SEQUENCE: 208

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 209
<211> LENGTH: 15
<212> TYPE: PRT
<213> ORGANISM: Homo sapiens

<400> SEQUENCE: 209

Leu Lys Glu Phe Thr Val Ser Gly Asn Ile Leu Thr Ile Arg Leu
1               5                   10                  15

<210> SEQ ID NO 210
<211> LENGTH: 25
<212> TYPE: PRT
<213> ORGANISM: Homo sapiens

<400> SEQUENCE: 210

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 211
<211> LENGTH: 25
<212> TYPE: PRT
<213> ORGANISM: Homo sapiens

<400> SEQUENCE: 211

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 212
<211> LENGTH: 11
<212> TYPE: PRT
<213> ORGANISM: Homo sapiens

<400> SEQUENCE: 212

Lys Glu Phe Thr Val Ser Gly Asn Ile Leu Thr
1               5                   10

<210> SEQ ID NO 213
<211> LENGTH: 14
<212> TYPE: PRT
<213> ORGANISM: Homo sapiens

<400> SEQUENCE: 213

Leu Leu Glu Phe Tyr Leu Ala Met Pro Phe Ala Thr Pro Met
1               5                   10

<210> SEQ ID NO 214
<211> LENGTH: 14
<212> TYPE: PRT
<213> ORGANISM: Homo sapiens

<400> SEQUENCE: 214

Ala Gly Ala Thr Gly Gly Arg Gly Pro Arg Gly Ala Gly Ala
1               5                   10

<210> SEQ ID NO 215
<211> LENGTH: 9
<212> TYPE: PRT
<213> ORGANISM: Homo sapiens

<400> SEQUENCE: 215

Leu Tyr Ala Thr Val Ile His Asp Ile
1               5

<210> SEQ ID NO 216
<211> LENGTH: 9
<212> TYPE: PRT
<213> ORGANISM: Homo sapiens

<400> SEQUENCE: 216

Ile Leu Asp Ser Ser Glu Glu Asp Lys
1               5

<210> SEQ ID NO 217
<211> LENGTH: 9
<212> TYPE: PRT
<213> ORGANISM: Homo sapiens

<400> SEQUENCE: 217

```
Lys Ala Ser Glu Lys Ile Phe Tyr Val
1               5
```

<210> SEQ ID NO 218
<211> LENGTH: 16
<212> TYPE: PRT
<213> ORGANISM: Homo sapiens

<400> SEQUENCE: 218

```
Glu Lys Ile Gln Lys Ala Phe Asp Asp Ile Ala Lys Tyr Phe Ser Lys
1               5                   10                  15
```

<210> SEQ ID NO 219
<211> LENGTH: 11
<212> TYPE: PRT
<213> ORGANISM: Homo sapiens

<400> SEQUENCE: 219

```
Phe Gly Arg Leu Gln Gly Ile Ser Pro Lys Ile
1               5                   10
```

<210> SEQ ID NO 220
<211> LENGTH: 18
<212> TYPE: PRT
<213> ORGANISM: Homo sapiens

<400> SEQUENCE: 220

```
Trp Glu Lys Met Lys Ala Ser Glu Lys Ile Phe Tyr Val Tyr Met Lys
1               5                   10                  15

Arg Lys
```

<210> SEQ ID NO 221
<211> LENGTH: 15
<212> TYPE: PRT
<213> ORGANISM: Homo sapiens

<400> SEQUENCE: 221

```
Lys Ile Phe Tyr Val Tyr Met Lys Arg Lys Tyr Glu Ala Met Thr
1               5                   10                  15
```

<210> SEQ ID NO 222
<211> LENGTH: 14
<212> TYPE: PRT
<213> ORGANISM: Homo sapiens

<400> SEQUENCE: 222

```
Lys Ile Phe Tyr Val Tyr Met Lys Arg Lys Tyr Glu Ala Met
1               5                   10
```

<210> SEQ ID NO 223
<211> LENGTH: 20
<212> TYPE: PRT
<213> ORGANISM: Homo sapiens

<400> SEQUENCE: 223

```
Ile Asn Lys Thr Ser Gly Pro Lys Arg Gly Lys His Ala Trp Thr His
1               5                   10                  15

Arg Leu Arg Glu
            20
```

<210> SEQ ID NO 224
<211> LENGTH: 20
<212> TYPE: PRT

```
<213> ORGANISM: Homo sapiens

<400> SEQUENCE: 224

Tyr Phe Ser Lys Lys Glu Trp Glu Lys Met Lys Ser Ser Glu Lys Ile
1               5                   10                  15

Val Tyr Val Tyr
            20

<210> SEQ ID NO 225
<211> LENGTH: 20
<212> TYPE: PRT
<213> ORGANISM: Homo sapiens

<400> SEQUENCE: 225

Met Lys Leu Asn Tyr Glu Val Met Thr Lys Leu Gly Phe Lys Val Thr
1               5                   10                  15

Leu Pro Pro Phe
            20

<210> SEQ ID NO 226
<211> LENGTH: 20
<212> TYPE: PRT
<213> ORGANISM: Homo sapiens

<400> SEQUENCE: 226

Lys His Ala Trp Thr His Arg Leu Arg Glu Arg Lys Gln Leu Val Val
1               5                   10                  15

Tyr Glu Glu Ile
            20

<210> SEQ ID NO 227
<211> LENGTH: 20
<212> TYPE: PRT
<213> ORGANISM: Homo sapiens

<400> SEQUENCE: 227

Leu Gly Phe Lys Val Thr Leu Pro Pro Phe Met Arg Ser Lys Arg Ala
1               5                   10                  15

Ala Asp Phe His
            20

<210> SEQ ID NO 228
<211> LENGTH: 20
<212> TYPE: PRT
<213> ORGANISM: Homo sapiens

<400> SEQUENCE: 228

Lys Ser Ser Glu Lys Ile Val Tyr Val Tyr Met Lys Leu Asn Tyr Glu
1               5                   10                  15

Val Met Thr Lys
            20

<210> SEQ ID NO 229
<211> LENGTH: 20
<212> TYPE: PRT
<213> ORGANISM: Homo sapiens

<400> SEQUENCE: 229

Lys His Ala Trp Thr His Arg Leu Arg Glu Arg Lys Gln Leu Val Val
1               5                   10                  15

Tyr Glu Glu Ile
            20
```

```
<210> SEQ ID NO 230
<211> LENGTH: 9
<212> TYPE: PRT
<213> ORGANISM: Homo sapiens

<400> SEQUENCE: 230

Ser Leu Gly Trp Leu Phe Leu Leu Leu
1               5

<210> SEQ ID NO 231
<211> LENGTH: 9
<212> TYPE: PRT
<213> ORGANISM: Homo sapiens

<400> SEQUENCE: 231

Leu Ser Arg Leu Ser Asn Arg Leu Leu
1               5

<210> SEQ ID NO 232
<211> LENGTH: 9
<212> TYPE: PRT
<213> ORGANISM: Homo sapiens

<400> SEQUENCE: 232

Leu Ser Arg Leu Ser Asn Arg Leu Leu
1               5

<210> SEQ ID NO 233
<211> LENGTH: 15
<212> TYPE: PRT
<213> ORGANISM: Homo sapiens

<400> SEQUENCE: 233

Cys Glu Phe His Ala Cys Trp Pro Ala Phe Thr Val Leu Gly Glu
1               5                   10                  15

<210> SEQ ID NO 234
<211> LENGTH: 15
<212> TYPE: PRT
<213> ORGANISM: Homo sapiens

<400> SEQUENCE: 234

Cys Glu Phe His Ala Cys Trp Pro Ala Phe Thr Val Leu Gly Glu
1               5                   10                  15

<210> SEQ ID NO 235
<211> LENGTH: 15
<212> TYPE: PRT
<213> ORGANISM: Homo sapiens

<400> SEQUENCE: 235

Cys Glu Phe His Ala Cys Trp Pro Ala Phe Thr Val Leu Gly Glu
1               5                   10                  15

<210> SEQ ID NO 236
<211> LENGTH: 10
<212> TYPE: PRT
<213> ORGANISM: Homo sapiens

<400> SEQUENCE: 236

Glu Val Ile Ser Cys Lys Leu Ile Lys Arg
1               5                   10
```

<210> SEQ ID NO 237
<211> LENGTH: 9
<212> TYPE: PRT
<213> ORGANISM: Homo sapiens

<400> SEQUENCE: 237

Arg Gln Lys Lys Ile Arg Ile Gln Leu
1               5

<210> SEQ ID NO 238
<211> LENGTH: 16
<212> TYPE: PRT
<213> ORGANISM: Homo sapiens

<400> SEQUENCE: 238

His Leu Gly Ser Arg Gln Lys Lys Ile Arg Ile Gln Leu Arg Ser Gln
1               5                   10                  15

<210> SEQ ID NO 239
<211> LENGTH: 17
<212> TYPE: PRT
<213> ORGANISM: Homo sapiens

<400> SEQUENCE: 239

Cys Ala Thr Trp Lys Val Ile Cys Lys Ser Cys Ile Ser Gln Thr Pro
1               5                   10                  15

Gly

<210> SEQ ID NO 240
<211> LENGTH: 9
<212> TYPE: PRT
<213> ORGANISM: Homo sapiens

<400> SEQUENCE: 240

Tyr Leu Ser Gly Ala Asn Leu Asn Leu
1               5

<210> SEQ ID NO 241
<211> LENGTH: 9
<212> TYPE: PRT
<213> ORGANISM: Homo sapiens

<400> SEQUENCE: 241

Ile Met Ile Gly Val Leu Val Gly Val
1               5

<210> SEQ ID NO 242
<211> LENGTH: 9
<212> TYPE: PRT
<213> ORGANISM: Homo sapiens

<400> SEQUENCE: 242

Gly Val Leu Val Gly Val Ala Leu Ile
1               5

<210> SEQ ID NO 243
<211> LENGTH: 9
<212> TYPE: PRT
<213> ORGANISM: Homo sapiens

<400> SEQUENCE: 243

His Leu Phe Gly Tyr Ser Trp Tyr Lys
1               5

```
<210> SEQ ID NO 244
<211> LENGTH: 10
<212> TYPE: PRT
<213> ORGANISM: Homo sapiens

<400> SEQUENCE: 244

Gln Tyr Ser Trp Phe Val Asn Gly Thr Phe
1               5                   10

<210> SEQ ID NO 245
<211> LENGTH: 9
<212> TYPE: PRT
<213> ORGANISM: Homo sapiens

<400> SEQUENCE: 245

Thr Tyr Ala Cys Phe Val Ser Asn Leu
1               5

<210> SEQ ID NO 246
<211> LENGTH: 15
<212> TYPE: PRT
<213> ORGANISM: Homo sapiens

<400> SEQUENCE: 246

Ala Tyr Val Cys Gly Ile Gln Asn Ser Val Ser Ala Asn Arg Ser
1               5                   10                  15

<210> SEQ ID NO 247
<211> LENGTH: 25
<212> TYPE: PRT
<213> ORGANISM: Homo sapiens

<400> SEQUENCE: 247

Asp Thr Gly Phe Tyr Thr Leu His Val Ile Lys Ser Asp Leu Val Asn
1               5                   10                  15

Glu Glu Ala Thr Gly Gln Phe Arg Val
            20                  25

<210> SEQ ID NO 248
<211> LENGTH: 15
<212> TYPE: PRT
<213> ORGANISM: Homo sapiens

<400> SEQUENCE: 248

Tyr Ser Trp Arg Ile Asn Gly Ile Pro Gln Gln His Thr Gln Val
1               5                   10                  15

<210> SEQ ID NO 249
<211> LENGTH: 13
<212> TYPE: PRT
<213> ORGANISM: Homo sapiens

<400> SEQUENCE: 249

Thr Tyr Tyr Arg Pro Gly Val Asn Leu Ser Leu Ser Cys
1               5                   10

<210> SEQ ID NO 250
<211> LENGTH: 13
<212> TYPE: PRT
<213> ORGANISM: Homo sapiens

<400> SEQUENCE: 250

Glu Ile Ile Tyr Pro Asn Ala Ser Leu Leu Ile Gln Asn
1               5                   10
```

```
<210> SEQ ID NO 251
<211> LENGTH: 15
<212> TYPE: PRT
<213> ORGANISM: Homo sapiens

<400> SEQUENCE: 251

Tyr Ala Cys Phe Val Ser Asn Leu Ala Thr Gly Arg Asn Asn Ser
1               5                   10                  15

<210> SEQ ID NO 252
<211> LENGTH: 13
<212> TYPE: PRT
<213> ORGANISM: Homo sapiens

<400> SEQUENCE: 252

Leu Trp Trp Val Asn Asn Gln Ser Leu Pro Val Ser Pro
1               5                   10

<210> SEQ ID NO 253
<211> LENGTH: 13
<212> TYPE: PRT
<213> ORGANISM: Homo sapiens

<400> SEQUENCE: 253

Leu Trp Trp Val Asn Asn Gln Ser Leu Pro Val Ser Pro
1               5                   10

<210> SEQ ID NO 254
<211> LENGTH: 13
<212> TYPE: PRT
<213> ORGANISM: Homo sapiens

<400> SEQUENCE: 254

Leu Trp Trp Val Asn Asn Gln Ser Leu Pro Val Ser Pro
1               5                   10

<210> SEQ ID NO 255
<211> LENGTH: 13
<212> TYPE: PRT
<213> ORGANISM: Homo sapiens

<400> SEQUENCE: 255

Glu Ile Ile Tyr Pro Asn Ala Ser Leu Leu Ile Gln Asn
1               5                   10

<210> SEQ ID NO 256
<211> LENGTH: 13
<212> TYPE: PRT
<213> ORGANISM: Homo sapiens

<400> SEQUENCE: 256

Asn Ser Ile Val Lys Ser Ile Thr Val Ser Ala Ser Gly
1               5                   10

<210> SEQ ID NO 257
<211> LENGTH: 9
<212> TYPE: PRT
<213> ORGANISM: Homo sapiens

<400> SEQUENCE: 257

Lys Thr Trp Gly Gln Tyr Trp Gln Val
1               5

<210> SEQ ID NO 258
```

```
<211> LENGTH: 10
<212> TYPE: PRT
<213> ORGANISM: Homo sapiens
<220> FEATURE:
<221> NAME/KEY: misc_feature
<222> LOCATION: (1)..(1)
<223> OTHER INFORMATION: May or may not be present

<400> SEQUENCE: 258

Ala Met Leu Gly Thr His Thr Met Glu Val
1               5                   10

<210> SEQ ID NO 259
<211> LENGTH: 9
<212> TYPE: PRT
<213> ORGANISM: Homo sapiens

<400> SEQUENCE: 259

Ile Thr Asp Gln Val Pro Phe Ser Val
1               5

<210> SEQ ID NO 260
<211> LENGTH: 9
<212> TYPE: PRT
<213> ORGANISM: Homo sapiens

<400> SEQUENCE: 260

Tyr Leu Glu Pro Gly Pro Val Thr Ala
1               5

<210> SEQ ID NO 261
<211> LENGTH: 10
<212> TYPE: PRT
<213> ORGANISM: Homo sapiens

<400> SEQUENCE: 261

Leu Leu Asp Gly Thr Ala Thr Leu Arg Leu
1               5                   10

<210> SEQ ID NO 262
<211> LENGTH: 10
<212> TYPE: PRT
<213> ORGANISM: Homo sapiens

<400> SEQUENCE: 262

Val Leu Tyr Arg Tyr Gly Ser Phe Ser Val
1               5                   10

<210> SEQ ID NO 263
<211> LENGTH: 10
<212> TYPE: PRT
<213> ORGANISM: Homo sapiens

<400> SEQUENCE: 263

Ser Leu Ala Asp Thr Asn Ser Leu Ala Val
1               5                   10

<210> SEQ ID NO 264
<211> LENGTH: 9
<212> TYPE: PRT
<213> ORGANISM: Homo sapiens

<400> SEQUENCE: 264

Arg Leu Met Lys Gln Asp Phe Ser Val
1               5
```

<210> SEQ ID NO 265
<211> LENGTH: 9
<212> TYPE: PRT
<213> ORGANISM: Homo sapiens

<400> SEQUENCE: 265

Arg Leu Pro Arg Ile Phe Cys Ser Cys
1               5

<210> SEQ ID NO 266
<211> LENGTH: 9
<212> TYPE: PRT
<213> ORGANISM: Homo sapiens

<400> SEQUENCE: 266

Leu Ile Tyr Arg Arg Arg Leu Met Lys
1               5

<210> SEQ ID NO 267
<211> LENGTH: 9
<212> TYPE: PRT
<213> ORGANISM: Homo sapiens

<400> SEQUENCE: 267

Ala Leu Leu Ala Val Gly Ala Thr Lys
1               5

<210> SEQ ID NO 268
<211> LENGTH: 10
<212> TYPE: PRT
<213> ORGANISM: Homo sapiens

<400> SEQUENCE: 268

Ile Ala Leu Asn Phe Pro Gly Ser Gln Lys
1               5                   10

<210> SEQ ID NO 269
<211> LENGTH: 9
<212> TYPE: PRT
<213> ORGANISM: Homo sapiens

<400> SEQUENCE: 269

Ala Leu Asn Phe Pro Gly Ser Gln Lys
1               5

<210> SEQ ID NO 270
<211> LENGTH: 9
<212> TYPE: PRT
<213> ORGANISM: Homo sapiens

<400> SEQUENCE: 270

Ala Leu Asn Phe Pro Gly Ser Gln Lys
1               5

<210> SEQ ID NO 271
<211> LENGTH: 9
<212> TYPE: PRT
<213> ORGANISM: Homo sapiens

<400> SEQUENCE: 271

Val Tyr Phe Phe Leu Pro Asp His Leu
1               5

<210> SEQ ID NO 272

```
<211> LENGTH: 9
<212> TYPE: PRT
<213> ORGANISM: Homo sapiens

<400> SEQUENCE: 272

Arg Thr Lys Gln Leu Tyr Pro Glu Trp
1               5

<210> SEQ ID NO 273
<211> LENGTH: 10
<212> TYPE: PRT
<213> ORGANISM: Homo sapiens

<400> SEQUENCE: 273

His Thr Met Glu Val Thr Val Tyr His Arg
1               5                   10

<210> SEQ ID NO 274
<211> LENGTH: 9
<212> TYPE: PRT
<213> ORGANISM: Homo sapiens

<400> SEQUENCE: 274

Ser Ser Pro Gly Cys Gln Pro Pro Ala
1               5

<210> SEQ ID NO 275
<211> LENGTH: 10
<212> TYPE: PRT
<213> ORGANISM: Homo sapiens

<400> SEQUENCE: 275

Val Pro Leu Asp Cys Val Leu Tyr Arg Tyr
1               5                   10

<210> SEQ ID NO 276
<211> LENGTH: 9
<212> TYPE: PRT
<213> ORGANISM: Homo sapiens

<400> SEQUENCE: 276

Leu Pro His Ser Ser Ser His Trp Leu
1               5

<210> SEQ ID NO 277
<211> LENGTH: 8
<212> TYPE: PRT
<213> ORGANISM: Homo sapiens

<400> SEQUENCE: 277

Ser Asn Asp Gly Pro Thr Leu Ile
1               5

<210> SEQ ID NO 278
<211> LENGTH: 15
<212> TYPE: PRT
<213> ORGANISM: Homo sapiens

<400> SEQUENCE: 278

Gly Arg Ala Met Leu Gly Thr His Thr Met Glu Val Thr Val Tyr
1               5                   10                  15

<210> SEQ ID NO 279
<211> LENGTH: 16
<212> TYPE: PRT
```

<213> ORGANISM: Homo sapiens

<400> SEQUENCE: 279

Trp Asn Arg Gln Leu Tyr Pro Glu Trp Thr Glu Ala Gln Arg Leu Asp
1               5                   10                  15

<210> SEQ ID NO 280
<211> LENGTH: 18
<212> TYPE: PRT
<213> ORGANISM: Homo sapiens

<400> SEQUENCE: 280

Thr Thr Glu Trp Val Glu Thr Thr Ala Arg Glu Leu Pro Ile Pro Glu
1               5                   10                  15

Pro Glu

<210> SEQ ID NO 281
<211> LENGTH: 17
<212> TYPE: PRT
<213> ORGANISM: Homo sapiens

<400> SEQUENCE: 281

Thr Gly Arg Ala Met Leu Gly Thr His Thr Met Glu Val Thr Val Tyr
1               5                   10                  15

His

<210> SEQ ID NO 282
<211> LENGTH: 15
<212> TYPE: PRT
<213> ORGANISM: Homo sapiens

<400> SEQUENCE: 282

Gly Arg Ala Met Leu Gly Thr His Thr Met Glu Val Thr Val Tyr
1               5                   10                  15

<210> SEQ ID NO 283
<211> LENGTH: 9
<212> TYPE: PRT
<213> ORGANISM: Homo sapiens

<400> SEQUENCE: 283

Pro Leu Leu Glu Asn Val Ile Ser Lys
1               5

<210> SEQ ID NO 284
<211> LENGTH: 10
<212> TYPE: PRT
<213> ORGANISM: Homo sapiens
<220> FEATURE:
<221> NAME/KEY: misc_feature
<222> LOCATION: (1)..(1)
<223> OTHER INFORMATION: May or may not be present

<400> SEQUENCE: 284

Glu Ala Ala Gly Ile Gly Ile Leu Thr Val
1               5                   10

<210> SEQ ID NO 285
<211> LENGTH: 9
<212> TYPE: PRT
<213> ORGANISM: Homo sapiens

<400> SEQUENCE: 285

Ile Leu Thr Val Ile Leu Gly Val Leu

```
1               5

<210> SEQ ID NO 286
<211> LENGTH: 10
<212> TYPE: PRT
<213> ORGANISM: Homo sapiens

<400> SEQUENCE: 286

Glu Ala Ala Gly Ile Gly Ile Leu Thr Val
1               5                   10

<210> SEQ ID NO 287
<211> LENGTH: 11
<212> TYPE: PRT
<213> ORGANISM: Homo sapiens
<220> FEATURE:
<221> NAME/KEY: misc_feature
<222> LOCATION: (11)..(11)
<223> OTHER INFORMATION: May or may not be present

<400> SEQUENCE: 287

Ala Glu Glu Ala Ala Gly Ile Gly Ile Leu Thr
1               5                   10

<210> SEQ ID NO 288
<211> LENGTH: 11
<212> TYPE: PRT
<213> ORGANISM: Homo sapiens

<400> SEQUENCE: 288

Arg Asn Gly Tyr Arg Ala Leu Met Asp Lys Ser
1               5                   10

<210> SEQ ID NO 289
<211> LENGTH: 30
<212> TYPE: PRT
<213> ORGANISM: Homo sapiens

<400> SEQUENCE: 289

Tyr Thr Thr Ala Glu Glu Ala Ala Gly Ile Gly Ile Leu Thr Val Ile
1               5                   10                  15

Leu Gly Val Leu Leu Ile Gly Cys Trp Tyr Cys Arg Arg
            20                  25                  30

<210> SEQ ID NO 290
<211> LENGTH: 12
<212> TYPE: PRT
<213> ORGANISM: Homo sapiens

<400> SEQUENCE: 290

Glu Glu Ala Ala Gly Ile Gly Ile Leu Thr Val Ile
1               5                   10

<210> SEQ ID NO 291
<211> LENGTH: 14
<212> TYPE: PRT
<213> ORGANISM: Homo sapiens

<400> SEQUENCE: 291

Ala Ala Gly Ile Gly Ile Leu Thr Val Ile Leu Gly Val Leu
1               5                   10

<210> SEQ ID NO 292
<211> LENGTH: 12
<212> TYPE: PRT
```

<213> ORGANISM: Homo sapiens

<400> SEQUENCE: 292

Ala Pro Pro Ala Tyr Glu Lys Leu Ser Ala Glu Gln
1               5                   10

<210> SEQ ID NO 293
<211> LENGTH: 12
<212> TYPE: PRT
<213> ORGANISM: Homo sapiens

<400> SEQUENCE: 293

Glu Glu Ala Ala Gly Ile Gly Ile Leu Thr Val Ile
1               5                   10

<210> SEQ ID NO 294
<211> LENGTH: 23
<212> TYPE: PRT
<213> ORGANISM: Homo sapiens

<400> SEQUENCE: 294

Arg Asn Gly Tyr Arg Ala Leu Met Asp Lys Ser Leu His Val Gly Thr
1               5                   10                  15

Gln Cys Ala Leu Thr Arg Arg
            20

<210> SEQ ID NO 295
<211> LENGTH: 20
<212> TYPE: PRT
<213> ORGANISM: Homo sapiens

<400> SEQUENCE: 295

Met Pro Arg Glu Asp Ala His Phe Ile Tyr Gly Tyr Pro Lys Lys Gly
1               5                   10                  15

His Gly His Ser
            20

<210> SEQ ID NO 296
<211> LENGTH: 20
<212> TYPE: PRT
<213> ORGANISM: Homo sapiens

<400> SEQUENCE: 296

Lys Asn Cys Glu Pro Val Val Pro Asn Ala Pro Pro Ala Tyr Glu Lys
1               5                   10                  15

Leu Ser Ala Glu
            20

<210> SEQ ID NO 297
<211> LENGTH: 9
<212> TYPE: PRT
<213> ORGANISM: Homo sapiens

<400> SEQUENCE: 297

Ser Leu Ser Lys Ile Leu Asp Thr Val
1               5

<210> SEQ ID NO 298
<211> LENGTH: 9
<212> TYPE: PRT
<213> ORGANISM: Homo sapiens

<400> SEQUENCE: 298

Leu Tyr Ser Ala Cys Phe Trp Trp Leu
1               5

<210> SEQ ID NO 299
<211> LENGTH: 9
<212> TYPE: PRT
<213> ORGANISM: Homo sapiens

<400> SEQUENCE: 299

Phe Leu Phe Leu Leu Phe Phe Trp Leu
1               5

<210> SEQ ID NO 300
<211> LENGTH: 9
<212> TYPE: PRT
<213> ORGANISM: Homo sapiens

<400> SEQUENCE: 300

Thr Leu Met Ser Ala Met Thr Asn Leu
1               5

<210> SEQ ID NO 301
<211> LENGTH: 9
<212> TYPE: PRT
<213> ORGANISM: Homo sapiens

<400> SEQUENCE: 301

Ala Leu Asp Val Tyr Asn Gly Leu Leu
1               5

<210> SEQ ID NO 302
<211> LENGTH: 10
<212> TYPE: PRT
<213> ORGANISM: Homo sapiens

<400> SEQUENCE: 302

Phe Leu Thr Pro Lys Lys Leu Gln Cys Val
1               5                   10

<210> SEQ ID NO 303
<211> LENGTH: 10
<212> TYPE: PRT
<213> ORGANISM: Homo sapiens

<400> SEQUENCE: 303

Val Ile Ser Asn Asp Val Cys Ala Gln Val
1               5                   10

<210> SEQ ID NO 304
<211> LENGTH: 9
<212> TYPE: PRT
<213> ORGANISM: Homo sapiens

<400> SEQUENCE: 304

Val Leu His Trp Asp Pro Glu Thr Val
1               5

<210> SEQ ID NO 305
<211> LENGTH: 9
<212> TYPE: PRT
<213> ORGANISM: Homo sapiens

<400> SEQUENCE: 305

Met Ser Leu Gln Arg Gln Phe Leu Arg
1               5

<210> SEQ ID NO 306
<211> LENGTH: 21
<212> TYPE: PRT
<213> ORGANISM: Homo sapiens

<400> SEQUENCE: 306

Ile Ser Pro Asn Ser Val Phe Ser Gln Trp Arg Val Val Cys Asp Ser
1               5                   10                  15

Leu Glu Asp Tyr Asp
            20

<210> SEQ ID NO 307
<211> LENGTH: 10
<212> TYPE: PRT
<213> ORGANISM: Homo sapiens

<400> SEQUENCE: 307

Ser Leu Pro Tyr Trp Asn Phe Ala Thr Gly
1               5                   10

<210> SEQ ID NO 308
<211> LENGTH: 15
<212> TYPE: PRT
<213> ORGANISM: Homo sapiens

<400> SEQUENCE: 308

Ser Gln Trp Arg Val Val Cys Asp Ser Leu Glu Asp Tyr Asp Thr
1               5                   10                  15

<210> SEQ ID NO 309
<211> LENGTH: 9
<212> TYPE: PRT
<213> ORGANISM: Homo sapiens

<400> SEQUENCE: 309

Ser Val Tyr Asp Phe Phe Val Trp Leu
1               5

<210> SEQ ID NO 310
<211> LENGTH: 9
<212> TYPE: PRT
<213> ORGANISM: Homo sapiens

<400> SEQUENCE: 310

Thr Leu Asp Ser Gln Val Met Ser Leu
1               5

<210> SEQ ID NO 311
<211> LENGTH: 9
<212> TYPE: PRT
<213> ORGANISM: Homo sapiens

<400> SEQUENCE: 311

Leu Leu Gly Pro Gly Arg Pro Tyr Arg
1               5

<210> SEQ ID NO 312
<211> LENGTH: 9
<212> TYPE: PRT
<213> ORGANISM: Homo sapiens

<400> SEQUENCE: 312

Leu Leu Gly Pro Gly Arg Pro Tyr Arg

```
<210> SEQ ID NO 313
<211> LENGTH: 9
<212> TYPE: PRT
<213> ORGANISM: Homo sapiens

<400> SEQUENCE: 313

Ala Asn Asp Pro Ile Phe Val Val Leu
1               5

<210> SEQ ID NO 314
<211> LENGTH: 15
<212> TYPE: PRT
<213> ORGANISM: Homo sapiens

<400> SEQUENCE: 314

Gln Cys Thr Glu Val Arg Ala Asp Thr Arg Pro Trp Ser Gly Pro
1               5                   10                  15

<210> SEQ ID NO 315
<211> LENGTH: 10
<212> TYPE: PRT
<213> ORGANISM: Homo sapiens

<400> SEQUENCE: 315

Ala Leu Pro Tyr Trp Asn Phe Ala Thr Gly
1               5                   10

<210> SEQ ID NO 316
<211> LENGTH: 9
<212> TYPE: PRT
<213> ORGANISM: Homo sapiens

<400> SEQUENCE: 316

Lys Cys Asp Ile Cys Thr Asp Glu Tyr
1               5

<210> SEQ ID NO 317
<211> LENGTH: 11
<212> TYPE: PRT
<213> ORGANISM: Homo sapiens

<400> SEQUENCE: 317

Ser Ser Asp Tyr Val Ile Pro Ile Gly Thr Tyr
1               5                   10

<210> SEQ ID NO 318
<211> LENGTH: 9
<212> TYPE: PRT
<213> ORGANISM: Homo sapiens

<400> SEQUENCE: 318

Met Leu Leu Ala Val Leu Tyr Cys Leu
1               5

<210> SEQ ID NO 319
<211> LENGTH: 10
<212> TYPE: PRT
<213> ORGANISM: Homo sapiens

<400> SEQUENCE: 319

Cys Leu Leu Trp Ser Phe Gln Thr Ser Ala
1               5                   10
```

<210> SEQ ID NO 320
<211> LENGTH: 9
<212> TYPE: PRT
<213> ORGANISM: Homo sapiens

<400> SEQUENCE: 320

Tyr Met Asp Gly Thr Met Ser Gln Val
1               5

<210> SEQ ID NO 321
<211> LENGTH: 9
<212> TYPE: PRT
<213> ORGANISM: Homo sapiens

<400> SEQUENCE: 321

Ala Phe Leu Pro Trp His Arg Leu Phe
1               5

<210> SEQ ID NO 322
<211> LENGTH: 11
<212> TYPE: PRT
<213> ORGANISM: Homo sapiens

<400> SEQUENCE: 322

Ile Tyr Met Asp Gly Thr Ala Asp Phe Ser Phe
1               5                   10

<210> SEQ ID NO 323
<211> LENGTH: 9
<212> TYPE: PRT
<213> ORGANISM: Homo sapiens

<400> SEQUENCE: 323

Gln Cys Ser Gly Asn Phe Met Gly Phe
1               5

<210> SEQ ID NO 324
<211> LENGTH: 12
<212> TYPE: PRT
<213> ORGANISM: Homo sapiens

<400> SEQUENCE: 324

Thr Pro Arg Leu Pro Ser Ser Ala Asp Val Glu Phe
1               5                   10

<210> SEQ ID NO 325
<211> LENGTH: 9
<212> TYPE: PRT
<213> ORGANISM: Homo sapiens

<400> SEQUENCE: 325

Leu Pro Ser Ser Ala Asp Val Glu Phe
1               5

<210> SEQ ID NO 326
<211> LENGTH: 10
<212> TYPE: PRT
<213> ORGANISM: Homo sapiens

<400> SEQUENCE: 326

Leu His His Ala Phe Val Asp Ser Ile Phe
1               5                   10

<210> SEQ ID NO 327

```
<211> LENGTH: 9
<212> TYPE: PRT
<213> ORGANISM: Homo sapiens

<400> SEQUENCE: 327

Ser Glu Ile Trp Arg Asp Ile Asp Phe
1               5

<210> SEQ ID NO 328
<211> LENGTH: 15
<212> TYPE: PRT
<213> ORGANISM: Homo sapiens

<400> SEQUENCE: 328

Gln Asn Ile Leu Leu Ser Asn Ala Pro Leu Gly Pro Gln Phe Pro
1               5                   10                  15

<210> SEQ ID NO 329
<211> LENGTH: 13
<212> TYPE: PRT
<213> ORGANISM: Homo sapiens

<400> SEQUENCE: 329

Ser Tyr Leu Gln Asp Ser Asp Pro Asp Ser Phe Gln Asp
1               5                   10

<210> SEQ ID NO 330
<211> LENGTH: 21
<212> TYPE: PRT
<213> ORGANISM: Homo sapiens

<400> SEQUENCE: 330

Phe Leu Leu His His Ala Phe Val Asp Ser Ile Phe Glu Gln Trp Leu
1               5                   10                  15

Gln Arg His Arg Pro
            20

<210> SEQ ID NO 331
<211> LENGTH: 9
<212> TYPE: PRT
<213> ORGANISM: Homo sapiens

<400> SEQUENCE: 331

Ser Val Ala Ser Thr Ile Thr Gly Val
1               5

<210> SEQ ID NO 332
<211> LENGTH: 10
<212> TYPE: PRT
<213> ORGANISM: Homo sapiens

<400> SEQUENCE: 332

Arg Ser Asp Ser Gly Gln Gln Ala Arg Tyr
1               5                   10

<210> SEQ ID NO 333
<211> LENGTH: 9
<212> TYPE: PRT
<213> ORGANISM: Homo sapiens

<400> SEQUENCE: 333

Leu Leu Tyr Lys Leu Ala Asp Leu Ile
1               5
```

```
<210> SEQ ID NO 334
<211> LENGTH: 10
<212> TYPE: PRT
<213> ORGANISM: Homo sapiens

<400> SEQUENCE: 334

Tyr Leu Asn Asp His Leu Glu Pro Trp Ile
1               5                   10

<210> SEQ ID NO 335
<211> LENGTH: 9
<212> TYPE: PRT
<213> ORGANISM: Homo sapiens

<400> SEQUENCE: 335

Cys Gln Trp Gly Arg Leu Trp Gln Leu
1               5

<210> SEQ ID NO 336
<211> LENGTH: 10
<212> TYPE: PRT
<213> ORGANISM: Homo sapiens

<400> SEQUENCE: 336

Val Leu Leu Gln Ala Gly Ser Leu His Ala
1               5                   10

<210> SEQ ID NO 337
<211> LENGTH: 9
<212> TYPE: PRT
<213> ORGANISM: Homo sapiens

<400> SEQUENCE: 337

Lys Phe Leu Asp Ala Leu Ile Ser Leu
1               5

<210> SEQ ID NO 338
<211> LENGTH: 9
<212> TYPE: PRT
<213> ORGANISM: Homo sapiens

<400> SEQUENCE: 338

Lys Val His Pro Val Ile Trp Ser Leu
1               5

<210> SEQ ID NO 339
<211> LENGTH: 10
<212> TYPE: PRT
<213> ORGANISM: Homo sapiens

<400> SEQUENCE: 339

Leu Met Leu Gln Asn Ala Leu Thr Thr Met
1               5                   10

<210> SEQ ID NO 340
<211> LENGTH: 9
<212> TYPE: PRT
<213> ORGANISM: Homo sapiens

<400> SEQUENCE: 340

Leu Leu Gly Ala Thr Cys Met Phe Val
1               5

<210> SEQ ID NO 341
<211> LENGTH: 15
```

```
<212> TYPE: PRT
<213> ORGANISM: Homo sapiens

<400> SEQUENCE: 341

Asn Pro Pro Ser Met Val Ala Ala Gly Ser Val Val Ala Ala Val
1               5                   10                  15

<210> SEQ ID NO 342
<211> LENGTH: 10
<212> TYPE: PRT
<213> ORGANISM: Homo sapiens

<400> SEQUENCE: 342

Ala Leu Gly Gly His Pro Leu Leu Gly Val
1               5                   10

<210> SEQ ID NO 343
<211> LENGTH: 9
<212> TYPE: PRT
<213> ORGANISM: Homo sapiens

<400> SEQUENCE: 343

Thr Met Asn Gly Ser Lys Ser Pro Val
1               5

<210> SEQ ID NO 344
<211> LENGTH: 9
<212> TYPE: PRT
<213> ORGANISM: Homo sapiens

<400> SEQUENCE: 344

Arg Tyr Gln Leu Asp Pro Lys Phe Ile
1               5

<210> SEQ ID NO 345
<211> LENGTH: 12
<212> TYPE: PRT
<213> ORGANISM: Homo sapiens

<400> SEQUENCE: 345

Asp Val Thr Phe Asn Ile Ile Cys Lys Lys Cys Gly
1               5                   10

<210> SEQ ID NO 346
<211> LENGTH: 9
<212> TYPE: PRT
<213> ORGANISM: Homo sapiens

<400> SEQUENCE: 346

Phe Met Val Glu Asp Glu Thr Val Leu
1               5

<210> SEQ ID NO 347
<211> LENGTH: 10
<212> TYPE: PRT
<213> ORGANISM: Homo sapiens

<400> SEQUENCE: 347

Phe Ile Asn Asp Glu Ile Phe Val Glu Leu
1               5                   10

<210> SEQ ID NO 348
<211> LENGTH: 9
<212> TYPE: PRT
<213> ORGANISM: Homo sapiens
```

```
<400> SEQUENCE: 348

Lys Tyr Asp Cys Phe Leu His Pro Phe
1               5

<210> SEQ ID NO 349
<211> LENGTH: 9
<212> TYPE: PRT
<213> ORGANISM: Homo sapiens

<400> SEQUENCE: 349

Lys Tyr Val Gly Ile Glu Arg Glu Met
1               5

<210> SEQ ID NO 350
<211> LENGTH: 9
<212> TYPE: PRT
<213> ORGANISM: Homo sapiens

<400> SEQUENCE: 350

Asn Thr Tyr Ala Ser Pro Arg Phe Lys
1               5

<210> SEQ ID NO 351
<211> LENGTH: 9
<212> TYPE: PRT
<213> ORGANISM: Homo sapiens

<400> SEQUENCE: 351

Phe Val Gly Glu Phe Phe Thr Asp Val
1               5

<210> SEQ ID NO 352
<211> LENGTH: 9
<212> TYPE: PRT
<213> ORGANISM: Homo sapiens

<400> SEQUENCE: 352

Glu Tyr Ile Leu Ser Leu Glu Glu Leu
1               5

<210> SEQ ID NO 353
<211> LENGTH: 9
<212> TYPE: PRT
<213> ORGANISM: Homo sapiens

<400> SEQUENCE: 353

His Leu Ser Thr Ala Phe Ala Arg Val
1               5

<210> SEQ ID NO 354
<211> LENGTH: 9
<212> TYPE: PRT
<213> ORGANISM: Homo sapiens

<400> SEQUENCE: 354

Lys Ile Phe Gly Ser Leu Ala Phe Leu
1               5

<210> SEQ ID NO 355
<211> LENGTH: 9
<212> TYPE: PRT
<213> ORGANISM: Homo sapiens

<400> SEQUENCE: 355
```

Ile Ile Ser Ala Val Val Gly Ile Leu
1               5

<210> SEQ ID NO 356
<211> LENGTH: 9
<212> TYPE: PRT
<213> ORGANISM: Homo sapiens

<400> SEQUENCE: 356

Ala Leu Cys Arg Trp Gly Leu Leu Leu
1               5

<210> SEQ ID NO 357
<211> LENGTH: 9
<212> TYPE: PRT
<213> ORGANISM: Homo sapiens

<400> SEQUENCE: 357

Ile Leu His Asn Gly Ala Tyr Ser Leu
1               5

<210> SEQ ID NO 358
<211> LENGTH: 9
<212> TYPE: PRT
<213> ORGANISM: Homo sapiens

<400> SEQUENCE: 358

Arg Leu Leu Gln Glu Thr Glu Leu Val
1               5

<210> SEQ ID NO 359
<211> LENGTH: 9
<212> TYPE: PRT
<213> ORGANISM: Homo sapiens

<400> SEQUENCE: 359

Val Val Leu Gly Val Val Phe Gly Ile
1               5

<210> SEQ ID NO 360
<211> LENGTH: 10
<212> TYPE: PRT
<213> ORGANISM: Homo sapiens

<400> SEQUENCE: 360

Tyr Met Ile Met Val Lys Cys Trp Met Ile
1               5                   10

<210> SEQ ID NO 361
<211> LENGTH: 9
<212> TYPE: PRT
<213> ORGANISM: Homo sapiens

<400> SEQUENCE: 361

His Leu Tyr Gln Gly Cys Gln Val Val
1               5

<210> SEQ ID NO 362
<211> LENGTH: 10
<212> TYPE: PRT
<213> ORGANISM: Homo sapiens

<400> SEQUENCE: 362

Tyr Leu Val Pro Gln Gln Gly Phe Phe Cys

<210> SEQ ID NO 363
<211> LENGTH: 9
<212> TYPE: PRT
<213> ORGANISM: Homo sapiens

<400> SEQUENCE: 363

Pro Leu Gln Pro Glu Gln Leu Gln Val
1               5

<210> SEQ ID NO 364
<211> LENGTH: 9
<212> TYPE: PRT
<213> ORGANISM: Homo sapiens

<400> SEQUENCE: 364

Thr Leu Glu Glu Ile Thr Gly Tyr Leu
1               5

<210> SEQ ID NO 365
<211> LENGTH: 9
<212> TYPE: PRT
<213> ORGANISM: Homo sapiens

<400> SEQUENCE: 365

Ala Leu Ile His His Asn Thr His Leu
1               5

<210> SEQ ID NO 366
<211> LENGTH: 9
<212> TYPE: PRT
<213> ORGANISM: Homo sapiens

<400> SEQUENCE: 366

Pro Leu Thr Ser Ile Ile Ser Ala Val
1               5

<210> SEQ ID NO 367
<211> LENGTH: 9
<212> TYPE: PRT
<213> ORGANISM: Homo sapiens

<400> SEQUENCE: 367

Val Leu Arg Glu Asn Thr Ser Pro Lys
1               5

<210> SEQ ID NO 368
<211> LENGTH: 9
<212> TYPE: PRT
<213> ORGANISM: Homo sapiens

<400> SEQUENCE: 368

Thr Tyr Leu Pro Thr Asn Ala Ser Leu
1               5

<210> SEQ ID NO 369
<211> LENGTH: 9
<212> TYPE: PRT
<213> ORGANISM: Homo sapiens

<400> SEQUENCE: 369

Ala Leu Leu Glu Ile Ala Ser Cys Leu
1               5

```
<210> SEQ ID NO 370
<211> LENGTH: 9
<212> TYPE: PRT
<213> ORGANISM: Homo sapiens

<400> SEQUENCE: 370

Asn Leu Ser Ser Ala Glu Val Val Val
1               5

<210> SEQ ID NO 371
<211> LENGTH: 9
<212> TYPE: PRT
<213> ORGANISM: Homo sapiens

<400> SEQUENCE: 371

Arg Leu Leu Val Pro Thr Gln Phe Val
1               5

<210> SEQ ID NO 372
<211> LENGTH: 9
<212> TYPE: PRT
<213> ORGANISM: Homo sapiens

<400> SEQUENCE: 372

Trp Leu Pro Phe Gly Phe Ile Leu Ile
1               5

<210> SEQ ID NO 373
<211> LENGTH: 9
<212> TYPE: PRT
<213> ORGANISM: Homo sapiens

<400> SEQUENCE: 373

Ser Pro Arg Trp Trp Pro Thr Cys Leu
1               5

<210> SEQ ID NO 374
<211> LENGTH: 9
<212> TYPE: PRT
<213> ORGANISM: Homo sapiens

<400> SEQUENCE: 374

Gly Val Ala Leu Gln Thr Met Lys Gln
1               5

<210> SEQ ID NO 375
<211> LENGTH: 9
<212> TYPE: PRT
<213> ORGANISM: Homo sapiens

<400> SEQUENCE: 375

Phe Met Asn Lys Phe Ile Tyr Glu Ile
1               5

<210> SEQ ID NO 376
<211> LENGTH: 10
<212> TYPE: PRT
<213> ORGANISM: Homo sapiens

<400> SEQUENCE: 376

Gln Leu Ala Val Ser Val Ile Leu Arg Val
1               5                   10

<210> SEQ ID NO 377
```

```
<211> LENGTH: 9
<212> TYPE: PRT
<213> ORGANISM: Homo sapiens

<400> SEQUENCE: 377

Phe Leu Gly Tyr Leu Ile Leu Gly Val
1               5

<210> SEQ ID NO 378
<211> LENGTH: 15
<212> TYPE: PRT
<213> ORGANISM: Homo sapiens

<400> SEQUENCE: 378

Ser Val Ser Glu Ser Asp Thr Ile Arg Ser Ile Ser Ile Ala Ser
1               5                   10                  15

<210> SEQ ID NO 379
<211> LENGTH: 15
<212> TYPE: PRT
<213> ORGANISM: Homo sapiens

<400> SEQUENCE: 379

Leu Leu Ala Asn Gly Arg Met Pro Thr Val Leu Gln Cys Val Asn
1               5                   10                  15

<210> SEQ ID NO 380
<211> LENGTH: 15
<212> TYPE: PRT
<213> ORGANISM: Homo sapiens

<400> SEQUENCE: 380

Arg Met Pro Thr Val Leu Gln Cys Val Asn Val Ser Val Val Ser
1               5                   10                  15

<210> SEQ ID NO 381
<211> LENGTH: 9
<212> TYPE: PRT
<213> ORGANISM: Homo sapiens

<400> SEQUENCE: 381

Leu Leu Ser Asp Asp Val Val Val
1               5

<210> SEQ ID NO 382
<211> LENGTH: 10
<212> TYPE: PRT
<213> ORGANISM: Homo sapiens

<400> SEQUENCE: 382

Ala Gln Pro Asp Thr Ala Pro Leu Pro Val
1               5                   10

<210> SEQ ID NO 383
<211> LENGTH: 9
<212> TYPE: PRT
<213> ORGANISM: Homo sapiens

<400> SEQUENCE: 383

Cys Ile Ala Glu Gln Tyr His Thr Val
1               5

<210> SEQ ID NO 384
<211> LENGTH: 10
<212> TYPE: PRT
```

<213> ORGANISM: Homo sapiens

<400> SEQUENCE: 384

Phe Leu Pro Glu Phe Gly Ile Ser Ser Ala
1               5                   10

<210> SEQ ID NO 385
<211> LENGTH: 14
<212> TYPE: PRT
<213> ORGANISM: Homo sapiens

<400> SEQUENCE: 385

Leu Pro Ala Val Val Gly Leu Ser Pro Gly Glu Gln Glu Tyr
1               5                   10

<210> SEQ ID NO 386
<211> LENGTH: 16
<212> TYPE: PRT
<213> ORGANISM: Homo sapiens

<400> SEQUENCE: 386

Val Gly Gln Asp Val Ser Val Leu Phe Arg Val Thr Gly Ala Leu Gln
1               5                   10                  15

<210> SEQ ID NO 387
<211> LENGTH: 8
<212> TYPE: PRT
<213> ORGANISM: Homo sapiens

<400> SEQUENCE: 387

Val Leu Phe Tyr Leu Gly Gln Tyr
1               5

<210> SEQ ID NO 388
<211> LENGTH: 9
<212> TYPE: PRT
<213> ORGANISM: Homo sapiens

<400> SEQUENCE: 388

Thr Leu Asn Asp Glu Cys Trp Pro Ala
1               5

<210> SEQ ID NO 389
<211> LENGTH: 11
<212> TYPE: PRT
<213> ORGANISM: Homo sapiens

<400> SEQUENCE: 389

Phe Gly Arg Leu Gln Gly Ile Ser Pro Lys Ile
1               5                   10

<210> SEQ ID NO 390
<211> LENGTH: 14
<212> TYPE: PRT
<213> ORGANISM: Homo sapiens

<400> SEQUENCE: 390

Cys Pro Pro Trp His Pro Ser Glu Arg Ile Ser Ser Thr Leu
1               5                   10

<210> SEQ ID NO 391
<211> LENGTH: 9
<212> TYPE: PRT
<213> ORGANISM: Homo sapiens

<400> SEQUENCE: 391

Gly Leu Pro Pro Asp Val Gln Arg Val
1               5

<210> SEQ ID NO 392
<211> LENGTH: 12
<212> TYPE: PRT
<213> ORGANISM: Homo sapiens

<400> SEQUENCE: 392

Ser Leu Phe Pro Asn Ser Pro Lys Trp Thr Ser Lys
1               5                   10

<210> SEQ ID NO 393
<211> LENGTH: 9
<212> TYPE: PRT
<213> ORGANISM: Homo sapiens

<400> SEQUENCE: 393

Ser Thr Ala Pro Pro Val His Asn Val
1               5

<210> SEQ ID NO 394
<211> LENGTH: 9
<212> TYPE: PRT
<213> ORGANISM: Homo sapiens

<400> SEQUENCE: 394

Leu Leu Leu Leu Thr Val Leu Thr Val
1               5

<210> SEQ ID NO 395
<211> LENGTH: 12
<212> TYPE: PRT
<213> ORGANISM: Homo sapiens

<400> SEQUENCE: 395

Pro Gly Ser Thr Ala Pro Pro Ala His Gly Val Thr
1               5                   10

<210> SEQ ID NO 396
<211> LENGTH: 9
<212> TYPE: PRT
<213> ORGANISM: Homo sapiens

<400> SEQUENCE: 396

Thr Cys Gln Pro Thr Cys Arg Ser Leu
1               5

<210> SEQ ID NO 397
<211> LENGTH: 9
<212> TYPE: PRT
<213> ORGANISM: Homo sapiens

<400> SEQUENCE: 397

Leu Leu Gly Arg Asn Ser Phe Glu Val
1               5

<210> SEQ ID NO 398
<211> LENGTH: 9
<212> TYPE: PRT
<213> ORGANISM: Homo sapiens

<400> SEQUENCE: 398

```
Arg Met Pro Glu Ala Ala Pro Pro Val
1               5
```

<210> SEQ ID NO 399
<211> LENGTH: 9
<212> TYPE: PRT
<213> ORGANISM: Homo sapiens

<400> SEQUENCE: 399

```
Ser Gln Lys Thr Tyr Gln Gly Ser Tyr
1               5
```

<210> SEQ ID NO 400
<211> LENGTH: 13
<212> TYPE: PRT
<213> ORGANISM: Homo sapiens

<400> SEQUENCE: 400

```
Pro Gly Thr Arg Val Arg Ala Met Ala Ile Tyr Lys Gln
1               5                   10
```

<210> SEQ ID NO 401
<211> LENGTH: 12
<212> TYPE: PRT
<213> ORGANISM: Homo sapiens

<400> SEQUENCE: 401

```
His Leu Ile Arg Val Glu Gly Asn Leu Arg Val Glu
1               5                   10
```

<210> SEQ ID NO 402
<211> LENGTH: 9
<212> TYPE: PRT
<213> ORGANISM: Homo sapiens

<400> SEQUENCE: 402

```
Thr Leu Pro Gly Tyr Pro Pro His Val
1               5
```

<210> SEQ ID NO 403
<211> LENGTH: 12
<212> TYPE: PRT
<213> ORGANISM: Homo sapiens

<400> SEQUENCE: 403

```
Cys Thr Ala Cys Arg Trp Lys Lys Ala Cys Gln Arg
1               5                   10
```

<210> SEQ ID NO 404
<211> LENGTH: 9
<212> TYPE: PRT
<213> ORGANISM: Homo sapiens

<400> SEQUENCE: 404

```
Val Leu Asp Gly Leu Asp Val Leu Leu
1               5
```

<210> SEQ ID NO 405
<211> LENGTH: 10
<212> TYPE: PRT
<213> ORGANISM: Homo sapiens

<400> SEQUENCE: 405

```
Ser Leu Tyr Ser Phe Pro Glu Pro Glu Ala
1               5                   10
```

<210> SEQ ID NO 406
<211> LENGTH: 10
<212> TYPE: PRT
<213> ORGANISM: Homo sapiens

<400> SEQUENCE: 406

Ala Leu Tyr Val Asp Ser Leu Phe Phe Leu
1               5                   10

<210> SEQ ID NO 407
<211> LENGTH: 9
<212> TYPE: PRT
<213> ORGANISM: Homo sapiens

<400> SEQUENCE: 407

Ser Leu Leu Gln His Leu Ile Gly Leu
1               5

<210> SEQ ID NO 408
<211> LENGTH: 9
<212> TYPE: PRT
<213> ORGANISM: Homo sapiens

<400> SEQUENCE: 408

Leu Tyr Val Asp Ser Leu Phe Phe Leu
1               5

<210> SEQ ID NO 409
<211> LENGTH: 9
<212> TYPE: PRT
<213> ORGANISM: Homo sapiens

<400> SEQUENCE: 409

Asn Tyr Ala Arg Thr Glu Asp Phe Phe
1               5

<210> SEQ ID NO 410
<211> LENGTH: 9
<212> TYPE: PRT
<213> ORGANISM: Homo sapiens

<400> SEQUENCE: 410

Leu Lys Leu Ser Gly Val Val Arg Leu
1               5

<210> SEQ ID NO 411
<211> LENGTH: 10
<212> TYPE: PRT
<213> ORGANISM: Homo sapiens

<400> SEQUENCE: 411

Pro Leu Pro Pro Ala Arg Asn Gly Gly Leu
1               5                   10

<210> SEQ ID NO 412
<211> LENGTH: 10
<212> TYPE: PRT
<213> ORGANISM: Homo sapiens

<400> SEQUENCE: 412

Ser Pro Ser Ser Asn Arg Ile Arg Asn Thr
1               5                   10

```
<210> SEQ ID NO 413
<211> LENGTH: 9
<212> TYPE: PRT
<213> ORGANISM: Homo sapiens

<400> SEQUENCE: 413

Leu Ala Ala Leu Pro His Ser Cys Leu
1               5

<210> SEQ ID NO 414
<211> LENGTH: 10
<212> TYPE: PRT
<213> ORGANISM: Homo sapiens

<400> SEQUENCE: 414

Gly Leu Ala Ser Phe Lys Ser Phe Leu Lys
1               5                   10

<210> SEQ ID NO 415
<211> LENGTH: 10
<212> TYPE: PRT
<213> ORGANISM: Homo sapiens

<400> SEQUENCE: 415

Arg Ala Gly Leu Gln Val Arg Lys Asn Lys
1               5                   10

<210> SEQ ID NO 416
<211> LENGTH: 10
<212> TYPE: PRT
<213> ORGANISM: Homo sapiens
<220> FEATURE:
<221> NAME/KEY: misc_feature
<222> LOCATION: (10)..(10)
<223> OTHER INFORMATION: May or may not be present

<400> SEQUENCE: 416

Ala Leu Trp Pro Trp Leu Leu Met Ala Thr
1               5                   10

<210> SEQ ID NO 417
<211> LENGTH: 9
<212> TYPE: PRT
<213> ORGANISM: Homo sapiens

<400> SEQUENCE: 417

Asn Ser Gln Pro Val Trp Leu Cys Leu
1               5

<210> SEQ ID NO 418
<211> LENGTH: 9
<212> TYPE: PRT
<213> ORGANISM: Homo sapiens

<400> SEQUENCE: 418

Leu Pro Arg Trp Pro Pro Pro Gln Leu
1               5

<210> SEQ ID NO 419
<211> LENGTH: 9
<212> TYPE: PRT
<213> ORGANISM: Homo sapiens

<400> SEQUENCE: 419

Lys Met Asp Ala Glu His Pro Glu Leu
1               5
```

```
<210> SEQ ID NO 420
<211> LENGTH: 9
<212> TYPE: PRT
<213> ORGANISM: Homo sapiens

<400> SEQUENCE: 420

Ala Trp Ile Ser Lys Pro Pro Gly Val
1               5

<210> SEQ ID NO 421
<211> LENGTH: 10
<212> TYPE: PRT
<213> ORGANISM: Homo sapiens

<400> SEQUENCE: 421

Ser Ala Trp Ile Ser Lys Pro Pro Gly Val
1               5                   10

<210> SEQ ID NO 422
<211> LENGTH: 9
<212> TYPE: PRT
<213> ORGANISM: Homo sapiens

<400> SEQUENCE: 422

Met Ile Ala Val Phe Leu Pro Ile Val
1               5

<210> SEQ ID NO 423
<211> LENGTH: 15
<212> TYPE: PRT
<213> ORGANISM: Homo sapiens

<400> SEQUENCE: 423

His Gln Gln Tyr Phe Tyr Lys Ile Pro Ile Leu Val Ile Asn Lys
1               5                   10                  15

<210> SEQ ID NO 424
<211> LENGTH: 10
<212> TYPE: PRT
<213> ORGANISM: Homo sapiens

<400> SEQUENCE: 424

Glu Leu Thr Leu Gly Glu Phe Leu Lys Leu
1               5                   10

<210> SEQ ID NO 425
<211> LENGTH: 15
<212> TYPE: PRT
<213> ORGANISM: Homo sapiens

<400> SEQUENCE: 425

Thr Leu Gly Glu Phe Leu Lys Leu Asp Arg Glu Arg Ala Lys Asn
1               5                   10                  15

<210> SEQ ID NO 426
<211> LENGTH: 9
<212> TYPE: PRT
<213> ORGANISM: Homo sapiens

<400> SEQUENCE: 426

Ile Leu Ala Lys Phe Leu His Trp Leu
1               5
```

-continued

```
<210> SEQ ID NO 427
<211> LENGTH: 9
<212> TYPE: PRT
<213> ORGANISM: Homo sapiens

<400> SEQUENCE: 427

Arg Leu Val Asp Asp Phe Leu Leu Val
1               5

<210> SEQ ID NO 428
<211> LENGTH: 15
<212> TYPE: PRT
<213> ORGANISM: Homo sapiens

<400> SEQUENCE: 428

Arg Pro Gly Leu Leu Gly Ala Ser Val Leu Gly Leu Asp Asp Ile
1               5                   10                  15

<210> SEQ ID NO 429
<211> LENGTH: 15
<212> TYPE: PRT
<213> ORGANISM: Homo sapiens

<400> SEQUENCE: 429

Leu Thr Asp Leu Gln Pro Tyr Met Arg Gln Phe Val Ala His Leu
1               5                   10                  15

<210> SEQ ID NO 430
<211> LENGTH: 9
<212> TYPE: PRT
<213> ORGANISM: Homo sapiens

<400> SEQUENCE: 430

Ser Arg Phe Gly Gly Ala Val Val Arg
1               5

<210> SEQ ID NO 431
<211> LENGTH: 11
<212> TYPE: PRT
<213> ORGANISM: Homo sapiens

<400> SEQUENCE: 431

Thr Ser Glu Lys Arg Pro Phe Met Cys Ala Tyr
1               5                   10

<210> SEQ ID NO 432
<211> LENGTH: 9
<212> TYPE: PRT
<213> ORGANISM: Homo sapiens

<400> SEQUENCE: 432

Cys Met Thr Trp Asn Gln Met Asn Leu
1               5

<210> SEQ ID NO 433
<211> LENGTH: 11
<212> TYPE: PRT
<213> ORGANISM: Homo sapiens

<400> SEQUENCE: 433

Leu Ser His Leu Gln Met His Ser Arg Lys His
1               5                   10

<210> SEQ ID NO 434
<211> LENGTH: 16
```

```
<212> TYPE: PRT
<213> ORGANISM: Homo sapiens

<400> SEQUENCE: 434

Lys Arg Tyr Phe Lys Leu Ser His Leu Gln Met His Ser Arg Lys His
1               5                   10                  15

<210> SEQ ID NO 435
<211> LENGTH: 10
<212> TYPE: PRT
<213> ORGANISM: Homo sapiens

<400> SEQUENCE: 435

Ala Ser Gly Pro Gly Gly Gly Ala Pro Arg
1               5                   10

<210> SEQ ID NO 436
<211> LENGTH: 10
<212> TYPE: PRT
<213> ORGANISM: Homo sapiens

<400> SEQUENCE: 436

Thr Val Ser Gly Asn Ile Leu Thr Ile Arg
1               5                   10

<210> SEQ ID NO 437
<211> LENGTH: 13
<212> TYPE: PRT
<213> ORGANISM: Homo sapiens

<400> SEQUENCE: 437

Pro Phe Ala Thr Pro Met Glu Ala Glu Leu Ala Arg Arg
1               5                   10

<210> SEQ ID NO 438
<211> LENGTH: 10
<212> TYPE: PRT
<213> ORGANISM: Homo sapiens

<400> SEQUENCE: 438

Val Leu Leu Lys Glu Phe Thr Val Ser Gly
1               5                   10

<210> SEQ ID NO 439
<211> LENGTH: 9
<212> TYPE: PRT
<213> ORGANISM: Homo sapiens

<400> SEQUENCE: 439

Glu Val Asp Pro Thr Ser Asn Thr Tyr
1               5

<210> SEQ ID NO 440
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Gly Gly Gly Gly Arg Gly Asp Ser Pro
1               5
```

COMBINATION VACCINE DEVICES AND METHODS OF KILLING CANCER CELLS

RELATED APPLICATIONS

This application is a national stage application, filed under 35 U.S.C. § 371, of PCT International Application No. PCT/US2015/028468, filed on Apr. 30, 2015, which claims the benefit of priority under 35 U.S.C. § 119(e) to U.S. Provisional Application No. 61/986,600, filed Apr. 30, 2014, which is incorporated herein by reference in its entirety.

GOVERNMENT SUPPORT

The invention made with Government support awarded by the National Institutes of Health Grant No. R01 EB015498. The Government has certain rights in the invention.

INCORPORATION BY REFERENCE OF SEQUENCE LISTING

The content of the text file named "29297_109001WO_SL.txt," which was created on Oct. 13, 2016 and is 168 KB in size, is hereby incorporated herein by reference in its entirety.

BACKGROUND OF THE INVENTION

Many cancers are recalcitrant to treatment because they co-opt the host immune system and evade the endogenous anti-tumor immune response. One such mechanism by which cancer cells evade the immune system is by upregulating immune-inhibitory proteins. Thus, agents that block these immune-inhibitory proteins have been explored as potential therapies that re-enable the endogenous anti-tumor immune response. However, these agents when used alone are ineffective in killing poorly immunogenic tumors. Thus, there is a need for compositions and methods to prevent or treat cancer by promoting the endogenous anti-tumor immune response, in particular in poorly immunogenic tumors. This invention addresses this need.

SUMMARY OF THE INVENTION

The invention features material-based cancer vaccines (e.g., cancer vaccine devices) in combination with immune checkpoint antibodies to boost T cell activity and anti-tumor immune responses.

A device of the invention comprises an inhibitor of an immune-inhibitory protein; a scaffold composition; a cell recruitment composition; and a bioactive composition, where the bioactive composition is incorporated into or coated onto the scaffold composition, and where the bioactive composition causes modification of cells in or recruited to the device.

For example, an immune-inhibitory protein is a protein that decreases and/or inhibits the activity of an immune cell. For example, an immune-inhibitory protein decreases and/or inhibits the activity of a T cell, B cell, NK cell, or dendritic cell. For example, a decrease in activity or inhibition of a T cell, B cell, NK cell, or dendritic cell decreases an endogenous immune response against an antigen (e.g., a cancer cell antigen). For example, the immune-inhibitory protein decreases and/or inhibits a T cell effector activity and/or an NK cell killing activity. In some cases, an immune-inhibitory protein reduces or inhibits the activity of a cytotoxic T-lymphocyte (CTL). For example an immune-inhibitory protein reduces or inhibits CTL-mediated lysis of a target cell. For example, an immune-inhibitory protein is an immune checkpoint protein (e.g., CTLA4 or PD1). For example, an immune-inhibitory protein (e.g., CTLA4) competes with CD28 for binding to CD80 and/or CD86, thereby interfering with T cell activation. See, e.g., Pardoll et al. Nat. Reviews Cancer. (2012) 12:252-264, incorporated herein by reference. For example, an immune inhibitory protein (e.g., PD1, PDL1, or PDL2) inhibits a kinase or phosphatase (e.g., SHP2) involved in T cell activation. For example, an immune inhibitory protein modulates the duration of T cell-antigen presenting cell (APC) contact or T cell-target cell contact. For example, an immune-inhibitory protein (e.g., CTLA4 or PD1) enhances the immunosuppressive function of a Treg cell.

In some embodiments, the immune-inhibitory protein is cytotoxic T-lymphocyte-associated antigen 4 (CTLA4), programmed cell death protein 1 (PD1), programmed cell death protein 1 ligand (PDL1), lymphocyte activation gene 3 (LAG3), B7-H3, B7-H4, or T cell membrane protein 3 (TIM3). For example, the immune-inhibitory protein is CTLA4. In other examples, the immune-inhibitory protein is PD1.

In some cases, the device comprises an inhibitor of CTLA4 and an inhibitor of PD1. For example, the inhibitor comprises a protein, peptide, or nucleic acid, e.g., an antibody or fragment thereof. In some examples, the antibody or fragment thereof binds to CTLA4. Exemplary anti-CTLA4 antibodies or fragments thereof include Ipilimumab, Tremelimumab, or a fragment thereof. In other examples, the inhibitor binds to PD1, and the inhibitor is a protein, e.g., MDX-1106, MK3475, CT-011, AMP-224, or a fragment thereof. In some cases, the inhibitor is a PDL2-immunoglobulin (Ig) fusion protein.

In some embodiments, the inhibitor is a protein, and the inhibitor, e.g., MDX-1105, binds to PDL1.

Other exemplary inhibitors are proteins that bind to LAG3, e.g., a LAG3-Ig fusion protein, such as IMP321; or proteins that bind to B7-H3, e.g., MGA271.

The cell recruitment composition of the device recruits an immune cell. The immune cell comprises an antigen presenting cell, e.g., a dendritic cell, a macrophage, a T cell, a B cell, or a natural killer (NK) cell.

The device contains a scaffold that comprises open, interconnected macropores. The device further comprises a deployment signal capable of inducing or promoting migration of cells, where in some examples, the deployment signal comprises a protein, peptide, or nucleic acid. For example, the deployment signal comprises i) one or more factors that induces migration of cells and has or is capable of forming a gradient; ii) a nucleic acid molecule encoding a protein that induces migration of cells out of the device; or iii) depletion or diffusion of the cell recruitment composition.

Exemplary cell recruitment compositions comprise a cytokine, chemokine, or growth factor. For example, the cell recruitment composition comprises GM-CSF, Flt3L, or CCL20.

In some cases, the bioactive composition of the device comprises a target antigen composition.

In some embodiments, the cell recruitment composition recruits an immune cell to the device, where the immune cells encounters the target antigen, and where the immune cell resides until a deployment signal induces egress of the immune cell to a lymph node tissue outside of the device.

In some examples, the level of immune activation of the immune cell at egress is greater than that prior to entering the device.

For example, the immune cell is antigen-primed at egress compared to the level of priming prior to entering the device. In some cases, the immune cells recruited to the device remain resident in the device for 2 hours to 4 weeks, e.g., 2 hours to 24 hours, 2 to 6 days, or 1 to 4 weeks.

In some cases, the target antigen composition of the device comprises a cancer antigen or a cancer derived antigen. The cancer antigen, cancer derived antigen, or cancer cell is, e.g., derived from a melanoma, a central nervous system (CNS) cancer, a CNS germ cell tumor, a lung cancer, leukemia, multiple myeloma, a renal cancer, a malignant glioma, a medulloblatoma, a breast cancer, an ovarian cancer, a prostate cancer, a bladder cancer, a fibrosarcoma, a pancreatic cancer, a gastric cancer, a head and neck cancer, or a colorectal cancer. For example, a cancer cell is derived from a solid cancer or hematological cancer. The hematological cancer is, e.g., a leukemia or a lymphoma. A leukemia is acute lymphoblastic leukemia (ALL), acute myelogenous leukemia (AML), chronic lymphocytic leukemia (CLL), small lymphocytic lymphoma (SLL), chronic myelogenous leukemia (CML), or acute monocytic leukemia (AMoL). A lymphoma is follicular lymphoma, Hodgkin's lymphoma (e.g., Nodular sclerosing subtype, mixed-cellularity subtype, lymphocyte-rich subtype, or lymphocyte depleted subtype), or Non-Hodgkin's lymphoma. Exemplary solid cancers include but are not limited to melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), and lung cancer (e.g., non-small cell lung cancer).

The device is administered to a subject in need thereof. For example, the subject is a mammal, e.g., a human. The subject was previously treated with a cancer therapy (e.g., for NSCLC, metastatic melanoma, or RCC) prior to administration with a device/vaccine and/or inhibitor of the invention. For example, the subject was previously treated with an inhibitor of the invention. For example, the subject was previously treated with one or more inhibitors of the invention. For example, the subject was previously treated with an inhibitor of the invention in the absence of co-administration with a cancer vaccine (e.g., a cancer vaccine device of the invention). The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

In some cases, the device contains a cancer-derived antigen. Exemplary cancer-derived antigens are described herein. For example, a cancer-derived antigen/tumor antigen comprises an antigen that is unique to tumor cells and/or arising from a mutation, e.g., an antigen shown in Table 1. In another example, a cancer-derived antigen comprises a shared antigen, e.g., a tumor specific antigen, a differentiation antigen, and/or an overexpressed antigen, e.g., as shown in Tables 2-4. In some examples, a cancer-derived antigen comprises a peptide comprising an amino acid sequence selected from the group consisting of SEQ ID NOs: 35-434.

For example, a cancer-derived antigen is selected from the group consisting of MAGE series of antigens, MART-1/ melanA, Tyrosinase, ganglioside, gp100, GD-2, 0-acetylated GD-3, GM-2, MUC-1, Sos1, Protein kinase C-binding protein, Reverse transcriptase protein, AKAP protein, VRK1, KIAA1735, T7-1, T11-3, T11-9, *Homo Sapiens* telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen se1-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195, and Carcinoembryonic antigen (CEA).

In other cases, the bioactive composition of the device comprises a tumor lysate, e.g., comprising lysate derived from a melanoma tumor. In other cases, the bioactive composition comprises irradiated tumor cells, e.g., comprising a melanoma cell (e.g., a B16-F10 cell).

The bioactive composition can also comprise a cancer cell surface antigen, or a viral or bacterial antigen.

In some embodiments, the device further comprises an adjuvant, e.g., a CpG rich oligonucleotide, such as a condensed CpG oligonucleotide. Exemplary condensed CpG oligonucleotides include PEI-CpG.

In some examples, the scaffold further comprises an RGD-modified alginate. In other cases, the device further comprises a toll-like receptor (TLR) agonist, e.g., a TLR agonist that preferentially binds to TLR3. For example, the TLR agonist comprises a TLR3 agonist, e.g., polyinosine-polycytidylic acid (poly I:C) or PEI-poly (LC).

In some cases, the scaffold comprises a hydrogel or porous polymer, said scaffold comprising a polymer or co-polymer of polylactic acid, polyglycolic acid, PLGA, alginate, gelatin, collagen, agarose, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly (uronic acid), poly(anhydride) or poly(vinylpyrrolidone). For example, a preferred polymer is PLG or alginate.

For example, the porous polymer is produced by gas-foaming.

In some cases, the device is in the form of a bead, pellet, sheet, or disc.

The invention also features a method of killing a cancer cell in a subject in need thereof comprising administering the device described herein.

In addition, the invention provides a method of killing a cancer cell in a subject in need thereof comprising administering: a) an inhibitor of an immune-inhibitory protein; and b) a device comprising i) a scaffold composition, ii) a cell recruitment composition, and
  iii) a bioactive composition, where the bioactive composition is incorporated into or coated onto the scaffold composition, and wherein the bioactive composition causes modification of cells in or recruited to the device.

For example, the scaffold comprises open, interconnected macropores, and wherein migration of the modified cells to another site in the body is promoted by the open, interconnected macropores and by the deployment signal.

In some cases, the other site in the body is a nearby or remote tissue target.

For example, the inhibitor is present in or on the device. Alternatively, or in addition,
  the inhibitor is coated in or on the scaffold composition.

In some cases, the inhibitor is not present in or on the device, e.g., the inhibitor is not coated in or on the scaffold composition. For example, the inhibitor and the device are formulated separately.

In other cases, the inhibitor and the device are formulated together.

In some example, the inhibitor and the device are administered to the subject simultaneously. Alternatively, the inhibitor and the device are administered to the subject sequentially.

In some embodiments, the device is implanted subcutaneously into the subject. For example, the inhibitor is administered intravenously, intraperitoneally, subcutaneously, orally, intradermally, by inhalation, transmucosally, or rectally. For example, the inhibitor is administered by injection, infusion, or inhalation.

In some cases, the inhibitor is administered at a dosage of 0.01-10 mg/kg (e.g., 0.01, 0.05, 0.1, 0.5, 1, 5, or 10 mg/kg) bodyweight. For example, the inhibitor is administered in an amount of 0.01-30 mg (e.g., 0.01, 0.05, 0.1, 0.5, 1, 5, 10, 20, or 30 mg) per dose.

In some methods of the invention, the subject comprises a cancer cell, where the cancer cell is poorly immunogenic. For example, the cancer cell is resistant to cytotoxic T-lymphocyte (CTL)-mediated lysis and/or is resistant to natural killer (NK) cell mediated killing. In other examples, the subject does not comprise an autoantibody. For example, an autoantibody is an antibody produced by the immune system that is directed against one or more of an individual's own protein, e.g., regardless of whether the individual is immunized with a tumor lysate or a specific purified antigen. For example, the autoantibody is directed against a cancer cell. In some cases, the subject does not comprise an autoantibody against a cancer cell.

In some cases, the invention provides methods utilizing a combination of a cancer vaccine device with an inhibitor of an immune-inhibitory protein. For example, the inhibitor of an immune-inhibitory protein comprises an inhibitor of CTLA4 and an inhibitor of PD1. In some cases, the inhibitor of CTLA4 comprises an anti-CTLA-4 antibody and the inhibitor of PD1 comprises an anti-PD1 antibody. Preferably, intratumoral cytotoxic T cells are enhanced relative to immunosuppressive Treg cells after administration of the vaccine and antibodies. That is, the utilization of a combination of a cancer vaccine device along with an inhibitor of an immune-inhibitory protein results in the preferential generation and expansion of intratumoral effector T cells (e.g., cytotoxic T cells) as compared to immunosuppressive cells, e.g., Treg cells. For example, the methods described herein result in an intratumoral ratio of CD8(+) effector T cells to Treg cells that is at least doubled as compared to vaccination alone. In other examples, the cancer vaccine device and inhibitor of an immune-inhibitory protein results in at least a 2-fold increase in the intratumoral ratio of CD8(+) effector T cells to Treg cells, e.g., at least a 3-fold increase; at least a 4-fold incease, at least a 5-fold increase, at least a 6-fold increase, at least a 7-fold increase, at least an 8-fold increase, at least a 9-fold increase, at least a 10-fold increase, at least an 11-fold increase, at least a 12-fold increase, at least a 13-fold increase, at least a 14-fold increase, at least a 15-fold increase, at least a 16-fold increase, at least a 17-fold increase, at least an 18-fold increase, at least a 19-fold increase, or at least a 20-fold increase in the intratumoral ratio of CD8(+) effector T cells to Treg cells.

In some cases, the inhibitor of an immune-inhibitory protein is administered prior to, concurrently with, and/or subsequent to administration of the cancer vaccine device to maintain efficacy and tumor inhibition effects. Preferably, antibody treatment continues after the cancer vaccine device is administered. For example, antibody treatment continues for at least one day, e.g., for two days, for three days, for four days, for five days, for six days, for seven days, for two weeks, for three weeks, for four weeks, for two months, for six months, for seven moths, for eight months, for nine months, for ten months, for eleven months, for twelve months, for two years, for three years, for four years, or for five years or more after the cancer vaccine device is administered.

In some cases, the scaffold comprises a hydrogel or porous polymer, e.g., a polymer or co-polymer of poly (D,L-lactide-co-glycolide) (PLG).

The composition and methods of making a vaccine of the invention are described in U.S. application Ser. No. 13/741,271, Publication No. 2013-0202707, and U.S. Pat. No. 8,067,237, the contents of which are incorporated herein in their entireties.

The invention provides a device and method for stimulating immune cells, such as dendritic cells, in situ. For example, presentation of Toll-like receptor (TLR) agonists in the context of the device is used for cancer vaccination. Incorporation and presentation of the TLR agonists embedded in structural polymeric devices specifically stimulates CD8(+) dendritic cells (DCs) (corresponding to CD141+ DCs in humans) and plasmacytoid DCs, which are subsets of DCs that are critical for cancer vaccination.

Accordingly, the invention provides a device comprising a porous polymeric structure composition, a tumor antigen, and a toll-like receptor (TLR) agonist. For example, the device comprises a polymeric structure composition, a tumor antigen, and a combination of toll-like receptor (TLR) agonists, where the TLR agonist is selected from the group consisting of TLR1, TLR2, TLR3, TLR4, TLR5, TLR6, TLR7, TLR8, TLR9, TLR10, TLR11, TLR12, and TLR13. For example, the polymeric structure comprises poly (D,L-lactide-co-glycolide) (PLG). Exemplary TLR agonists include pathogen associated molecular patterns (PAMPs), e.g., an infection-mimicking composition such as a bacterially-derived immunomodulator. TLR agonists include nucleic acid or lipid compositions (e.g., monophosphoryl lipid A (MPLA)).

Certain nucleic acids function as TLR agonists, e.g., TLR1 agonists, TLR2 agonists, TLR3 agonists, TLR4 agonists, TLR5 agonists, TLR6 agonists, TLR7 agonists, TLR8 agonists, TLR9 agonists, TLR10 agonists, TLR11 agonists, TLR12 agonists, or TLR13 agonists. In one example, the TLR agonist comprises a TLR9 agonist such as a cytosine-guanosine oligonucleotide (CpG-ODN), a poly(ethylenimine) (PEI)-condensed oligonucleotide (ODN) such as PEI-CpG-ODN, or double stranded deoxyribonucleic acid (DNA). TLR9 agonists are useful to stimulate plasmacytoid DCs. For example, the device comprises 5 µg, 10 µg, 25 µg, 50 µg, 100 µg, 250 µg, or 500 µg of CpG-ODN.

In another example, the TLR agonist comprises a TLR3 agonist such as polyinosine-polycytidylic acid (poly I:C), PEI-poly (I:C), polyadenylicpolyuridylic acid (poly (A:U)), PEI-poly (A:U), or double stranded ribonucleic acid (RNA).

TLR3 agonists are useful to stimulate CD8+ DCs in mice and CD141+ DCs in humans. A plurality of TLR agonists, e.g., a TLR3 agonist such as poly I:C and a TLR9 agonist such as CpG act in synergy to activate an anti-tumor immune response. For example, the device comprises a TLR3 agonist such as poly (I:C) and the TLR9 agonist (CpG-ODN) or a PEI-CpG-ODN. Preferably, the TLR agonist comprises the TLR3 agonist, poly (I:C) and the TLR9 agonist, CpG-ODN. The combination of poly (I:C) and CpG-ODN act synergistically as compared to the vaccines incorporating CpG-ODN or P(I:C) alone.

In some cases, the TLR agonist comprises a TLR4 agonist selected from the group consisting of lipopolysaccharide (LPS), monophosphoryl lipid A (MPLA), a heat shock protein, fibrinogen, heparin sulfate or a fragment thereof, hyaluronic acid or a fragment thereof, nickel, an opoid, α1-acid glycoprotein (ACP), RC-529, murine β-defensin 2, and complete Freund's adjuvant (CFA). In other cases, the TLR agonist comprises a TLR5 agonist, wherein the TLR5 agonist is flagellin. Other suitable TLR agonists include TRL7 agonists selected from the group consisting of single-stranded RNA, guanosine analogs, imidazoginolines, and loxorbine.

Preferably, the TLR agonist is present at a concentration effective to induce the local production of interleukin-12 (IL-12) by dendritic cells.

In some embodiments, the device contains an immunogenic factor/infection-mimicking composition, e.g., a toll-like receptor ligand, a CpG-ODN sequence or derivative thereof, a tumor antigen, a growth factor, a heat-shock protein, a product of cell death, or a cytokine.

The invention also provides a device comprising a porous polymeric structure composition, a disease-associated antigen, and a toll-like receptor (TLR) agonist, wherein the TLR agonist preferentially binds to TLR3. In some cases, the polymeric structure composition comprises poly-lactide-co-glycolide (PLG). The TLR3 agonist is present in an amount to preferentially stimulate CD8+ dendritic cells or CD141+ dendritic cells.

Preferably, the TLR agonist comprises a TLR3 agonist. In some cases, the TLR3 agonist comprises polyinosine-polycytidylic acid (poly I:C) or PEI-poly (I:C). For example, the TLR agonist comprises a nucleic acid. In other cases, the TLR agonist further comprises a TLR9 agonist. For example, the TLR9 agonist comprises a cytosine-guanosine oligonucleotide (CpG-ODN) or a PEI-CpG-ODN. Optionally, the device comprises a combination of TLR agonists, the combination comprising a TLR3 agonist and a TLR9 agonist. For example, the TLR3 agonist comprises poly (I:C) and the TLR9 agonist comprises CpG-ODN.

Alternatively, the device comprises a combination of TLR agonists, the combination comprising a TLR3 agonist and a TLR4 agonist. For example, the TLR3 agonist comprises poly (I:C) and the TLR4 agonist comprises MPLA.

Optionally, the device further comprises a recruitment composition. Exemplary recruitment compositions include granulocyte macrophage colony stimulating factor (GM-CSF), Flt3L, and CCL20. For example, the recruitment composition comprises encapsulated GM-CSF.

In some cases, the disease-associated antigen comprises a tumor antigen. For example, the tumor antigen comprises a tumor lysate, purified protein tumor antigen, or synthesized tumor antigen.

Optionally, the TLR agonist further comprises pathogen associated molecular patterns (PAMPs). For example, the PAMP comprises a monophosphoryl lipid A (MPLA).

Also provided is a device comprising a polymeric structure composition, a tumor antigen, and a combination of TLR agonists, wherein the TLR agonist is selected from the group consisting of TLR1, TLR2, TLR3, TLR4, TLR5, TLR6, TLR7, TLR8, TLR9, TLR10, TLR11, TLR12, and TLR13.

A method for eliciting an anti-tumor immune response is carried out by contacting or implanting into a subject a device comprising a polymeric structure composition, a tumor antigen, and a TLR agonist, wherein the TLR agonist preferentially binds to TLR3. For example, the TLR agonist comprises a TLR3 agonist. Alternatively, the TLR agonist comprises a TLR3 agonist and a TLR9 agonist.

Preferably, the anti-tumor immune response comprises activation of a CD8+ dendritic cell or a CD141+ dendritic cell. In some cases, the anti-tumor immune response comprises activation of a plasmacytoid dendritic cell or a CD141+ dendritic cell. Alternatively, the anti-tumor immune response comprises a reduction in tumor burden.

Preferably, the TLR agonist is present at a concentration effective to induce production of interleukin-12 (IL-12) by dendritic cells.

Optionally, the device further comprises granulocyte macrophage colony stimulating factor (GM-CSF). In some examples, the GM-CSF is encapsulated. Another optional recruitment composition is a cytokine. For example, the device comprises 1 µg, 3 µg, 5 µg, 10 µg, 25 µg, or 50 µg of GM-CSF.

The device also contains a tumor antigen, e.g., in the form of a tumor lysate (cultured cells or patient-derived primary cells) or purified tumor antigen such as a chemically synthesized/synthetic protein, a recombinant (e.g., biochemically-purified) protein/antigen (e.g., purified from a tumor cell). In some cases, the recombinant protein/antigen is made in a prokaryotic cell. In other cases, the recombinant protein/antigen is made in a eukaryotic (e.g., mammalian) cell.

Also with in the invention is a method for eliciting an anti-tumor immune response by contacting a subject, e.g., implanting into a subject, a device comprising a porous polymeric structure composition, a tumor antigen, and a TLR agonist. For example, the TLR agonist is selected from the group consisting of TLR1, TLR2, TLR3, TLR4, TLR5, TLR6, TLR7, TLR8, TLR9, TLR10, TLR11, TLR12, and TLR13. The device described above is associated with advantages over earlier vaccines. The most significant advantage is its ability to stimulate critical subsets of DCs that mediate potent anti-tumor activity. The method involves administering to a subject a device that contains a TLR3 agonist and/or a TLR9 agonist, which leads to elicitation of an anti-tumor immune response characterized by activation of plasmacytoid DCs and/or CD141+ DCs in the subject to which the vaccine was administered. The vaccine is useful for prophylaxis as well as therapy.

The device is administered, e.g., topically applied or implanted, and is present over a period of time, e.g., indwelling, while constantly recruiting, educating, and dispersing or sending cells forth to lymph nodes or sites of disease or infection in the body. Improvements over existing devices include long term, ongoing activation of cells that enter the device and concomitant long term, ongoing egress of immunologically activated, e.g., antigen primed cells. The device includes a scaffold composition, a recruitment composition, and a deployment composition. The deployment composition that mediates prolonged and continuous egress of primed cells is an infection-mimicking composition such as a bacterially-derived immunomodulator. In preferred embodiments, the bacterially-derived immunomodulator is a nucleic acid such as a cytosine-guanosine oligonucleotide (CpG-ODN).

The methods are used to treat a wide variety of diseases and to develop vaccines against a wide variety of antigens. In a preferred embodiment, the invention is used to develop a cancer vaccine. Another preferred embodiment of the invention comprises an infection-mimicking microenvironment with means to activate the host immune system and subsequently induce an immune response. The use of a synthetic cytosine-guanosine oligodeoxynucleotide (CpG-ODN) sequence with exogenous granulocyte macrophage colony stimulating factor (GM-CSF) provides a method for controlling dendritic cell migration and modulating antigen-specific immune responses. The approach of using of this synthetic cytosine-gyanosine oligonucleotide (CpG-ODN) sequence and/or poly (LC), e.g., condensed oligonucleotides (e.g., PEI-CpG-ODN, or PEI-poly (LC)), demonstrates significant improvements over earlier immune therapies. See, e.g., US 2012-0100182, e.g., at page 14, [0106]-page 15, [0110]; and page 24, [0176], incorporated herein by reference.

Devices perform three primary functions, e.g. attracting cells to the device, presenting an immunogenic factor, and inducing cell migration away from the device, e.g., to drain lymph nodes where activated immune cells exert their anti-tumor actions. Each of these primary functions are performed by the scaffold and/or biological composition(s). Various combinations of either the scaffold or biological composition achieve at least one primary function in exemplary devices. For example, the scaffold composition performs each of the three primary functions in some devices. In an alternative example, the scaffold composition performs one primary function, e.g. attracts cells to the device (preferably, dendritic cells), whereas the biological composition performs two primary functions, e.g. presents an immunogenic factor and induces cells (preferably, dendritic cells) to migrate away from the device, while some devices, for instance, are the inverse combination. Exemplary secondary functions of the scaffold and/or biological compositions include, but are not limited to, targeting the device to a particular cell or tissue type, adhering/releasing the device to/from the surface of one or more cells or tissues, and modulating the stability/degradation of the device.

The invention comprises a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition. Alternatively the bioactive composition incorporated into or coated onto the scaffold composition attracts a dendritic cell, introduces an immunogenic factor into the dendritic cell thereby activating the dendritic cell, and induces the dendritic cell to migrate away from the scaffold composition. In other preferred embodiments, the scaffold composition or bioactive composition separately attract a dendritic cell to the device, introduce an immunogenic factor into the dendritic cell, and induce the dendritic cell to migrate away from the device.

DCs include conventional DCs as well as specific subsets of DCs. The TLR agonists, e.g., TLR3 agonists, preferentially attract and stimulate CD141+ DCs in the human (CD8+ DCs in the mouse). The TLR9 agonist, e.g., CpG, preferentially attract and stimulate plasmacytoid DCs.

In preferred embodiments, the recruitment composition is GM-CSF, e.g., encapsulated GM-CSF. The device temporally controls local GM-CSF concentration, thereby controlling recruitment, residence, and subsequent dispersement/deployment of immune cells to lymph nodes or tissue sites distant from location of the device, e.g., sites of infection or tumor location. The concentration of GM-CSF determines whether if functions as a recruitment element or a deployment element. Accordingly, a method of programming dendritic cells in situ is carried out by introducing to a subject a device comprising scaffold composition and encapsulated recruitment composition. A pulse of recruitment composition is released from the device within 1-7 days of introduction of the device, leaving a residual amount of the recruitment composition in or on the device. The pulse is followed by slow release of the residual amount over several weeks. The local concentration of the recruitment composition and the temporal pattern of release mediates recruitment, retention, and subsequent release of dendritic cells from the device. For example, the pulse comprises at least 50, 60, 75, 90, or 95% of the amount of the recruitment composition associated with the device. An exemplary temporal release profile comprises a pulse characterized by release of at least 60% of the amount of the recruitment composition associated with the device in 1-5 days following the introduction of the device to a subject. Following the pulse, the residual amount is slowly released over an extended period of time (e.g., 1, 2, 3, 4, 5, 6, 7, 8, 9, 10, 12 days or 2, 3, 4, 5 or more weeks) following the pulse period. Other recruitment compositions include Flt3L and/or CCL20. The recruitment compounds are used individually or in combination.

The method of making a scaffold is earned out by providing a scaffold composition, incorporating into or coating onto the scaffold composition a first bioactive composition comprising polypeptides with means for attracting or repelling a dendritic cell, and contacting the scaffold composition with a second bioactive composition, wherein the second bioactive composition is covalently or non-covalently associated with the scaffold composition wherein the second bioactive composition comprises a immunogenic factor. In an alternate embodiment of this method, the linking and contacting steps are repeated to yield a plurality of layers, wherein the second bioactive composition comprises a combination of compounds with means to activate a dendritic cell.

Methods comprise continuous in situ dendritic cell programming, comprising administering to a subject, a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition. The devices recruit and stimulate a heterogeneous population of dendritic cells. Each subset is specialized and contributes significantly to the generation of an immune response. For example, the device mediates CpG-ODN presentation and enrichment of a subset of dendritic cells, plasmacytoid DC (pDC), or CD141+ DCs, which are particularly important in development of anti-tumor immunity.

Methods comprise increasing vaccine efficacy, comprising administering to a subject, a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition, thereby increasing the effectiveness of a vaccination procedure.

Methods comprise vaccinating a subject against cancer, comprising administering to a subject, a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition, thereby conferring upon a subject anti-tumor immunity, e.g., IL-12 production, and reduced tumor burden. In the case of a localized or solid tumor, the device is administered or implanted at or near the tumor site or site from which the tumor was excised or surgically removed. For example, the device is implanted at a distance of 1, 3, 5, 10, 15, 20, 25, 40 mm from a tumor site or site of excision, e.g., the PLG vaccine device is administered 16-21 mm away from a tumor mass.

Immunogenic factors include TLR ligands. For example, the immunogenic factor used is a modified TLR-9 ligand sequence, PEI-CpG-ODN. Preferably, the TLR ligand is a TLR3 agonist such as poly (I:C) or condensed PEI-poly (I:C).

Scaffold compositions comprise a non-biodegradable material. Exemplary non-biodegradable materials include, but are not limited to, metal, plastic polymer, or silk polymer. Moreover, scaffold compositions are composed of a biocompatible material. This biocompatible material is non-toxic or non-immunogenic.

Bioactive compositions are covalently or non-covalently linked to the scaffold composition. Bioactive compositions comprise an element, either covalently or non-covalently bonded to the surface of the scaffold composition, with means to attract a dendritic cell. Alternatively, or in addition, bioactive compositions comprise an element, either covalently or non-covalently bonded to the surface of the scaffold composition, with means to introduce an immunogenic factor into a dendritic cell. Alternatively, or further in addition, bioactive compositions comprises an element, either covalently or non-covalently bonded to the surface of the scaffold composition, with means to induce a dendritic cell to migrate away from the scaffold composition.

The element of the bioactive composition with means to manipulate a dendritic cell is a secreted or membrane-bound amino acid, peptide, polypeptide, protein, nucleotide, dinucleotide, oligonucleotide, polynucleotide, polymer, small molecule or compound. In a preferred embodiment, this element is granulocyte macrophage colony stimulating factor (GM-CSF), because this element attracts dendritic cells to the scaffold composition. In another preferred embodiment, this element is a PEI-CpG-ODN sequence because this element has means to introduce CpG-ODN sequences into a dendritic cell thereby activating the cell. In some embodiments, this element is a polynucleotide or polypeptide encoding for CCR7, a chemokine receptor that mediates dendritic cell migration towards lymph nodes and away from the scaffold composition. The CCR7 element is introduced into a dendritic cell simultaneously or sequentially with PEI-CpG-ODN sequences to enhance dendritic cell migration away from the scaffold composition.

Scaffold compositions of the present invention contain an external surface. Scaffold compositions of the present invention alternatively, or in addition, contain an internal surface. External or internal surfaces of the scaffold compositions are solid or porous. Pore size is less than about 10 nm, in the range of about 100 nm-20 μm in diameter, or greater than about 20 μm, e.g., up to and including 1000 μm. In preferred embodiments, the size of the pores allows the migration into and subsequent exit of cells such as DCs from the device. For example, the pores are nanoporous, microporous, or macroporous. For example, the diameter of nanopores are less than about 10 nm; micropore are in the range of about 100 μm-20 μm in diameter; and, macropores are greater than about 20 μm (preferably greater than about 100 μm and even more preferably greater than about 400 μm, e.g., greater than 600 μm or greater than 800 μm). In one example, the scaffold is macroporous with open, interconnected pores of about 100-500 μm in diameter, e.g., 100-200, 200-400, or 400-500 μm. The size of the pores and the interconnected architecture allows the cells to enter, traverse within the volume of the device via the interconnected pores, and then leave the device via the pores to go to locations in the body outside of the device, e.g. to a tumor site, where an immune response is mounted against tumor cells. The activated DCs migrate away from the device and mount an immune response to solid tumors at discrete locations or throughout the body in the case of metastatic tumor cells or blood tumors such as leukemias.

Scaffold compositions of the present invention comprise one or more compartments.

Devices of the present invention are administered or implanted orally, systemically, sub- or trans-cunataneously, as an arterial stent, or surgically.

The devices and methods of the invention provide a solution to several problems associated with protocols for continuous cell programming in situ. In situ cell programming systems that stimulate immune responses of the cells and induce their outward migration to populate infected or diseased bodily tissues enhance the success of recovery, e.g., the specific elimination of diseased tissue. Such a device that controls cell function and/or behavior, e.g., locomotion, contains a scaffold composition and one or more bioactive compositions. The bioactive composition is incorporated into or coated onto the scaffold composition. The scaffold composition and/or bioactive composition temporally and spatially (directionally) controls dendritic cell attraction, programming, and migration.

The devices mediate active recruitment, modification, and release of host cells from the material in vivo, thereby improving the function of cells that have contacted the scaffold. For example, the device attracts or recruits cells already resident in the body to the scaffold material, and programs or reprograms the resident cells to a desired fate (e g, immune activation).

This device includes a scaffold composition which incorporates or is coated with a bioactive composition; the device regulates attraction, activation, and migration of dendritic cells. Depending on the application for which the device is designed, the device regulates attraction, activation, and/or migration of dendritic cells through the physical or chemical characteristics of the scaffold itself. For example, the scaffold composition is differentially permeable, allowing cell migration only in certain physical areas of the scaffold. The permeability of the scaffold composition is regulated, for example, by selecting or engineering a material for greater or smaller pore size, density, polymer cross-linking, stiffness, toughness, ductility, or viscoelascticity. The scaffold composition contains physical channels or paths through which cells can move more easily towards a targeted area of egress of the device or of a compartment within the device. The scaffold composition is optionally organized into compartments or layers, each with a different permeability, so that the time required for a cell to move through the device is precisely and predictably controlled. Migration is also regulated by the degradation, de- or re-hydration, oxygenation, chemical or pH alteration, or ongoing self-assembly of the scaffold composition.

Attraction, activation, and/or migration are regulated by a bioactive composition. The device controls and directs the activation and migration of cells through its structure. Chemical affinities are used to channel cells towards a specific area of egress. For example, cytokines are used to attract or retard the migration of cells. By varying the density and mixture of those bioactive substances, the device controls the timing of the migration. The density and mixture of these bioactive substances is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/excretion of compositions by resident support cells. The physical or chemical structure of the scaffold also regulates the diffusion of bioactive agents through the device.

The bioactive composition includes one or more compounds that regulate cell function and/or behavior. The bioactive composition is covalently linked to the scaffold composition or non-covalently associated with the scaffold.

Signal transduction events that participate in the process of cell migration are initiated in response to immune mediators. Thus, the device optionally contains a second bioactive composition that comprises GM-CSF, a CpG-ODN or poly (LC) sequence, a cancer antigen, and/or an immunomodulator.

In some cases, the second bioactive composition is covalently linked to the scaffold composition, keeping the composition relatively immobilized in or on the scaffold composition. In other cases, the second bioactive composition is noncovalently associated with the scaffold. Noncovalent bonds are generally one to three orders of magnitude weaker than covalent bonds permitting diffusion of the factor out of the scaffold and into surrounding tissues. Noncovalent bonds include electrostatic, hydrogen, van der Waals, π aromatic, and hydrophobic.

The scaffold composition is biocompatible. The composition is bio-degradable/erodable or resistant to breakdown in the body. Relatively permanent (degradation resistant) scaffold compositions include metals and some polymers such as silk. Preferably, the scaffold composition degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

Exemplary scaffold compositions include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly (uronic acids), poly(vinylpyrrolidone) and copolymers or graft copolymers of any of the above. One preferred scaffold composition includes an RGD-modified alginate. In other examples, the scaffold composition includes crosslinked polymers, e.g., crosslinked alginates, gelatins, or derivatives thereof, such as those that are methacrylated.

Another preferred scaffold composition a macroporous poly-lactide-co-glycolide (PLG). For example, the PLG matrix includes GM-CSF, danger signals, and a target antigen, e.g., a cancer antigen and serves as a residence for recruited DCs as they are programmed. The recruitment element, GM-CSF, is encapsulated into the PLG scaffolds. PLG matrices that comprise the encapsulated GM-CSF provide a pulse of the dendritic cell recruitment composition and then a gradual slower rate of release. The pulse comprises at least 40, 50, 60, 75, 80% or more of the initial amount of bioactive composition with the remaining percent being released gradually over then next days or weeks after administration to the site in or on the subject to be treated. For example, release is approximately 60% of bioactive GM-CSF load within the first 5 days, followed by slow and sustained release of bioactive GM-CSF over the next 10 days. This release profile mediates a rate of diffusion of the factor through the surrounding tissue to effectively recruit resident DCs.

Porosity of the scaffold composition influences migration of the cells through the device. Pores are nanoporous, microporous, or macroporous. For example, the diameter of nanopores are less than about 10 nm; micropore are in the range of about 100 nm-20 μm in diameter; and, macropores are greater than about 20 μm (preferably greater than about 100 μm and even more preferably greater than about 400 μm). In other examples, the pore size ranges from less than 10 nm to about 1000 μm. In some cases, the average pore size ranges from about 250 μm to about 500 μm. In some cases, the porous architecture is random or aligned. In one example, the scaffold is macroporous with aligned pores of about 400-500 μm in diameter.

A method of making a scaffold is carried out by providing a scaffold composition and covalently linking or noncovalently associating the scaffold composition with a first bioactive composition. Exemplary devices and methods of making them are described in US 2012/0100182, PCT/US2010/057630, and PCT/US2012/35505, each of which is hereby incorporated by reference. The first bioactive composition preferably contains granulocyte macrophage colony stimulating factor. The scaffold composition is also contacted with a second bioactive composition, preferably one or more cytosine-guanosine oligonucleotide (CpG-ODN) sequences. The second bioactive composition is associated with the scaffold composition to yield a doped scaffold, i.e., a scaffold composition that includes one or more bioactive substances. The contacting steps are optionally repeated to yield a plurality of doped scaffolds, e.g., each of the contacting steps is characterized by a different amount of the second bioactive composition to yield a gradient of the second bioactive composition in the scaffold device. Rather than altering the amount of composition, subsequent contacting steps involve a different bioactive composition, i.e., a third, fourth, fifth, sixth . . . , composition or mixture of compositions, that is distinguished from the prior compositions or mixtures of prior doping steps by the structure or chemical formula of the factor(s). The method optionally involves adhering individual niches, layers, or components to one another and/or insertion of semi-permeable, permeable, or nonpermeable membranes within or at one or more boundaries of the device to further control/regulate locomotion of cells or bioactive compositions.

Therapeutic applications of the device include the instruction of immune cells. For example, the method includes the steps of providing a device that includes scaffold composition with a bioactive composition incorporated therein or thereon and a mammalian cell bound to the scaffold and contacting a mammalian tissue with the device, e.g., by implanting or affixing the device into or onto a mammalian tissue. At the time of administering or implanting the device, exemplary relative amounts of each component, recruiting composition (e.g., GM-CSF, Flt3L, or CCL20), danger signal (e.g., CpG-ODN), and antigen (e.g., purified tumor antigen or tumor cell lysate) are as follows: GM-CSF: 0.5 µg-500 µg; CpG-ODN: 50 µg-3,000 µg; and Tumor antigen/lysate: 100 µg-10,000 µg.

A method of modulating an activity of a cell, e.g., a host cell, is carried out by administering to a mammal a device containing a scaffold composition and a recruitment composition incorporated therein or thereon, and then contacting the cell with a deployment signal. The cells leave the device after encountering antigen (and other factors) and thus being activated to seek out tumor cells in the body to which an immune response is mounted. The activity of the cell at egress differs from that prior to entering the device. Cells are recruited into the device and remain resident in the device for a period of time, e.g., minutes; 0.2, 0.5, 1, 2, 4, 6, 12, 24 hours; 2, 4, 6, days; weeks (1-4), months (2, 4, 6, 8, 10, 12) or years, during which the cells are exposed to structural elements and bioactive compositions that lead to a change in the activity or level of activity of the cells. Encountering the antigen and other compounds in the device induces egress of the altered (re-educated or reprogrammed) cells, and the cells migrate out of the device and into surrounding tissues or remote target locations to seek out and mediate immunity against diseased cells such as tumor cells.

The deployment signal is a composition such as protein, peptide, or nucleic acid or a state of activation of the cell. For example, having ingested antigen, DCs become activated and migrate to lymph nodes, the spleen, and other anatomical locations, where they meet up with T cells to further propagate an antigen-specific immune response, e.g., anti-cancer response. For example, cells migrating into the device only encounter the deployment signal once they have entered the device. In some cases, the deployment signal is a nucleic acid molecule, e.g., a plasmid containing sequence encoding a protein that induces migration of the cell out of the device and into surrounding tissues. The deployment signal occurs when the cell encounters the plasmid in the device, the DNA becomes internalized in the cell (i.e., the cell is transfected), and the cell manufactures the gene product encoded by the DNA. In some cases, the molecule that signals deployment is an element of the device and is released from the device in delayed manner (e.g., temporally or spatially) relative to exposure of the cell to the recruitment composition. Alternatively, the deployment signal is a reduction in or absence of the recruitment composition. For example, a recruitment composition induces migration of cells into the device, and a reduction in the concentration or depletion, dissipation, or diffusion of the recruitment composition from the device results in egress of cells out of the device. In this manner, immune cells such as T cells, B cells, or dendritic cells (DCs) of an individual are recruited into the device, primed and activated to mount an immune response against an antigen-specific target. Optionally, an antigen corresponding to a target to which an immune response is desired is incorporated into or onto the scaffold structure. Cytokines, such as granulocyte macrophage colony stimulating factor (GM-CSF) are also a component of the device to amplify immune activation and/or induce migration of the primed cells to lymph nodes. Other cell specific recruitment compositions are described below.

The device recruit cells in vivo, modifies these cells, and then promotes their migration to another site in the body. This approach is exemplified herein in the context of dendritic cells and cancer vaccine development but is also useful to other vaccines such as those against microbial pathogens as well as cell therapies in general. Cells educated using the devices described herein promote regeneration of a tissue or organ immediately adjacent to the material, or at some distant site. Alternatively, the cells are educated to promote destruction of a tissue (locally or at a distant site). The methods are also useful for disease prevention, e.g., to promote cell-based maintenance of tissue structure and function to stop or retard disease progression or age-related tissue changes. The education of cells within the device, "programming" and "reprogramming" permits modification of the function or activity of any cell in the body to become a multipotent stem cell again and exert therapeutic effects.

The inability of traditional and ex vivo DC-based vaccination strategies to coordinate and sustain an immune response mediated by the heterogeneous DC network in cancer patients has led to limited clinical effectiveness of these approaches. The devices and methods described herein have distinct advantages, because preferential recruitment and expansion of pDCs dramatically improves immune responses to cancer antigens and reduces tumor progression compared to previous vaccine approaches.

Described herein is a material-based (e.g., PLG) vaccine which has been optimized, e.g., to control the presentation of GM-CSF and adjuvants, relative to other vaccine formulations in order to enhance T effector activity and downregulate Treg cells and other immunosuppressive mechanisms that may be induced by some adjuvants. The material-based vaccine represents a significant advantage over previous vaccine systems in that it creates a tumor and vaccine microenvironment that responds to an immune-inhibitory protein, e.g., anti-CTLA-4, by preferentially enhancing effector T cell generation and expansion over Treg cells.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques.

Similarly, "conservative amino acid substitutions," in one or a few amino acids in an amino acid sequence are substituted with different amino acids with highly similar properties are also readily identified as being highly similar to a particular amino acid sequence, or to a particular nucleic acid sequence which encodes an amino acid. Such conservatively substituted variations of any particular sequence are a feature of the present invention. Individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. See, e.g., Creighton (1984) Proteins, W.H. Freeman and Company, incorporated herein by reference.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to reduce or prevent cancer in a mammal Ultimately, the attending physician or veterinarian decides the appropriate amount and dosage regimen.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

BRIEF DESCRIPTION OF THE DRAWINGS

FIG. 9A is a bar graph showing the size of B16 melanoma tumors in mice treated with vaccine alone (V), or vaccine in combination with anti-PD-1 (+P), anti-CTLA4 (+C) or both anti-PD-1 and anti-CTLA4 (+P+C) at 35 days after inoculation of $10^5$ tumor cells. FIG. 9B is a bar graph that shows the numbers of CD8(+) T cells and FIG. 9C is a bar graph that shows the numbers of FoxP3(+) Tregs isolated from B16 tumors in mice treated with vaccine alone (V), or vaccine in combination with anti-PD-1 (+P), anti-CTLA4 (+C) or both anti-PD-1 and anti-CTLA4 (+P+C) at 35 days after inoculation of $10^5$ tumor cells. FIG. 9D is a bar graph that shows the CD8(+) T cell and FoxP3(+) Treg ratio in B16 tumors in mice treated with vaccine alone (V), or vaccine in combination with anti-PD-1 (+P), anti-CTLA4 (+C) or both anti-PD-1 and anti-CTLA4 (+P+C) at 35 days after inoculation of $10^5$ tumor cells. Values in B (n=8), C &D (n=5) represent mean and standard deviation. * P<0.05 ** P<0.01 as compared to other experimental conditions as noted.

FIG. 10A-FIG. 10E is a series of bar charts and a dot plot showing that PLG vaccine in combination with blockade antibodies enhances intratumoral T effector cell activity. FIG. 10A is a bar chart that shows the total number of CD3(+)CD8(+) T cells isolated from the B16 tumors of untreated mice (Control) and mice treated with PLG vaccines alone (Vax) or in combination with anti-PD-1 (+PD-1) and anti-CTLA-4 (+CTLA4) antibodies. FIG. 10B is a bar chart that shows the total number of CD3(+)FoxP3(+) T regulatory cells isolated from the B16 tumors of untreated mice (Control) and mice treated with PLG vaccines alone (Vax) or in combination with anti-PD-1 (+PD-1) and anti- CTLA-4 (+CTLA4) antibodies. FIG. 10C is a bar chart that shows the ratio of CD3(+)CD8(+) T cells to CD3(+)FoxP3 (+) T regulatory cells isolated from the B16 tumors of untreated mice (Control) and mice treated with PLG vaccines alone (Vax) or in combination with anti-PD-1 (+PD-1) and anti-CTLA-4 (+CTLA-4) antibodies. FIG. 10D is a series of FACS plots representing tumor infiltrating leukocytes in tumors of untreated mice (Control) and mice treated with PLG vaccines alone (Vax) or in combination with anti-PD-1 (+PD-1) and anti-CTLA-4 (+CTLA4) antibodies. Single cell suspensions were prepared from tumors at Day 18 and stained for activated, cytotoxic Tcell markers, CD8 (+) and CD107a. Numbers in FACS plots indicate the percentage of the cell population positive for both markers. FIG. 10E is a bar chart showing the numbers of CD8(+), tumor-infiltrating T cells positive for either IFNγ or CD107a in blank matrices (Control), PLG vaccines alone or vaccines in combination with anti-PD-1 and anti-CTLA-4. Values in A, B, C &D (n=5) represent mean and standard deviation. * P<0.05 ** P<0.01 as compared to the vaccine alone (V vs V+P; V vs V+C) unless otherwise noted.

DETAILED DESCRIPTION OF THE INVENTION

Prior to the invention, cancer vaccines typically depended on cumbersome and expensive manipulation of cells in the laboratory, and subsequent cell transplantation resulted in poor lymph node homing and limited efficacy. In terms of cancer treatment, many existing therapies become ineffective because cancers can co-opt immune checkpoint pathways to evade the endogenous immune response. Although agents have been identified and are used to prevent or minimize this ability of cancer cells to evade the immune system, these agents lack efficacy in poorly immunogenic tumors. The invention solves these problems by using materials for cancer vaccination that mimic key aspects of bacterial infection to directly control immune cell trafficking and activation in the body. The invention further combines these cancer vaccines with inhibitors of immune-inhibitory proteins (e g, immune checkpoint proteins), thereby enabling an endogenous immune response strong enough to eliminate tumors or minimize their progression. Also, the cancer vaccines work synergistically with the inhibitors of the immune-inhibitory proteins to lower the dosage of inhibitor required for efficacy in treating cancer compared to the dosage required when the inhibitor is used as a single agent.

Figure 1A:
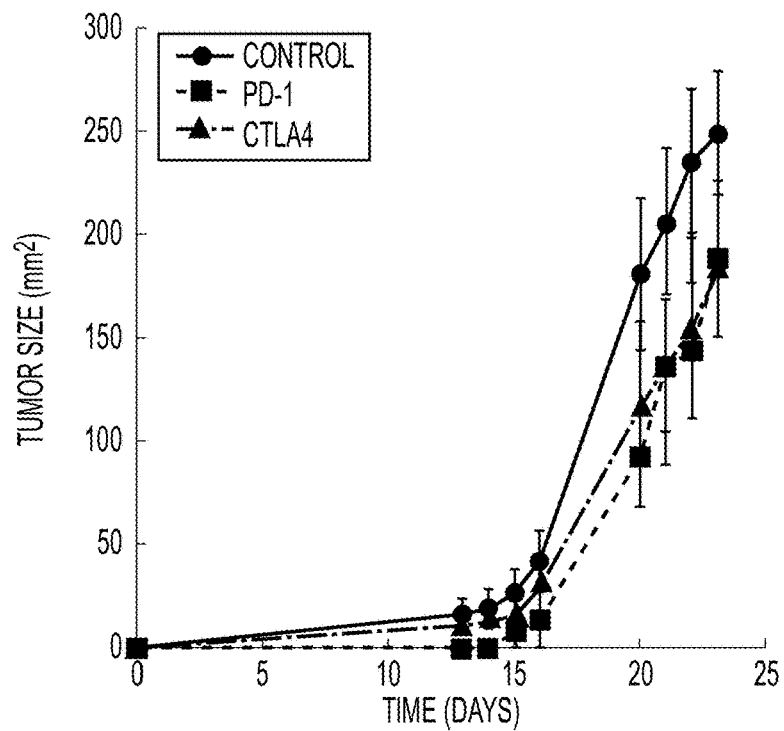
FIG. 1A is a graph of tumor size in melanoma tumor-bearing mice after several days with or without treatment with anti-PD1 or anti-CTLA4 antibodies. Values represent means and standard deviations (n=10).
Figure 1B:
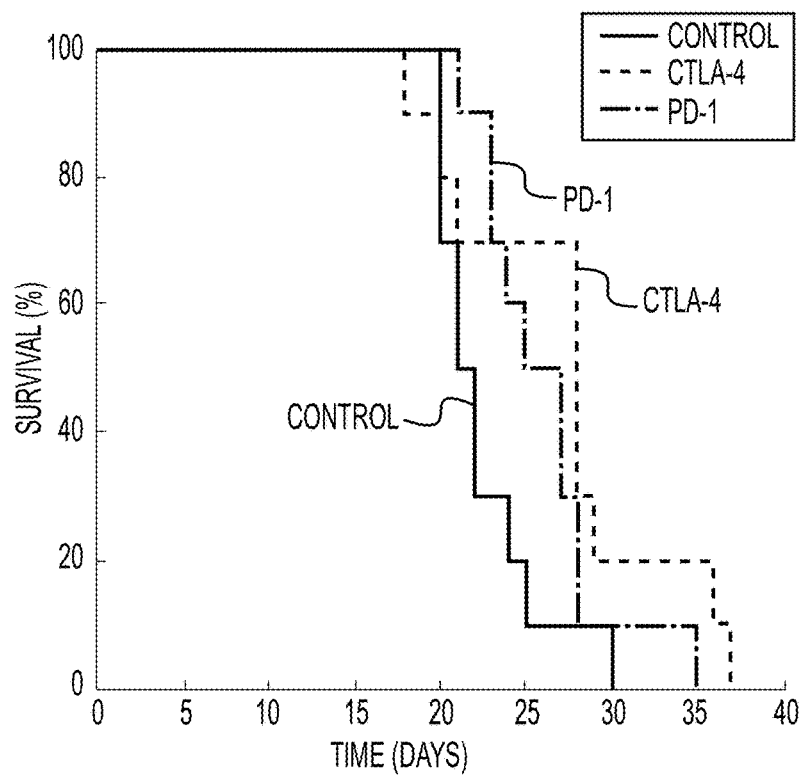
FIG. 1B is a Kaplar Meier survival curve showing the survival time of melanoma tumor-bearing mice with or without treatment with anti-PD1 or anti-CTLA4 antibodies.
Figure 5A:
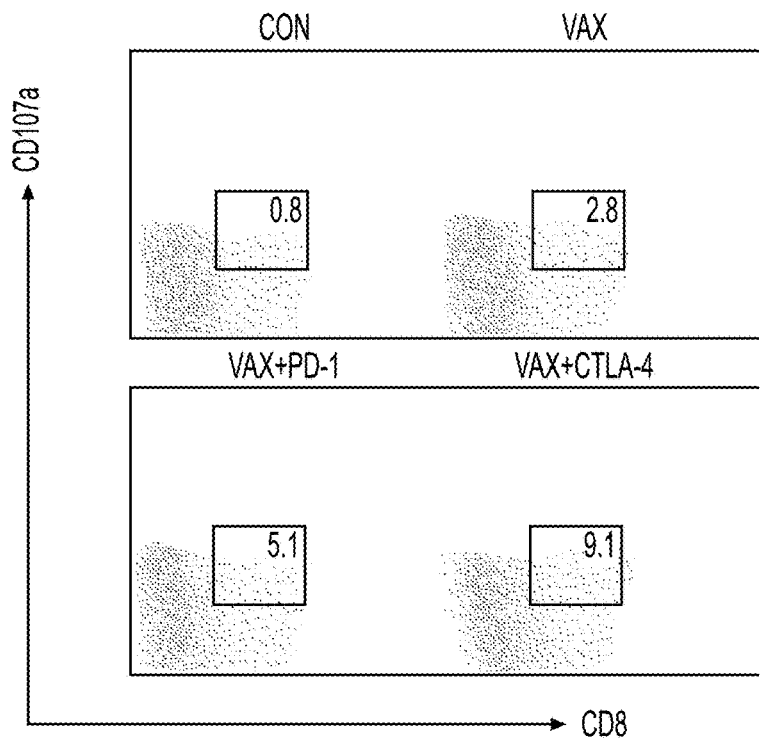
FIG. 5A is a set of flow cytometric scatterplots showing the percentage of the cell population isolated from the scaffolds that were positive for CD8 and CD107a in the four treatment groups.
Figure 5B:
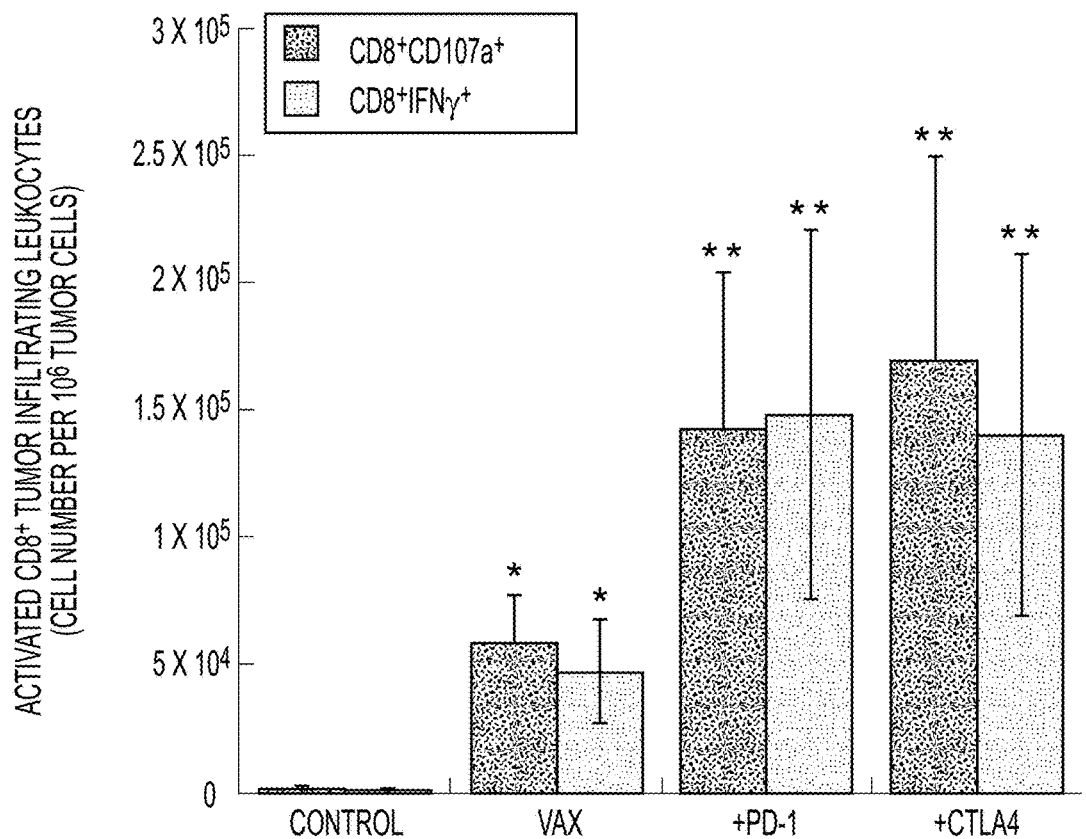
FIG. 5B is a bar graph showing the fold increase in number of activated CD8, scaffold-infiltrating T cells that were positive for CD107a and IFNγ in the four treatment groups. Values (n=5) represent mean and standard deviation. * P<0.05 ** P<0.01 as compared to all other experimental conditions unless otherwise noted.
Figure 6A:
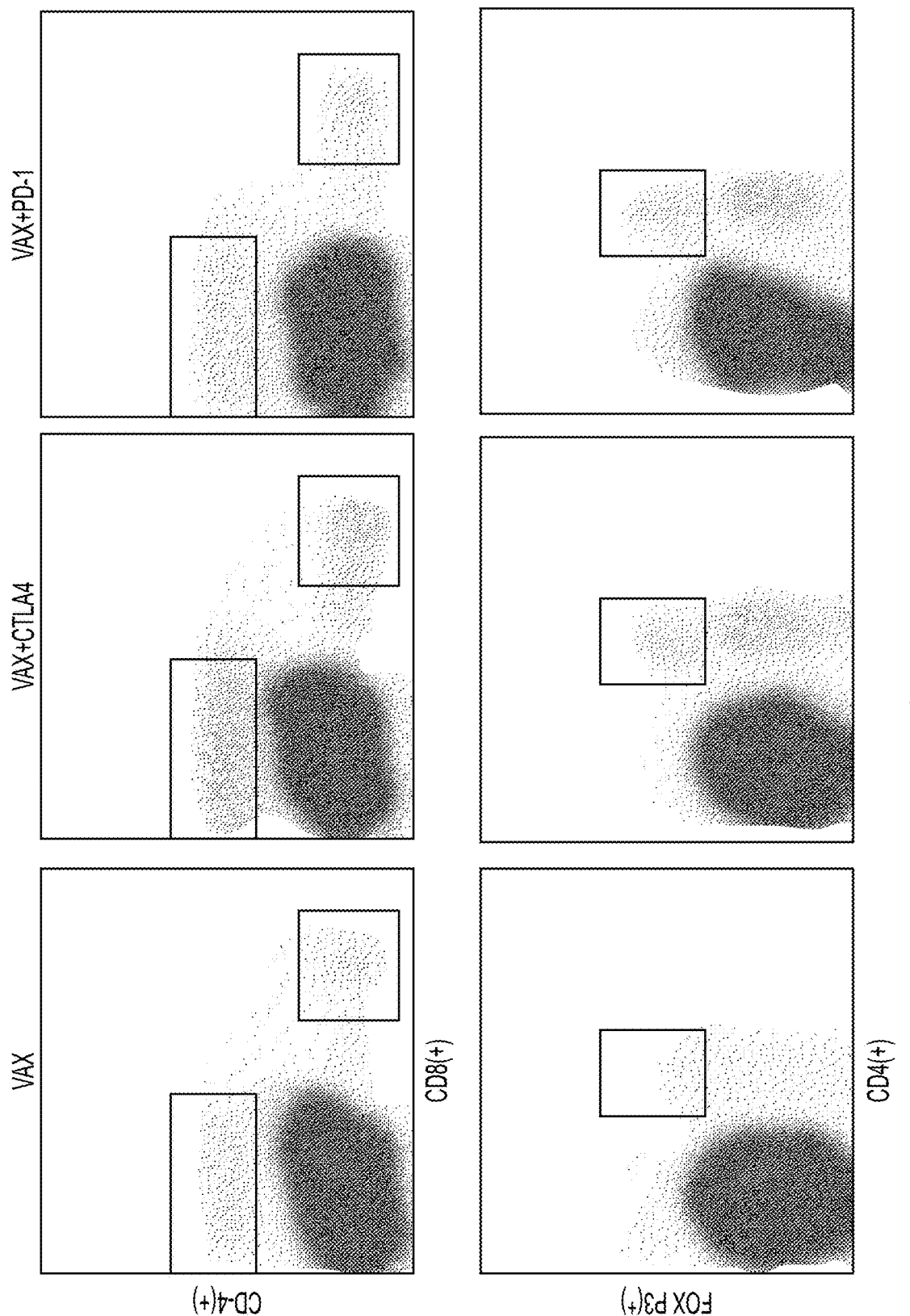
FIG. 6A is a panel of fluorescence activated cell sorting (FACS) scatterplots showing the proportion of T cell infiltrates isolated from PLG vaccine implants that express CD4, CD8, and/or FoxP3 in mice treated with vaccine only (VAX), vaccine plus anti-CTLA4 antibody (VAX+CTLA4), or vaccine plus anti-PD1 antibody (VAX+PD1).
Figure 6B:
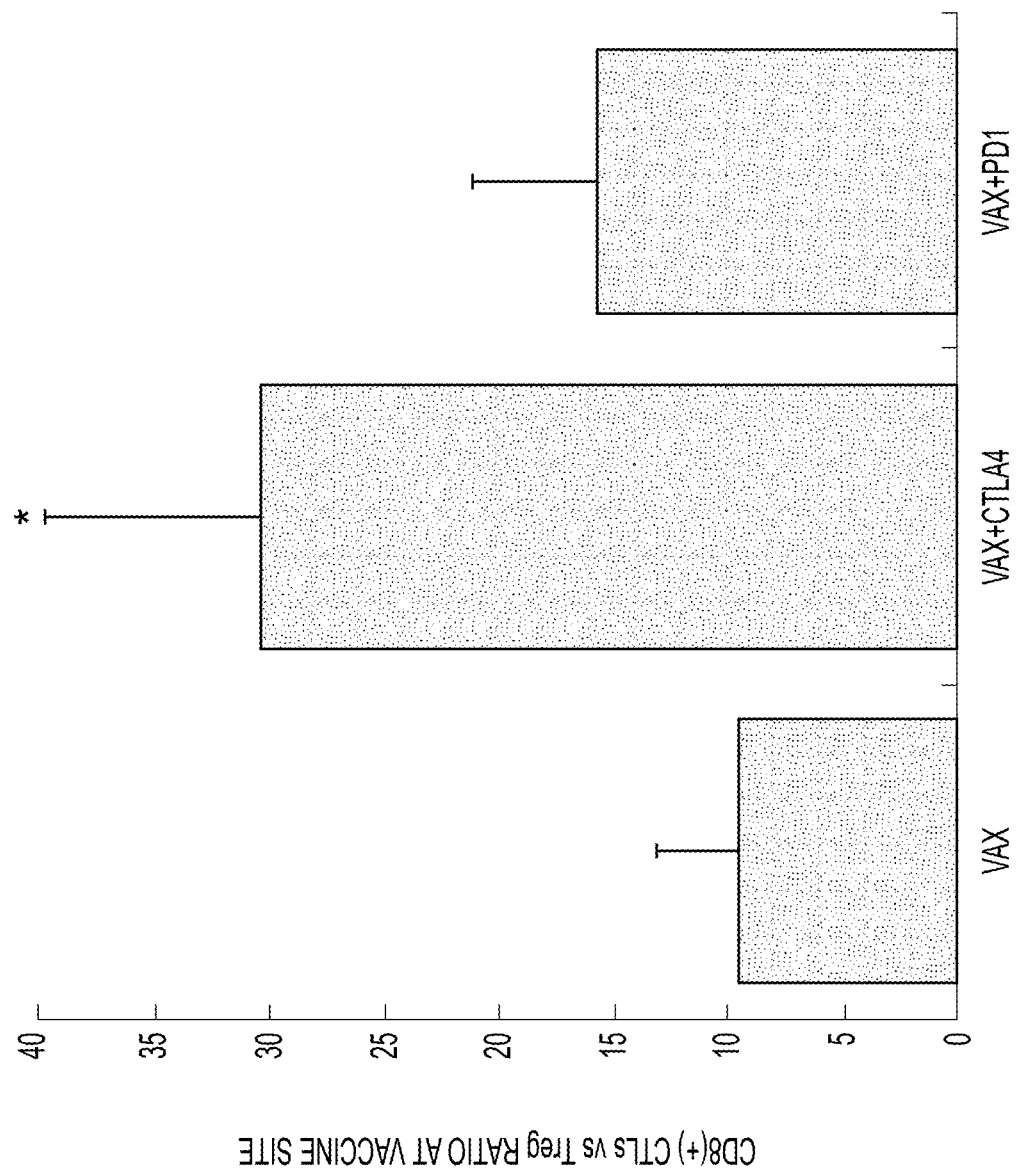
FIG. 6B is a bar graph showing the ratio of $CD3^+CD8^+$ effector T cells to $CD4^+FoxP3^+$ T cells at the vaccination site of mice treated with vaccine only (VAX), vaccine plus anti-CTLA4 antibody (VAX+CTLA4), or vaccine plus anti-PD1 antibody (VAX+PD1). Values represent mean and standard deviation (n=5). *P<0.05 **P<0.01 as compared to all other experimental conditions unless otherwise noted.

The results described herein demonstrate that poly(lactide-co-glcolide) (PLG) cancer vaccines produce significant numbers of antigen specific T cells in melanoma models. In summary, to test the effects of vaccine and antibody (e.g., anti-CTLA4 and/or anti-PD1 antibody) treatments in combination, an aggressive, therapeutic B16 melanoma model was utilized. In mice bearing B16 melanoma tumors, treatment with anti-CTLA4 and anti-PD1 antibodies alone had no effect on tumor size and survival outcomes in these animals (FIGS. 1A-B). PLG vaccination modestly suppressed tumor progression but did not affect long-term survival in any mice bearing B16 melanoma tumors. Surprisingly, the administration of CTLA-4 and PD-1 antibodies combined with PLG vaccines was able to promote long-term survival rates of 75% and 40%, respectively, in mice that would otherwise die when treated with each agent alone. These treatments synergize to promote significant T cell activity at tumor sites and locally within vaccines (FIGS. 3A-6B). The response is significantly skewed toward cytotoxic T cell activity relative to suppressive regulatory T cell activity, and these responses can be maintained for extended times when anti-CTLA4 antibodies are combined with vaccination (FIG. 6B).

Immune Checkpoint Pathways and Cancer

In healthy subjects, immune checkpoint pathways (also known as immune-inhibitory pathways) are important for maintaining self-tolerance and preventing autoimmunity. However, immune checkpoint pathways in cancer cells are often dysregulated, leading to the ability of tumors to evade the body's endogenous anti-tumor immune response. Cancers co-opt the immune checkpoint pathways by a number of ways, such as upregulating the expression of immune checkpoint proteins that normally serve immune-inhibitory roles. For example, inhibitory ligands and receptors that regulate T cell effector activity are often overexpressed in cancer cells.

An exemplary inhibitory receptor is cytotoxic T-lymphocyte-associated antigen 4 (CTLA4), also called CD152, which reduces the level of T cell activation. Another exemplary inhibitory receptor is programmed cell death protein 1 (PD1), also called CD279, which limits T effector cell activity. For example, cancer cells upregulate ligands for PD1 (e.g., programmed cell death protein ligand 1 (PDL1)), thereby blocking anti-tumor immune responses.

The blockade of immune checkpoints in cancer immunotherapy has emerged as a promising approach to combat this mechanism by which cancer cells evade the anti-tumor immune response. For example, antibodies directed against immune-inhibitory proteins, such as immune checkpoint proteins (also referred to as blockade antibodies herein) are being explored as potential anti-cancer therapeutics. See, e.g., Pardoll. Nat. Reviews Cancer. (2012) 12:252-264.

Immune-Inhibitory Proteins and their Inhibitors

Immune checkpoint proteins include the B7/CD28 receptor super family. CTLA-4 belongs to the immunoglobulin superfamily of receptors, which also includes programmed cell death protein 1 (PD-1), B and T lymphocyte attenuator (BTLA), T-cell immunoglobulin and mucin domain-containing protein 3 (TIM-3), and V-domain immunoglobulin suppressor of T cell activation (VISTA). Other immune regulatory checkpoint proteins include proteins in the TNF family (e.g., OX40 (also known as CD134) and 4-1BB ligand).

The amino acid sequence of *Mus musculus* VISTA, provided by Genbank Accession No. AEO22039.1, is shown below (SEQ ID NO: 1).

(SEQ ID NO: 1)
```
  1 mgvpavpeas sprwgtllla iflaasrglv aafkvttpys lyvcpegqna tltcrilgpv
 61 skghdvtiyk twylssrgev qmckehrpir nftlqhlqhh gshlkanash dqpqkhglel
121 asdhhgnfsi tlrnvtprds glycclviel knhhpeqrfy gsmelqvqag kgsgstcmas
181 neqdsdsita aalatgaciv gilclplill lvykqrqvas hrraqelvrm dssntqgien
241 pgfettppfq gmpeaktrpp lsyvaqrqps esgryllsdp stplsppgpg dvffpsldpv
301 pdspnseai
```

The mRNA sequence encoding *Mus musculus* VISTA, provided by Genbank Accession No. JN602184.1, is shown below (SEQ ID NO: 2), with the start and stop codons in bold.

(SEQ ID NO: 2)
```
  1 atgggtgtcc ccgcggtccc agaggccagc agcccgcgct ggggaaccct gctccttgct
 61 attttcctgg ctgcatccag aggtctggta gcagcttca aggtcaccac tccatattct
121 ctctatgtgt gtcccgaggg acagaatgcc accctcacct gcaggattct gggccccgtg
181 tccaaagggc acgatgtgac catctacaag acgtggtacc tcagctcacg aggcgaggtc
241 cagatgtgca agaacaccg gcccatacgc aacttcacat tgcagcacct tcagcaccac
301 ggaagccacc tgaaagccaa cgccagccat gaccagcccc agaagcatgg gctagagcta
361 gcttctgacc accacggtaa cttctctatc accctgcgca atgtgacccc aagggacagc
421 ggcctctact gctgtctagt gatagaatta aaaaccacc acccagaaca acggttctac
481 gggtccatgg agctacaggt acaggcaggc aaaggctcgg ggtccacatg catggcgtct
541 aatgagcagg acagtgacag catcacggct gcggccctgg ccaccggcgc ctgcatcgtg
601 ggaatcctct gcctccccct tatcctgctg ctggtctata gcagagaca ggtggcctct
661 caccgccgtg cccaggagtt ggtgaggatg gacagcagca cacccaagg aatcgaaaac
721 ccaggcttcg agaccactcc acccttccag gggatgcctg aggccaagac caggccgcca
781 ctgtcctatg tggcccagcg gcaaccttcg gagtcaggac ggtacctgct ctctgacccc
841 agcacacctc tgtcgcctcc aggccctggg gacgtctttt tcccatccct agatccagtc
901 cctgactccc ctaactctga agccatctaa
```

The amino acid sequence of human OX40 ligand, provided by Genbank Accession No. NP_003318.1, is shown below (SEQ ID NO: 3), with the signal peptide shown in underlined font and the mature peptide shown in italicized font.

(SEQ ID NO: 3)
```
  1 mcvgarrlgr gpcaallllg lglstvtqlh cvgdtypsnd rcchecrpgn gmvsrcsrsq
 61 ntvcrpcgpg fyndvvsskp ckpctwcnlr sgserkqlct atqdtvcrcr agtqpldsyk
121 pgvdcapcpp ghfspgdnqa ckpwtnctla gkhtlqpasn ssdaicedrd ppatqpqetq
181 gpparpitvq pteawprtsq gpstrpvevp ggravaailg lglvlgllgp laillalyll
241 rrdqrlppda hkppgggsfr tpiqeeqada hstlaki
```

The mRNA sequence encoding human OX40 ligand, provided by Genbank Accession No. NM_003327.3, is shown below (SEQ ID NO: 4), with the start and stop codons in bold.

```
                                                          (SEQ ID NO: 4)
   1 ccgcaaggaa aacccagact ctggcgacag cagagacgag gatgtgcgtg ggggctcggc
  61 ggctgggccg cgggccgtgt gcggctctgc tcctcctggg cctggggctg agcaccgtga
 121 cggggctcca ctgtgtcggg gacacctacc ccagcaacga ccggtgctgc cacgagtgca
 181 ggccaggcaa cgggatggtg agccgctgca gccgctccca gaacacggtg tgccgtccgt
 241 gcgggccggg cttctacaac gacgtggtca gctccaagcc gtgcaagccc tgcacgtggt
 301 gtaacctcag aagtgggagt gagcggaagc agctgtgcac ggccacacag gacacagtct
 361 gccgctgccg ggcgggcacc cagcccctgg acagctacaa gcctggagtt gactgtgccc
 421 cctgccctcc agggcacttc tccccaggcg acaaccaggc ctgcaagccc tggaccaact
 481 gcaccttggc tgggaagcac accctgcagc cggccagcaa tagctcggac gcaatctgtg
 541 aggacaggga cccccagcc acgcagcccc aggagaccca gggcccccg gccaggccca
 601 tcactgtcca gcccactgaa gcctggccca gaacctcaca gggaccctcc acccggcccg
 661 tggaggtccc cggggccgt gcggttgccg ccatcctggg cctgggcctg gtgctggggc
 721 tgctgggccc cctggccatc ctgctggccc tgtacctgct ccggagggac cagaggctgc
 781 cccccgatgc ccacaagccc ctgggggag gcagtttccg gacccccatc caagaggagc
 841 aggccgacgc ccactccacc ctggccaaga tctgacctgg gccaccaag gtggacgctg
 901 ggccccgcca ggctggagcc cggagggtct gctgggcgag cagggcaggt gcaggccgcc
 961 tgccccgcca cgctcctggg ccaactctgc accgttctag gtgccgatgg ctgcctccgg
1021 ctctctgctt acgtatgcca tgcataccct ctgccccgcg ggaccacaat aaaaaccttg
1081 gcagacggga gtctccgacc ggcaaaaaaa aaaaaaaaa
```

The amino acid sequence of human 4-1BB, provided by Genbank Accession No. NP_001552.2, is shown below (SEQ ID NO: 5), with the signal peptide in underlined font and the mature peptide in italicized font.

```
                                                          (SEQ ID NO: 5)
  1 mgnscyniva tlllvlnfer trslqdpcsn cpagtfcdnn rnqicspcpp nsfssaggqr
 61 tcdicrqckg vfrtrkecss tsnaecdctp gfhclgagcs mceqdckqgq eltkkgckdc
121 cfgtfndqkr gicrpwtncs ldgksvlvng tkerdvvcgp spadlspgas svtppapare
181 pghspqiisf flaltstall fllffltlrf svvkrgrkkl lyifkqpfmr pvqttqeedg
241 cscrfpeeee ggcel
```

The mRNA sequence of human 4-1BB, provided by Genbank Accession No. NM-001561.5, is shown below (SEQ ID NO: 6), with the start and stop codons in bold.

```
                                                          (SEQ ID NO: 6)
  1 caaggaggga tcccacagat gtcacagggc tgtcacagag ctgtggtggg aatttcccat
 61 gagaccccgc cctggctga gtcaccgcac tcctgtgttt gacctgaagt cctctcgagc
121 tgcagaagcc tgaagaccaa ggagtggaaa gttctccggc agccctgaga tctcaagagt
181 gacatttgtg agaccagcta atttgattaa aattctcttg gaatcagctt tgctagtatc
241 atacctgtgc cagatttcat catgggaaac agctgttaca acatagtagc cactctgttg
301 ctggtcctca actttgagag gacaagatca ttgcaggatc cttgtagtaa ctgcccagct
361 ggtacattct gtgataataa caggaatcag atttgcagtc cctgtcctcc aaatagtttc
421 tccagcgcag gtggacaaag gacctgtgac atatgcaggc agtgtaaagg tgttttcagg
```

-continued

```
 481 accaggaagg agtgttcctc caccagcaat gcagagtgtg actgcactcc agggtttcac
 541 tgcctggggg caggatgcag catgtgtgaa caggattgta acaaggtca agaactgaca
 601 aaaaaaggtt gtaaagactg ttgctttggg acatttaacg atcagaaacg tggcatctgt
 661 cgaccctgga caaactgttc tttggatgga agtctgtgc ttgtgaatgg gacgaaggag
 721 agggacgtgg tctgtggacc atctccagcc gacctctctc cgggagcatc ctctgtgacc
 781 ccgcctgccc ctgcgagaga gccaggacac tctccgcaga tcatctcctt ctttcttgcg
 841 ctgacgtcga ctgcgttgct cttcctgctg ttcttcctca cgctccgttt ctctgttgtt
 901 aaacggggca gaaagaaact cctgtatata ttcaaacaac catttatgag accagtacaa
 961 actactcaag aggaagatgg ctgtagctgc cgatttccag aagaagaaga aggaggatgt
1021 gaactgtgaa atggaagtca ataggctgt tgggactttc ttgaaaagaa gcaaggaaat
1081 atgagtcatc cgctatcaca gctttcaaaa gcaagaacac catcctacat aatacccagg
1141 attcccccaa cacacgttct tttctaaatg ccaatgagtt ggcctttaaa aatgcaccac
1201 ttttttttt tttttgacag gtctcactc tgtcacccag gctggagtgc agtggcacca
1261 ccatggctct ctgcagcctt gacctctggg agctcaagtg atcctcctgc ctcagtctcc
1321 tgagtagctg gaactacaag gaagggccac cacacctgac taactttttt gttttttgtt
1381 tggtaaagat ggcatttcac catgttgtac aggctggtct caaactccta ggttcacttt
1441 ggcctcccaa agtgctggga ttacagacat gaactgccag gcccggccaa ataatgcac
1501 cacttttaac agaacagaca gatgaggaca gagctggtga taaaaaaaaa aaaaaaaaag
1561 cattttctag ataccactta acaggtttga gctagttttt ttgaaatcca aagaaaatta
1621 tagtttaaat tcaattacat agtccagtgg tccaactata attataatca aaatcaatgc
1681 aggtttgttt tttggtgcta atatgacata tgacaataag ccacgaggtg cagtaagtac
1741 ccgactaaag tttccgtggg ttctgtcatg taacacgaca tgctccaccg tcagggggga
1801 gtatgagcag agtgcctgag tttagggtca aggacaaaaa acctcaggcc tggaggaagt
1861 tttggaaaga gttcaagtgt ctgtatatcc tatggtcttc tccatcctca caccttctgc
1921 ctttgtcctg ctcccttta agccaggtta cattctaaaa attcttaact tttaacataa
1981 tattttatac caaagccaat aaatgaactg catatgatag gtatgaagta cagtgagaaa
2041 attaacacct gtgagctcat tgtcctacca cagcactaga gtgggggccg ccaaactccc
2101 atggccaaac ctggtgcacc atttgccttt gtttgtctgt tggtttgctt gagacagtct
2161 tgctctgttg cccaggctgg aatggagtgg ctattcacag gcacaatcat agcacacttt
2221 agccttaaac tcctgggctc aagtgatcca cccgcctcag tctcccaagt agctgggatt
2281 acaggtgcaa acctggcatg cctgccattg tttggcttat gatctaagga tagctttta
2341 aattttattc attttatttt tttttgagac agtgtctcac tctgtctccc aggctggagt
2401 acagtggtac aatcttggat caccgcctcc cagtttcaag tgatctccct gcctcagcct
2461 cctaagtagc tgggactaca ggtatgtgcc accacgcctg gctaattttt atatttttag
2521 tagagacggg gtttcaccat gttgtccagg ctggtctcaa actcctgacc tcaggtgatc
2581 tgcccacctc tgcctcccaa agtgctggga ttacaggcat gagccaccat gcctggccat
2641 ttcttacact tttgtatgac atgcctattg caagcttgcg tgcctctgtc ccatgttatt
2701 ttactctggg atttaggtgg agggagcagc ttctatttgg aacattggcc atcgcatggc
2761 aaatgggtat ctgtcacttc tgctcctatt tagttggttc tactataacc tttagagcaa
2821 atcctgcagc caagccaggc atcaataggg cagaaaagta tattctgtaa ataggggtga
```

-continued

```
2881 ggagaagata tttctgaaca atagtctact gcagtaccaa attgcttttc aaagtggctg 2941 ttctaatgta ctcccgtcag tcatataagt gtcatgtaag tatcccattg atccacatcc 3001 ttgctaccct ctggtactat caggtgccct taattttgcc aagccagtgg gtatagaatg 3061 agatctcact gtggtcttag tttgcatttg cttggttact gatgagcacc ttgtcaaata 3121 tttatatacc atttgtgttt atttttttaa ataaaatgct tgctcatgct tttttgccca 3181 tttgcaaaaa aacttggggc cgggtgcagt ggctcatgcc tgtagtccca gctctttggg 3241 aggccaaggt gggcagatcg cttgagccca ggagttcgag accagccttg caacatggc 3301 gaaaccctgt ctttacaaaa aatacaaaaa ttagccgggt gtggtggtgt gcacctgaag 3361 tcccagctac tcagtaggtt cgctttgagc ctggaggca gaggttgcag tgagctggga 3421 ccgcatcact acacttcagc ctgggcaaca gagaaaaacc ttttctcaga aacaaacaaa 3481 cccaaatgtg gttgtttgtc ctgattccta aaaggtcttt atgtattcta gataataatc 3541 tttggtcagt tatatgtgtt aaaaaatatc ttctttgtgg ccaggcacgg tagctcacac 3601 ctgtaatccc agcactttgc ggggctgagg tgggtggatc atctgaggtc aagagttcaa 3661 gatcagcctg gccaacacag tgaaacccca tctctactaa acatgtacaa aacttagctg 3721 ggtatggtgg cgggtgcctg taaccccagc tgctccagag gctgtggcag aagaatcgct 3781 tgaacccagg aggcagaggt tgcagcgagc caagattgtg ccattgcact ccagactggg 3841 tgacaagagt gaaattctgc ctatctatct atctatctat ctatatctat atatatatat 3901 atatatatcc tttgtaattt attttttccct ttttaaaatt ttttataaaa ttctttttta 3961 tttttatttt tagcagaggt gaggtttctg aggtttcatt atgttgccca ggctggtctt 4021 gaactcctga gctcaagtga tcctcccacc tcagccttcc aaagtgctgg aattgcagac 4081 atgagccacc gcgcccctcc tgttttctc taattaatgg tgtctttctt tgtcttctg 4141 gtaataagca aaagttctt catttgattt ggttaaattt ataactgttt tctcatatgg 4201 ttaacatttt ttcttgcctg gctaaagaaa tccttttctg cccaatacta taaagaggtt 4261 tgcccacatt ttattccaaa agttttaagt tttgtctttc atcttgaagt ctaatgtatc 4321 aggaactggc ttttgtgcct gttgggaggt agtgatccaa ttccatgtct tgcatgtagg 4381 taaccactgg tccctgcgcc atgtattcaa tacgtcgtct ttctcctgcg ggtctgcaat 4441 ctcacctacc atccatcaag tttccatagg gccatgggtc tgcttctggg ctccctgttc 4501 tgttccattg tcaatttgtc tatcctgtgc cagtatcaca ctgtgtttat tacaatagct 4561 ttgtaacagc tctcgatatc cggtaggaca tctccctcca ccttctttt ctacttcaga 4621 agtgtcttag ctaggtcagg cacggtggct cacgcctgta atcccagcac tttgggaggc 4681 cgacgcggat ggatcacctg aggtcaggag ttttgagaca gcctggccaa catggtgaaa 4741 ccccatctct actaaaaaat acaaaaatta gtcaggcatg gtggcatgtg cctgtaatcc 4801 cagctatttg ggaggctgag gccggagaat tgcttgaacc cggggggcgg aggttgcagt 4861 gagccgagat cgtaccattg cactccagcc tgggtgacag agcgaaactc tgtctcagga 4921 aaaaaagaa aagagatgtc ttggttattc ttggttcttt attattcaat ataaattta 4981 gaagctgaat ttgaaaagat ttggattgga atttcattaa atctacaggt caatttaggg 5041 agagttgata attttacaga attgagtcat ctggtgttcc aataagaata agagaacaat 5101 tattggctgt acaattcttg ccaaatagta ggcaaagcaa agcttaggaa gtatactggt 5161 gccatttcag gaacaaagct aggtgcgaat attttgtct ttctgaatca tgatgctgta 5221 agttctaaag tgatttctcc tcttggcttt ggacacatgg tgtttaatta cctactgctg 5281 actatccaca aacagaaaga gactggtcat gccccacagg gttggggtat ccaagataat
```

```
5341 ggagcgaggc tctcatgtgt cctaggttac acaccgaaaa tccacagttt attctgtgaa 5401 gaaaggaggc tatgtttatg atacagactg tgatattttt atcatagcct attctggtat 5461 catgtgcaaa agctataaat gaaaaacaca ggaacttggc atgtgagtca ttgctccccc 5521 taaatgacaa ttaataagga aggaacattg agacagaata aaatgatccc cttctgggtt 5581 taatttagaa agttccataa ttaggtttaa tagaaataaa tgtaaatttc tatgattaaa 5641 aataaattag cacatttagg gatacacaaa ttataaatca ttttctaaat gctaaaaaca 5701 agctcaggtt tttttcagaa gaaagtttta attttttttc tttagtggaa gatatcactc 5761 tgacggaaag ttttgatgtg aggggcggat gactataaag tgggcatctt cccccacagg 5821 aagatgtttc catctgtggg tgagaggtgc ccaccgcagc tagggcaggt tacatgtgcc 5881 ctgtgtgtgg taggacttgg agagtgatct ttatcaacgt ttttatttaa aagactatct 5941 aataaaacac aaaactatga tgttcacagg aaaaaaagaa taagaaaaaa agaaaaaaaa 6001 a
```

CTLA4 is a receptor expressed only on T cells, and it reduces the level of T cell activation by interfering with the activity of T cell co-stimulatory receptor, CD28. CTLA4 is a target of cancer immunotherapies (e.g., by antibodies that bind to and block CTLA4). Ipilimumab (manufactured by Bristol-Myers Squibb) is a fully humanized anti-CTLA4 antibody that has been approved by the Food and Drug Administration (FDA) for the treatment of melanoma (in particular, unresectable or metastatic melanoma) and is undergoing clinical trials for use in other cancers. Tremelimumab (manufactured by Pfizer; CAS number 745013-59-6) is a fully humanized IgG2 monoclonal anti-CTLA4 antibody that is undergoing clinical trials for the treatment of melanoma.

The amino acid sequence of human CTLA4, provided by Genbank Accession No. P16410.3, is shown below (SEQ ID NO: 7).

```
                                                       (SEQ ID NO: 7)
  1 maclgfqrhk aqlnlatrtw pctllffllf ipvfckamhv aqpavvlass rgiasfvcey 61 aspgkatevr vtvlrqadsq vtevcaatym mgneltfldd sictgtssgn qvnltiqglr 121 amdtglyick velmypppyy lgigngtqiy vidpepcpds dfllwilaav ssglffysfl 181 ltavslskml kkrsplttgv yvkmpptepe cekqfqpyfi pin
```

Amino acid residues 36-223 of SEQ ID NO: 7 corresponds to the mature sequence of CTLA4.

The mRNA sequence of human CTLA4, provided by Genbank Accession No. AF414120.1, is shown below (SEQ ID NO: 8).

```
                                                       (SEQ ID NO: 8)
  1 cttctgtgtg tgcacatgtg taatacatat ctgggatcaa agctatctat ataaagtcct 61 tgattctgtg tgggttcaaa cacatttcaa agcttcagga tcctgaaagg ttttgctcta 121 cttcctgaag acctgaacac cgctcccata aagccatggc ttgccttgga tttcagcggc 181 acaaggctca gctgaacctg gctaccagga cctggccctg cactctcctg ttttttcttc 241 tcttcatccc tgtcttctgc aaagcaatgc acgtggccca gcctgctgtg gtactggcca 301 gcagccgagg catcgccagc tttgtgtgtg agtatgcatc tccaggcaaa gccactgagg 361 tccgggtgac agtgcttcgg caggctgaca gccaggtgac tgaagtctgt gcggcaacct 421 acatgatggg gaatgagttg accttcctag atgattccat ctgcacgggc acctccagtg 481 gaaatcaagt gaacctcact atccaaggac tgagggccat ggacacggga ctctacatct 541 gcaaggtgga gctcatgtac ccaccgccat actacctggg cataggcaac ggaacccaga 601 tttatgtaat tgatccagaa ccgtgcccag attctgactt cctcctctgg atccttgcag 661 cagttagttc ggggttgttt ttttatagct ttctcctcac agctgtttct ttgagcaaaa
```

```
 721 tgctaaagaa aagaagccct cttacaacag gggtctatgt gaaaatgccc ccaacagagc 781 cagaatgtga aaagcaattt cagccttatt ttattcccat caattgagaa accattatga 841 agaagagagt ccatatttca atttccaaga gctgaggcaa ttctaacttt tttgctatcc 901 agctattttt atttgtttgt gcatttgggg ggaattcatc tctctttaat ataaagttgg 961 atgcggaacc caaattacgt gtactacaat ttaaagcaaa ggagtagaaa gacagagctg 1021 ggatgtttct gtcacatcag ctccactttc agtgaaagca tcacttggga ttaatatggg 1081 gatgcagcat tatgatgtgg gtcaaggaat taagttaggg aatggcacag cccaaagaag 1141 gaaaaggcag ggagcgaggg agaagactat attgtacaca ccttatattt acgtatgaga 1201 cgtttatagc cgaaatgatc ttttcaagtt aaattttatg cctttttattt cttaaacaaa 1261 tgtatgatta catcaaggct tcaaaaatac tcacatggct atgttttagc cagtgatgct 1321 aaaggttgta ttgcatatat acatatatat atatatatat atatatatat atatatatat 1381 atatatatat tttaatttga tagtattgtg catagagcca cgtatgtttt tgtgtatttg 1441 ttaatggttt gaatataaac actatatggc agtgtctttc caccttgggt cccagggaag 1501 ttttgtggag gagctcagga cactaataca ccaggtagaa cacaaggtca tttgctaact 1561 agcttggaaa ctggatgagg tcatagcagt gcttgattgc gtggaattgt gctgagttgg 1621 tgttgacatg tgctttgggg cttttacacc agttcctttc aatggtttgc aaggaagcca 1681 cagctggtgg tatctgagtt gacttgacag aacactgtct tgaagacaat ggcttactcc 1741 aggagaccca caggtatgac cttctaggaa gctccagttc gatgggccca attcttacaa 1801 acatgtggtt aatgccatgg acagaagaag gcagcaggtg gcagaatggg gtgcatgaag 1861 gtttctgaaa attaacactg cttgtgtttt taactcaata ttttccatga aaatgcaaca 1921 acatgtataa tatttttaat taaataaaaa tctgtggtgg tcgttttaaa aaaaaaaaaa 1981 aaaaaaaaaa aaaaaaaaaa aaaaaaaaaa aaaaaaaaaa aaaaa
```

The atg start codon and the stop codon are bolded and underlined.

Blockade of CTLA4 enables a pre-existing endogenous anti-tumor immune response to destroy tumors. Thus, in the presence of an endogenous anti-tumor immune response in a subject, inhibition of CTLA4 lifts the resistance to the immune response and allows the body's immune cells to destroy the cancer cells. However, in poorly immunogenic tumors, the endogenous immune response is either does not exist or is too weak to kill the cancer cells, and inhibition of CTLA4 alone has minimal efficacy.

The role of PD1 is to limit T cell activity in peripheral tissues during an immune response to infection and to minimize autoimmunity. PD1 is expressed on activated lymphocytes, including activated T effector cells, B cells, and natural killer (NK) cells. Ligands for PD1 include PD1 ligand 1 (PDL1, also called B7-H1 and CD274), and PDL2 (also called B7-DC and CD273). PD1 inhibits lymphocyte function when bound to its ligands. In subjects with cancer, PD1 is often expressed on a large percentage of tumor-infiltrating lymphocytes. Also, PDL1 is overexpressed in cancers such as melanoma, ovarian, renal, and lung cancer. PDL2 is overexpressed in cells from lymphomas, such as B cell lymphoma (e.g., primary mediastinal B cell lymphoma, follicular cell B cell lymphoma, and Hodgkin's disease). Thus, PD1 and its ligands are main players in immune inhibition in the tumor microenvironment, and are therefore targets for cancer immunotherapy.

The mRNA sequence encoding human PD1, provided by Genbank Accession No. NM_005018.2, is shown below (SEQ ID NO: 9).

```
                                                            (SEQ ID NO: 9)
  1 agtttcccct ccgctcacct ccgcctgagc agtggagaag gcggcactct ggtggggctg 61 ctccaggcat gcagatccca caggcgccct ggccagtcgt ctgggcggtg ctacaactgg 121 gctggcggcc aggatggttc ttagactccc cagacaggcc ctggaacccc cccaccttct 181 ccccagccct gctcgtggtg accgaagggg acaacgccac cttcacctgc agcttctcca 241 acacatcgga gagcttcgtg ctaaactggt accgcatgag ccccagcaac cagacggaca 301 agctggccgc cttccccgag gaccgcagcc agcccggcca ggactgccgc ttccgtgtca
```

```
 361 cacaactgcc caacgggcgt gacttccaca tgagcgtggt cagggcccgg cgcaatgaca
 421 gcggcaccta cctctgtggg gccatctccc tggcccccaa ggcgcagatc aaagagagcc
 481 tgcgggcaga gctcagggtg acagagagaa gggcagaagt gcccacagcc caccccagcc
 541 cctcacccag gccagccggc cagttccaaa ccctggtggt tggtgtcgtg ggcggcctgc
 601 tgggcagcct ggtgctgcta gtctgggtcc tggccgtcat ctgctcccgg gccgcacgag
 661 ggacaatagg agccaggcgc accggccagc ccctgaagga ggaccctca gccgtgcctg
 721 tgttctctgt ggactatggg gagctggatt ccagtggcg agagaagacc ccggagcccc
 781 ccgtgccctg tgtccctgag cagacggagt atgccaccat tgtctttcct agcggaatgg
 841 gcacctcatc ccccgcccgc aggggctcag ctgacggccc tcggagtgcc cagccactga
 901 ggcctgagga tggacactgc tcttggcccc tctgaccggc ttccttggcc accagtgttc
 961 tgcagaccct ccaccatgag cccgggtcag cgcatttcct caggagaagc aggcagggtg
1021 caggccattg caggccgtcc aggggctgag ctgcctgggg gcgaccgggg ctccagcctg
1081 cacctgcacc aggcacagcc ccaccacagg actcatgtct caatgcccac agtgagccca
1141 ggcagcaggt gtcaccgtcc cctacaggga gggccagatg cagtcactgc ttcaggtcct
1201 gccagcacag agctgcctgc gtccagctcc ctgaatctct gctgctgctg ctgctgctgc
1261 tgctgctgcc tgcggcccgg ggctgaaggc gccgtggccc tgcctgacgc cccggagcct
1321 cctgcctgaa cttgggggct ggttggagat ggccttggag cagccaaggt gcccctggca
1381 gtggcatccc gaaacgccct ggacgcaggg cccaagactg gcacaggag tgggaggtac
1441 atggggctgg ggactcccca ggagttatct gctccctgca ggcctagaga agtttcaggg
1501 aaggtcagaa gagctcctgg ctgtggtggg cagggcagga aacccctcca cctttacaca
1561 tgcccaggca gcacctcagg ccctttgtgg ggcagggaag ctgaggcagt aagcgggcag
1621 gcagagctgg aggcctttca ggcccagcca gcactctggc ctcctgccgc cgcattccac
1681 cccagcccct cacaccactc gggagaggga catcctacgg tcccaaggtc aggagggcag
1741 ggctggggtt gactcaggcc cctcccagct gtggccacct gggtgttggg agggcagaag
1801 tgcaggcacc tagggccccc catgtgccca ccctgggagc tctccttgga acccattcct
1861 gaaattattt aaaggggttg gccgggctcc caccagggcc tgggtgggaa ggtacaggcg
1921 ttcccccggg gcctagtacc cccgccgtgg cctatccact cctcacatcc acacactgca
1981 cccccactcc tggggcaggg ccaccagcat ccaggcggcc agcaggcacc tgagtggctg
2041 ggacaaggga tccccttcc ctgtggttct attatattat aattataatt aaatatgaga
2101 gcatgctaag gaaaa
```

The atg start codon and the stop codon are bolded and underlined.
The amino acid sequence of human PD1, provided by Genbank Accession No. NP_005009.2, is shown below (SEQ ID NO: 10).

```
                                                      (SEQ ID NO: 10)
  1 mqipqapwpv vwavlqlgwr pgwfldspdr pwnppptfspa llvvtegdna tftcsfsnts 61 esfvlnwyrm spsnqtdkla afpedrsqpg qdcrfrvtql pngrdfhmsv vrarrndsgt 121 ylcgaislap kaqikeslra elrvterrae vptahpspsp rpagqfqtlv vgvvggllgs 181 lvllvwvlav icsraargti garrtgqplk edpsavpvfs vdygeldfqw rektpeppvp 241 cvpeqteyat ivfpsgmgts sparrgsadg prsaqplrpe dghcswpl
```

Residues 1-20 of SEQ ID NO: 10 correspond to the signal peptide sequence, and residues 21-288 of SEQ ID NO: 10 correspond to the mature peptide sequence.

The amino acid sequence of human PDL1 is provided by Genbank Accession No. Q9NZQ7.1, incorporated herein by reference, and is shown below (SEQ ID NO: 11).

```
                                                     (SEQ ID NO: 11)
   1 mrifavfifm tywhllnaft vtvpkdlyvv eygsnmtiec kfpvekqldl aalivyweme 61 dkniiqfvhg eedlkvqhss yrqrarllkd qlslgnaalq itdvklqdag vyrcmisygg 121 adykritvkv napynkinqr ilvvdpvtse heltcqaegy pkaeviwtss dhqvlsgktt 181 ttnskreekl fnvtstlrin tttneifyct frrldpeenh taelvipelp lahppnerth 241 lvilgaillc lgvaltfifr lrkgrmmdvk kcgiqdtnsk kqsdthleet
```

The mRNA sequence encoding human PDL1 is provided by Genbank Accession No. AY291313.1, incorporated herein by reference, and is shown below (SEQ ID NO: 12), with the start and stop codons in bold.

```
                                                     (SEQ ID NO: 12)
   1 atgaggatat ttgctgtctt tatattcatg acctactggc atttgctgaa cgccccatac 61 aacaaaatca accaaagaat tttggttgtg gatccagtca cctctgaaca tgaactgaca 121 tgtcaggctg agggctaccc caaggccgaa gtcatctgga caagcagtga ccatcaagtc 181 ctgagtggta agaccaccac caccaattcc aagagagagg agaagctttt caatgtgacc 241 agcacactga aatcaacac aacaactaat gagatttct actgcacttt taggagatta 301 gatcctgagg aaaaccatac agctgaattg gtcatcccag aactacctct ggcacatcct 361 ccaaatgaaa ggactcactt ggtaattctg ggagccatct tattatgcct tggtgtagca 421 ctgacattca tcttccgttt aagaaaaggg agaatgatgg atgtgaaaaa atgtggcatc 481 caagatacaa actcaaagaa gcaaagtgat acacatttgg aggagacta a
```

The amino acid sequence of human PDL2 is provided by Genbank Accession No. Q9BQ51.2, incorporated herein by reference, and is shown below (SEQ ID NO: 13).

```
                                                     (SEQ ID NO: 13)
   1 miflllmlsl elqlhqiaal ftvtvpkely iiehgsnvtl ecnfdtgshv nlgaitaslq 61 kvendtsphr eratlleeql plgkasfhip qvqvrdegqy qciiiygvaw dykyltlkvk 121 asyrkinthi lkvpetdeve ltcqatgypl aevswpnvsv pantshsrtp eglyqvtsvl 181 rlkpppgrnf scvfwnthvr eltlasidlq sqmeprthpt wllhifipfc iiafifiatv 241 ialrkqlcqk lysskdttkr pvtttkrevn sai
```

The mRNA sequence encoding human PDL2 is provided by Genbank Accession No. AF344424.1, incorporated herein by reference, and is shown below (SEQ ID NO: 14), with the start and stop codons in bold.

```
                                                     (SEQ ID NO: 14)
   1 gcaaaccta agctgaatga caactttc ttctcttgaa tatatcttaa cgccaaattt 61 tgagtgcttt tttgttaccc atcctcatat gtcccagctg gaaagaatcc tgggttggag 121 ctactgcatg ttgattgttt tgttttcct tttggctgtt cattttggtg gctactataa 181 ggaaatctaa cacaaacagc aactgttttt tgttgtttac ttttgcatct ttacttgtgg 241 agctgtggca agtcctcata tcaaatacag aacatgatct tcctcctgct aatgttgagc
```

```
 301 ctggaattgc agcttcacca gatagcagct ttattcacag tgacagtccc taaggaactg 361 tacataatag agcatggcag caatgtgacc ctggaatgca actttgacac tggaagtcat 421 gtgaaccttg gagcaataac agccagtttg caaaaggtgg aaaatgatac atccccacac 481 cgtgaaagag ccactttgct ggaggagcag ctgcccctag ggaaggcctc gttccacata 541 cctcaagtcc aagtgaggga cgaaggacag taccaatgca taatcatcta tggggtcgcc 601 tgggactaca agtacctgac tctgaaagtc aaagcttcct acaggaaaat aaacactcac 661 atcctaaagg ttccagaaac agatgaggta gagctcacct gccaggctac aggttatcct 721 ctggcagaag tatcctggcc aaacgtcagc gttcctgcca acaccagcca ctccaggacc 781 cctgaaggcc tctaccaggt caccagtgtt ctgcgcctaa agccaccccc tgcagaaac 841 ttcagctgtg tgttctggaa tactcacgtg agggaactta ctttggccag cattgacctt 901 caaagtcaga tggaacccag gacccatcca acttggctgc ttcacatttt catcccctcc 961 tgcatcattg ctttcatttt catagccaca gtgatagccc taagaaaaca actctgtcaa 1021 aagctgtatt cttcaaaaga cacaacaaaa agacctgtca ccacaacaaa gagggaagtg 1081 aacagtgcta tctgaacctg tggtcttggg agccagggtg acctgatatg acatctaaag 1141 aagcttctgg actctgaaca agaattcggt ggcctgcaga gcttgccatt tgcactttc 1201 aaatgccttt ggatgaccca gca
```

MDX-1106 (also called BMS-936558; manufactured by Bristol Myers Squibb) is an anti-PD1 human monoclonal antibody that is undergoing clinical trials for use in melanoma, renal, and lung cancers. See, e.g., Clinical Trials Identifier No. NCT00730639. MK-3475 (manufactured by Merck) is a monoclonal IgG4 antibody against PD1 and is undergoing clinical trials for use in previously-treated patients with Non-Small Cell Lung Cancer (NSCLC). CT-011 (also called pidilizumab, produced by Cure Tech) is a humanized monoclonal antibody against PD1 and is undergoing clinical trials for use in metastatic colorectal cancer, metastatic melanoma, and lymphoma. AMP-224 (developed by GlaxoSmithKline and Amplimmune) is an Fc fusion protein containing a ligand of PD1. AMP-224 blocks the interaction between PD1 and PDL2 or PDL1. AMP-224 is undergoing clinical trials for use in cancer. See, e.g., Clinical Trials Identifier No. NCT01352884. MDX1105 (produced by Bristol-Myers Squibb) is a fully human monoclonal IgG4 anti-PDL1 antibody and clinical trials are undergoing for its use in cancer (e.g., relapsed/refractory renal cell carcinoma, NSCLC, colorectal adenocarcinoma, malignant melanoma, advanced/metastatic epithelial ovarian cancer, gastric cancer, pancreatic cancer, and breast cancer). See, e.g., Clinical Trial Identifier No. NCT00729664.

In addition to immune checkpoint receptors, B7 family immune-inhibitory ligands are also immune-inhibitory proteins that are candidate targets for cancer immunotherapy. For example, B7-H3 (also called CD276) and B7-H4 (also called B7-S1, B7x, or VCTN1) have been implicated in immune inhibition. In addition, B7-H3 and B7-H4 are overexpressed on cancer cells and on tumor infiltrating cells. MGA271 (produced by Macrogenics) is a humanized IgG1/kappa monoclonal antibody against B7-H3 and is currently undergoing clinical trials for use in refractory B7-H3-expressing neoplasms (e.g., prostate cancer and melanoma). See, e.g., Clinical Trial Identifier No. NCT01391143.

The amino acid sequence of human B7-H3 is provided by Genbank Accession No. Q5ZPR3.1, incorporated herein by reference. The mRNA sequence encoding human B7-H3 is provided by Genbank Accession No. AJ583695.1, incorporated herein by reference.

The amino acid sequence of human B7-H4 is provided by Genbank Accession No. Q7Z7D3.1, incorporated herein by reference. The mRNA sequence encoding human B7-H4 is provided by Genbank Accession No. DQ103757.1, incorporated herein by reference.

A number of other proteins have been shown to be associated with inhibition of immune cell activity and are thus also potential targets for cancer immunotherapy. These proteins include lymphocyte activation gene 3 (LAG3, or CD223), 2B4 (CD244), B and T lymphocyte attenuator (BTLA, CD272), T membrane protein 3 (TIM3, HAVcr2), adenosine A2a receptor (A2aR), and killer inhibitory receptors. Killer inhibitor receptors include killer cell immunoglobulin-like receptors (KIRs) and C-type leptin receptors, both of which regulate the killing activity of NK cells. IMP321 (produced by Immutep) is a soluble LAG3-Ig fusion protein that targets LAG3 and is currently being studied for use in advanced renal cell adenocarcinoma and advanced pancreatic adenocarcinoma. See, e.g., Brignone et al. Clin. Cancer Res. (2009) 15:6225-6231 and Wang-Gillam et al. Invest. New Drugs (2013) 31:707-13.

The amino acid sequence of human BTLA is provided by Genbank Accession No. NP_861445.3, incorporated herein by reference, and is shown below (SEQ ID NO: 15), with the signal peptide shown in underlined font and the mature peptide shown in italicized font.

(SEQ ID NO: 15)
```
  1 mktlpamlgt gklfwvffli pyldiwnihq kescdvqlyi krqsehsila gdpfelecpv
 61 kycanrphvt wcklngttcv kledrqtswk eeknisffil hfepvlpndn gsyrcsanfq
121 snlieshstt lyvtdvksas erpskdemas rpwllysllp lgglpllitt cfclfcclrr
181 hqgkqnelsd tagreinlvd ahlkseqtea strqnsqvll setgiydndp dlcfrmqegs
241 evysnpclee nkpgivyasl nhsvigpnsr larnvkeapt eyasicvrs
```

The mRNA sequence encoding human BTLA is provided by Genbank Accession No. NM_181780.3, incorporated herein by reference, and is shown below (SEQ ID NO: 16), with the start and stop codons shown in bold.

(SEQ ID NO: 16)
```
   1 gtctttctgt tcactttttt tcacaaaatc atccaggctc ttcctactct cctctcttac
  61 cacctctctc ttctttttt ttttttttta gttatttcac agatgccact ggggtaggta
 121 aactgaccca actctgcagc actcagaaga cgaagcaaag ccttctactt gagcagtttt
 181 tccatcactg atatgtgcag gaaatgaaga cattgcctgc catgcttgga actgggaaat
 241 tattttgggt cttcttctta atcccatatc tggacatctg aacatccat gggaaagaat
 301 catgtgatgt acagctttat ataaagagac aatctgaaca ctccatctta gcaggagatc
 361 cctttgaact agaatgccct gtgaaatact gtgctaacag gcctcatgtg acttggtgca
 421 agctcaatgg aacaacatgt gtaaaacttg aagatagaca aacaagttgg aaggaagaga
 481 agaacatttc atttttcatt ctacatttg aaccagtgct tcctaatgac aatgggtcat
 541 accgctgttc tgcaaatttt cagtctaatc tcattgaaag ccactcaaca actctttatg
 601 tgacagatgt aaaaagtgcc tcagaacgac cctccaagga cgaaatggca agcagaccct
 661 ggctcctgta tagtttactt cctttgggg gattgcctct actcatcact acctgtttct
 721 gcctgttctg ctgcctgaga aggcaccaag gaaagcaaaa tgaactctct gacacagcag
 781 gaagggaaat taacctggtt gatgctcacc ttaagagtga gcaaacagaa gcaagcacca
 841 ggcaaaattc ccaagtactg ctatcagaaa ctggaattta tgataatgac cctgaccttt
 901 gtttcaggat gcaggaaggg tctgaagttt attctaatcc atgcctggaa gaaaacaaac
 961 caggcattgt ttatgcttcc ctgaaccatt ctgtcattgg accgaactca agactggcaa
1021 gaaatgtaaa agaagcacca acagaatatg catccatatg tgtgaggagt taagtctgtt
1081 tctgactcca acagggacca ttgaatgatc agcatgttga catcattgtc tgggctcaac
1141 aggatgtcaa ataatatttc tcaatttgag aatttttact ttagaaatgt tcatgttagt
1201 gcttgggtct taagggtcca taggataaat gattaaaatt tctctcagaa acttatttgg
1261 gagcttttta tattatagcc ttgaataaca aaatctctcc aaaactggtt gacatcatga
1321 gtagcagaat agtagaacgt ttaaacttag ctacatttta cccaatatac aaactcgatc
1381 ttgcctttga agctattgga aagacttgta gggaaaagag gtttgtgtta cctgcatcag
1441 ttcactacac actcttgaaa acaaaatgtc ccaatttgac taaccaacca taaatacagt
1501 aatgattgta tatttcaagt cagtcttcca aaataagaaa ttttgctgt gtcagtctaa
1561 gaatggtgtt tcttaaatgc aaaggagaaa tcattttagg cttgatgtaa gaaaatgaaa
1621 ataataaatg gtgcaataaa aatatagaat ataccaattg gatatagggt agatgttcca
1681 catacctggc aaacaaatgc ttatatctac tctgttagat tgataagcaa atataggtat
1741 taatggagca gtcaacgtat agcacattta tgaggaaagt agagactcac tgggtcacat
1801 agactaatgg ataggaatgt gacataatgc tgctgaatta atatacttat ggcatctga
1861 atagtttaaa agttagtcag aataggtatc actgggcaag tgaagatagc ttaaactgct
```

```
1921 tcatgcttga cttgatagca agttaaagtg caattaatgg aatggaggaa aacccagaat 1981 atttaattgg tctgtagggg tcaatttgct ttcattcacc acatctgcat cttgctgttc 2041 ttcttactaa ggaatcaggg caaatcatct gtagtgacat attttagttt gctaatcatt 2101 tattttaaaa tactgaggtt gcagccactt aagagtatag caaaagatgg attcagattt 2161 ttggactttc caaagtactt gagttaaact atttcaaaaa tagcctataa ttttattcaa 2221 cagtttgagg ctattcgaat tctcaggtgc tgctactgaa taatgtaata gtcttcatac 2281 aaagtggata gcaaaggtta aaatccattt caacaaatat gtgagctgag ctgctgcaca 2341 aaggaatgtg atgtgtgtgt gtgtgtgtgt gtgtgtgtgt gttaggtggg gtgggtgaca 2401 acagaaatgg tgcacgagaa actgatcaaa ttgacattat attttcagtt tgcttatgaa 2461 gctcaaaata ctagagtaaa tgggtcatta aagaaaataa tatgtgaaat tatggagttt 2521 agaatacaag tggggtatat atacaaaaag acaaaactga ggttttgtgg tggagagatt 2581 ttcttaagta acactggcat taagttttag ctccttagat ttgggggtgc aaatattctt 2641 ttgagtcact gttattttgc caattacacc tagaatttca agcaaccaat tcgagatagg 2701 ctgttttagc caggctgcat ttgtggacaa cttatgtaag aaagacatgt tagaatagct 2761 gcttgtggta ttcttaaaaa tagaaacagg aaatatgggg aggatacatt tagctgtcct 2821 cttatcagat gaacacacga aattgaacag ttccttcatg attctctcaa acttaaaagc 2881 aaaatatttc tgtcttattt aaaatatcct tagtatgtct tatagtaaag ataatgctga 2941 taatgatttc atctctaaga tgtattaata tatttgtact gtttgccaaa atcacaaatc 3001 atttatgttt ttattccttt tcaaaatggt gtcagagaca tacatgcatt ttcccaaatg 3061 actctacttc actattattt acatggctta tttcattagt ttatagaggg tttgagaaaa 3121 agaatatgta gataatttaa tggtttttca caaattttaa gcttgtgatt gtgctcaatg 3181 agaaggtaaa gttattaaaa cttatttgaa atcaaa
```

The amino acid sequence of human TIM3 is provided by Genbank Accession No. Q8TDQ0.3, incorporated herein by reference, and is shown below (SEQ ID NO: 17).

```
                                                          (SEQ ID NO: 17)
  1 mfshlpfdcv llllllllltr sseveyraev gqnaylpcfy tpaapgnlvp vcwgkgacpv 61 fecgnvvlrt derdvnywts rywlngdfrk gdvsltienv tladsgiycc riqipgimnd 121 ekfnlklvik pakvtpaptr qrdftaafpr mlttrghgpa etqtlgslpd inltqistla 181 nelrdsrlan dlrdsgatir igiyigagic aglalalifg alifkwyshs kekiqnlsli 241 slanlppsgl anavaegirs eeniytieen vyeveepney ycyvssrqqp sqplgcrfam 301 p
```

The mRNA sequence encoding human TIM3 is provided by Genbank Accession No. AF450242.1, incorporated herein by reference, and is shown below (SEQ ID NO: 18).

```
                                                          (SEQ ID NO: 18)
  1 ggagagttaa aactgtgcct aacagaggtg tcctctgact tttcttctgc aagctccatg 61 ttttcacatc ttccctttga ctgtgtcctg ctgctgctgc tgctactact tacaaggtcc 121 tcagaagtgg aatacagagc ggaggtcggt cagaatgcct atctgccctg cttctacacc 181 ccagccgccc cagggaacct cgtgcccgtc tgctggggca aggagcctg tcctgtgttt 241 gaatgtggca acgtggtgct caggactgat gaaagggatg tgaattattg gacatccaga
```

```
 301 tactggctaa atggggattt ccgcaaagga gatgtgtccc tgaccataga gaatgtgact 361 ctagcagaca gtgggatcta ctgctgccgg atccaaatcc caggcataat gaatgatgaa 421 aaatttaacc tgaagttggt catcaaacca gccaaggtca cccctgcacc gactctgcag 481 agagacttca ctgcagcctt tccaaggatg cttaccacca ggggacatgg cccagcagag 541 acacagacac tggggagcct ccctgatata aatctaacac aaatatccac attggccaat 601 gagttacggg actctagatt ggccaatgac ttacgggact ctggagcaac catcagaata 661 ggcatctaca tcggagcagg gatctgtgct gggctggctc tggctcttat cttcggcgct 721 ttaattttca aatggtattc tcatagcaaa gagaagatac agaatttaag cctcatctct 781 ttggccaacc tccctccctc aggattggca aatgcagtag cagagggaat tcgctcagaa 841 gaaaacatct ataccattga agagaacgta tatgaagtgg aggagcccaa tgagtattat 901 tgctatgtca gcagcaggca gcaaccctca caacctttgg gttgtcgctt tgcaatgcca 961 tagatccaac caccttattt ttgagcttgg tgttttgtct ttttcagaaa ctatgagctg 1021 tgtcacctga ctggttttgg aggttctgtc cactgctatg gagcagagtt ttcccatttt 1081 cagaagataa tgactcacat gggaattgaa ctggga
```

Combination of Inhibitors with Vaccines

In the presence of an endogenous anti-tumor immune response in a subject, inhibition of an immune-inhibitory (e.g., immune checkpoint) protein described above lifts the resistance of cancer cells to the immune response and allows the body's immune cells to destroy the cancer. However, in poorly immunogenic tumors, the endogenous immune response either does not exist or is too weak to kill the cancer cells, and inhibition of immune-inhibitory proteins has minimal efficacy.

To address this problem, the invention provides a combination of a cancer vaccine device with an inhibitor of an immune-inhibitory protein. As described in detail in the working examples, this combination surprisingly led to a greater decrease in tumor size and a longer survival time compared to administration of inhibitor alone. Described herein is a material-based (e.g., PLG) vaccine which has been optimized, e.g., to control the presentation of GM-CSF and adjuvants, relative to other vaccine formulations in order to enhance T effector activity and downregulate Treg cells and other immunosuppressive mechanisms that may be induced by some adjuvants. The material-based vaccine represents a significant advantage over previous vaccine systems in that it creates a tumor and vaccine microenvironment that responds to an immune-inhibitory protein, e.g., anti-CTLA-4, by preferentially enhancing effector T cell generation and expansion over Treg cells.

The invention features a cancer vaccine device that comprises one or more (e.g., 1, 2, 3, 4, 5, 6, or more) inhibitors to an immune-inhibitory protein. For example, the inhibitor(s) is incorporated into or onto the cancer vaccine device, e.g., incorporated into or onto a scaffold composition within the device. Administration of a cancer vaccine device containing the inhibitor(s) allows for localized delivery of the inhibitor(s), e.g., at the same site as vaccine.

The inhibitor can be encapsulated in the vaccine device during fabrication of the device. Alternatively, the inhibitor is added to the vaccine device after it is fabricated. For example, the inhibitor is encapsulated in the PLG microspheres utilized to fabricate the vaccine, combined with the CpG and sucrose added to the PLG prior to foaming, or added to the vaccine device after fabrication, e.g., by adsorbing to the surface of the device, or by placing the inhibitor in a sustained release formulation that is subsequently combined with the vaccine device.

For example, the cancer vaccine device comprises an anti-CTLA4 antibody and/or an anti-PD1 antibody.

The invention also provides a method of killing a cancer cell, slowing cancer progression, reducing a tumor size, prolonging the survival time of a cancer patient, and/or treating cancer by administering a cancer vaccine in combination with an inhibitor of an immune-inhibitory protein.

For example, the vaccine and the inhibitor are formulated separately, i.e., the inhibitor is not included within the vaccine device. In some embodiments, the vaccine and one or more (e.g., 1, 2, 3, 4, 5, 6, or more) inhibitor(s) are administered simultaneously. In other cases, the vaccine and the inhibitor(s) are administered sequentially. For example, the inhibitor(s) is administered at least 6 hours (e.g., 6 h, 12 h, 24 h, 2 days, 3 days, 4 days, 5 days, 6 days, 7 days, 1.5 weeks, 2 weeks, 3 weeks, 4 weeks, or more) prior to administration of the vaccine. In other cases, the vaccine is administered at least 6 hours (e.g., 6 h, 12 h, 24 h, 2 days, 3 days, 4 days, 5 days, 6 days, 7 days, 1.5 weeks, 2 weeks, 3 weeks, 4 weeks, or more) prior to administration of the inhibitor(s). In other embodiments, the vaccine and the inhibitor are formulated together, e.g., the inhibitor is included within or coated onto the vaccine device.

For example, an anti-CTLA4 antibody and/or anti-PD1 antibody are administered in combination with the vaccine device (e.g., administered simultaneously or sequentially).

The combination of inhibitor(s) and vaccine in provides certain advantages. For example, the combination synergistically induces the activity of T effector cells that infiltrate tumors. Also, the combination enhances local T effector cell activity (e.g., T cells in close proximity to the implanted vaccine device, and/or T cells in the vaccine draining lymph nodes). Also, the combination of inhibitor(s) and vaccine in the same device provides advantages over non-device vaccines used in combination with the inhibitor(s). In particular, inclusion of the inhibitor(s) in the vaccine device allows for targeting of local and/or specific immune cells (such as those specifically recruited to the device). Unlike systemic administration of the inhibitor(s), this local administration of the inhibitor(s) in some cases leads to lower toxicity and a lower dosage needed for efficacy.

In some cases, the inhibitor is administered prior to the vaccine device. For example, after administration of the inhibitor (e.g., antibody), e.g., within a week, immune cells infiltrate into the tumor site. The infiltration can cause a transient increase in tumor size. After administration (e.g., implantation) of the vaccine device, regression in tumor size occurs. For example, regression in tumor size occurs at least 1 weeks (e.g., 1, 2, 3, 4, 5, 6, 7, 8, 9, 10, 11, 12, 13, 14, 15, 16, 17, 18, 19, 20, 30, 40, 50, 60 weeks or more) after administration of the vaccine device. In some cases, the combination of the inhibitor and the vaccine device causes a reduction in tumor size (e.g., a reduction of at least 10%, e.g., 10%, 20%, 30%, 40%, 50%, 60%, 70%, 80%, 90%, 95%, or more) compared to the tumor size prior to administration of the inhibitor and/or vaccine device. In some examples, the combination of the inhibitor and the vaccine device causes total eradication of the tumor.

Tumor size is determined by standard methods in the art. For example, tumor size is the weight of the tumor or the area of the tumor. Tumor size (area in $mm^2$) is, e.g., the product of the two longest diameters of the tumor. Tumor diameters can be measured using standard methods (e.g., with calipers). In other examples, the weight of a tumor is a measure of its size.

Cancer Vaccine Device

In the cancer vaccine, presentation of toll like receptor (TLR) agonists for cancer vaccination leads to improved activation of immune cells. The vaccines and methods comprise incorporation and presentation of TLR agonists embedded in structural polymeric devices. CD8(+) Dendritic cells (DCs) and plasmacytoid DCs (as well as conventional DCs) play important roles in cancer vaccination; these cells are preferentially recruited and activated using the TLR-agonist containing structural polymeric device. The device is manufactured as a tiny bioengineered porous disc filled with tumor-specific antigens and TLR agonists. The disc is implanted into the body, e.g., inserted under the skin, where it activates the immune system to destroy cancer cells. This approach reprograms cells that are already in the body.

In some examples, the device includes a recruitment component. Thus, the device optionally includes a recruitment molecule such as a cytokine. In those situations, polymers were designed to first release a cytokine to recruit and house host dendritic cells (DCs), and subsequently present cancer antigens and danger signals to activate the resident DCs and dramatically enhance their homing to lymph nodes. Specific and protective anti-tumor immunity was generated with these materials. For example, a 90% survival rate was achieved in animals that otherwise die from cancer within 25 days. These materials are useful in cancer and other vaccines to program and control the trafficking of a variety of cell types in the body.

A polymer system was designed to not only serve as a drug delivery device, but also as a physical, antigen-presenting structure to which the DCs are recruited, and where DCs reside while they are activated using a material (poly [lactide-co-glycolide]) (PLG) and bioactive molecules (e.g., GM-CSF and CpG-ODN). These bioactive molecules have excellent safety profiles. The material system serves as an effective cancer vaccine, eliminating the time, expense and regulatory burden inherent to existing cell therapies and reducing or eliminating the need for multiple, systemic injections and high total drug loading. The devices described herein utilize infection-mimicking materials to program DCs in situ.

The invention includes macroporous polymer matrices that regulate the trafficking and activation of DCs in vivo by precisely controlling the presentation of GM-CSF and CpG-oligonucleotide (CpG-ODN) adjuvants (Ali et al., 2009 Nat Mater, 2: 151-8; Ali et al., 2009 Sci Transl Med, 1:8-19). When applied as cancer vaccines, these matrices have led induced CTL-mediated eradication of melanoma tumors (Ali et al., 2009 Sci Transl Med, 1:8-19).

A macroporous poly-lactide-co-glycolide (PLG) matrix presents GM-CSF, danger signals, and cancer antigens in a defined spatiotemporal manner in vivo, and serve as a residence for recruited DCs as they are programmed. GM-CSF is encapsulated into PLG scaffolds using a high pressure $CO_2$ foaming process, as described in US 2013-0202707. The GM-CSF release profile from the matrix allows diffusion of the factor through the surrounding tissue to effectively recruit resident DCs.

In situ dendritic cell targeting systems are utilized to therapeutically manipulate the immune system with TLR agonists. As described in detail in US 2013-0202707 (incorporated herein by reference), macroporous polymeric scaffolds are designed that deliver three different classes of TLR agonists in vivo: CpG-ODN, monophosphoryl lipid A (MPLA), and polyinosinic:polycytidylic acid (P(I:C)) in combination with GM-CSF, Flt3L, or CCL20 to augment DC recruitment and activation. Various subsets of DCs are recruited and utilized for in situ vaccination. The ability of these systems to effect immune protection and tumor regression required CD8(+) DCs and correlates strongly with plasmacytoid DCs(pDCs) and IL-12 production, regardless of the TLR agonist type or dose.

Inflammatory Mediators

Dendritic Cell (DC) proliferation, migration and maturation are sensitive to inflammatory mediators, and granulocyte macrophage colony stimulating factor (GM-CSF) has been identified as a potent stimulator of immune responses, specifically against cancer antigens. GM-CSF also has the ability to recruit and program these antigen-presenting immune cells. Additionally, Cytosine-guanosine (CpG) oligonucleotide (CpG-ODN) sequences found in bacterial DNA are potent immunomodulators that stimulate DC activation, leading to specific T-cell responses. Creating an infection mimicking microenvironment by the presentation of exogenous GM-CSF and CpG-ODN provides an avenue to precisely control the number and timing of DC migration and modulate antigen specific immune responses.

The vertebrate immune system employs various mechanisms for pathogen recognition, making it adept at generating antigen-specific responses and clearing infection. Immunity is controlled by antigen presenting cells (APCs), especially dendritic cells (DCs), which capture antigens and are activated by stimuli, unique 'danger signals' of the invading pathogen, such as CpG dinucleotide sequences in bacterial DNA (Bancbereau J, and Steinman R M. Nature. 392, 245-252. (1998); Klinman D M. Nat. Rev. Immunol. 4, 249-58 (2004); each incorporated herein by reference).

However, cancerous cells, derived from self-tissues, are void of the danger signals required to signal DC maturation and instead promote an immunosuppressive microenvironment that allows cells to escape immunity. Key elements of infection are inflammatory cytokines and danger signals. A polymeric material system is ideal to present these factors in the required spatiotemporal manner to provide an infection-mimicking microenvironment in situ that useful as a vaccine. These infection mimics provide the continuous programming of host DCs, providing for efficient DC activation and dispersement in situ. These infection-mimicking devices are used for numerous vaccine applications, including melanoma cancer vaccines.

In many infections, inflammatory cytokines and danger signals stimulate specific DC responses that mediate immune recognition and pathogen clearance. For example, upon bacterial invasion and release of toxins, skin cells such as fibroblasts, keratinocytes and melanocytes are damaged, resulting in the release of inflammatory cytokines, such as GM-CSF (Hamilton J. Trends in Immunol. 23, 403-408. (2002); Hamilton J., and Anderson G. Growth Factors. 22(4), 225-231. (2004); each herein incorporated by reference), that act to recruit Langerhans DC (skin) and DC precursors (monocytes; blood) (Hamilton J. Trends in Immunol. 23, 403-408. (2002); Hamilton J., and Anderson G. Growth Factors. 22(4), 225-231. (2004); Bowne W. B., et al. Cytokines Cell Mol Ther. 5(4), 217-25. (1999); Dranoff, G. Nat. Rev. Cancer 4, 11-22 (2004); each herein incorporated by reference). As DCs arrive to the site of infection, they begin to differentiate and increase in phagocytic ability in response to the inflammation (Mellman I., and Steinman R. M. Cell. 106, 255-258. (2001), incorporated herein by reference). DCs that ingest bacteria or their products begin to process antigens, and DC maturation proceeds via endosomal TLR9 signaling stimulated by CpG dinucleotide sequences in bacterial DNA (Krieg A. M., Hartmann G., and Weiner G. J. CpG DNA: A potent signal for growth, activation, and maturation of human dendritic cells. Proc Natl Acad Sci USA. 16, 9305-9310 (1999), incorporated herein by reference). Mature DCs then home to the lymph nodes where they prime antigen specific T-cell responses that clear infection.

CpG-ODNs are potent "danger signals" that upregulate DC expression of CCR7, CD80/86 costimulatory molecules, and MHC-antigen complexes. Importantly, TLR9 signaling induces DCs into promoting Th1-like, cytotoxic T cell responses by cytokine production (e.g., type 1 IFN) and cross-presentation of antigen onto MHCI molecules. The presentation of these signals concurrently with tumor antigens provides the danger signal needed to promote immune responses that effectively fight cancerous cells.

Different classes of CPG-ODNs promote different immune responses depending on the ODN's specific structure and sequence. The ODN utilized in the present invention, CpG-ODN 1826, has been successfully tested in various mouse vaccination models, including melanoma. CpG-ODN 1826 has shown a beneficial effect alone or when used as adjuvant for peptide vaccines and whole cell vaccines. Moreover, ODN 1826 has been shown to directly promote DC maturation and cytokine production. This particular CpG ODN sequence also indirectly activates Th1 cells and NK cells and, thus, enhances adaptive cellular immune responses.

Vector systems that promote CpG internalization into DCs to enhance delivery and its localization to TLR9 have been developed. The amine-rich polycation, polyethylimine (PEI) has been extensively used to condense plasmid DNA, via association with DNA phosphate groups, resulting in small, positively charge condensates facilitating cell membrane association and DNA uptake into cells (Godbey W. T., Wu K. K., and Mikos, A. G. J. of Biomed Mater Res, 1999, 45, 268-275; Godbey W. T., Wu K. K., and Mikos, A. G. Proc Natl Acad Sci USA. 96(9), 5177-81. (1999); each herein incorporated by reference). Consequently, PEI has been utilized as a non-viral vector to enhance gene transfection and to fabricate PEI-DNA loaded PLG matrices that promoted long-term gene expression in host cells in situ (Huang Y C, Riddle F, Rice K G, and Mooney D J. Hum Gene Ther. 5, 609-17. (2005), incorporated herein by reference). Therefore, CpG-ODNs were condensed with PEI molecules in the present invention. The PEI condensation enhances DC internalization of CpG-ODN, and the subsequent decondensation of PEI-CpG-ODN within DCs promotes DC activation (US 2013-0202707, incorporated herein by reference, e.g., at page 86, lines 1-7; and FIG. 3).

To appropriately mimic infection and program cells in situ, the PLG system of the invention was designed to not only serve as a drug delivery device that releases inflammatory cytokines (e.g., GM-CSF), but also as a physical structure to which the DCs are recruited and reside while they are activated by danger signals (e.g., CpG-ODNs). The ability to control DC recruitment to and DC residence within porous PLG matrices is achieved using temporal control over the delivery of GM-CSF in situ, which results in batches of programmed DCs being dispersed only when GM-CSF levels were designed to subside in situ. For example, this system disperses at least 5% (e.g., about 6%) of programmed DCs to the lymph nodes and induces protective anti-tumor immunity in at least 20% (e.g., about 23%) of mice when applied as a cancer vaccine. The cell programming and dispersement efficiency is improved using an overriding secondary signal (CpG-ODN) that continuously releases DCs from GM-CSF inhibition and promotes DC maturation and dispersement in the presence of high GM-CSF levels in situ. For example, PLG matrices were fabricated to locally present synthetic CpG-ODN with exogenous GM-CSF allowing for DCs recruited by GM-CSF to be stimulated by CpG-ODN in situ.

Dendritic Cells

Dendritic cells (DCs) are immune cells within the mammalian immune system and are derived from hematopoietic bone marrow progenitor cells. More specifically, dendritic cells can be categorized into lymphoid (or plasmacytoid) dendritic cell (pDC) and myeloid dendritic cell (mDC) subdivisions having arisen from a lymphoid (or plasmacytoid) or myeloid precursor cell, respectively. From the progenitor cell, regardless of the progenitor cell type, an immature dendritic cell is born. Immature dendritic cells are characterized by high endocytic activity and low T-cell activation potential. Thus, immature dendritic cells constitutively sample their immediate surrounding environment for pathogens. Exemplary pathogens include, but are not limited to, a virus or a bacteria. Sampling is accomplished by pattern recognition receptors (PRRs) such as the toll-like receptors (TLRs). Dendritic cells activate and mature once a pathogen is recognized by a pattern recognition receptor, such as a toll-like receptor.

Mature dendritic cells not only phagocytose pathogens and break them down, but also, degrade their proteins, and present pieces of these proteins, also referred to as antigens, on their cell surfaces using MHC (Major Histocompatibility Complex) molecules (Classes I, II, and III). Mature dendritic cells also upregulate cell-surface receptors that serve as co-receptors for T-cell activation. Exemplary co-receptors include, but are not limited to, CD80, CD86, and CD40. Simultaneously, mature dendritic cells upregulate chemotactic receptors, such as CCR7, that allows the cell to migrate through the blood stream or the lymphatic system to the spleen or lymph node, respectively.

Dendritic cells are present in external tissues that are in contact with the external environment such as the skin (dendritic cells residing in skin are also referred to as Langerhans cells). Alternatively, dendritic cells are present in internal tissues that are in contact with the external environment such as linings of the nose, lungs, stomach, and intestines. Finally, immature dendritic cells reside in the blood stream. Once activated, dendritic cells from all off these tissues migrate to lymphoid tissues where they present antigens and interact with T cells and B cells to initiate an immune response. One signaling system of particular importance for the present invention involves the chemokine receptor CCR7 expressed on the surface of dendritic cells and the chemokine receptor ligand CCL19 secreted by lymph node structures to attract migrating mature dendritic cells toward high concentrations of immune cells. Exemplary immune cells activated by contact with mature dendritic cells include, but are not limited to, helper T cells, killer T cells, and B cells. Although multiple cell types within the immune system present antigens, including macrophages and B lymphocytes, dendritic cells are the most potent activators of all antigen-presenting cells.

Dendritic cells earned their name from the characteristic cell shape comprising multiple dendrites extending from the cell body. The functional benefit of this cell shape is a significantly increased cell surface and contact area to the surroundings compared to the cell volume. Immature dendritic cells sometimes lack the characteristic dendrite formations and are referred to as veiled cells. Veiled cells possess large cytoplasmic veils rather than dendrites.

Plasmacytoid dendritic cells (pDCs) are innate immune cells that circulate in the blood and are found in peripheral lymphoid organs. They constitute <0.4% of peripheral blood mononuclear cells (PBMC). In humans, these cells express the surface markers CD123, BDCA-2(CD303) and BDCA-4(CD304), but do not express high levels of CD11c or CD14, which distinguishes them from conventional dendritic cells or monocytes, respectively. Mouse pDC express CD11c, B220, BST-2 (mPDCA) and Siglec-H and are negative for CD11b. As components of the innate immune system, these cells express intracellular Toll-like receptors 7 and 9 which detect ssRNA and CpG DNA motifs, respectively. Upon stimulation and subsequent activation, these cells produce large amounts of type I interferon (mainly IFN-α (alpha) and IFN-3 (beta)), which are critical pleiotropic anti-viral compounds mediating a wide range of effects. The CD8− subset presents antigen using the class II pathway to CD4+ helper T cells. The CD8+ subset presents antigens using the class I pathway. The peptide/MHC class I molecules are presented to CD8+ T cells which go on to become cytotoxic T lymphocytes (CTL). The CD8 cell surface protein in the mouse corresponds to the CD141 cell surface protein in the human. CD8/CD141-positive cells express TLR3 and are preferentially activated by TLR3 agonists.

Toll-Like Receptors (TLRs)

TLRs are a class of single transmembrane domain, non-catalytic, receptors that recognize structurally conserved molecules referred to as pathogen-associated molecular patterns (PAMPs). PAMPs are present on microbes and are distinguishable from host molecules. TLRs are present in all vertebrates. Thirteen TLRs (referred to as TLRs1-13, consecutively) have been identified in humans and mice. Humans comprise TLRs 1-10.

TLRs and interleukin-1 (IL-1) receptors comprise a receptor superfamily the members of which all share a TIR domain (Toll-IL-1 receptor). TIR domains exist in three varieties with three distinct functions. TIR domains of subgroup 1 are present in receptors for interleukins produced by macrophages, monocytes, and dendritic cells. TIR domains of subgroup 2 are present in classical TLRs which bind directly or indirectly to molecules of microbial origin. TIR domains of subgroup 3 are present in cytosolic adaptor proteins that mediate signaling between proteins comprising TIR domains of subgroups 1 and 2.

TLR ligands comprise molecules that are constantly associated with and highly specific for a threat to the host's survival such as a pathogen or cellular stress. TLR ligands are highly specific for pathogens and not the host. Exemplary pathogenic molecules include, but are not limited to, lipopolysaccharides (LPS), lipoproteins, lipoarabinomannan, flagellin, double-stranded RNA, and unmethylated CpG islands of DNA.

In one preferred embodiment of the present invention, the Toll-Like receptor 9 (TLR9) is activated by specific unmethylated CpG-containing sequences in bacterial DNA or synthetic oligonucleotides (ODNs) found in the endosomal compartment of dendritic cells. Methylation status of the CpG site is a crucial distinction between bacterial and mammalian DNA, as well as between normal and cancerous tissue. Unmethylated ODNs including one or more CpG motifs mimic the effects of bacterial DNA. Alternatively, or in addition, unmethylated ODNs including one or more CpG motifs occur within oncogenes present within malignant tumor cells.

One or more sequences of the TLR-9 receptor recognizes one or more CpG-ODN sequences of the present invention. TLR-9 receptors encompassed by the present invention are described by the following sequences.

Human TLR-9, isoform A, is encoded by the following mRNA sequence (NCBI Accession No. NM_017442 and SEQ ID NO: 19; the start codon for all mRNA sequences presented herein is bolded and capitalized):

```
                                                      (SEQ ID NO: 19)
  1 ggaggtcttg tttccggaag atgttgcaag gctgtggtga aggcaggtgc agcctagcct 61 cctgctcaag ctacaccctg gccctccacg catgaggccc tgcagaactc tggagatggt 121 gcctacaagg gcagaaaagg acaagtcggc agccgctgtc ctgagggcac cagctgtggt 181 gcaggagcca agacctgagg gtggaagtgt cctcttagaa tggggagtgc ccagcaaggt 241 gtacccgcta ctggtgctat ccagaattcc catctctccc tgctctctgc ctgagctctg 301 ggccttagct cctccctggg cttggtagag acaggtgtg aggccctcat gggatgtagg 361 ctgtctgaga ggggagtgga aagaggaagg ggtgaaggag ctgtctgcca tttgactatg 421 caaatggcct ttgactcatg ggaccctgtc ctcctcactg ggggcagggt ggagtggagg 481 gggagctact aggctggtat aaaaatctta cttcctctat tctctgagcc gctgctgccc
```

-continued

```
 541 ctgtgggaag ggacctcgag tgtgaagcat ccttccctgt agctgctgtc cagtctgccc
 601 gccagaccct ctggagaagc ccctgccccc cagcATGggt ttctgccgca cgcccctgca
 661 cccgctgtct cctggtgc aggccatcat gctggccatg accctggccc tgggtacctt
 721 gcctgccttc ctaccctgtg agctccagcc cacggcctg gtgaactgca actggctgtt
 781 cctgaagtct gtgccccact tctccatggc agcacccgt ggcaatgtca ccagcctttc
 841 cttgtcctcc aaccgcatcc accacctcca tgattctgac tttgccccacc tgcccagcct
 901 gcggcatctc aacctcaagt ggaactgccc gccggttggc ctcagcccca tgcacttccc
 961 ctgccacatg accatcgagc ccagcacctt cttggctgtg cccaccctgg aagagctaaa
1021 cctgagctac aacaacatca tgactgtgcc tgcgctgccc aaatccctca tatccctgtc
1081 cctcagccat accaacatcc tgatgctaga ctctgccagc ctcgccggcc tgcatgccct
1141 gcgcttccta ttcatggacg gcaactgtta ttacaagaac ccctgcaggc aggcactgga
1201 ggtggcccccg ggtgccctcc ttggcctggg caacctcacc cacctgtcac tcaagtacaa
1261 caacctcact gtggtgcccc gcaacctgcc ttccagcctg gagtatctgc tgttgtccta
1321 caaccgcatc gtcaaactgg cgcctgagga cctggccaat ctgaccgccc tgcgtgtgct
1381 cgatgtgggc ggaaattgcc gccgctgcga ccacgctccc aaccctgca tggagtgccc
1441 tcgtcacttc ccccagctac atcccgatac cttcagccac ctgagccgtc ttgaaggcct
1501 ggtgttgaag gacagttctc tctcctggct gaatgccagt tggttccgtg ggctgggaaa
1561 cctccgagtg ctggacctga gtgagaactt cctctacaaa tgcatcacta aaaccaaggc
1621 cttccagggc ctaacacagc tgcgcaagct taacctgtcc ttcaattacc aaaagagggt
1681 gtcctttgcc cacctgtctc tggccccttc cttcgggagc ctggtcgccc tgaaggagct
1741 ggacatgcac ggcatcttct ccgctcact cgatgagacc acgctccggc cactggcccg
1801 cctgcccatg ctccagactc tgcgtctgca gatgaacttc atcaaccagg cccagctcgg
1861 catcttcagg gccttccctg gcctgcgcta cgtggacctg tcggacaacc gcatcagcgg
1921 agcttcggag ctgacagcca ccatgggggga ggcagatgga ggggagaagg tctggctgca
1981 gcctggggac cttgctccgg ccccagtgga cactcccagc tctgaagact tcaggcccaa
2041 ctgcagcacc ctcaacttca ccttggatct gtcacggaac aacctggtga ccgtgcagcc
2101 ggagatgttt gcccagctct cgcacctgca gtgcctgcgc ctgagccaca ctgcatctc
2161 gcaggcagtc aatggctccc agttcctgcc gctgaccggt ctgcaggtgc tagacctgtc
2221 ccacaataag ctgaccctct accacgagca ctcattcacg gagctaccac gactggaggc
2281 cctggacctc agctacaaca gccagccctt tggcatgcag ggcgtgggcc acaacttcag
2341 cttcgtggct cacctgcgca ccctgcgcca cctcagcctg gcccacaaca catccacag
2401 ccaagtgtcc cagcagctct gcagtacgtc gctgcgggcc ctggacttca gcggcaatgc
2461 actgggccat atgtgggccg agggagacct ctatctgcac ttcttccaag gcctgagcgg
2521 tttgatctgg ctggacttgt cccagaaccg cctgcacacc ctcctgcccc aaaccctgcg
2581 caacctcccc aagagcctac aggtgctgcg tctccgtgac aattacctgg ccttctttaa
2641 gtggtggagc ctccacttcc tgcccaaact ggaagtcctc gacctggcag gaaaccagct
2701 gaaggccctg accaatggca gcctgcctgc tggcacccgg ctccggaggc tggatgtcag
2761 ctgcaacagc atcagcttcg tggcccccgg cttcttttcc aaggccaagg agctgcgaga
2821 gctcaacctt agcgccaacg ccctcaagac agtggaccac tcctggtttg gcccctggc
2881 gagtgccctg caaatactag atgtaagcgc caaccctctg cactgcgcct gtggggcggc
```

```
2941 ctttatggac ttcctgctgg aggtgcaggc tgccgtgccc ggtctgccca gccgggtgaa 3001 gtgtggcagt ccgggccagc tccagggcct cagcatcttt gcacaggacc tgcgcctctg 3061 cctggatgag gccctctcct gggactgttt cgccctctcg ctgctggctg tggctctggg 3121 cctgggtgtg cccatgctgc atcacctctg tggctgggac ctctggtact gcttccacct 3181 gtgcctggcc tggcttccct ggcgggggcg gcaaagtggg cgagatgagg atgccctgcc 3241 ctacgatgcc ttcgtggtct tcgacaaaac gcagagcgca gtggcagact gggtgtacaa 3301 cgagcttcgg gggcagctgg aggagtgccg tgggcgctgg gcactccgcc tgtgcctgga 3361 ggaacgcgac tggctgcctg gcaaaaccct ctttgagaac ctgtgggcct cggtctatgg 3421 cagccgcaag acgctgtttg tgctggccca cacggaccgg gtcagtggtc tcttgcgcgc 3481 cagcttcctg ctggcccagc agcgcctgct ggaggaccgc aaggacgtcg tggtgctggt 3541 gatcctgagc cctgacggcc gccgctcccg ctatgtgcgg ctgcgccagc gcctctgccg 3601 ccagagtgtc ctcctctggc cccaccagcc cagtggtcag cgcagcttct gggcccagct 3661 gggcatggcc ctgaccaggg acaaccacca cttctataac cggaacttct gccagggacc 3721 cacggccgaa tagccgtgag ccggaatcct gcacggtgcc acctccacac tcacctcacc 3781 tctgcctgcc tggtctgacc ctccctgct cgcctccctc accccacacc tgacacagag 3841 caggcactca ataaatgcta ccgaaggc
```

Human TLR-9, isoform A, is encoded by the following amino acid sequence (NCBI Accession No. NP_059138 and SEQ ID NO: 20):

```
                                            (SEQ ID NO: 20)
MGFCRSALHPLSLLVQAIMLAMTLALGTLPAFLPCELQPHGLVNCNWLFL

KSVPHFSMAAPRGNVTSLSLSSNRIHHLHDSDFAHLPSLRHLNLKWNCPP

VGLSPMHFPCHMTIEPSTFLAVPTLEELNLSYNNIMTVPALPKSLISLSL

SHTNILMLDSASLAGLHALRFLFMDGNCYYKNPCRQALEVAPGALLGLGN

LTHLSLKYNNLTVVPRNLPSSLEYLLLSYNRIVKLAPEDLANLTALRVLD

VGGNCRRCDHAPNPCMECPRHFPQLHPDTFSHLSRLEGLVLKDSSLSWLN

ASWFRGLGNLRVLDLSENFLYKCITKTKAFQGLTQLRKLNLSFNYQKRVS

FAHLSLAPSFGSLVALKELDMHGIFFRSLDETTLRPLARLPMLQTLRLQM

NFINQAQLGIFRAFPGLRYVDLSDNRISGASELTATMGEADGGEKVWLQP

GDLAPAPVDTPSSEDFRPNCSTLNFTLDLSRNNLVTVQPEMFAQLSHLQC

LRLSHNCISQAVNGSQFLPLTGLQVLDLSHNKLDLYHEHSFTELPRLEAL

DLSYNSQPFGMQGVGHNFSFVAHLRTLRHLSLAHNNIHSQVSQQLCSTSL

RALDFSGNALGHMWAEGDLYLHFFQGLSGLIWLDLSQNRLHTLLPQTLRN

LPKSLQVLRLRDNYLAFFKWWSLHFLPKLEVLDLAGNQLKALTNGSLPAG

TRLRRLDVSCNSISFVAPGFFSKAKELRELNLSANALKTVDHSWFGPLAS

ALQILDVSANPLHCACGAAFMDFLLEVQAAVPGLPSRVKCGSPGQLQGLS

IFAQDLRLCLDEALSWDCFALSLLAVALGLGVPMLHHLCGWDLWYCFHLC

LAWLPWRGRQSGRDEDALPYDAFVVFDKTQSAVADWVYNELRGQLEECRG

RWALRLCLEERDWLPGKTLFENLWASVYGSRKTLFVLAHTDRVSGLLRAS

FLLAQQRLLEDRKDVVVLVILSPDGRRSRYVRLRQRLCRQSVLLWPHQPS

GQRSFWAQLGMALTRDNHHFYNRNFCQGPTAE
```

Human TLR3 is encoded by the following mRNA sequence (GenBank Accesion No. NM_003265.2 (GI: 19718735), incorporated herein by reference; SEQ ID NO: 21):

```
                                            (SEQ ID NO: 21)
  1 cactttcgag agtgccgtct atttgccaca cacttccctg atgaaatgtc tggatttgga 61 ctaaagaaaa aaggaaaggc tagcagtcat ccaacagaat cATGagacag actttgcctt 121 gtatctactt ttgggggggc cttttgccct ttgggatgct gtgtgcatcc tccaccacca 181 agtgcactgt tagccatgaa gttgctgact gcagccacct gaagttgact caggtacccg 241 atgatctacc cacaaacata acagtgttga accttaccca taatcaactc agaagattac 301 cagccgccaa cttcacaagg tatagccagc taactagctt ggatgtagga tttaacacca 361 tctcaaaact ggagccagaa ttgtgccaga acttcccat gttaaaagtt ttgaacctcc 421 agcacaatga gctatctcaa ctttctgata aaacctttgc cttctgcacg aatttgactg
```

-continued

```
 481 aactccatct catgtccaac tcaatccaga aaattaaaaa taatcccttt gtcaagcaga
 541 agaatttaat cacattagat ctgtctcata atggcttgtc atctacaaaa ttaggaactc
 601 aggttcagct ggaaaatctc aagagcttc tattatcaaa caataaaatt caagcgctaa
 661 aaagtgaaga actggatatc tttgccaatt catctttaaa aaaattagag ttgtcatcga
 721 atcaaattaa agagttttct ccagggtgtt tcacgcaat tggaagatta tttggcctct
 781 ttctgaacaa tgtccagctg ggtcccagcc ttacagagaa gctatgtttg gaattagcaa
 841 acacaagcat tcggaatctg tctctgagta acagccagct gtccaccacc agcaatacaa
 901 ctttcttggg actaaagtgg acaaatctca ctatgctcga tctttcctac aacaacttaa
 961 atgtggttgg taacgattcc tttgcttggc ttccacaact agaatatttc ttcctagagt
1021 ataataatat acagcatttg ttttctcact ctttgcacgg gcttttcaat gtgaggtacc
1081 tgaatttgaa acggtctttt actaaacaaa gtatttccct tgcctcactc cccaagattg
1141 atgattttc ttttcagtgg ctaaaatgtt tggagcacct taacatggaa gataatgata
1201 ttccaggcat aaaaagcaat atgttcacag gattgataaa cctgaaatac ttaagtctat
1261 ccaactcctt tacaagtttg cgaactttga caaatgaaac atttgtatca cttgctcatt
1321 ctcccttaca catactcaac ctaaccaaga ataaaatctc aaaaatagag agtgatgctt
1381 tctcttggtt gggccaccta gaagtacttg acctgggcct taatgaaatt gggcaagaac
1441 tcacaggcca ggaatggaga ggtctagaaa atatttcga atctatctt tcctacaaca
1501 agtacctgca gctgactagg aactcctttg ccttggtccc aagccttcaa cgactgatgc
1561 tccgaagggt ggcccttaaa aatgtggata gctctccttc accattccag cctcttcgta
1621 acttgaccat tctggatcta agcaacaaca acatagccaa cataaatgat gacatgttgg
1681 agggtcttga gaaactagaa attctcgatt tgcagcataa caacttagca cggctctgga
1741 aacacgcaaa ccctggtggt cccatttatt tcctaaaggg tctgtctcac ctccacatcc
1801 ttaacttgga gtccaacggc tttgacgaga tcccagttga ggtcttcaag gatttatttg
1861 aactaaagat catcgattta ggattgaata atttaaacac acttccagca tctgtcttta
1921 ataatcaggt gtctctaaag tcattgaacc ttcagaagaa tctcataaca tccgttgaga
1981 agaaggtttt cgggccagct ttcaggaacc tgactgagtt agatatgcgc tttaatccct
2041 ttgattgcac gtgtgaaagt attgcctggt ttgttaattg gattaacgag acccatacca
2101 acatccctga gctgtcaagc cactaccttt gcaacactcc acctcactat catgggttcc
2161 cagtgagact ttttgataca tcatcttgca aagacagtgc ccccttttgaa ctctttttca
2221 tgatcaatac cagtatcctg ttgattttta tctttattgt acttctcatc cactttgagg
2281 gctggaggat atctttttat tggaatgttt cagtacatcg agttcttggt ttcaaagaaa
2341 tagacagaca gacagaacag tttgaatatg cagcatatat aattcatgcc tataaagata
2401 aggattgggt ctgggaacat ttctcttcaa tggaaaagga agaccaatct ctcaaatttt
2461 gtctggaaga aagggacttt gaggcgggtg ttttgaact agaagcaatt gttaacagca
2521 tcaaaagaag cagaaaaatt attttttgtta taacacacca tctattaaaa gacccattat
2581 gcaaaagatt caaggtacat catgcagttc aacaagctat tgaacaaaat ctggattcca
2641 ttatattggt tttccttgag gagattccag attataaact gaaccatgca ctctgtttgc
2701 gaagaggaat gtttaaatct cactgcatct tgaactggcc agttcagaaa gaacggatag
2761 gtgcctttcg tcataaattg caagtagcac ttggatccaa aaactctgta cattaaattt
2821 atttaaatat tcaattagca aaggagaaac tttctcaatt taaaaagttc tatggcaaat
2881 ttaagttttc cataaaggtg ttataatttg tttattcata tttgtaaatg attatattct
```

```
2941 atcacaatta catctcttct aggaaaatgt gtctccttat ttcaggccta tttttgacaa 3001 ttgacttaat tttacccaaa ataaaacata taagcacgta aaaaaaaaaa aaaaaaa
```

Human TLR3 is encoded by the following amino acid sequence (GenBank Accesion No. ABC86910.1 (GI: 86161330), incorporated herein by reference; SEQ ID NO: 22):

```
                                                      (SEQ ID NO: 22)
  1 mrqtlpciyf wggllpfgml cassttkctv shevadcshl kltqvpddlp tnitvlnlth 61 nqlrrlpaan ftrysqltsl dvgfntiskl epelcqklpm lkvlnlqhne lsqlsdktfa 121 fctnltelhl msnsiqkikn npfvkqknli tldlshngls stklgtqvql enlqelllsn 181 nkiqalksee ldifansslk klelssnqik efspgcfhai grlfglflnn vqlgpsltek 241 lclelantsi rnlslsnsql sttsnttflg lkwtnltmld lsynnlnvvg ndsfawlpql 301 eyffleynni qhlfshslhg lfnvrylnlk rsftkqsisl aslpkiddfs fqwlkclehl 361 nmedndipgi ksnmftglin lkylslsnsf tslrtltnet fvslahsplh ilnltknkis 421 kiesdafswl ghlevldlgl neigqeltgq ewrglenife iylsynkylq ltrnsfalvp 481 slqrlmlrrv alknvdssps pfqplrnlti ldlsnnnian inddmlegle kleildlqhn 541 nlarlwkhan pggpiyflkg lshlhilnle sngfdeipve vfkdlfelki idlglnnlnt 601 lpasvfnnqv slkslnlqkn litsvekkvf gpafrnltel dmrfnpfdct cesiawfvnw 661 inethtnipe lsshylcntp phyhgfpvrl fdtssckdsa pfelffmint sillififiv 721 llihfegwri sfywnvsvhr vlgfkeidrq teqfeyaayi ihaykdkdwv wehfssmeke 781 dqslkfclee rdfeagvfel eaivnsikrs rkiifvithh llkdplckrf kvhhavqqai 841 eqnldsiilv fleeipdykl nhalclrrgm fkshcilnwp vqkerigafr hklqvalgsk 901 nsvh
```

The nucleic acid sequence of human TLR1 is provided in GenBank Accession No. NM_003263.3 (GI:41350336), incorporated herein by reference. The amino acid sequence of human TLR1 is provided in GenBank Accession No. NP_003254.2 (GI:41350337), incorporated herein by reference.

The nucleic acid sequence of human TLR2 is provided in GenBank Accession No. NM_003264.3 (GI:68160956), incorporated herein by reference. The amino acid sequence of human TLR2 is provided in GenBank Accession No. NP_003255.2 (GI:19718734), incorporated herein by reference.

The nucleic acid sequence of human TLR4 is provided in GenBank Accession No. NM_138554.4 (GI:373432600), incorporated herein by reference. The amino acid sequence of human TLR4 is provided in GenBank Accession No. NP_612564.1 (GI:19924149), incorporated herein by reference.

The nucleic acid sequence of human TLR5 is provided in GenBank Accession No. NM_003268.5 (GI:281427130), incorporated herein by reference. The amino acid sequence of human TLR5 is provided in GenBank Accession No. NP_003259.2 (GI:16751843), incorporated herein by reference.

The nucleic acid sequence of human TLR6 is provided in GenBank Accession No. NM_006068.4 (GI:318067953), incorporated herein by reference. The amino acid sequence of human TLR6 is provided in GenBank Accession No. NP_006059.2 (GI:20143971), incorporated herein by reference.

The nucleic acid sequence of human TLR7 is provided in GenBank Accession No. NM_016562.3 (GI:67944638), incorporated herein by reference. The amino acid sequence of human TLR7 is provided in GenBank Accession No. NP_057646.1 (GI:7706093), incorporated herein by reference.

The nucleic acid sequence of human TLR8 is provided in GenBank Accession No. NM_138636.4 (GI:257196253), incorporated herein by reference. The amino acid sequence of human TLR8 is provided in GenBank Accession No. NP_619542.1 (GI:20302168), incorporated herein by reference.

The nucleic acid sequence of human TLR10 is provided in GenBank Accession No. NM_030956.3 (GI:306140488), incorporated herein by reference. The amino acid sequence of human TLR10 is provided in GenBank Accession No. NP_112218.2 (GI:62865618), incorporated herein by reference.

The nucleic acid sequence of mouse TLR11 is provided in GenBank Accession No. NM_205819.3 (GI:408684412), incorporated herein by reference. The amino acid sequence of mouse TLR11 is provided in GenBank Accession No. NP_991388.2 (GI:408684413), incorporated herein by reference.

The nucleic acid sequence of mouse TLR12 is provided in GenBank Accession No. NM_205823.2 (GI:148539900), incorporated herein by reference. The amino acid sequence of mouse TLR12 is provided in GenBank Accession No. NP_991392.1 (GI:45430001), incorporated herein by reference.

The nucleic acid sequence of mouse TLR13 is provided in GenBank Accession No. NM_205820.1 (GI:45429998), incorporated herein by reference. The amino acid sequence of mouse TLR13 is provided in GenBank Accession No. NP_991389.1 (GI:45429999), incorporated herein by reference.

A representative list of TLR agonists (both synthetic and natural ligands), along with their corresponding receptor is provided in the table below.

Scaffold devices described herein comprise and release GM-CSF polypeptides to attract host DCs to the device. Contemplated GM-CSF polypeptides are isolated from endogenous sources or synthesized in vivo or in vitro. Endogenous GM-CSF polypeptides are isolated from healthy human tissue. Synthetic GM-CSF polypeptides are synthesized in vivo following transfection or transformation of template DNA into a host organism or cell, e.g. a mammal or cultured human cell line. Alternatively, synthetic GM-CSF polypeptides are synthesized in vitro by polymerase chain reaction (PCR) or other art-recognized methods Sambrook, J., Fritsch, E. F., and Maniatis, T., Molecular Cloning:

| Receptor | Pathogen Associated Ligands (PAMPS) [1] | Ligand Natural host | Synthetic Ligands |
|---|---|---|---|
| TLR 1 | multiple triacyl lipopeptides | Bacteria | Pam3Cys-* |
| TLR 2 | multiple glycolipids | Bacteria | CFA |
|  | multiple lipopoptides | Bacteria | MALP2-** |
|  | multiple lipoproteins | Bacteria | Pam2Cys** |
|  | lipoteichoic acid | Gram Positive Bacteria | FSL-1 |
|  | HSP 70, or other heat shock proteins | Host cells | Hib-OMPC |
|  | zymosan (Beta-glucan) | Fungi |  |
|  | Numerous others |  |  |
| TLR 3 | Double stranded RNA | viruses | Poly (I:C); Low and High molecular weight Poly (A:U) |
| TLR 4 | lipopolysacharides (LPS): or LPS derivatives such as MPLA | Gram negative bacteria | AGP |
|  | several heat shock proteins | Bacteria and host cells | MPLA |
|  | fibrinogen | host cells | RC-529 |
|  | heparin sulfate fragments | host cells | MDF2β |
|  | hyaluronic acid fragments | host cells | CFA |
|  | nickel |  |  |
|  | Various opoid drugs |  |  |
| TLR 5 | Flagellin | Bacteria | Flagellin |
| TLR 6 | multiple diacyl lipopeptides | Mycoplasma | FSL1-** Pam2Cys** MALP2-** |
| TLR 7 | Viral asRNA (influenza, VSV, HIV, HCV) | RNA viruses | Guanosine analogs; imidazoquinolinos (e.g. Imiquimod, Aldara ® R848, Resiquimod ®), Loxorbine |
| TLR 8 | small synthetic compounds; single-stranded RNA | RNA, Human and viral | Imidazoquinoline; Loxoribine; ssPolyU, 3M-012 |
| TLR 9 | Unmethylated CpG Oligodeoxynucleotide DNA DNA; dsDNA viruses (HSV, MCMV); Homozoin (*Plasmodium*) | Bacteria, DNA viruses | CpG-oligonucleotides, numerous sequences have been synthesized (e.g CpG-ODN 2006, 1826, 2395) |
| TLR 10 | unknown |  |  |
| TLR 11 | Profilin | Toxoplasma gondii |  |
| TLR 12 | Profilin | Toxoplasma gondii |  |
| TLR 13 [2][3] | bacterial ribosomal RNA sequence *CGGAAAGACC* (SEQ ID NO: 23) | Virus, bacteria |  |

*Ligands recognized by TLR1 and TLR2
**Ligands recognized by TLR2 and TLR6
References
Meyer T, StockMath E. Clinical investigation of Toll-like receptor agonists. Expert opinion on investigational drugs. 2008; 17: 1051-1065. [PubMed]
van Duin D, Medzhitov R, Shaw AC. Triggering TLR signaling in vaccination. Trends in immunology. 2006; 27: 49-55
Kumat H, Kawai T, Akira S. Toll-like receptors and innate immunity. Biochemical and biophysical research communications. 2009; 388: 621-625.
Walterbaugh C, Doan T, Malvoid R. Vaas S (2008), *Immunology*. Lippincod's illustrated reviews. Philadelphia: Wollers Kumat Health/Lippincot Williams & Windra. pp. 17.
Shi Z, Csi Z, Sanchez A, et al. (February 2011). *A noval Toll-like receptor that recognizes vesicular stomachis virus*. 286. pp. 4517-24.
Oldenburg M. Kruger A, Fardl R, et al. (August 2012). *TLR13 recognizes bacterial 23S rRNA devoid of erythromycin resistance-forming modification*. S37.pp, 1111-5.
S. Gnjabic, N. B. Sawhney, N. Shardwaj Toll-like receptor agonists: are they good adjuvants? Cancer 3, 16 (4) (2010), pp. 382-391.

Granulocyte Macrophage Colony Stimulating Factor (GM-CSF)

Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

A Laboratory Manual. Cold Spring Harbor Laboratory Press, NY, Vol. 1, 2, 3 (1989), herein incorporated by reference).

GM-CSF polypeptides are modified to increase protein stability in vivo. Alternatively, GM-CSF polypeptides are engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). GM-CSF polypeptides of the present invention are modified at one or more of these amino acid residues with respect to glycosylation state.

GM-CSF polypeptides are recombinant. Alternatively GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In a preferred embodiment, GM-CSF is a recombinant human protein (PeproTech, Catalog #300-03). Alternatively, GM-CSF is a recombinant murine (mouse) protein (PeproTech, Catalog #315-03). Finally, GM-CSF is a humanized derivative of a recombinant mouse protein.

Human Recombinant GM-CSF (PeproTech, Catalog #300-03) is encoded by the following polypeptide sequence (SEQ ID NO: 24):

```
                                              (SEQ ID NO: 24)
MAPARSPSPS TQPWEHVNAI QEARRLLNLS RDTAAEMNET

VEVISEMFDL QEPTCLQTRL ELYKQGLRGS LTKLKGPLTM

MASHYKQHCP PTPETSCATQ IITFESFKEN LKDFLLVIPF

DCWEPVQE
```

Murine Recombinant GM-CSF (PeproTech, Catalog #315-03) is encoded by the following polypeptide sequence (SEQ ID NO: 25):

```
                                              (SEQ ID NO: 25)
MAPTRSPITV TRPWKHVEAI KEALNLLDDM PVTLNEEVEV

VSNEFSFKKL TCVQTRLKIF EQGLRGNFTK LKGALNMTAS

YYQTYCPPTP ETDCETQVTT YADFIDSLKT FLTDIPFECK KPVQK
```

Human Endogenous GM-CSF is encoded by the following mRNA sequence (NCBI Accession No. NM_000758 and SEQ ID NO: 26):

```
                                                    (SEQ ID NO: 26)
   1 acacagagag aaaggctaaa gttctctgga ggatgtggct gcagagcctg ctgctcttgg 61 gcactgtggc ctgcagcatc tctgcacccg cccgctcgcc cagcccagc acgcagccct 121 gggagcatgt gaatgccatc caggaggccc ggcgtctcct gaacctgagt agagacactg 181 ctgctgagat gaatgaaaca gtagaagtca tctcagaaat gtttgacctc caggagccga 241 cctgcctaca gacccgcctg gagctgtaca agcagggcct gcggggcagc ctcaccaagc 301 tcaagggccc cttgaccatg atggccagcc actacaagca gcactgccct ccaacccccgg 361 aaacttcctg tgcaacccag attatcacct ttgaaagttt caaagagaac ctgaaggact 421 ttctgcttgt catcccttt gactgctggg agccagtcca ggagtgagac cggccagatg 481 aggctggcca agccggggag ctgctctctc atgaaacaag agctagaaac tcaggatggt 541 catcttggag ggaccaaggg gtgggccaca gccatggtgg gagtggcctg gacctgccct 601 gggccacact gaccctgata caggcatggc agaagaatgg gaatatttta tactgacaga 661 aatcagtaat atttatatat ttatatttt aaaatattta tttatttat tatttaagtt 721 catattccat atttattcaa gatgtttac cgtaataatt attattaaaa atatgcttct 781 a
```

Human Endogenous GM-CSF is encoded by the following amino acid sequence (NCBI Accession No. NP_000749.2 and SEQ ID NO: 27):

```
                                              (SEQ ID NO: 27)
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMAS

HYKQHCPPTPETSCATQIITFESFKENLKDFLLVIPFDCWEPVQE
```

GM-CSF signaling is a potent chemotactic factor for conventional DCs and significantly enhanced surface expression of MHC(II) and CD86(+), which are utilized for priming T cell immunity. In contrast, Flt3L vaccines led to greater numbers of plasmacytoid DCs (pDCs), correlating with increased levels of T cell priming cytokines that amplify T cell responses. Thus, as described in US 2013-0202707, incorporated herein by reference, 3D polymer matrices modified to present inflammatory cytokines are utilized to effectively mobilize and activate different DC subsets in vivo for immunotherapy.

An exemplary amino acid sequence of human Flt3 is provided below (GenBank Accession No.: P49771.1 (GI: 1706818), incorporated herein by reference; SEQ ID NO: 28):

```
                                                              (SEQ ID NO: 28)
  1 mtvlapawsp ttyllllll1 ssglsgtqdc sfqhspissd favkirelsd yllqdypvtv 61 asnlqdeelc gglwrlvlaq rwmerlktva gskmqgller vnteihfvtk cafqpppscl 121 rfvqtnisrl lqetseqlva lkpwitrqnf srclelqcqp dsstlpppws prpleatapt 181 apqppllll1 llpvgllll1a aawclhwqrt rrrtprpgeq vppvspqdl llveh
```

Cytosine-Guanosine (CpG) Oligonucleotide (CpG-ODN) Sequences

CpG sites are regions of deoxyribonucleic acid (DNA) where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silences while oncogenes, or cancer-inducing genes, are expressed. Importantly, CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

The present invention comprises CpG dinucleotides and oligonucleotides. Contemplated CpG oligonucleotides are isolated from endogenous sources or synthesized in vivo or in vitro. Exemplary sources of endogenous CpG oligonucleotides include, but are not limited to, microorganisms, bacteria, fungi, protozoa, viruses, molds, or parasites. Alternatively, endogenous CpG oligonucleotides are isolated from mammalian benign or malignant neoplastic tumors. Synthetic CpG oligonucleotides are synthesized in vivo following transfection or transformation of template DNA into a host organism. Alternatively, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), incorporated herein by reference).

CpG oligonucleotides are presented for cellular uptake by dendritic cells. In one embodiment, naked CpG oligonucleotides are used. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are bound to one or more compounds to increase the stability of the oligonucleotide within the scaffold and/or dendritic cell.

CpG oligonucleotides are condensed prior to cellular uptake. In one preferred embodiment, CpG oligonucleotides are condensed using polyethylimine (PEI), a cationic polymer that increases the efficiency of cellular uptake into dendritic cells.

CpG oligonucleotides of the present invention can be divided into multiple classes. For example, exemplary CpG-ODNs encompassed by compositions, methods and devices of the present invention are stimulatory, neutral, or suppressive. The term "stimulatory" used herein is meant to describe a class of CpG-ODN sequences that activate TLR9. The term "neutral" used herein is meant to describe a class of CpG-ODN sequences that do not activate TLR9. The term "suppressive" used herein is meant to describe a class of CpG-ODN sequences that inhibit TLR9. The term "activate TLR9" describes a process by which TLR9 initiates intracellular signaling.

Simulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-α production from plasmacytoid dendritic cells (pDC). Type A CpG ODNs weakly stimulate TLR9-dependent NF-κB signaling.

Type B stimulatory CpG ODNs contain a full phosphorothioate backbone with one or more CpG dinucleotides. Following TLR9 activation, these CpG-ODNs strongly activate B cells. In contrast to Type A Cpg-ODNs, Type B CpG-ODNS weakly stimulate IFN-α secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-α production from pDC. Simlar to Type B CpG ODNs, Type C CpG ODNs induce strong B cell stimulation.

Exemplary stimulatory CpG ODNs comprise, but are not limited to, ODN 1585, ODN 1668, ODN 1826, ODN 2006, ODN 2006-G5, ODN 2216, ODN 2336, ODN 2395, ODN M362 (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgacgttcctgacgtt, wherein CpG elements are bolded, SEQ ID NO: 29).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Suppressive CpG ODNs that inhibit TLR9 are encompassed by the present invention. Exemplary potent inhibitory sequences are (TTAGGG)$_4$ (SEQ ID NO: 30) (oligonucleotide TTAGGG, InvivoGen), found in mammalian telomeres and ODN 2088 (InvivoGen), derived from a murine stimulatory CpG ODN by replacement of 3 bases. Suppressive ODNs disrupt the colocalization of CpG ODNs with TLR9 in endosomal vesicles without affecting cellular binding and uptake. Suppressive CpG ODNs encompassed by the present invention are used to fine-tune, attenuate, reverse, or oppose the action of a stimulatory CpG-ODN.

Alternatively, or in addition, compositions, methods, or devices of the present invention comprising suppressive CpG ODNs are used to treat autoimmune conditions or prevent immune responses following transplant procedures.

Cancer Antigens

Compositions, methods, and devices of the present invention comprise cancer antigens with means to vaccinate and/or provide protective immunity to a subject to whom such a device was administered. Cancer antigens are used alone or in combination with GM-CSF, CpG-ODN sequences, or immunomodulators. Moreover, cancer antigens are used simultaneously or sequentially with GM-CSF, CpG-ODN sequences, or immunomodulators.

Exemplary cancer antigens encompassed by the compositions, methods, and devices of the present invention include, but are not limited to, tumor lysates extracted from biopsies (e.g., from melanoma tumor biopsies, or from B16-F10 tumors isolated from mice challenged with B16-F10 melanoma tumor cells), irradiated tumor cells (e.g., irradiated melanoma cells), antigens from lung cancer, antigens from breast cancers (e.g., Her2, e.g., purified Her2 or a fragment thereof), antigens from glioma cancers, prostate (e.g., prostate cancer) antigens (e.g., prostatic acid phosphatase), MAGE series of antigens (MAGE-1 is an example), MART-1/melanA, tyrosinase, ganglioside, gp100, GD-2, 0-acetylated GD-3, GM-2, MUC-1, Sos1, Protein kinase C-binding protein, Reverse transcriptase protein, AKAP protein, VRK1, KIAA1735, T7-1, T11-3, T11-9, *Homo Sapiens* telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen se1-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologic ally defined breast cancer antigen NY-BR-16, Chromogranin A; parathyroid secretory protein 1, DUPAN-2, CA 19-9, CA 72-4, CA 195, Carcinoembryonic antigen (CEA).

The amino acid sequence of human prostatic acid phosphatase is provided by Genbank Accession No. AAA60022.1, and is shown below (SEQ ID NO: 31), with the signal peptide shown in underlined font and the mature peptide shown in italicized font.

```
                                                        (SEQ ID NO: 31)
  1 mraaplllar aaslalascf cffcwldrsv lakelkfvtl vfrhgdrspi dtfptdpike 61 sswpqgfgql tqlgmeqhye lgeyirkryr kflndsykhe qvyirstdvd rtlmsrmtnl 121 aalfppegvs iwnpillwqp ipvhtvplse dqllylpfrn cprfqelese tlkseefqkr 181 lhpykdfiat lgklsglhgq dlfgiwskvy dplysesvhn ftlpswated tmtklrelse 241 lsllslygih kqkeksrlqg gvlvneilnh mkratqipsy kklimysand ttvtglqmal 301 dvynglippy aschltelyf ekgeyfvemy yrnetqhepy plmlpgcsps cplerfaelv 361 gpvipqdwst evmttnshqg tedstd
```

The mRNA sequence encoding human prostatic acid phosphatase is provided by Genbank Accession No. M24902.1, and is shown below (SEQ ID NO: 32), with the start and stop codons in bold.

```
                                                        (SEQ ID NO: 32)
  1 ggccagaaac agctctcctc aacatgagag ctgcacccct cctcctggcc agggcagcaa 61 gcttagcctt ggcttcttgt ttctgctttt tttgctggct agaccgaagt gtactagcca 121 aggagttgaa gtttgtgact tggtgtttc ggcatggaga ccgaagtccc attgacacct 181 ttcccactga ccccataaag gaatcctcat ggcacaagg atttggccaa ctcacccagc 241 tgggcatgga gcagcattat gaacttggag agtatataag aaagagatat agaaaattct 301 tgaatgactc ctataaacat gaacaggttt atattcgaag cacagacgtt gaccggactt 361 tgatgagtcg tatgacaaac ctggcagccc tgtttccccc agaaggtgtc agcatctgga
```

-continued

```
 421 atcctatcct actctggcag cccatcccgg tgcacacagt tcctctttct gaagatcagt
 481 tgctatacct gcctttcagg aactgccctc gttttcaaga acttgagagt gagactttga
 541 aatcagagga attccagaag aggctgcacc cttataagga ttttatagct accttgggaa
 601 aactttcagg attacatggc caggaccttt ttggaatttg gagtaaagtc tacgaccctt
 661 tatattctga gagtgttcac aatttcactt taccctcctg ggccactgag acaccatga
 721 ctaagttgag agaattgtca gaattgtccc tcctgtccct ctatggaatt cacaagcaga
 781 aagagaaatc taggctccaa gggggtgtcc tggtcaatga aatcctcaat cacatgaaga
 841 gagcaactca gataccaagc tacaaaaaac ttatcatgta ttctgcgcat gacactactg
 901 tgactggcct acagatggcg ctagatgttt acaacggact ccttcctccc tatgcttctt
 961 gccacttgac ggaattgtac tttgagaagg gggagtactt tgtggagatg tactaccgga
1021 atgagacgca gcacgagccg tatcccctca tgctacctgg ctgcagcccc agctgtcctc
1081 tggagaggtt tgctgagctg gttggccctg tgatccctca agactggtcc acggaggtta
1141 tgaccacaaa cagccatcaa ggtactgagg acagtacaga ttagtgtgca cagagatctc
1201 tgtagaaaga gtagctgccc ттттctcaggg cagatgatgc tttgagaaca tactttggcc
1261 attacccccc agctttgagg aaaatgggct ttggatgatt attttatgtt ttaggggacc
1321 cccaacctca ggcaattcca tcctcttcac ccgaccctgc ccccacttg cataaaactt
1381 agctaagttt tgtttgttt ttcagcgtta atgtaaaggg gcagcagtgc caaaatataa
1441 cagagataaa gcttaggtca aagttcatag agttcccatg aactatatga ctggccacac
1501 aggatctttt gтaттттaagg attctgagat tttgcttgag caggattaga taaggctgtt
1561 ctttaaatgt ctgaaatgga acagatttca aaaaaaaccc cacaatctag ggtgggaaca
1621 aggaaggaaa gatgtgaata ggctgatggg caaaaaacca atttacccat cagttccagc
1681 cttctctcaa ggagaggcaa agaaaggaga tacagtggag acatctggaa agttttctcc
1741 actggaaaac tgctactatc тgттттттaтa tttctgttaa aatatatgag gctacagaac
1801 taaaaattaa aacctctttg tgtcccttgg tcctggaaca tttatgttcc ttttaaagaa
1861 acaaaaatca aactttacag aaagatttga tgtatgtaat acatatagca gctcttgaag
1921 таттаттаттс атагсааата агтсатстга тгагаасааг статтгггс асасасст
1981 aggaaagaga gcaccacgtg atggagtttc tccagaagct ccagtgataa gagatgttga
2041 ctctaaagtt gatttaaggc caggcatggt ggtttacgcc taaatccca gcatttgggg
2101 agtccgaggt gggcagatca cttgagctca ggaggtcaag atcagcctgg caacatggt
2161 gaaacстттgт ctctacataa aатасааaaa ттгагтггgg саттгтгтг тгтгссгата
2221 gtccactact tgtggggcta aggcaggagg atcacttgag ccccggaggt cgaggctaca
2281 gtgagccaag agtgcactac tgtactccag ccagggcaag agagcgagac cctgtctcaa
2341 taaataaata aataaataaa taaataaata aataaataaa taaataaaaa caaagttgat
2401 taagaaagga agtataggct aggcacagtg gctcacacct gtaatccttg cattttggaa
2461 ggctgaggca ggaggatcac tttaggcctg tgtgttcaa gaccagcctg gtcaacatag
2521 tgagacactg tctctaccaa aaaaaggaag gaagggacac ататсааасг gааасааат
2581 tagaaatgta attatgttat gttctaagtg cctccaagtt caaaacttat tggaatgttg
2641 agagtgtggt tacgaaatac gttaggagga caaaaggaat gtgtaagtct ttaatgcccg
2701 ататсттсаг аааасстаад сааасттаса ггтсстдстд аааствстсаа
2761 agaaatcatg atatagcttt gccatgtggc agatctacat gtctagagaa cactgtgctc
2821 tattaccatt atggataaag atgagatggt ttctagagat ggtttctact ggctgccaga
```

-continued

```
2881 atctagagca aagccatccc cgctcctggt tggtcacaga atgactgaca aagacatcga
2941 ttgatatgct tctttgtgtt atttccctcc caagtaaatg tttgtccttg ggtccatttt
3001 ctatgcttgt aactgtcttc tagcagtgag ccaaatgtaa aatagtgaat aaagtcatta
3061 ttaggaagtt caaaagcatt gcttttataa tgaactt
```

The amino acid sequence of human Her2 is provided by Genbank Accession No. P04626.1, and is shown below (SEQ ID NO: 33).

```
                                                          (SEQ ID NO: 33)
   1 melaalcrwg lllallppga astqvctgtd mklrlpaspe thldmlrhly qgcqvvqgnl
  61 eltylptnas lsflgdigev qgyvliahnq vrqvplqrlr ivrgtqlfed nyalavldng
 121 dplnnttpvt gaspgglrel qlrslteilk ggvliqrnpq lcyqdtilwk difhknngla
 181 ltlidtnrsr achpcspmck gsrcwgesse dcqsltrtvc aggcarckgp lptdccheqc
 241 aagctgpkhs dclaclhfnh sgicelhcpa lvtyntdtfe smpnpegryt fgascvtacp
 301 ynylstdvgs ctlvcplhnq evtaedgtqr cekcskpcar vcyglgmehl revravtsan
 361 iqefagckki fgslaflpes fdgdpasnta plqpeqlqvf etleeitgyl yisawpdslp
 421 dlsvfqnlqv irgrilhnga ysltlqglgi swlglrslre lgsglalihh nthlcfvhtv
 481 pwdqlfrnph qallhtanrp edecvgegla chqlcarghc wgpgptqcvn csqflrgqec
 541 veecrvlqgl preyvnarhc lpchpecqpq ngsvtcfgpe adqcvacahy kdppfcvarc
 601 psgvkpdlsy mpiwkfpdee gacqpcpinc thscvdlddk gcpaeqrasp ltsiisavvg
 661 illvvvlgvv fgilikrrqq kirkytmrrl lgetelvepl tpsgampnqa qmrilketel
 721 rkvkvlgsga fgtvykgiwi pdgenvkipv aikvlrents pkankeilde ayvmagvgsp
 781 yvsrllgicl tstvqlvtql mpygclldhv renrgrlgsq dllnwcmqia kgmsyledvr
 841 lvhrdlaarn vlvkspnhvk itdfglarll dideteyhad ggkvpikwma lesilrrrft
 901 hqsdvwsygv tvwelmtfga kpydgipare ipdllekger lpqppictid vymimvkcwm
 961 idsecrprfr elvsefsrma rdpqrfvviq nedlgpaspl dstfyrslle dddmgdlvda
1021 eeylvpqqgf fcpdpapgag gmvhhrhrss strsgggdlt lglepseeea prsplapseg
1081 agsdvfdgdl gmgaakglqs lpthdpsplq rysedptvpl psetdgyvap ltcspqpeyv
1141 nqpdvrpqpp spregplpaa rpagatlerp ktlspgkngv vkdvfafgga venpeyltpq
1201 ggaapqphpp pafspafdnl yywdqdpper gappstfkgt ptaenpeylg ldvpv
```

The mRNA sequence encoding human Her2 is provided by Genbank Accession No. NM_004448.3, and is shown below (SEQ ID NO: 34), with the start and stop codons in bold.

```
                                                          (SEQ ID NO: 34)
   1 gcttgctccc aatcacagga gaaggaggag gtggaggagg agggctgctt gaggaagtat
  61 aagaatgaag ttgtgaagct gagattcccc tccattggga ccggagaaac caggggagcc
 121 ccccgggcag ccgcgcgccc cttcccacgg ggcccttttac tgcgccgcgc gcccggcccc
 181 caccccctcgc agcacccgc gccccgcgcc ctcccagccg gtccagccg gagccatggg
 241 gccgagccg cagtgagcac catggagctg gcggccttgt gccgctgggg gctcctcctc
 301 gccctcttgc cccccggagc cgcgagcacc caagtgtgca ccggcacaga catgaagctg
 361 cggctccctg ccagtcccga gacccacctg gacatgctcc gccacctcta ccagggctgc
 421 caggtggtgc agggaaacct ggaactcacc tacctgccca ccaatgccag cctgtccttc
```

-continued

```
 481 ctgcaggata tccaggaggt gcagggctac gtgctcatcg ctcacaacca agtgaggcag 541 gtcccactgc agaggctgcg gattgtgcga ggcacccagc tctttgagga caactatgcc 601 ctggccgtgc tagacaatgg agacccgctg aacaatacca ccctgtcac agggcctcc 661 ccaggaggcc tgcgggagct gcagcttcga agcctcacag agatcttgaa aggaggggtc 721 ttgatccagc ggaaccccca gctctgctac caggacacga ttttgtggaa ggacatcttc 781 cacaagaaca accagctggc tctcacactg atagacacca accgctctcg ggcctgccac 841 ccctgttctc cgatgtgtaa gggctcccgc tgctggggag agagttctga ggattgtcag 901 agcctgacgc gcactgtctg tgccggtggc tgtgcccgct gcaaggggcc actgcccact 961 gactgctgcc atgagcagtg tgctgccggc tgcacgggcc caagcactc tgactgcctg 1021 gcctgcctcc acttcaacca cagtggcatc tgtgagctgc actgcccagc cctggtcacc 1081 tacaacacag acacgtttga gtccatgccc aatcccgagg ccggtatac attcggcgcc 1141 agctgtgtga ctgcctgtcc ctacaactac ctttctacgg acgtgggatc ctgcaccctc 1201 gtctgccccc tgcacaacca agaggtgaca gcagaggatg aacacagcg gtgtgagaag 1261 tgcagcaagc cctgtgcccg agtgtgctat ggtctgggca tggagcactt gcgagaggtg 1321 agggcagtta ccagtgccaa tatccaggag tttgctggct gcaagaagat ctttgggagc 1381 ctggcatttc tgccggagag ctttgatggg acccagcct caacactgc cccgctccag 1441 ccagagcagc tccaagtgtt tgagactctg aagagatca caggttacct atacatctca 1501 gcatggccgg acagcctgcc tgacctcagc gtcttccaga acctgcaagt aatccgggga 1561 cgaattctgc acaatggcgc ctactcgctg accctgcaag ggctgggcat cagctggctg 1621 gggctgcgct cactgaggga actgggcagt ggactggccc tcatccacca taacacccac 1681 ctctgcttcg tgcacacggt gccctgggac cagctctttc ggaacccgca ccaagctctg 1741 ctccacactg ccaaccggcc agaggacgag tgtgtgggcg agggcctggc ctgccaccag 1801 ctgtgcgccc gagggcactg ctggggtcca gggcccaccc agtgtgtcaa ctgcagccag 1861 ttccttcggg gccaggagtg cgtggaggaa tgccgagtac tgcagggct ccccagggag 1921 tatgtgaatg ccaggcactg tttgccgtgc caccctgagt gtcagcccca gaatggctca 1981 gtgacctgtt ttggaccgga ggctgaccag tgtgtggcct gtcccacta taaggaccct 2041 cccttctgcg tggcccgctg ccccagcggt gtgaaacctg acctctccta catgcccatc 2101 tggaagttt cagatgagga gggcgcatgc cagccttgcc ccatcaactg cacccactcc 2161 tgtgtggacc tggatgacaa gggctgcccc gccgagcaga gagccagccc tctgacgtcc 2221 atcatctctg cggtggttgg cattctgctg gtcgtggtct tggggtggt cttgggatc 2281 ctcatcaagc gacggcagca aagatccgg aagtacacga tgcggagact gctgcaggaa 2341 acggagctgg tggagccgct gacacctagc ggagcgatgc caaccaggc gcagatgcgg 2401 atcctgaaag agacggagct gaggaaggtg aaggtgcttg gatctggcgc ttttggcaca 2461 gtctacaagg gcatctggat ccctgatggg gagaatgtga aaattccagt ggccatcaaa 2521 gtgttgaggg aaaacacatc ccccaaagcc aacaaagaaa tcttagacga agcatacgtg 2581 atggctggtg tgggctcccc atatgtctcc cgccttctgg gcatctgcct gacatccacg 2641 gtgcagctgc tgacacagct tatgcccat ggctgcctct tagaccatgt ccgggaaaac 2701 cgcggacgcc tgggctccca ggacctgctg aactggtgta tgcagattgc caaggggatg 2761 agctacctga aggatgtgcg gctcgtacac agggacttgg ccgctcggaa cgtgctggtc 2821 aagagtccca accatgtcaa aattacagac ttcgggctgg ctcggctgct ggacattgac
```

```
-continued
2881 gagacagagt accatgcaga tgggggcaag gtgcccatca agtggatggc gctggagtcc 2941 attctccgcc ggcggttcac ccaccagagt gatgtgtgga gttatggtgt gactgtgtgg 3001 gagctgatga cttttggggc caaaccttac gatgggatcc cagcccggga gatccctgac 3061 ctgctggaaa aggggggagcg gctgccccag cccccatct gcaccattga tgtctacatg 3121 atcatggtca aatgttggat gattgactct gaatgtcggc caagattccg ggagttggtg 3181 tctgaattct cccgcatggc cagggacccc cagcgctttg tggtcatcca gaatgaggac 3241 ttgggcccag ccagtccctt ggacagcacc ttctaccgct cactgctgga ggacgatgac 3301 atgggggacc tggtggatgc tgaggagtat ctggtacccc agcagggctt cttctgtcca 3361 gaccctgccc cgggcgctgg gggcatggtc caccacaggc accgcagctc atctaccagg 3421 agtggcggtg gggacctgac actagggctg gagccctctg aagaggaggc ccccaggtct 3481 ccactggcac cctccgaagg ggctggctcc gatgtatttg atggtgacct gggaatgggg 3541 gcagccaagg ggctgcaaag cctccccaca catgacccca gccctctaca gcggtacagt 3601 gaggacccca cagtacccct gccctctgag actgatggct acgttgcccc cctgacctgc 3661 agcccccagc ctgaatatgt gaaccagcca gatgttcggc cccagccccc ttcgccccga 3721 gagggccctc tgcctgctgc ccgacctgct ggtgccactc tggaaaggcc caagactctc 3781 tccccaggga agaatggggt cgtcaaagac gttttttgcct ttggggggtgc cgtggagaac 3841 cccgagtact tgacacccca gggaggagct gccctcagc cccaccctcc tcctgccttc 3901 agcccagcct tcgacaacct ctattactgg gaccaggacc caccagagcg gggggctcca 3961 cccagcacct tcaaagggac acctacggca gagaacccag agtacctggg tctggacgtg 4021 ccagtgtgaa ccagaaggcc aagtccgcag aagccctgat gtgtcctcag ggagcaggga 4081 aggcctgact tctgctggca tcaagaggtg ggagggccct ccgaccactt ccaggggaac 4141 ctgccatgcc aggaacctgt cctaaggaac cttccttcct gcttgagttc ccagatggct 4201 ggaaggggtc cagcctcgtt ggaagaggaa cagcactggg gagtctttgt ggattctgag 4261 gccctgccca atgagactct agggtccagt ggatgccaca gcccagcttg gcccttttcct 4321 tccagatcct gggtactgaa agccttaggg aagctggcct gagagggggaa gcggccctaa 4381 gggagtgtct aagaacaaaa gcgacccatt cagagactgt ccctgaaacc tagtactgcc 4441 ccccatgagg aaggaacagc aatggtgtca gtatccaggc tttgtacaga gtgctttttct 4501 gtttagtttt tactttttttt gttttgttttt tttaaagatg aaataaagac ccaggggggag 4561 aatgggtgtt gtatggggag gcaagtgtgg ggggtccttc tccacaccca ctttgtccat 4621 ttgcaaatat attttggaaa acagctaaaa aaaaaaaaaa aaaa
```

In some embodiments, tumor antigens are classified into 4 major groups based on their expression profile. See van der Bruggen P, Stroobant V, Vigneron N, Van den Eynde B. Peptide database: T cell-defined tumor antigens. *Cancer Immun* 2013. URL: www.cancerimmunity.org/peptide/, incorporated herein by reference. Exemplary tumor antigens and their classification are summarized below as follows:

1) Unique Antigens: Unique to tumor cells (Table 1). These antigens arise from mutations in the gene that encodes the protein antigen. Commonly, the mutation(s) affects the coding sequence of the gene. In some examples, the mutation(s) are unique to the tumor of an individual subject or a small number of subjects. These unique antigens are generally not shared by tumors from different subjects.

2) Shared Antigens: Tumor specific antigens (Table 2). Shared antigens, unlike unique antigens, are expressed in multiple independent tumors. Tumor specific antigens are expressed in multiple tumors but not in normal cells. For example, these antigens are encoded by "cancer-germline" genes.

3) Shared Antigens: Differentiation antigens (Table 3). Differentiation antigens are expressed in the tumor as well as in the normal tissue from which the tumor originated. For example, these antigens are expressed in a particular lineage of cells during a developmental stage. Since these antigens are not tumor-specific, targeting these antigens for cancer immunotherapy may cause autoimmunity toward the corresponding normal tissue, depending on whether the normal tissue is dispensible and whether the tissue expressing the antigen is surgically removed during the course of cancer treatment.

4) Shared Antigens: Overexpressed antigens (Table 4). These antigens are expressed in a variety of normal tissues and are overexpressed in tumor cells.

For example, tables of tumor peptides, e.g., considered to be tumor antigens based on their recognition by T lymphocytes that also recognize tumor cells expressing the parent proteins. Each table below includes the protein or gene name, GeneCard information about the protein/gene, a peptide sequence from the protein (e.g., a minimum sequence for antigen specificity, e.g., recognized by T cells), and the position of the peptide in the full length protein sequence. In some examples, the peptide shown in the tables below is a human leukocyte antigen (HLA) presenting molecule, e.g., the peptide is presented onto a major histocompatibility complex (MHC) molecule. In Table 1, the underlined amino acid(s) are those that are different from the sequence of the version of the protein found in non-tumor cells, i.e., tumor cells contain a mutated form of the protein(s) where the mutation(s) are underlined in Table 1.

TABLE 1

| Gene/protein | GeneCard information, incorporated herein by reference | Peptide | SEQ ID NO: | Position |
|---|---|---|---|---|
| alpha-actinin-4 | http://www.genecards.org/cgi-bin/carddisp.pl?gene=ACTN4 | FIAS<u>N</u>GVKLV | 35 | 118-127 |
| ARTC1 | http://www.genecards.org/cgi-bin/carddisp.pl?gene=BBX | YSVYFNLPADTIYTN[d] | 36 | |
| BCR-ABL fusion protein (b3a2) | http://www.genecards.org/cgi-bin/carddisp.pl?gene=ABL1 | SSKAL<u>Q</u>RPV<br>GFKQSSKAL<br>ATGFKQSSKAL<u>Q</u>RPVAS<br>ATGFKQSSKAL<u>Q</u>RPVAS | 37<br>38<br>39<br>40 | 926-934<br>922-930<br>920-936<br>920-936 |
| B-RAF | http://www.genecards.org/cgi-bin/carddisp.pl?gene=BRAF | EDLTVKIGDFGLAT<br><u>E</u>KSRWSGSHQFEQLS | 41 | 586-614 |
| CASP-5 | http://www.genecards.org/cgi-bin/carddisp.pl?gene=CASP5 | FLIIW<u>Q</u>NTM[c] | 42 | 67-75 |
| CASP-8 | http://www.genecards.org/cgi-bin/carddisp.pl?gene=CASP8 | FPSDSW<u>C</u>YF | 43 | 476-484 |
| beta-catenin | http://www.genecards.org/cgi-bin/carddisp.pl?gene=CTNNB1 | SYLDSGIH<u>F</u> | 44 | 29-37 |
| cdc27 | http://www.genecards.org/cgi-bin/carddisp.pl?gene=CDC27 | FSWAMDLDPKGAb | 45 | 760-771 |
| CDK4 | http://www.genecards.org/cgi-bin/carddisp.pl?gene=CDK4 | A<u>C</u>DPHSGHFV | 46 | 23-32 |
| CDKN2A | http://www.genecards.org/cgi-bin/carddisp.pl?gene=CDKN2A | AVCPWTWLR[c] | 47 | 125-133 (p14ARF-ORF3) 111-119 (p16INK4a-ORF3) |
| CLPP | http://www.genecards.org/cgi-bin/carddisp.pl?gene=CLPP&search=clpp | ILDKVlvHL | 48 | 240-248 |
| COA-1 | http://www.genecards.org/cgi-bin/carddisp.pl?gene=UBXN11 | TLYQDDTLTLQAAG[b]<br>TLYQDDTLTLQAAG[b] | 49<br>50 | 447-460<br>447-460 |
| dek-can fusion protein | http://www.genecards.org/cgi-bin/carddisp.pl?gene=DEK<br>http://www.genecards.org/cgi-bin/carddisp.pl?gene=NUP214 | TMKQICKKEIRRLHQY | 51 | 342-357 |
| EFTUD2 | http://www.genecards.org/cgi-bin/carddisp.pl?gene=EFTUD2 | KILDAVVAQ<u>K</u> | 52 | 668-677 |
| Elongation factor 2 | http://www.genecards.org/cgi-bin/carddisp.pl?gene=EEF2 | ETVSEQ<u>S</u>NV | 53 | 581-589 |
| ETV6-AML1 fusion protein | http://www.genecards.org/cgi-bin/carddisp.pl?gene=ETV6<br>http://www.genecards.org/cgi-bin/carddisp.pl?gene=RUNX1 | RIAECILGM<br>IGRIAECILG<u>M</u>NPSR<br>IGRIAECILG<u>M</u>NPSR | 54<br>55<br>56 | 334-342<br>332-346<br>332-346 |
| FLT3-ITD | http://www.genecards.org/cgi-bin/carddisp.pl?gene=FLT3 | YVDFREYEY<u>Y</u> | 57 | 591-600 |
| FN1 | http://www.genecards.org/cgi-bin/carddisp.pl?gene=FN1 | MIFE<u>K</u>HGERRTTPP | 58 | 2050-2063 |

TABLE 1-continued

| Gene/protein | GeneCard information, incorporated herein by reference | Peptide | SEQ ID NO: | Position |
|---|---|---|---|---|
| GPNMB | http://www.genecards.org/cgi-bin/carddisp.pl?gene=GPNMB | TLDWLLQTPK | 59 | 179-188 |
| LDLR-fucosyltransferaseASfusion protein | http://www.genecards.org/cgi-bin/carddisp.pl?gene=LDLR http://www.genecards.org/cgi-bin/carddisp.pl?gene=FUT1 | WRRAPAPGA PVTWRRAPA | 60 61 | 315-323 312-320 |
| HLA-A2[a] | http://www.genecards.org/cgi-bin/carddisp.pl?gene=HLA-A | | | |
| HLA-A11[a] | http://www.genecards.org/cgi-bin/carddisp.pl?gene=HLA-A | | | |
| hsp70-2 | http://www.genecards.org/cgi-bin/carddisp.pl?gene=HSPA2 | SLFEGIDIYT | 62 | 286-295 |
| | | AEPINIQTW | 63 | 262-270 |
| MART2 | http://www.genecards.org/cgi-bin/carddisp.pl?gene=HHAT | FLEGNEVGKTY | 64 | 446-455 |
| ME1 | http://www.genecards.org/cgi-bin/carddisp.pl?gene=ME1 | FLDEFMEGV | 65 | 224-232 |
| MUM-1 | http://www.ncbi.nlm.nih.gov/nuccore/11094678 | EEKLIVVLF | 66 | 30-38 |
| MUM-2 | http://www.genecards.org/cgi-bin/carddisp.pl?gene=TRAPPC1 | SELFRSGLDSY FRSGLDSYV | 67 68 | 123-133 126-134 |
| MUM-3 | http://www.genecards.org/cgi-bin/carddisp.pl?gene=PAPOLG | EAFIQPITR | 69 | 322-330 |
| neo-PAP | http://www.genecards.org/cgi-bin/carddisp.pl?gene=PAPOLG | RVIKNSIRLTL[b] | 70 | 724-734 |
| Myosin class I | http://www.genecards.org/cgi-bin/carddisp.pl?gene=MYO1B | KINKNPKYK | 71 | 911-919 |
| NFYC | http://www.genecards.org/cgi-bin/carddisp.pl?gene=NFYC | QQITKTEV | 72 | 275-282 |
| OGT | http://www.genecards.org/cgi-bin/carddisp.pl?gene=OGT | SLYKESPFPL[c] | 73 | 28-37 |
| OS-9 | http://www.genecards.org/cgi-bin/carddisp.pl?gene=OS9 | KELEGILLL | 74 | 438-446 |
| p53 | http://www.genecards.org/cgi-bin/carddisp.pl?gene=TP53 | VVPCEPPEV | 75 | 217-225 |

TABLE 1-continued

| Gene/protein | GeneCard information, incorporated herein by reference | Peptide | SEQ ID NO: | Position |
|---|---|---|---|---|
| pml-RARalpha fusion protein | http://www.genecards.org/cgi-bin/carddisp.pl?gene=PML<br>http://www.genecards.org/cgi-bin/carddisp.pl?gene=RARA | NSNHVASGAGEAA<u>I</u>ETQSSSSEEIV | 76 | |
| PRDX5 | http://www.genecards.org/cgi-bin/carddisp.pl?gene=PRDX5 | LLLDDL<u>L</u>VSI | 77 | 163-172 |
| PTPRK | http://www.genecards.org/cgi-bin/carddisp.pl?gene=PTPRK | PYYFAAELPP<u>R</u>NLPEP | 78 | 667-682 |
| K-ras | http://www.genecards.org/cgi-bin/carddisp.pl?gene=KRAS | VVVGA<u>V</u>GVG | 79 | 7-15 |
| N-ras | http://www.genecards.org/cgi-bin/carddisp.pl?gene=NRAS | ILDTAG<u>R</u>EEY | 80 | 55-64 |
| RBAF600 | http://www.genecards.org/cgi-bin/carddisp.pl?gene=UBR4 | <u>R</u>PHVPESAF | 81 | 329-337 |
| SIRT2 | http://www.genecards.org/cgi-bin/carddisp.pl?gene=SIRT2 | KIFSEVTLK | 82 | 192-200 |
| SNRPD1 | http://www.genecards.org/cgi-bin/carddisp.pl?gene=SNRPD1 | SHETV<u>I</u>IEL | 83 | 11-19 |
| SYT-SSX1 or SYT-SSX2 fusion protein | http://www.genecards.org/cgi-bin/carddisp.pl?gene=SS18<br>http://www.genecards.org/cgi-bin/carddisp.pl?gene=SSX1<br>http://www.genecards.org/cgi-bin/carddisp.pl?gene=SSX2 | QRPYGYDQIM | 84 | 402-410 (SYT)<br>111-112 (SSX2) |
| TGF-betaRII | http://www.genecards.org/cgi-bin/carddisp.pl?gene=TGFBR2 | RLSSCVPVA[c] | 85 | 131-139 |
| Triosephosphate isomerase | http://www.genecards.org/cgi-bin/carddisp.pl?gene=TPI1 | GELIGI<u>L</u>NAAKVPAD | 86 | 23-37 |

[a]The mutation affects the HLA gene itself.
[b]The mutation is not located in the region encoding the peptide.
[c]Frameshift product.
[d]The mutation creates a start codon (ATG) that opens an alternative open reading frame (ORF) encoding the antigenic peptide, which is recognized by regulatory T cells (Tregs).

TABLE 2

| Gene/Protein | GeneCard information, incorporated herein by reference | Peptide | SEQ ID NO: | Position |
|---|---|---|---|---|
| BAGE-1 | http://www.genecards.org/cgi-bin/carddisp.pl?gene=BAGE | AARAVFLAL | 87 | 2-10 |
| Cyclin-A1 | http://www.genecards.org/cgi-bin/carddisp.pl?gene=CCNA1&search=cyclin-a1 | FLDRFLSCM | 88 | 227-235 |
| | | SLIAAAAFCLA | 89 | 341-351 |
| GAGE-1,2,8 | http://www.genecards.org/cgi-bin/carddisp.pl?gene=GAGE1<br>http://www.genecards.org/cgi-bin/carddisp.pl?gene=GAGE2A<br>http://www.genecards.org/cgi-bin/carddisp.pl?gene=GAGE8 | YRPRPRRY | 90 | 9-16 |
| GAGE-3,4,5,6,7 | http://www.genecards.org/cgi-bin/carddisp.pl?gene=GAGE3<br>http://www.genecards.org/cgi-bin/carddisp.pl?gene=GAGE4<br>http://www.genecards.org/cgi-bin/carddisp.pl?gene=GAGE5<br>http://www.genecards.org/cgi-bin/carddisp.pl?gene=GAGE6<br>http://www.genecards.org/cgi-bin/carddisp.pl?gene=GAGE7 | YYWPRPRRY | 91 | 10-18 |
| GnTV[f] | http://www.genecards.org/cgi-bin/carddisp.pl?gene=MGAT5 | VLPDVFIRC(V) | 92 | intron |
| HERV-K-MEL | | MLAVISCAV | 93 | 1-9 |
| KK-LC-1 | http://www.genecards.org/cgi-bin/carddisp.pl?gene=CXorf61 | RQKRILVNL | 94 | 76-84 |
| KM-HN-1 | http://www.genecards.org/cgi-bin/carddisp.pl?gene=CCDC110 | NYNNFYRFL | 95 | 196-204 |
| | | EYSKECLKEF | 96 | 499-508 |
| | | EYLSLSDKI | 97 | 770-778 |
| LAGE-1 | http://www.genecards.org/cgi-bin/carddisp.pl?gene=CTAG2 | MLMAQEALAFL | 98 | ORF2 (1-11) |
| | | SLLMWITQC | 99 | 157-165 |
| | | LAAQERRVPR | 100 | ORF2 (18-27) |
| | | ELVRRILSR | 101 | 103-111 |
| | | APRGVRMAV | 102 | ORF2 (46-54) |
| | | SLLMWITQCFLPVF | 103 | 157-170 |
| | | QGAMLAAQERRVPRAAEVPR | 104 | ORF2 (14-33) |
| | | AADHRQLQLSISSCLQQL | 105 | 139-156 |
| | | CLSRRPWKRSWSAGSCPGMPHL | 106 | ORF2 (81-102) |
| | | CLSRRPWKRSWSAGSCPGMPHL | 107 | ORF2 (81-102) |
| | | ILSRDAAPLPRPG | 108 | 108-120 |
| | | AGATGGRGPRGAGA | 109 | 37-50 |
| MAGE-A1 | http://www.genecards.org/cgi-bin/carddisp.pl?gene=MAGEA1 | EADPTGHSY | 110 | 161-169 |
| | | KVLEYVIKV | 111 | 278-286 |
| | | SLFRAVITK | 112 | 96-104 |
| | | EVYDGREHSA | 113 | 222-231 |
| | | RVRFFFPSL | 114 | 289-298 |
| | | EADPTGHSY | 115 | 161-169 |
| | | REPVTKAEML | 116 | 120-129 |
| | | KEADPTGHSY | 117 | 160-169 |
| | | DPARYEFLW | 118 | 258-266 |
| | | ITKKVADLVGF | 119 | 102-112 |
| | | SAFPTTINF | 120 | 62-70 |
| | | SAYGEPRKL | 121 | 230-238 |
| | | RVRFFFPSL | 122 | 289-298 |
| | | SAYGEPRKL | 123 | 230-238 |
| | | TSCILESLFRAVITK | 124 | 90-104 |
| | | PRALAETSYVKVLEY | 125 | 268-282 |
| | | FLLLKYRAREPVTKAE | 126 | 112-127 |
| | | EYVIKVSARVRF | 127 | 281-292 |
| MAGE-A2 | http://www.genecards.org/cgi-bin/carddisp.pl?gene=MAGEA2 | YLQLVFGIEV | 128 | 157-166 |
| | | EYLQLVFGI | 129 | 156-164 |
| | | REPVTKAEML | 130 | 127-136 |
| | | EGDCAPEEK | 131 | 212-220 |
| | | LLKYRAREPVTKAE | 132 | 121-134 |
| MAGE-A3 | http://www.genecards.org/cgi-bin/carddisp.pl?gene=MAGEA3 | EVDPIGHLY | 133 | 168-176 |
| | | FLWGPRALV[d] | 134 | 271-279 |
| | | KVAELVHFL | 135 | 112-120 |
| | | TFPDLESEF | 136 | 97-105 |
| | | VAELVHFLL | 137 | 113-121 |

TABLE 2-continued

| Gene/Protein | GeneCard information, incorporated herein by reference | Peptide | SEQ ID NO: | Position |
|---|---|---|---|---|
| | | MEVDPIGHLY | 138 | 167-176 |
| | | EVDPIGHLY | 139 | 168-176 |
| | | REPVTKAEML | 140 | 127-136 |
| | | AELVHFLLL[i] | 141 | 114-122 |
| | | MEVDPIGHLY | 142 | 167-176 |
| | | WQYFFPVIF | 143 | 143-151 |
| | | EGDCAPEEK | 144 | 212-220 |
| | | KKLLTQHFVQENYLEY | 145 | 243-258 |
| | | RKVAELVHFLLLKYR | 146 | 111-125 |
| | | KKLLTQHFVQENYLEY | 147 | 243-258 |
| | | ACYEFLWGPRALVETS | 148 | 267-282 |
| | | RKVAELVHFLLLKYR | 149 | 111-125 |
| | | VIFSKASSSLQL | 150 | 149-160 |
| | | VIFSKASSSLQL | 151 | 149-160 |
| | | VFGIELMEVDPIGHL | 152 | 161-175 |
| | | GDNQIMPKAGLLIIV | 153 | 191-205 |
| | | TSYVKVLHHMVKISG | 154 | 281-295 |
| | | RKVAELVHFLLLKYRA | 155 | 111-126 |
| | | FLLLKYRAREPVTKAE | 156 | 119-134 |
| MAGE-A4 | http://www.genecards.org/cgi-bin/carddisp.pl?gene=MAGEA4 | EVDPASNTY[j] | 157 | 169-177 |
| | | GVYDGREHTV | 158 | 230-239 |
| | | NYKRCFPVI | 159 | 143-151 |
| | | SESLKMIF | 160 | 156-163 |
| MAGE-A6 | http://www.genecards.org/cgi-bin/carddisp.pl?gene=MAGEA6 | MVKISGGPR | 161 | 290-298 |
| | | EVDPIGHVY | 162 | 168-176 |
| | | REPVTKAEML | 163 | 127-136 |
| | | EGDCAPEEK | 164 | 212-220 |
| | | ISGGPRISY | 165 | 293-301 |
| | | LLKYRAREPVTKAE | 166 | 121-134 |
| MAGE-A9 | http://www.genecards.org/cgi-bin/carddisp.pl?gene=MAGEA9 | ALSVMGVYV | 167 | 223-231 |
| MAGE-A10 | http://www.genecards.org/cgi-bin/carddisp.pl?gene=MAGEA10 | GLYDGMEHL[l] | 168 | 254-262 |
| | | DPARYEFLW | 169 | 290-298 |
| MAGE-A12 | http://www.genecards.org/cgi-bin/carddisp.pl?gene=MAGEA12 | FLWGPRALV[e] | 170 | 271-279 |
| | | VRIGHLYIL | 171 | 170-178 |
| | | EGDCAPEEK | 172 | 212-220 |
| | | REPFTKAEMLGSVIR | 173 | 127-141 |
| | | AELVHFLLLKYRAR | 174 | 114-127 |
| MAGE-C1 | http://www.genecards.org/cgi-bin/carddisp.pl?gene=MAGEC1 | ILFGISLREV | 175 | 959-968 |
| | | KVVEFLAML | 176 | 1083-1091 |
| | | SSALLSIFQSSPE | 177 | 137-149 |
| | | SFSYTLLSL | 178 | 450-458 |
| | | VSSFFSYTL | 179 | 779-787 |
| MAGE-C2 | http://www.genecards.org/cgi-bin/carddisp.pl?gene=MAGEC2 | LLFGLALIEV | 180 | 191-200 |
| | | ALKDVEERV | 181 | 336-344 |
| | | SESIKKKVL | 182 | 307-315 |
| | | ASSTLYLVF | 183 | 42-50 |
| | | SSTLYLVFSPSSFST | 184 | 43-57 |
| mucin[k] | http://www.genecards.org/cgi-bin/carddisp.pl?gene=MUC1 | PDTRPAPGSTAPPAHGVTSA | 185 | |
| NA88-A | | QGQHFLQKV | 186 | |
| NY-ESO-1/ LAGE-2 | http://www.genecards.org/cgi-bin/carddisp.pl?gene=CTAG1B | SLLMWITQC | 187 | 157-165 |
| | | MLMAQEALAFL | 188 | (1-11) |
| | | ASGPGGGAPR | | 53-62 |
| | | LAAQERRVPR | 189 | ORF2 |
| | | LAAQERRVPR | 190 | (18-27) |
| | | TVSGNILTIR | | 127-136 |
| | | APRGPHGGAASGL | 191 | 60-72 |
| | | MPFATPMEA | 192 | 94-102 |
| | | KEFTVSGNILTI | 193 | 124-135 |

TABLE 2-continued

| Gene/Protein | GeneCard information, incorporated herein by reference | Peptide | SEQ ID NO: | Position |
|---|---|---|---|---|
| | | MPFATPMEA | 194 | 94-102 |
| | | LAMPFATPM | 195 | 92-100 |
| | | ARGPESRLL | 196 | 80-88 |
| | | SLLMWITQCFLPVF | 197 | 157-170 |
| | | LLEFYLAMPFATPM EAELARRSLAQ | 198 | 87-111 |
| | | LLEFYLAMPFATPM EAELARRSLAQ | 199 | 87-111 |
| | | EFYLAMPFATPM | 200 | 89-100 |
| | | PGVLLKEFTVSGNI LTIRLTAADHR | 201 | 119-143 |
| | | RLLEFYLAMPFA | 202 | 86-97 |
| | | QGAMLAAQERRVP RAAEVPR | 203 | ORF2 |
| | | QGAMLAAQERRVP RAAEVPR PFATPMEAELARR | 204 | (14-33) 95-107 |
| | | PGVLLKEFTVSGNI LTIRLT | 205 | 119-138 |
| | | PGVLLKEFTVSGNI LTIRLT VLLKEFTVSG | 206 | 119-138 121-130 |
| | | AADHRQLQLSISSC LQQL | 207 | 139-156 |
| | | LLEFYLAMPFATPM EAELARRSLAQ | 208 | 87-111 |
| | | LKEFTVSGNILTIRL | 209 | 123-137 |
| | | PGVLLKEFTVSGNI LTIRLTAADHR | 210 | 119-143 |
| | | LLEFYLAMPFATPM EAELARRSLAQ | 211 | 87-111 |
| | | KEFTVSGNILT | 212 | 124-134 |
| | | LLEFYLAMPFATPM | 213 | 87-100 |
| | | AGATGGRGPRGAGA | 214 | 37-50 |
| | | LYATVIHDI | 215 | 715-723 |
| SAGE | http://www.genecards.org/cgi-bin/carddisp.pl?gene=SAGE1 | ILDSSEEDK | 216 | 103-111 |
| Sp17 | http://www.genecards.org/cgi-bin/carddisp.pl?gene=SPA17 | KASEKIFYV | 217 | 41-49 |
| SSX-2 | http://www.genecards.org/cgi-bin/carddisp.pl?gene=SSX2 | EKIQKAFDDIAKYF SK | 218 | 19-34 |
| | | FGRLQGISPKI | 219 | 101-111 |
| | | WEKMKASEKIFYV YMKRK | 220 | 37-54 |
| | | KIFYVMKRKYEA MT | 221 | 45-59 |
| | | KIFYVMKRKYEAM | 222 | 45-58 |
| | | INKTSGPKRGKHA WTHRLRE | 223 | 151-170 |
| SSX-4 | http://www.genecards.org/cgi-bin/carddisp.pl?gene=SSX4 | YFSKKEWEKMKSS EKIVYVY | 224 | 31-50 |
| | | MKLNYEVMTKLGF KVTLPPF | 225 | 51-70 |
| | | KHAWTHRLRERKQ LVVYEEI | 226 | 161-180 |
| | | LGFKVTLPPFMRSK RAADFH | 227 | 61-80 |
| | | KSSEKIVYVYMKL NYEVMTK | 228 | 41-60 |
| | | KHAWTHRLRERKQ LVVYEEI | 229 | 161-180 |
| | | SLGWLFLLL | 230 | 78-86 |
| TAG-1 | | LSRLSNRLL | 231 | 42-50 |
| | | LSRLSNRLL | 232 | 42-50 |
| TAG-2 | | CEFHACWPAFTVL GE | 233 | 34-48 |
| TRAG-3 | http://www.genecards.org/cgi-bin/carddisp.pl?gene=CSAG2 | CEFHACWPAFTVL GE | 234 | 34-48 |
| | | CEFHACWPAFTVL GE | 235 | 34-48 |

TABLE 2-continued

| Gene/Protein | GeneCard information, incorporated herein by reference | Peptide | SEQ ID NO: | Position |
|---|---|---|---|---|
| | | EVISCKLIKR | 236 | intron 2 |
| TRP2-INT2[g] | http://www.genecards.org/cgi-bin/carddisp.pl?gene=DCT | RQKKIRIQL | 237 | 21-29 |
| XAGE-1b/GAGED2a | http://www.genecards.org/cgi-bin/carddisp.pl?gene=XGE1BA | HLGSRQKKIRIQLRSQ | 238 | 17-32 |
| | | CATWKVICKSCISQTPG | 239 | 33-49 |

[d]Only processed by the intermediate proteasome β5i (Guillaume et al. Proc. Natl. Acad. Sci. U.S.A. 107.43(2010): 18599-604).
[e]Same peptide as MAGE-A3/A2 (aa 271-279).
[f]Aberrant transcript of N-acetyl glucosaminyl transferase V (GnTV) that is found only in melanomas.
[g]Incompletely spliced transcript found only in melanomas.
[i]The processing of this peptide requires the immunoproteasome.
[j]This peptide is encoded by allele MAGE-4a, which is expressed in one third of MAGE-4 positive tumor samples. The other allele, namely MAGE-4b, encodes peptide EVDPTSNTY.
[k]MHC-unrestricted recognition by CTL of a repeated motif that is unmasked in tumors due to mucin underglycosylation. Mucin underglycosylation also occurs in breast duct epithelial cells during lactation, but only at the extracellular apical surface, which is not accessible to T cells.
[l]Only processed by the intermediate proteasome β1iβ5i (Guillaume et al. 2010).

TABLE 3

| Gene/protein | GeneCard information, incorporated herein by reference | Peptide | SEQ ID NO: | Position |
|---|---|---|---|---|
| CEA | http://www.genecards.org/cgi-bin/carddisp.pl?gene=CEACAM5 | YLSGANLNL[g] | 240 | 605-613 |
| | | IMIGVLVGV | 241 | 691-699 |
| | | GVLVGVALI | 242 | 694-702 |
| | | HLFGYSWYK | 243 | 61-69 |
| | | QYSWFVNGTF | 244 | 268-277 |
| | | TYACFVSNL | 245 | 652-660 |
| | | AYVCGIQNSVSANRS | 246 | 568-582 |
| | | DTGFYTLHVIKSDLVNEEATGQFRV | 247 | 116-140 |
| | | YSWRINGIPQQHTQV | 248 | 625-639 |
| | | TYYRPGVNLSLSC | 249 | 425-437 |
| | | EIIYPNASLLIQN | 250 | 99-111 |
| | | YACFVSNLATGRNNS | 251 | 653-667 |
| | | LWWVNNQSLPVSP | 252 | 177-189 and 355-367 |
| | | LWWVNNQSLPVSP | 253 | 177-189 and 355-367 |
| | | LWWVNNQSLPVSP | 254 | 177-189 and 355-367 |
| | | EIIYPNASLLIQN | 255 | 99-111 |
| | | NSIVKSITVSASG | 256 | 666-678 |
| gp100/Pmel17 | http://www.genecards.org/cgi-bin/carddisp.pl?gene=SILV | KTWGQYWQV | 257 | 154-162 |
| | | (A)MLGTHTMEV | 258 | 177(8)-186 |
| | | ITDQVPFSV | 259 | 209-217 |
| | | YLEPGPVTA | 260 | 280-288 |
| | | LLDGTATLRL | 261 | 457-466 |
| | | VLYRYGSFSV | 262 | 476-485 |
| | | SLADTNSLAV | 263 | 570-579 |
| | | RLMKQDFSV | 264 | 619-627 |
| | | RLPRIFCSC | 265 | 639-647 |
| | | LIYRRRLMK | 266 | 614-622 |
| | | ALLAVGATK | 267 | 17-25 |
| | | IALNFPGSQK | 268 | 86-95 |
| | | ALNFPGSQK | 269 | 87-95 |
| | | ALNFPGSQK | 270 | 87-95 |
| | | VYFFLPDHL | 271 | intron 4 |
| | | RTKQLYPEW | 272 | 40-42 and 47-52[e] |
| | | HTMEVTVYHR | 273 | 182-191 |
| | | SSPGCQPPA | 274 | 529-537 |
| | | VPLDCVLYRY | 275 | 471-480 |
| | | LPHSSSHWL | 276 | 630-638 |
| | | SNDGPTLI | 277 | 71-78 |
| | | GRAMLGTHTMEVTVY | 278 | 175-189 |

TABLE 3-continued

| Gene/protein | GeneCard information, incorporated herein by reference | Peptide | SEQ ID NO: | Position |
|---|---|---|---|---|
| | | WNRQLYPEWTEAQRLD | 279 | 44-59 |
| | | TTEWVETTARELPIPEPE | 280 | 420-437 |
| | | TGRAMLGTHTMEVTVYH | 281 | 174-190 |
| | | GRAMLGTHTMEVTVY | 282 | 175-189 |
| mamma-globin-A | http://www.genecards.org/cgi-bin/carddisp.pl?gene=SCGB2A2 | PLLENVISK | 283 | 23-31 |
| Melan-A/MART-1 | http://www.genecards.org/cgi-bin/carddisp.pl?gene=MLANA | (E)AAGIGILTV | 284 | 26(27)-35 |
| | | ILTVILGVL | 285 | 32-40 |
| | | EAAGIGILTV | 286 | 26-35 |
| | | AEEAAGIGIL(T) | 287 | 24-33(34) |
| | | RNGYRALMDKS | 288 | 51-61 |
| | | YTTAEEAAGIGILTVILGVLLLIGCWYCRR | 2892 | 21-50 |
| | | EEAAGIGILTVI | 290 | 25-36 |
| | | AAGIGILTVILGVL | 291 | 27-40 |
| | | APPAYEKLpSAEQ$^f$ | 292 | 100-111 |
| | | EEAAGIGILTVI | 293 | 25-36 |
| | | RNGYRALMDKSLHVGTQCALTRR | 294 | 51-73 |
| | | MPREDAHFIYGYPKKGHGHS | 295 | 1-20 |
| | | KNCEPVVPNAPPAYEKLSAE | 296 | 91-110 |
| NY-BR-1 | http://www.genecards.org/cgi-bin/carddisp.pl?gene=ANKRD30A | SLSKILDTV | 297 | 904-912 |
| OA1 | http://www.genecards.org/cgi-bin/carddisp.pl?gene=GPR143 | LYSACFWWL | 298 | 126-134 |
| PAP | http://www.genecards.org/cgi-bin/carddisp.pl?gene=ACPP | FLELLFEWL | 299 | 18-26 |
| | | TLMSAMTNL | 300 | 112-120 |
| | | ALDVYNGLL | 301 | 299-307 |
| PSA | http://www.genecards.org/cgi-bin/carddisp.pl?gene=KLK3 | FLTPKKLQCV | 302 | 165-174 |
| | | VISNDVCAQV | 303 | 178-187 |
| RAB38/NY-MEL-1 | http://www.genecards.org/cgi-bin/carddisp.pl?gene=RAB38 | VLHWDPETV | 304 | 50-58 |
| TRP-1/gp75 | http://www.genecards.org/cgi-bin/carddisp.pl?gene=TYRP1 | MSLQRQFLR | 305 | alt. ORF |
| | | ISPNSVFSQWRVVCDSLEDYD | 306 | 277-297 |
| | | SLPYWNFATG | 307 | 245-254 |
| | | SQWRVVCDSLEDYDT | 308 | 284-298 |
| TRP-2 | http://www.genecards.org/cgi-bin/carddisp.pl?gene=DCT | SVYDFFVWL | 309 | 180-188 |
| | | TLDSQVMSL | 310 | 360-368 |
| | | LLGPGRPYR | 311 | 197-205 |
| | | LLGPGRPYR | 312 | 197-205 |
| | | ANDPIFVVL | 313 | 387-395 |
| | | QCTEVRADTRPWSGP | 314 | 60-74 |
| | | ALPYWNFATG | 315 | 241-250 |
| tyrosinase | http://www.genecards.org/cgi-bin/carddisp.pl?gene=TYR | KCDICTDEY | 316 | 243-251 |
| | | SSDYVIPIGTY | 317 | 146-156 |
| | | MLLAVLYCL | 318 | 1-9 |
| | | CLLWSFQTSA | 319 | 8-17 |
| | | YMDGTMSQV | 320 | 369-377 |
| | | AFLPWHRLF | 321 | 206-214 |
| | | IYMDGTADFSF | 322 | 368-373 and 336-340$^e$ |
| | | QCSGNFMGF | 323 | 90-98 |
| | | TPRLPSSADVEF | 324 | 309-320 |
| | | LPSSADVEF | 325 | 312-320 |
| | | LHHAFVDSIF | 326 | 388-397 |
| | | SEIWRDIDF$^d$ | 327 | 192-200 |
| | | QNILLSNAPLGPQFP | 328 | 56-70 |
| | | SYLQDSDPDSFQD | 329 | 450-462 |

TABLE 3-continued

| Gene/protein | GeneCard information, incorporated herein by reference | Peptide | SEQ ID NO: | Position |
|---|---|---|---|---|
| | | FLLHHAFVDSIEEQWLQRHRP | 330 | 386-406 |

[d] Different alleles encoding tyrosinase have been described. In 50% of Caucasians, the serine residue of nonapeptide SEIWRDIDF is replaced by a tyrosine.
[e] The peptide is composed of two non-contiguous fragments that are spliced by the proteasome.
[f] Phosphopeptide.
[g] Seems to be poorly processed by tumor cells (Fauquembergue et al. J. Immunother. 33.4(2010): 402-13).

TABLE 4

| Gene/Protein | GeneCard information, incorporated herein by reference | Peptide | SEQ ID NO: | Position |
|---|---|---|---|---|
| adipophilin | http://www.genecards.org/cgi-bin/carddisp.pl?gene=PLIN2 | SVASTITGV | 331 | 129-137 |
| AIM-2 | http://www.genecards.org/cgi-bin/carddisp.pl?gene=LOC51152 | RSDSGQQARY | 332 | intron |
| ALDH1A1 | http://www.genecards.org/cgi-bin/carddisp.pl?gene=ALDH1A1 | LLYKLADLI | 333 | 88-96 |
| BCLX (L) | http://www.genecards.org/cgi-bin/carddisp.pl?gene=BCL2L1 | YLNDHLEPWI | 334 | 173-182 |
| BING-4 | http://www.genecards.org/cgi-bin/carddisp.pl?gene=WDR46 | CQWGRLWQL | 335 | ORF2 |
| CALCA | http://www.genecards.org/cgi-bin/carddisp.pl?gene=CALCA | VLLQAGSLHA | 336 | 16-25 |
| CD45 | http://www.genecards.org/cgi-bin/carddisp.pl?gene=PTPRC | KFLDALISL | 337 | 556-564 |
| CPSF | http://www.genecards.org/cgi-bin/carddisp.pl?gene=CPSF1 | KVHPVIWSL | 338 | 250-258 |
| | | LMLQNALTTM | 339 | 1360-1369 |
| cyclin D1 | http://www.genecards.org/cgi-bin/carddisp.pl?gene=CCND1 | LLGATCMFV | 340 | 101-109 |
| | | NPPSMVAAGSVVAAV | 341 | 198-212 |
| DKK1 | http://www.genecards.org/cgi-bin/carddisp.pl?gene=DKK1 | ALGGHPLLGV | 342 | 20-29 |
| ENAH (hMena) | http://www.genecards.org/cgi-bin/carddisp.pl?gene=ENAH | TMNGSKSPV | 343 | 502-510 |
| EpCAM | http://www.genecards.org/cgi-bin/carddisp.pl?gene=EPCAM | RYQLDPKFI | 344 | 173-181 |
| EphA3 | http://www.genecards.org/cgi-bin/carddisp.pl?gene=EPHA3 | DVTFNIICKKCG | 345 | 356-367 |
| EZH2 | http://www.genecards.org/cgi-bin/carddisp.pl?gene=EZH2 | FMVEDETVL | 346 | 120-128 |
| | | FINDEIFVEL | 347 | 165-174 |
| | | KYDCFLHPF | 348 | 291-299 |
| | | KYVGIEREM | 349 | 735-743 |
| FGF5 | http://www.genecards.org/cgi-bin/carddisp.pl?gene=FGF5 | NTYASPRFK[f] | 350 | 172-176 and 204-207 |
| glypican-3 | http://www.genecards.org/cgi-bin/carddisp.pl?gene=GPC3&search=GLYPICAN-3 | FVGEFFTDV | 351 | 144-152 |
| | | EYILSLEEL | 352 | 298-306 |
| G250/MN/CAIX | http://www.genecards.org/cgi-bin/carddisp.pl?gene=CA9 | HLSTAFARV | 353 | 254-262 |
| HER-2/neu | http://www.genecards.org/cgi-bin/carddisp.pl?gene=ERBB2 | KIFGSLAFL | 354 | 369-377 |
| | | IISAVVGIL | 355 | 654-662 |
| | | ALCRWGLLL | 356 | 5-13 |
| | | ILHNGAYSL | 357 | 435-443 |
| | | RLLQETELV | 358 | 689-697 |
| | | VVLGVVFGI | 359 | 665-673 |
| | | YMIMVKCWMI | 360 | 952-961 |
| | | HLYQGCQVV | 361 | 48-56 |
| | | YLVPQQGFFC | 362 | 1023-1032 |
| | | PLQPEQLQV | 363 | 391-399 |
| | | TLEEITGYL | 364 | 402-410 |
| | | ALIHHNTHL | 365 | 466-474 |
| | | PLTSIISAV | 366 | 650-658 |
| | | VLRENTSPK | 367 | 754-762 |
| | | TYLPTNASL | 368 | 63-71 |
| IDO1 | http://www.genecards.org/cgi-bin/carddisp.pl?gene=IDO1 | ALLEIASCL | 369 | 199-207 |

TABLE 4-continued

| Gene/Protein | GeneCard information, incorporated herein by reference | Peptide | SEQ ID NO: | Position |
|---|---|---|---|---|
| IGF2B3 | http://www.genecards.org/cgi-bin/carddisp.pl?gene=GPC3&search=GLYPICAN-3 | NLSSAEVVV<br>RLLVPTQFV | 370<br>371 | 515-523<br>199-207 |
| IL13Ralpha2 | http://www.genecards.org/cgi-bin/carddisp.pl?gene=IL13RA2 | WLPFGFILI | 372 | 345-353 |
| Intestinal carboxyl esterase | http://www.genecards.org/cgi-bin/carddisp.pl?gene=CES2 | SPRWWPTCL | 373 | alt. ORF |
| alpha foetoprotein | http://www.genecards.org/cgi-bin/carddisp.pl?gene=AFP | GVALQTMKQ<br>FMNKFIYEI<br>QLAVSVILRV | 374<br>375<br>376 | 542-550<br>158-166<br>364-373 |
| Kallikrein 4 | http://www.genecards.org/cgi-bin/carddisp.pl?gene=KLK4 | FLGYLILGV<br>SVSESDTIRSISIAS<br>LLANGRMPTVLQCVN<br>RMPTVLQCVNVSVVS | 377<br>378<br>379<br>380 | 11-19<br>125-139<br>155-169<br>160-174 |
| KIF20A | http://www.genecards.org/cgi-bin/carddisp.pl?gene=KIF20A&search=KIF20A | LLSDDDVVV<br>AQPDTAPLPV<br>CIAEQYHTV | 381<br>382<br>383 | 12-20<br>284-293<br>809-817 |
| Lengsin | http://www.genecards.org/cgi-bin/carddisp.pl?gene=CSF1 | FLPEFGISSA | 384 | 270-279 |
| M-CSF | http://www.genecards.org/cgi-bin/carddisp.pl?gene=CSF1 | LPAVVGLSPGEQEY | 385 | alt. ORF |
| MCSP | http://www.genecards.org/cgi-bin/carddisp.pl?gene=CSPG4 | VGQDVSVLFRVTGALQ | 386 | 693-708 |
| mdm-2 | http://www.genecards.org/cgi-bin/carddisp.pl?gene=MDM2 | VLFYLGQY | 387 | 53-60 |
| Meloe | | TLNDECWPA<br>FGRLQGISPKI<br>CPPWHPSERISSTL | 388<br>389<br>390 | 36-44<br>32-44<br>24-37 |
| MMP-2 | http://www.genecards.org/cgi-bin/carddisp.pl?gene=MMP2 | GLPPDVQRV[h] | 391 | 560-568 |
| MMP-7 | http://www.genecards.org/cgi-bin/carddisp.pl?gene=MMP7 | SLFPNSPKWTSK | 392 | 96-107 |
| MUC1 | http://www.genecards.org/cgi-bin/carddisp.pl?gene=MUC1 | STAPPVHNV<br>LLLLTVLTV<br>PGSTAPPAHGVT | 393<br>394<br>395 | 950-958<br>12-20<br>repeated region |
| MUC5AC | http://www.genecards.org/cgi-bin/carddisp.pl?gene=MUC5AC | TCQPTCRSL | 396 | 716-724 |
| p53 | http://www.genecards.org/cgi-bin/carddisp.pl?gene=TP53 | LLGRNSFEV<br>RMPEAAPPV<br>SQKTYQGSY<br>PGTRVRAMAIYKQ<br>HLIRVEGNLRVE | 397<br>398<br>399<br>400<br>401 | 264-272<br>65-73<br>99-107<br>153-165<br>193-204 |
| PAX5 | http://www.genecards.org/cgi-bin/carddisp.pl?gene=PAX5 | TLPGYPPHV | 402 | 311-319 |
| PBF | http://www.genecards.org/cgi-bin/carddisp.pl?gene=ZNF395 | CTACRWKKACQR | 403 | 499-510 |
| PRAME | http://www.genecards.org/cgi-bin/carddisp.pl?gene=PRAME | VLDGLDVLL<br>SLYSFPEPEA<br>ALYVDSLFFL<br>SLLQHLIGL<br>LYVDSLEFL[c] | 404<br>405<br>406<br>407<br>408 | 100-108<br>142-151<br>300-309<br>425-433<br>301-309 |
| PSMA | http://www.genecards.org/cgi-bin/carddisp.pl?gene=FOLH1 | NYARTEDFF | 409 | 178-186 |
| RAGE-1 | http://www.genecards.org/cgi-bin/carddisp.pl?gene=RAGE | LKLSGVVRL<br>PLPPARNGGL[g]<br>SPSSNRIRNT | 410<br>411<br>412 | 352-360<br>32-40<br>11-20 |
| RGS5 | http://www.genecards.org/cgi-bin/carddisp.pl?gene=RGS5 | LAALPHSCL<br>GLASFKSFLK | 413<br>414 | 5-13<br>74-83 |
| RhoC | http://www.genecards.org/cgi-bin/carddisp.pl?gene=RhoC | RAGLQVRKNK | 415 | 176-185 |
| RNF43 | http://www.genecards.org/cgi-bin/carddisp.pl?gene=RNF43 | ALWPWLLMA(T)<br>NSQPVWLCL | 416<br>417 | 11-19 (20)<br>721-729 |

TABLE 4-continued

| Gene/Protein | GeneCard information, incorporated herein by reference | Peptide | SEQ ID NO: | Position |
|---|---|---|---|---|
| RU2AS | http://www.genecards.org/cgi-bin/carddisp.pl?gene=DCDC2 | LPRWPPPQL | 418 | antisense |
| secernin 1 | http://www.genecards.org/cgi-bin/carddisp.pl?gene=SCRN1 | KMDAEHPEL | 419 | 196-204 |
| SOX10 | http://www.genecards.org/cgi-bin/carddisp.pl?gene=SOX10 | AWISKPPGV | 420 | 332-340 |
|  |  | SAWISKPPGV | 421 | 331-340 |
| STEAP1 | http://www.genecards.org/cgi-bin/carddisp.pl?gene=STEAP1 | MIAVFLPIV | 422 | 292-300 |
|  |  | HQQYFYKIPILVINK | 423 | 102-116 |
| survivin | http://www.genecards.org/cgi-bin/carddisp.pl?gene=BIRCS | ELTLGEFLKL | 424 | 95-104 |
|  |  | TLGEFLKLDRERAKN | 425 | 97-111 |
| Telomerase | http://www.genecards.org/cgi-bin/carddisp.pl?gene=TERT | ILAKFLHWL[e] | 426 | 540-548 |
|  |  | RLVDDFLLV | 427 | 865-873 |
|  |  | RPGLLGASVLGLDDI | 428 | 672-686 |
|  |  | LTDLQPYMRQFVAHL | 429 | 766-780 |
| VEGF | http://www.genecards.org/cgi-bin/carddisp.pl?gene=VEGFA | SRFGGAVVR[i] | 430 |  |
| WT1 | http://www.genecards.org/cgi-bin/carddisp.pl?gene=WT1 | TSEKRPFMCAY | 431 | 317-327 |
|  |  | CMTWNQMNL | 432 | 235-243 |
|  |  | LSHLQMHSRKH | 433 | 337-347 |
|  |  | KRYFKLSHLQMHSRKH | 434 | 332-347 |

[c]The antigen is recognized by CTLs bearing an NK inhibitory receptor that prevents lysis of cells expressing certain HLA-C molecules.
[e]Poorly or not processed (Parkhurst, 2004; Ayyoub, 2001).
[f]The peptide is composed of two non-contiguous fragments that are spliced.
[g]Alternative transcript.
[h]MMP-2 is expressed ubiquitously but melanoma cells cross-present, in an αvβ3-dependent manner, an antigen derived from secreted MMP-2.
[i]The epitope is located in the untranslated region.

Immunomodulators

Compositions, methods, and devices of the present invention comprise immunomodulators including, but not limited to, TLR ligands, growth factors, and products of dying cells, e.g. heat shock proteins, with means to stimulate dendritic cell activation. Immunomodulators are used alone or in combination with GM-CSF, CpG-ODN sequences, or cancer antigens Immunomodulators are used simultaneously or sequentially with GM-CSF, CpG-ODN sequences, or cancer antigens.

All known TLR ligands found either on a cell surface or an internal cellular compartment are encompassed by the compositions, methods, and devices of the present invention. Exemplary TLR ligands include, but are not limited to, triacyl lipoproteins (TLR1); lipoproteins, gram positive peptidoglycan, lipteichoic acids, fungi, and viral glycoproteins (TLR2); double-stranded RNA, poly I:C (TLR 3); lipopolysaccaride, viral glycoproteins (TLR 4); flagellin (TLR5); diacyl lipoproteins (TLR6); small synthetic compounds, single-stranded RNA (TLR7 and TLR 8); unmethylated CpG DNA (TLR9); Profilin (TLR11). Also included as TRL ligands are host molecules like fibronectin and heat shock proteins (HSPs). Host TLR ligands are also encompassed by the present invention. The role of TLRs in innate immunity and the signaling molecules used to activate and inhibit them are known in the art (for a review, see Holger K. Frank B., Hessel E., and Coffman R L. Therapeutic targeting of innate immunity with Toll-like receptor agonists and antagonists. Nature Medicine 13, 552-559 (2007), incorporated herein by reference).

All known growth factors are encompassed by the compositions, methods, and devices of the present invention. Exemplary growth factors include, but are not limited to, transforming growth factor beta (TGF-β), granulocyte-colony stimulating factor (G-CSF), granulocyte-macrophage colony stimulating factor (GM-CSF), nerve growth factor (NGF), neurotrophins, Platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF or FGF-2), epidermal growth factor (EGF), hepatocyte growth factor (HGF). The present invention encompasses cytokines as well as growth factors for stimulating dendritic cell activation. Exemplary cytokines include, but are not limited to, IL-1, IL-2, IL-3, IL-4, IL-5, IL-6, IL-8, IL-10, IL-12 IL-15, IL-17, IL-18, TNF-α, IFN-γ, and IFN-α.

Indications of cell death and products of dying cells stimulate dendritic cell activation. As such, all products of dying cells are encompassed by the compositions, methods, and devices of the present invention. Exemplary cell death products include, but are not limited to, any intracellular feature of a cell such as organelles, vesicles, cytoskeletal elements, proteins, DNA, and RNA. Of particular interest are heat shock proteins expressed when a cell is under stress and which are released upon cell death. Exemplary heat shock proteins include, but are not limited to, Hsp10, Hsp20, Hsp27, Hsp33, Hsp40, Hsp60, Hsp70, Hsp71, Hsp72, Grp78, Hsx70, Hsp84, Hsp90, Grp94, Hsp100, Hsp104, Hsp110.

Microenvironments and Vaccine Efficiency

The devices/scaffold described herein represent an infection-mimicking microenvironment. Each device constitutes a factory that attracts/accepts, educates/stimulates and sends forth to surrounding bodily tissues activated dendritic cells that are capable of stimulating/enhancing an immune response to a particular antigen. Specifically, the scaffold devices are implanted or coated with pathogenic molecules to mimic and infectious microenvironment to further activate the dendritic cell response.

Appropriately mimicking aspects of infection with material systems dramatically impacts tumor progression when applied as cancer vaccines by continuously recruiting, activating and homing DCs to LNs. The first PLG vaccine, using GM-CSF alone, led to a batch process where host DCs were recruited by GM-CSF to reside at a site of tumor antigen presentation, and were trapped until GM-CSF levels fell and the cells could become activated and disperse (see US 2008/0044900 A1, incorporated herein by reference). Temporal variation of the local GM-CSF concentration allowed control over the number of recruited DCs, and the timing of their activation and dispersement. Although the best GM-CSF-based vaccine was able to confer protective immunity in nearly a quarter of the animals tested, approximately 26% of the recruited DCs were activated (~240,000 DCs) and approximately 6% of DCs dispersed to the LNs. High levels of GM-CSF recruited large numbers of DC, but also limited DC activation, leaving potentially therapeutic DCs entrapped within scaffolds. These results motivated the development of an improved system that mimicked bacterial infection by locally presenting CpG-ODNs as an overriding 'danger signal', that opposed GM-CSF inhibition of DC activation and dispersement. These devices described herein represent significant advances by mediating increased and continuous egress of DCs.

CpG-ODN molecules were condensed with PEI to not only promote ODN uptake into DCs and localization to its TLR-9 receptor, but also to electrostatically immobilize it in PLG matrices to be presented simultaneously with tumor antigens. In vitro results indicated that PEI-CpG-ODN condensates can decondense within DCs and stimulate TLR signaling that promoted DC activation and dispersement toward the lymph node derived chemokine, CCL19, in the presence of inhibitory levels of GM-CSF (500 ng/ml) (US 2013-0202707, incorporated herein by reference).

As described in detail in US 2013-0202707, the vaccine devices of the invention advantageously allow for fine control of cell behavior and programming in situ.

Scaffold Compositions and Architecture

Components of the scaffolds are organized in a variety of geometric shapes (e.g., discs, beads, pellets), niches, planar layers (e.g., thin sheets). For example, discs of about 0.1-200 millimeters in diameter, e.g., 5, 10, 20, 40, 50 millimeters are implanted subcutaneously. The disc may have a thickness of 0.1 to 10 milimeters, e.g., 1, 2, 5 milimeters. The discs are readily compressed or lyophilized for administration to a patient. An exemplary disc for subcutaneous administration has the following dimensions: 8 milimeters in diameter and 1 milimeter in thickness. Multicomponent scaffolds are optionally constructed in concentric layers each of which is characterized by different physical qualities (% polymer, % crosslinking of polymer, chemical composition of scaffold, pore size, porosity, and pore architecture, stiffness, toughness, ductility, viscoelasticity, and or composition of bioactive substances such as growth factors, homing/migration factors, differentiation factors. Each niche has a specific effect on a cell population, e.g., promoting or inhibiting a specific cellular function, proliferation, differentiation, elaboration of secreted factors or enzymes, or migration. Cells incubated in the scaffold are educated and induced to migrate out of the scaffold to directly affect a target tissue, e.g., and injured tissue site. For example, stromal vascular cells and smooth muscle cells are useful in sheetlike structures are used for repair of vessel-like structures such as blood vessels or layers of the body cavity. For example, such structures are used to repair abdominal wall injuries or defects such as gastroschisis. Similarly, sheetlike scaffolds seeded with dermal stem cells and/or keratinocytes are used in bandages or wound dressings for regeneration of dermal tissue. The device is placed or transplanted on or next to a target tissue, in a protected location in the body, next to blood vessels, or outside the body as in the case of an external wound dressing. Devices are introduced into or onto a bodily tissue using a variety of known methods and tools, e.g., spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches. Devices can also be assembled in place, for example by senquentially injecting or inserting matrix materials. Scaffold devices are optionally recharged with cells or with bioactive compounds, e.g., by sequential injection or spraying of substances such as growth factors or differentiation factors.

A scaffold or scaffold device is the physical structure upon which or into which cells associate or attach, and a scaffold composition is the material from which the structure is made. For example, scaffold compositions include biodegradable or permanent materials such as those listed below. The mechanical characteristics of the scaffold vary according to the application or tissue type for which regeneration is sought. It is biodegradable (e.g., collagen, alginates, polysaccharides, polyethylene glycol (PEG), poly(glycolide) (PGA), poly(L-lactide) (PLA), or poly(lactide-co-glycolide) (PLGA), poly lactic-coglycolic acid, or permanent (e.g., silk). In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogenous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold.

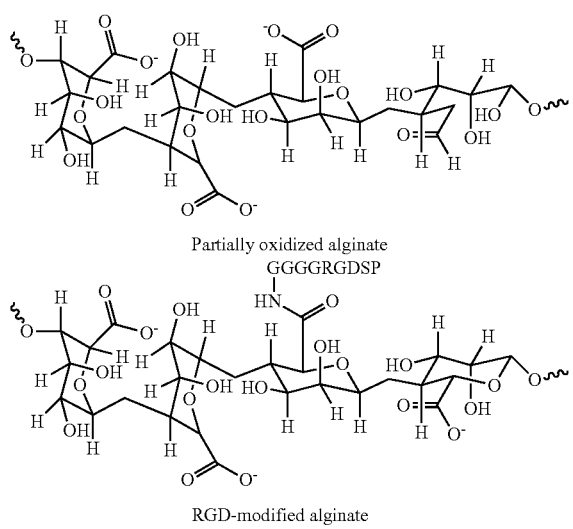

Partially oxidized alginate

RGD-modified alginate

The scaffold comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly (alkylene oxides) particularly poly(ethylene oxides), poly (allylamines) (PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

The scaffolds are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g., $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for dental applications, wound dressings chondrocyte transplantation and as a matrix for other cell types.

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer. U.S. Pat. No. 6,642,363, incorporated herein by reference, discloses methods for making and using polymers containing polysachharides such as alginates or modified alginates that are particularly useful for cell transplantation and tissue engineering applications.

Useful polysaccharides other than alginates include agarose and microbial polysaccharides such as those listed in the table below.

| Polysaccharide Scaffold Compositions | |
|---|---|
| Polymers[a] | Structure |
| Fungal | |
| Pullulan (N) | 1,4-;1,6-α-D-Glucan |
| Scleroglucan (N) | 1,3;1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-;1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2;1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N-neutral, A = anionic and C = cationic.

The scaffolds of the invention are porous or non-porous. For example, the scaffolds are nanoporous having a diameter of less than about 10 nm; microporous wherein the diameter of the pores are preferably in the range of about 100 nm-20 μm; or macroporous wherein the diameter of the pores are greater than about 20 μm, more preferably greater than about 100 μm and even more preferably greater than about 400 μm. In one example, the scaffold is macroporous with aligned pores of about 400-500 μm in diameter. The preparation of polymer matrices having the desired pore sizes and pore alignments are described in the Examples. Other methods of preparing porous hydrogel products are known in the art. (U.S. Pat. No. 6,511,650, incorporated herein by reference).

Bioactive Compositions

The device includes one or more bioactive compositions. Bioactive compositions are purified naturally-occurring, synthetically produced, or recombinant compounds, e.g., polypeptides, nucleic acids, small molecules, or other agents. For example, the compositions include GM-CSF, CpG-ODN, and tumor antigens or other antigens. For example, the compositions described herein include an inhibitor of an immune inhibitory protein (e.g., an inhibitor of CTLA4, PD1, PDL1, B7-H3, B7-H4, LAG3, 2B4, BTLA, TIM3, A2aR, or a killer inhibitory receptor). For example, the composition includes an antibody or fragment thereof or a protein that binds to an immune inhibitory protein (e.g., CTLA4, PD1, PDL1, B7-H3, B7-H4, LAG3, 2B4, BTLA, TIM3, A2aR, or a killer inhibitory receptor). In preferred embodiments, the composition includes an antibody of fragment thereof that binds to CTLA4, PD1, or PDL1.

The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

Coupling of the polypeptides, antibodies, or fragments thereof to the polymer matrix is accomplished using synthetic methods known to one of ordinary skill in the art. Approaches to coupling of peptides to polymers are discussed in Hirano and Mooney, Advanced Materials, p. 17-25 (2004). Other useful bonding chemistries include those discussed in Hermanson, *Bioconjugate Techniques*, p. 152-185 (1996), particularly by use of carbodiimide couplers, DCC and DIC (Woodward's Reagent K). Polypeptides contain a terminal amine group for such carbodiimide bonding. The amide bond formation is preferably catalyzed by 1-ethyl-3-(3-dimethylaminopropyl)carbodiimide (EDC), which is a water soluble enzyme commonly used in peptide synthesis.

Control of Release Kinetics of Bioactive Compositions

The release profile of bioactive compositions such as GM-CSF is controlled using a number of different techniques, e.g., encapsulation, nature of attachment/association with the scaffold, porosity of the scaffold, and particle size of the bioactive compositions.

For example, GM-CSF is encapsulated as one means by which to incorporate GM-CSF into the scaffolds. GM-CSF was first encapsulated into PLG microspheres, and then these GM-CSF loaded microspheres were then in a gas foaming process to develop macroporous PLG scaffolds. The incorporation of GM-CSF into the microspheres causes the GM-CSF to be more deeply embedded into the polymer, which causes the device to sustain the initial pulse of GM-CSF delivery over days 1-5. Other incorporation methods are optionally used to alter or fine tune the duration of the GM-CSF pulse as desired, which would in turn change the kinetics of DC recruitment. For example, foaming PLG particles mixed with lyophilized GM-CSF results in GM-CSF that is associated more with the surface of the polymer scaffold, and the protein diffuses more quickly.

Alternative methods for scaffold fabrication that modify release kinetics include modifying the physical structure of the scaffolds pores, thereby leading to different degradation times and release kinetics (change pore size or total porosity as a percentage of volume), e.g., as described in Riddle et al., Role of poly(lactide-co-glycolide) particle size on gas-foamed scaffolds. J Biomater Sci Polym Ed. 2004; 15(12): 1561-70. Another way to alter release kinetics is to modify the composition, i.e., the raw materials from which the scaffold is made, thereby altering the release properties. For example, different polymers, e.g., alginate, PLA, PGA, or using PLGA are used. Also, use of the polymers with different ratios of glycolic and lactic acid) leads to different release profiles. For example, a variety of PLGs, differing in composition (lactide to glycolide ratio) and molecular weight are used to prepare microspheres (5-50 μm) using known double emulsion (water/oil/water) process, followed by preparation of scaffolds using particulate PLG and PLG microspheres using gas foaming/particulate leaching techniques (Ennett et al., Temporally regulated delivery of VEGF in vitro and in vivo. J Biomed Mater Res A. 2006 October; 79(1). Another technique involves incorporating the protein into different compartments (e.g., encapsulating proteins PLG microspheres or simple mixing and lyophilizing with the polymer before foaming) Methods of making a scaffold described herein include using gas foaming, e.g., as described in detail in Harris et al. J. Biomed. Materials Res. Part A. 42.3(1998)396-402 and Sheridan et al. J. Control. Ra. 64(2000)91-102, both incorporated herein by reference.

In other embodiments, wires (e.g., a template containing multiple wires) are used as porogens, i.e., to create pores in the scaffold, e.g., to create aligned pores.

Charging and/or Recharging the Device

A bioactive composition such as GM-CSF is incorporated within different layers/compartments of the device, thereby allowing multiple pulses of GM-CSF to be delivered. Each pulse charges (or recharges) the device with an influx of DCs. Scaffolds are fabricated using a variety of methods to create multiple pulses of GM-CSF (or other bioactive agents). For example, such devices are made by incorporating the protein into different compartments (e.g., encapsulating proteins PLG microspheres or simple mixing and lyophilizing with the polymer before foaming) thereby creating 2 or more distinct release profiles (i.e., pulses) of the protein (e.g., as described in Richardson et al., Polymeric system for dual growth factor delivery. Nat Biotechnol. 2001 November; 19(11)).

Alternatively, the protein is encapsulated in fast degrading PLG microspheres (e.g. low MW, 50:50 ratio) and slow degrading PLG microspheres (high MW, 85:15 ratio). Then these microspheres are mixed together to be used later to fabricate the scaffolds. Therefore, the protein is encapsulated in both fast a degrading polymer and a slow degrading polymer, thereby resulting in at least 2 distinct releases kinetics and pulses of delivery. This method is utilized to create 3, 4, 5, or more different kinds of microspheres, the ratiometric characteristics of which differ, thereby leading to 3, 4, 5 or more pulses of release of the bioactive composition such as GM-CSF.

Another approach to making a device that delivers more than one pulse is to fabricate a layered scaffold. Layered scaffolds are made by compression molding on different scaffold formulations with another. For example, the raw materials (sucrose+PLG1+Protein) is compressed in a mold and a slightly varied formulation (sucrose+PLG2+Protein) is also compressed in a mold. Then these two layers are compressed together and then foamed, resulting in a bilayered scaffold with distinct spatial control of the concentration of the protein, e.g., as described in Chen et al., Pharm Res. Spatio-temporal VEGF and PDGF delivery patterns blood vessel formation and maturation. 2007 February; 24(2):258-64).

Device Construction

The scaffold structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into cell scaffold structures using methods known in the art, e.g., injection molding, lyophillization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The device is assembled in vivo in several ways. The scaffold is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In one example, the ungelled or unformed scaffold material is mixed with bioactive substances and cells prior to introduction into the body or while it is introduced. The resultant in vivo/in situ assembled scaffold contains a mixture of these substances and cells.

In situ assembly of the scaffold occurs as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the scaffold material by a radiation beam or through a heat or light conductor, such as a wire or fiber optic cable or an ultrasonic transducer. Alternatively, a shear-thinning material, such as an ampliphile, is used which re-cross links after the shear force exerted upon it, for example by its passage through a needle, has been relieved.

Suitable hydrogels for both in vivo and ex vivo assembly of scaffold devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A. 99:5133-5138. A method for reversible gellation following shear thinning is exemplified in Lee et al., 2003, Adv. Mat. 15:1828-1832.

A multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. Non-concentric compartments are formed by injecting material into different locations in a previously injected layer. A multi-headed injection device extrudes compartments in parallel and simultaneously. The layers are made of similar or different scaffolding compositions differentially doped with bioactive substances and different cell types. Alternatively, compartments self-organize based on their hydrophilic/phobic characteristics or on secondary interactions within each compartment.

Compartmentalized Device

In certain situations, a device containing compartments with distinct chemical and/or physical properties is useful. A compartmentalized device is designed and fabricated using different compositions or concentrations of compositions for each compartment.

Alternatively, the compartments are fabricated individually, and then adhered to each other (e.g., a "sandwich" with an inner compartment surrounded on one or all sides with the second compartment). This latter construction approach is accomplished using the intrinsic adhesiveness of each layer for the other, diffusion and interpenetration of polymer chains in each layer, polymerization or cross-linking of the second layer to the first, use of an adhesive (e.g., fibrin glue), or physical entrapment of one compartment in the other. The compartments self-assemble and interface appropriately, either in vitro or in vivo, depending on the presence of appropriate precursors (e.g., temperature sensitive oligopeptides, ionic strength sensitive oligopeptides, block polymers, cross-linkers and polymer chains (or combinations thereof), and precursors containing cell adhesion molecules that allow cell-controlled assembly).

Alternatively, the compartmentalized device is formed using a printing technology. Successive layers of a scaffold precursor doped with bioactive substances is placed on a substrate then cross linked, for example by self-assembling chemistries. When the cross linking is controlled by chemical-, photo- or heat-catalyzed polymerization, the thickness and pattern of each layer is controlled by a masque, allowing complex three dimensional patterns to be built up when un-cross-linked precursor material is washed away after each catalyzation. (W T Brinkman et al., Photo-cross-linking of type 1 collagen gels in the presence of smooth muscle cells: mechanical properties, cell viability, and function. *Biomacromolecules,* 2003 July-August; 4(4): 890-895; W. Ryu et al., The construction of three-dimensional microfluidic scaffolds of biodegradable polymers by solvent vapor based bonding of micro-molded layers. *Biomaterials,* 2007 February; 28(6): 1174-1184; Wright, Paul K. (2001). *21st Century manufacturing.* New Jersey: Prentice-Hall Inc.) Complex, multi-compartment layers are also built up using an inkjet device which "paints" different doped-scaffold precursors on different areas of the substrate. Julie Phillippi (Carnegie Mellon University) presentation at the annual meeting of the American Society for Cell Biology on Dec. 10, 2006; Print me a heart and a set of arteries, Aldhouse P., New Scientist 13 Apr. 2006 Issue 2547 p 19; Replacement organs, hot off the press, C. Choi, New Scientist, 25 Jan. 2003, v 2379. These layers are built-up into complex, three dimensional compartments. The device is also built using any of the following methods: Jetted Photopolymer, Selective Laser Sintering, Laminated Object Manufacturing, Fused Deposition Modeling, Single Jet Inkjet, Three Dimensional Printing, or Laminated Object Manufacturing.

The release profiles of bioactive substances from scaffold devices is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors). In both cases, the time frame of release determines the time over which effective cell delivery by the device is desired.

The bioactive substances are added to the scaffold compositions using known methods including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, long term presentation of a bioactive substance on the scaffold in a defined conformation. Exemplary reagents for covalent coupling of such substances are provided in the table below.

| Methods to covalently couple peptides/proteins to polymers | | |
| --- | --- | --- |
| Functional Group of Polymer | Coupling reagents and cross-linker | Reacting groups on proteins/ peptides |
| —OH | Cyanogen bromide (CNBr) Cyanuric chloride 4-(4,6-Dimethoxy-1,3,5-triazin-2-yl)-4-methyl-morpholinium chloride (DMT-MM) | —NH$_2$ |

Methods to covalently couple peptides/proteins to polymers

| Functional Group of Polymer | Coupling reagents and cross-linker | Reacting groups on proteins/peptides |
|---|---|---|
| —NH$_2$ | Diisocyanate compounds<br>Diisothoncyanate compounds<br>Glutaraldehyde<br>Succinic anhydride | —NH$_2$<br>—OH |
| —NH$_2$ | Nitrous Acid<br>Hydrazine + nitrous acid | —NH$_2$<br>—SH<br>—Ph—OH |
| —NH$_2$ | Carbodiimide compounds (e.g., EDC, DCC)[a]<br>DMT-MM | —COOH |
| —COOH | Thionyl chloride<br>N-hydroxysuccinimide<br>N-hydroxysulfosuccinimide + EDC | —NH$_2$ |
| —SH | Disulfide compound | —SH |

[a]EDC: 1-ethyl-3-(3-dimethylaminopropyl) carbodiimide hydrochloride; DCC: dicyclohexylcarbodiimide Bioactive substances suitable for use in the present invention include, but are not limited to: interferons, interleukins, chemokines, cytokines, colony stimulating factors, chemotactic factors, granulocyte/macrophage colony stimulating factor (GM-CSF). Splice variants of any of the above mentioned proteins, and small molecule agonists or antagonists thereof that may be used advantageously to activate dendritic cells are also contemplated herein.

Exemplary bioactive substances suitable for use in, on, or in combination with the vaccine device of the invention include an inhibitor of an immune-inhibitory protein. Exemplary immune-inhibitory proteins include immune checkpoint proteins (e.g., CTLA4, PD1, PDL1, and PDL2). Other exemplary immune inhibitory proteins include B7-H3, B7-H4, LAG3, 2B4, BTLA, TIM3, A2aR, and/or a killer inhibitory receptor. Exemplary inhibitors include small molecules, proteins, peptides, antibodies or fragments thereof, and nucleic acids. For example, an inhibitor is a nucleic acid, protein, antibody, or fragment thereof that binds to CTLA4, PD1, PDL1, PDL2, B7-H3, B7-H4, LAG3, 2B4, BTLA, TIM3, A2aR, and/or a killer inhibitory receptor. For example, an inhibitor is a nucleic acid that binds to a mRNA that encodes CTLA4, PD1, PDL1, PDL2, B7-H3, B7-H4, LAG3, 2B4, BTLA, TIM3, A2aR, and/or a killer inhibitory receptor. In some embodiments, the nucleic acid that binds to a mRNA of the inhibitor downregulates inhibitor expression at the mRNA and/or protein level.

A small molecule is a low molecular weight compound of less than 1000 Daltons, less than 800 Daltons, or less than 500 Daltons. Antibodies and fragments thereof described herein include, but are not limited to, polyclonal, monoclonal, chimeric, dAb (domain antibody), single chain, Fab, Fab' and F(ab')2 fragments, Fv, scFvs. A fragment of an antibody possess the immunological activity of its respective antibody. In some embodiments, a fragment of an antibody contains 1500 or less, 1250 of less, 1000 or less, 900 or less, 800 or less, 700 or less, 600 or less, 500 or less, 400 or less, 300 or less, 200 or less amino acids. For example, a protein or peptide inhibitor contains 1500 or less, 1250 of less, 1000 or less, 900 or less, 800 or less, 700 or less, 600 or less, 500 or less, 400 or less, 300 or less, 200 or less, 100 or less, 80 or less, 70 or less, 60 or less, 50 or less, 40 or less, 30 or less, 25 or less, 20 or less, 10 or less amino acids. For example, a nucleic acid inhibitor of the invention contains 400 or less, 300 or less, 200 or less, 150 or less, 100 or less, 90 or less, 80 or less, 70 or less, 60 or less, 50 or less, 40 or less, 35 or less, 30 or less, 28 or less, 26 or less, 24 or less, 22 or less, 20 or less, 18 or less, 16 or less, 14 or less, 12 or less, 10 or less nucleotides.

In some cases, a compound (e.g., small molecule) or macromolecule (e.g., nucleic acid, polypeptide, or protein) of the invention is purified and/or isolated. As used herein, an "isolated" or "purified" small molecule, nucleic acid molecule, polynucleotide, polypeptide, or protein (e.g., antibody or fragment thereof), is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally occurring state. Purified also defines a degree of sterility that is safe for administration to a human subject, e.g., lacking infectious or toxic agents.

By "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

For example, a nucleic acid inhibitor is a short interfering RNA, a short hairpin RNA, antisense RNA, aptamers, peptide nucleic acids (PNAs), microRNAs (miRNAs), or locked nucleic acids (LNAs). In some embodiments, the nucleic acid comprises modified oligonucleotides (e.g., 2'-o-methyl RNA).

Examples of cytokines as mentioned above include, but are not limited to IL-1, IL-2, IL-3, IL-4, IL-5, IL-6, IL-7, IL-8, IL-10, IL-12, IL-15, IL-17, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

Scaffolds of the invention optionally comprise at least one non-viral gene therapy vector such that either the transplanted cells or host cells in the vicinity of the implant would take up and express gene that lead to local availability of the desired factor for a desirable time frame. Such non-viral vectors include, but are not limited to, cationic lipids, polymers, targeting proteins, and calcium phosphate.

Scaffold Fabrication.

A 85:15, 120 kD copolymer of D,L-lactide and glycolide (PLG) (Alkermes, Cambridge, Mass.) was utilized in a gas-foaming process to form scaffolds with open, interconnected pores (Cohen S., Yoshioka T., Lucarelli, M., Hwang L. H., and Langer R. Pharm, Res. 8, 713-720 (1991); herein incorporated by reference). PLG microspheres encapsulating GM-CSF were made using standard double emulsion (Harris, E D., Kim, B. S., and Mooney. D. J. J. Biomed. Mater. Res. 42, 396-402 (1998): herein incorporated by reference). 16 mg of PLG microspheres were then mixed with 150 mg of the porogens, NaCl or sucrose (sieved to a particle size between 250 μm and 425 μm), and compression molded. The resulting disc was allowed to equilibrate within a high-pressure $CO_2$ environment, and a rapid reduction in pressure causes the polymer particles to expand and fuse into an interconnected structure. The NaCl was leached from the scaffolds by immersion in water yielding scaffolds that were 90% porous. To incorporate tumor lysates into PLG scaffolds, biopsies of B16-F10 tumors, that had grown subcutaneously in the backs of C57BL/6J mice (Jackson Laboratory, Bar Harbor Me.), were digested in collagenase (250 U/ml) (Worthington, Lakewood, N.J.) and suspended at a concentration equivalent to $10^7$ cells per ml after filtration through 40 µm cell strainers. The tumor cell suspension was subjected to 4 cycles of rapid freeze in liquid nitrogen and thaw (37° C.) and then centrifuged at 400 rpm for 10 mm. The supernatant (1 ml) containing tumor lysates was collected and lyophilized with the PLG microspheres and the resulting mixture was used to make PLG scaffold-based cancer vaccines. To incorporate CpG-ODNs into PLG scaffolds, PEI-CpG-ODN condensate solutions were vortexed with 60 µl of 50% (wt/vol) sucrose solution, lyophilized and mixed with dry sucrose to a final weight of 150 mg. The sucrose containing PEI-CpG-ODN condensate was then mixed with blank, GM-CSF and/or tumor lysate loaded PLG microspheres to make PLG cancer vaccines.

Scaffold compositions of the present invention comprise GM-CSF, Flt3L, and/or CCL20, and CpG-ODN sequences. A range of concentrations of each element are contemplated. In a preferred embodiment, the scaffold composition comprises PLG. With respect to GM-CSF, Flt3L, and/or CCL20, per 40 mg polymeric scaffold composition, 0-100 µg of GM-CSF, Flt3L, and/or CCL20 polypeptide is incorporated into or coated onto the scaffold composition. Alternatively, doses comprising 0-50 µg, 0-25 µg, 0-10 µg, 0-5 µg, and 0-3 µg of GM-CSF, Flt3L, and/or CCL20 are incorporated into the scaffold composition. In a preferred embodiment, 0-3 µg of GM-CSF, Flt3L, and/or CCL20 are incorporated into the scaffold composition. With respect to CpG-ODN sequences, or PEI-CpG-ODN condensates, per 40 mg polymeric scaffold composition, 0-1000 µg of PEI-CpG-ODN is incorporated into or coated onto the scaffold composition. Alternatively, doses comprising 0-500 µg, 0-250 µg, 0-100 µg (e.g., 100 µg), 0-50 µg, 0-25 µg, 0-10 µg, and 0-5 µg of PEI-CpG-ODN are incorporated into the scaffold composition. In a preferred embodiment, 0-50 µg of PEI-CpG-ODN are incorporated into the scaffold composition.

Vaccine Device

The biocompatible scaffolds are useful as delivery vehicles for cancer vaccines. The cancer vaccine stimulates an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells. Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. These treatments optionally involve cytokine exposure to activate the cells, genetic manipulation to overexpress cytokines from the cells, or priming with tumor specific antigens or cocktails of antigens, and expansion in culture. Dendritic cell vaccines activate antigen presenting cells directly, and their proliferation, activation and migration to lymph nodes is regulated by scaffold compositions to enhance their ability to elicit an immune response. Types of cancers to be treated include central nervous system (CNS) cancers, CNS Germ Cell tumor, lung cancer, Leukemia, Multiple Myeloma, Renal Cancer, Malignant Glioma, Medulloblastoma, and Melanoma.

For the purpose of eliciting an antigen-specific immune response, a scaffold device is implanted into a mammal. The device is tailored to activate immune cells and prime the cells with a specific antigen thereby enhancing immune defenses and destruction of undesired tissues and targeted microorganisms such as bacterial or viral pathogens. The device attracts appropriate immune cells, such as macrophages, T cells, B cells, NK cells, and dendritic cells, by containing and/or releasing signaling substances such as GM-CSF. These signaling substances are incorporated in the scaffold composition in such a way as to control their release spatially and temporally using the same techniques used to integrate other bioactive compounds in the scaffold composition.

Once the immune cells are inside the device, the device programs the immune cells to attack or cause other aspects of the immune system to attack undesired tissues (e.g., cancer, adipose deposits, or virus-infected or otherwise diseased cells) or microorganisms Immune cell activation is accomplished by exposing the resident immune cells to preparations of target-specific compositions, e.g., ligands found on the surface of the undesired tissues or organisms, such as cancer cell surface markers, viral proteins, oligonucleatides, peptide sequences or other specific antigens. For example, useful cancer cell-specific antigens and other tissue or organism-specific proteins are listed in the table below.

The device optionally contains multiple ligands or antigens in order to create a multivalent vaccine. The compositions are embedded in or coated on the surface of one or more compartments of the scaffold composition such that immune cells migrating through the device are exposed to the compositions in their traverse through the device. Antigens or other immune stimulatory molecules are exposed or become exposed to the cells as the scaffold composition degrades. The device may also contain vaccine adjuvants that program the immune cells to recognize ligands and enhance antigen presentation. Exemplary vaccine adjuvants include chemokines/cytokines, CpG rich oligonucleotides, or antibodies that are exposed concurrently with target cell-specific antigens or ligands.

The device attracts immune cells to migrate into a scaffold where they are educated in an antigen-specific manner and activated. The programmed immune cells are then induced to egress towards lymph nodes in a number of ways. The recruitment composition and deployment signal/composition, e.g., a lymph node migration inducing substance, is released in one or more bursts, programmed by the method of incorporation and/or release from the scaffold material, or controlled by the sequential degradation of scaffold compartments which contain the attractant. When a burst dissipates, the cells migrate away. Compartments containing repulsive substances are designed to degrade and release the repulsive substance in one or more bursts or steadily over time. Relative concentration of the repulsive substances cause the immune cells to migrate out of the device. Alternatively, cells which have been placed in or have migrated into the device are programmed to release repulsive substances or to change their own behavior. For example, localized gene therapy is carried out by cell exposure to plasmid DNA attached to the scaffold. Useful repulsive substances include chemokines and cytokines. Alternatively, the device may cause immune cells to egress by degrading and releasing them.

Target disease states, stimulatory molecules and antigens useful in vaccine device construction are listed below.

Bioactive Factors to Promote Immune Responses
a. Interleukins: IL-1, IL-2, IL-3, IL-4, IL-5, IL-6, IL-8, IL-10, IL-12 IL-15, IL-17, IL-18 etc.
b. TNF-α
c. IFN-γ
d. IFN-α
e. GM-CSF
f. G-CSF
g. Ftl-3 ligand
h. MIP-3 β (CCL19)
i. CCL21
j. M-CSF
k. MIF
l. CD40L
m. CD3
n. ICAM
o. Anti-CTLA4 proteins or antibodies or fragments thereof (e.g., ipilimumab or tremelimumab)
p. TGF-β
q. CPG rich DNA or oligonucleotides
r. Sugar moieties associated with Bacteria: Lipopolysacharides (LPS) is an example
s. Fas ligand
t. Trail
u. Lymphotactin
v. Mannan (M-FP)
w. Heat Shock Proteins (apg-2, Hsp70 and Hsp 90 are examples)
x. anti-PD1 proteins or antibodies (e.g., MDX-1106, MK3475, CT-011, or AMP-224)
y. anti-PDL1 or anti-PDL2 proteins or antibodies (e.g., MDX-1105)
z. anti-LAG3 proteins or antibodies or fragments thereof
aa. anti-B7-H3 proteins or antibodies or fragments thereof
bb. anti-B7-H4 proteins or antibodies or fragments thereof
cc. anti-TIM3 proteins or antibodies or fragments thereof
dd. anti-BTLA proteins or antibodies or fragments thereof
ee. anti-A2aR proteins or antibodies or fragments thereof
ff. anti-killer inhibitor receptor (KIR) (e.g., killer cell immunoglobulin-like receptor or C-type lectin receptor) proteins or antibodies or fragments thereof
gg. anti-TIM4 proteins or antibodies or fragments thereof
hh. anti-TIM2 proteins or antibodies or fragments thereof
ii. anti-OX40 proteins or antibodies or fragments thereof
jj. anti-4-1BB proteins or antibodies or fragments thereof
kk. anti-phosphatidylserine proteins or antibodies or fragments thereof (e.g., a monoclonal antibody against phosphatidylserine Diseases and Antigens—Vaccination Targets
a. Cancer: antigens and their sources
i. Tumor lysates extracted from biopsies (e.g., from melanoma tumor biopsies)
ii. Irradiated tumor cells (e.g., irradiated melanoma cells)
iii. Melanoma
1. MAGE series of antigens (MAGE-1 is an example)
2. MART-1/melanA
3. Tyrosinase
4. ganglioside
5. gp100
6. GD-2
7. O-acetylated GD-3
8. GM-2
9. B16-F10 tumor lysate, e.g., from mice challenged with B16-F10 melanoma tumor cells (ATCC, Manassas, N.J.)
10. tyrosinase-related protein (TRP)-2
11. lung cancer cell lysate or lung cancer cell antigen
12. glioma cancer cell lysate or glioma cancer cell antigen
13. prostate cancer cell lysate or prostate cancer cell antigen
iv. Breast Cancer
1. MUC-1
2. Sos1
3. Protein kinase C-binding protein
4. Reverse trascriptase protein
5. AKAP protein
6. VRK1
7. KIAA1735
8. T7-1, T11-3, T11-9
9. Her2 (also known as CD340)
v. Other General and Specific Cancer Antigens
1. *Homo Sapiens* telomerase ferment (hTRT)
2. Cytokeratin-19 (CYFRA21-1)
3. SQUAMOUS CELL CARCINOMA ANTIGEN 1 (SCCA-1), (PROTEIN T4-A)
4. SQUAMOUS CELL CARCINOMA ANTIGEN 2 (SCCA-2)
5. Ovarian carcinoma antigen CA125 (1A1-3B) (KIAA0049)
6. MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3)
7. CTCL tumor antigen se-1
8. CTCL tumor antigen se14-3
9. CTCL tumor antigen se20-4
10. CTCL tumor antigen se20-9
11. CTCL tumor antigen se33-1
12. CTCL tumor antigen se37-2
13. CTCL tumor antigen se57-1
14. CTCL tumor antigen se89-1
15. Prostate-specific membrane antigen
16. 5T4 oncofetal trophoblast glycoprotein
17. Orf73 Kaposi's sarcoma-associated herpesvirus
18. MAGE-C1 (cancer/testis antigen CT7)
19. MAGE-B1 ANTIGEN (MAGE-XP ANTIGEN) (DAM10)
20. MAGE-B2 ANTIGEN (DAM6)
21. MAGE-2 ANTIGEN
22. MAGE-4a antigen
23. MAGE-4b antigen
24. Colon cancer antigen NY-CO-45
25. Lung cancer antigen NY-LU-12 variant A
26. Cancer associated surface antigen
27. Adenocarcinoma antigen ART1
28. Paraneoplastic associated brain-testis-cancer antigen (onconeuronal antigen MA2; paraneoplastic neuronal antigen)
29. Neuro-oncological ventral antigen 2 (NOVA2)
30. Hepatocellular carcinoma antigen gene 520
31. TUMOR-ASSOCIATED ANTIGEN CO-029

32. Tumor-associated antigen MAGE-X2
33. Synovial sarcoma, X breakpoint 2
34. Squamous cell carcinoma antigen recognized by T cell
35. Serologically defined colon cancer antigen 1
36. Serologically defined breast cancer antigen NY-BR-15
37. Serologically defined breast cancer antigen NY-BR-16
38. Chromogranin A; parathyroid secretory protein 1
39. DUPAN-2
40. CA 19-9
41. CA 72-4
42. CA 195
43. Carcinoembryonic antigen (CEA)
b. AIDS (HIV Associated Antigens)
i. Gp120
ii. SIV229
iii. SIVE660
iv. SHIV89.6P
v. E92
vi. HCl
vii. OKM5
viii. FVIIIRAg
ix. HLA-DR (Ia) antigens
x. OKM1
xi. LFA-3
c. General Infectious Diseases and Associated Antigens
i. Tuberculosis
1. *Mycobacterium tuberculosis* antigen 5
2. *Mycobacterium tuberculosis* antigen 85
3. ESAT-6
4. CFP-10
5. Rv3871
6. GLU-S
ii. Malaria
1. CRA
2. RAP-2
3. MSP-2
4. AMA-1
iii. Possible mutant influenza and meningitis strains
d. Neuro Protection—Protect Against Neurological Diseases (e.g., Alzheimer's, Parkinsons, Prion Disease)
1. Classes of self CNS antigens
2. human alpha-synuclein (Parkinson's)
3. beta amyloid plaques (Alzheimer's)
e. Autoimmune Diseases (multiple sclerosis, Rheumatoid arthritis etc)
i. Disease linked MHC antigens
ii. Different classes of Self antigens
iii. Insulin
iv. Insulin peptide B9-23
v. glutamic acid
vi. decarboxylase 65 (GAD 65)
vii. HSP 60
Disease linked T-cell receptor (TCR)

Prior vaccines have been largely ineffective for patients with established cancer, as advanced disease requires potent and sustained activation of $CD8^+$ cytotoxic T lymphocytes (CTLs) to kill tumor cells and clear the disease. Subsets of dendritic cells (DCs) specialize in antigen cross-presentation and in the production of cytokines, which regulate both CTLs and T regulatory (Treg) cells that shut down effector T cell responses. Coordinated regulation of a DC network, and plasmacytoid DCs (pDCs) and $CD8^+$ DCs in particular, enhances host immunity in mice. Functionalized biomaterials incorporating various combinations of an inflammatory cytokine, immune danger signal, and tumor lysates are used in the vaccines described herein to control the activation and localization of host DC populations in situ.

Implantable synthetic polymer matrices (antigen-loaded acellular biomaterial device) that spatially and temporally control the in vivo presentation of cytokines, tumor antigens, and danger signals are utilized. GM-CSF is released from these polylactide-co-glycolide (PLG) [a FDA-approved biomaterial] matrices into the surrounding tissue to recruit DC precursors and DCs. CpG-rich oligonucleotides are immobilized on the matrices as danger signals, and antigen (tumor lysates) is released to matrix-resident DCs to program DC development and maturation. These matrices quantitatively regulate DC activation and trafficking in situ and induce prophylactic immunity against inoculations of murine B16-F10 melanoma cells (P. Schnorrer, G. M. Behrens, N. S. Wilson, J. L. Pooley, C. M. Smith, D. El-Sukkari, G. Davey, F. Kupresanin, M. Li, E. Maraskovsky, G. T. Belz, F. R. Carbone, K. Shortman, W. R. Heath, J. A. Villadangos, The dominant role of $CD8^+$ dendritic cells in cross-presentation is not dictated by antigen capture. Proc. Natl. Acad. Sci. U.S.A. 103, 10729-10734 (2006)). As described herein, this system administered repeatedly over time to controls the recruitment and activation of multiple DC and T cell subsets and is effective as a therapeutic vaccine against established tumors.

Matrix Fabrication

An exemplary protocol for matrix fabrication is described herein (see, e.g., US 2013-0202707, incorporated herein by reference). An 85:15, 120-kD copolymer of $_{D,L}$-lactide and glycolide (PLG) (Alkermes) was utilized in a gas-foaming process to form porous PLG matrices (L. D. Harris, B. S. Kim, D. J. Mooney, Open pore biodegradable matrices formed with gas foaming. *J. Biomed. Mater. Res.* 42, 396-402 (1998)). PLG microspheres encapsulating GM-CSF were first made with standard double emulsion (S. Cohen, T. Yoshioka, M. Lucarelli, L. H. Hwang, R. Langer, Controlled delivery systems for proteins based on poly(lactic/glycolic acid) microspheres. *Pharm. Res.* 8, 713-720 (1991)). PLG micro-spheres were then mixed with 150 mg of the porogen, sucrose (sieved to a particle size between 250 and 425 mm), and compression molded. The resulting disc was allowed to equilibrate within a high-pressure $CO_2$ environment, and a rapid reduction in pressure causes the polymer particles to expand and fuse into an interconnected structure. The sucrose was leached from the scaffolds by immersion in water, yielding scaffolds that were 90% porous. To incorporate tumor lysates into PLG scaffolds, the biopsies of B16-F10 tumors that had grown subcutaneously in the backs of C57BL/6J mice (Jackson Laboratory) were digested in collagenase (250 U/ml) (Worthington) and suspended at a concentration equivalent to $10^7$ cells per milliliter after filtration through 40-µm cell strainers. The tumor cell suspension was subjected to four cycles of rapid freeze in liquid nitrogen and thaw (37° C.) and then centrifuged at 400 rpm for 10 min. The supernatant (1 ml) containing tumor lysates was collected, incubated with the PLG microspheres, and lyophilized, and the resulting mixture was utilized in the high-pressure $CO_2$ process to foam macroporous PLG matrices incorporating tumor lysates.

To incorporate CpG-ODNs into PLG scaffolds, CpG-ODN 1826, 5'-tccatgacgttcctgacgtt-3' (Invivogen, San Diego, Calif.; SEQ ID NO: 29) was condensed with poly (ethylenimine) (PEI) ($M_n$ ~60,000; Sigma Aldrich) molecules by dropping ODN 1826 solutions into PEI solution while vortexing the mixture (L. D. Harris, B. S. Kim, D. J. Mooney, Open pore biodegradable matrices formed with gas foaming. J. Biomed. Mater. Res. 42, 396-402 (1998); S. Cohen, T. Yoshioka, M. Lucarelli, L. H. Hwang, R. Langer, Controlled delivery systems for proteins based on poly (lactic/glycolic acid) microspheres. Pharm. Res. 8, 713-720 (1991); Y. C. Huang, M. Connell, Y. Park, D. J. Mooney, K. G. Rice, Fabrication and in vitro testing of polymeric delivery system for condensed DNA. J. Biomed. Mater. Res. A 67, 1384-1392(2003)). The charge ratio between PEI and CpG-ODN ($NH_3^+:PO_4^-$) was kept constant at 7 during condensation. PEI-CpG-ODN condensate solutions were then vortexed with 60 μl of 50% (w/v) sucrose solution, lyophilized, and mixed with dry sucrose to a final weight of 150 mg. The sucrose containing PEI-CpG-ODN condensate was then mixed with blank, GM-CSF, and/or tumor lysate-loaded PLG microspheres to make PLG cancer vaccines.

To achieve controlled GM-CSF and TLR agonist presentation, macroporous, poly-lactide-co-glycolide (PLG) matrices quickly release GM-CSF (Ali et al., 2009 Nat Mater, 2: 151-8); e.g., approximately 60% of the protein was released by day 10 (US 2013-0202707, incorporated herein by reference), to induce the recruitment of DCs or their precursors. GM-CSF loaded PLG scaffolds were also modified to present TLR-activating, CpG-ODN, MPLA and P(I:C) molecules, as danger signals. Presentation of the TLR agonists was designed to provide a long-term, local signal to activate DCs. Importantly, the relatively high molecular weight and composition of the particular PLG chosen to fabricate scaffolds results in slow scaffold degradation, allowing for long-term analysis of the vaccine site and its regulation over DC activation and T cell immunity.

The vaccine system of the invention is capable of generating prophylactic immunity against poorly immunogenic B16-F10 melanoma (O. A. Ali, N. Huebsch, L. Cao, G. Dranoff, D. J. Mooney, Infection-mimicking materials to program dendritic cells in situ. Nat. Mater. 8, 151-158 (2009) and US 2013-0202707, incorporated herein by reference). As described in US 2013-0202707, incorporated herein by reference, the vaccine system promotes and extends CTL responses through naïve T cell differentiation induced by pDCs and CD8$^+$ DCs, the corresponding production of type 1 IFNs and IL-12, and inhibition of negative feedback mechanisms.

As described in US 2013-0202707, incorporated herein by reference, vaccine formulations containing various TLR agonists produce significant and systemic anti-melanoma CTLs in correlation with the activation of specific DC subsets and reduce tumor burden. Inclusion of TLR agonists was activates DCs, in general, increasing their surface expression of MHCII and the costimulatory molecule, CD86, indicating an enhanced capacity to present antigen and activate T cell populations. In particular, appropriate TLR signaling enhanced the generation of CD8(+) and pDC subsets at the vaccine site and stimulated the production of IFNs and the potent T cell growth factor, IL-12.

In some embodiments, three different types of pathogen associated molecular patterns (PAMPs) are incorporated into or onto structural polymeric devices such as PLG disc structures/scaffolds to act as adjuvants in vaccines (3 types; a short oligonucleotide (CpG-ODN); a synthetic RNA—(Poly(I:C); P(I:C)), a synthetic lipid (monophosphoryl lipid A; MPLA). Such vaccine formulations recruit and activate dendritic cells in situ.

Vaccine-dependent survival in an aggressive melanoma cancer model correlates strongly with the ability of the vaccine to specifically activate 2 subsets of dendritic cells—CD8(+) DCs and plasmacytoid DCs—regardless of the adjuvant utilized in the vaccine system. This correlation has been confirmed utilizing 4 different vaccine adjuvants in the PLG vaccine. These vaccines induce potent tumor rejection in a therapeutic model of melanoma, by activating specific T cell responses that have been detected at the vaccine site and at tumors. These findings demonstrate the PLG vaccine system's versatility in incorporating different types of agonists that stimulate different pathways in innate and adaptive immune responses.

The Role of Dendritic Cells in the Immune Response

Dendritic cells (DCs) orchestrate immune responses to infection and tumors by priming and propagating specific, cytotoxic T lymphocyte (CTL) responses. Immature DCs residing in peripheral tissue detect foreign substances (i.e., antigens) unique to invading pathogens, and are activated by stimuli, such as pathogen associated molecular patterns (PAMPs) or products of dying cells (i.e., "danger signals"), originating during pathogen induced inflammatory responses. Maturing DCs mature both process and present antigens on major histocompatibility complexes (MHC) receptors, and express the costimulatory molecules CD80 and CD86, both of which are required for effector T-cell stimulation. Another important result of DC maturation by 'danger signaling', is that DCs acquire the ability to home to the lymph nodes to engage and activate naive T-cells, enabling the T cells to recognize the antigens DCs are presenting.

The ability of particular DCs to initiate and control immune responses is a consequence of both their localization within tissues and their specialized capacity for mobilization. DCs originate from pluripotent stem cells in the bone marrow, enter the blood stream and localize into almost all organs. Based on the relative expression of a series of surface markers, different subsets of DCs or DC precursors can be identified in peripheral blood, including plasmacytoid DCs (pDCs) and conventional DCs (cDCs)2. pDCs are major type I interferon (IFN) producers, and specialize in activating adaptive immune responses to virus challenge via cytokine signaling. CD11c(+) cDCs, such as epidermal DCs, are especially adept at antigen presentation and co-stimulation of T cells.

Upon microbial invasion and inflammation, DCs rapidly migrate into the draining lymph nodes and primary sites of infection at rates that vastly outnumber other APCs, such as macrophages. The production of most DC subsets, including (pDCs) is controlled in the steady state by the cytokine Fms-related tyrosine kinase 3 ligand (FL). Other cytokines, such as GM-CSF and CCL20, released by damaged or infected cells, actively recruit and localize cDCs to the sites of inflammation. In inflammatory models, both in vivo and in vitro, these inflammatory cytokines have been shown to also enhance DC migration and proliferation and may regulate DC activation state. The quantity of DCs activated during infection or within tumors is correlated with the strength of the subsequent immune response and disease prognosis.

To generate sufficient numbers of dendritic cells (DCs) for immunotherapy, laboratory-based culture of DC precursors with inflammatory cytokines, such as granulocyte macrophage-colony stimulating factor (GM-CSF) and FL (Flt3) has often been used. DCs modified in vitro to present tumor antigens are capable of eliciting antitumor effects in murine models upon transplantation. Initial clinical testing of ex vivo DC-based vaccines has revealed the induction of tumor regression in a subset of cancer patients, but little survival benefit. Protocols involving the ex vivo manipulation of DCs are limited by the quantities and types of DCs that can be produced, poor engraftment efficiency and LN homing, and loss of DC activation upon injection in the in vivo environment.

To address these limitations, infection-mimicking materials of the device present inflammatory cytokines in combination with a danger signal to recruit and activate DCs in vivo. Also, nanoparticles containing cytosine-guanosine (CpG) rich oligonucleotide (CpG-ODN) sequences were immobilized onto scaffolds, as CpG-ODN are expressed in bacterial DNA, and are potent danger signals that can stimulate activation of matrix resident DCs.

CD141+ DCs and plasmacytoid DCs are critical for successful cancer vaccination (prophylactic and therapeutic). Plasmacytoid DCs look like plasma cells, but have certain characteristics similar to myeloid dendritic cells, can produce high amounts of interferon-alpha, and are characterized by TLR7 and TLR9. The TLR agonist, CpG, binds to TLR9. CD8+ DCs in mice are equivalent to CD141+ dendritic cells. CD141+ DCs are found in human lymph nodes, bone marrow, tonsil, and blood. They are characterized by high expression of toll-like receptor 3 (TLR3), production of IL-12p70 and IFN-β, and superior capacity to induce T helper 1 cell responses, when compared with the more commonly studied CD1c+ DC subset.

Polyinosine-polycytidylic acid (poly I:C)-activated CD141+ DCs have a superior capacity to cross-present antigens to CD8+ cytotoxic T lymphocytes than poly I:C-activated CD1c+ DCs. Thus, CD141+ DC subset represents an important functionally distinct human DC subtype with characteristics similar to those of the mouse CD8α+ DC subset. CD141+ DCs play a role in the induction of cytotoxic T lymphocyte responses and their activation is important for vaccination against cancers, viruses, and other pathogens.

p(I:C) in the vaccine device stimulates CD141+ DCs in humans (CD8+ DCs in mice) and CpG stimulates plasmacytoid DCs. Devices with one or both of these TLR agonists lead to potent DC activation and the generation of significant prophylactic and therapeutic anti-tumor immune responses. A combination of different TLR agonists, e.g., a combination of p(I:C) and CpG, in a device leads to a synergistic effect in the activation of a DC immune response against tumors.

PLG vaccines incorporating CpG-ODN and P(I:C) act synergistically to generate significant tumor inhibition, reduced tumor burden, and to generate improved anti-tumor immune responses.

Controlled Release of Cytokines and In Vivo DC Recruitment

Macroporous, poly-lactide-co-glycolide (PLG) matrices were designed to provide long-term and sustained release of GM-CSF, FL, and CCL20 and to house DCs for activation. These PLG scaffolds were 80-90% porous with an average pore size between 125-200 um to facilitate dendritic cell infiltration. The in vitro release kinetics for the three cytokines were similar, as the matrices quickly released protein with a burst over the first 5 days followed by sustained release over the next several weeks (US 2013-0202707, incorporated herein by reference).

In Vivo DC Activation

PLG scaffolds were modified to present nanoparticles containing TLR-activating, CpG-ODN, as an infection-mimicking danger signal in concert with delivery with inflammatory cytokines. This dramatically enhanced DC activation in situ over control conditions lacking cytokine signaling.

Controlled mobilization and activation of DCs and DC precursors is of particular interest in the development of ex vivo DC based vaccines, and more generally the design of material systems that activate the immune system in vivo. As described herein, polymers which mimic key aspects of microbial infection effectively recruit DCs for cancer vaccination. MCI scaffolds engineered to release GM-CSF, FL, and CCL20 led to significant numbers of resident DCs, and the co-presentation of danger signals led to DC maturation. Even though all vaccine formulations were capable of inducing tumor protection in a therapeutic model of B16-F10 melanoma, GM-CSF and FL vaccines produced more antigen specific CTLs, higher levels of Th1 priming cytokines, and greater survival rates when compared to CCL20.

pDCs, and their cDC counterparts are targeted to exploit their specialized abilities mediate anti-tumor T cell responses. In contrast to nanoparticle targeting systems, the polymer systems described herein not only serve as a antigen delivery devices to recruit and activate DCs, but also serve as a physical structure where DCs temporarily reside while they are activated.

The systems described herein demonstrated significant anti-tumor activity. In addition to the polymers, e.g., PLG, described herein, matrices are optionally fabricated from other more inflammatory polymers to boost immune responses and DC mobilization. Another important aspect of subsequent T cell priming by these cells is LN homing. The exit or dispersement of DCs after antigen exposure is optimized by incorporating different adjuvants into the material to activate migratory function. Alternatively, other matrix properties, including degradation kinetics and porosity are altered to promote further control over DC trafficking.

FL, CCL20 and GM-CSF are utilized in biomaterial systems to mimic infection-induced recruitment of DCs in situ. As described in US 2013-0202707, e.g., at page 111, line 17-page 113, line 17 (incorporated herein by reference), infection-mimicking porous devices are effective as therapeutic cancer vaccines.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not significantly react with other antigens. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked $V_H$:$V_L$ heterodimer, which can be expressed from a gene fusion including $V_H$- and $V_L$-encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "ERs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, an scFv, or a T-cell receptor. Epitopic determinants consist of chemically active surface groupings of molecules such as amino acids or sugar side chains and have specific three dimensional structural characteristics, as well as specific charge characteristics. For example, antibodies may be raised against N-terminal or C-terminal peptides of a polypeptide, linear or non-linear peptide sequences of a protein, as well as epitopes that comprise amino acids of a first antigen and those of a second antigen.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (Nature 361: 186-87 (1993)). The ratio of $K_{off}/K_{on}$ enables the cancellation of all parameters not related to affinity, and is equal to the dissociation constant $K_d$. Davies et al. (1990) Annual Rev Biochem 59:439-473). An antibody of the present invention is said to specifically bind to an antigen or epitope described herein (e.g., a CTLA, PD1, PDL1, or other immune inhibitory protein and/or tumor antigen) when the equilibrium binding constant ($K_d$) is ≤1 µM, preferably ≤100 nM, more preferably ≤10 nM, more preferably ≤1 nM, and most preferably ≤100 pM to about 1 pM, as measured by assays such as radioligand binding assays or similar assays known to those skilled in the art.

Routes of Administration

A pharmaceutical composition of the invention (e.g., an inhibitor described herein) is formulated to be compatible with its intended route of administration. Examples of routes of administration include parenteral, e.g., intravenous, intraperitoneal, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811, incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Dosages

The methods of the invention include administering one or more inhibitors of an immune-inhibitory protein described herein at a dosage of 0.01-10 mg/kg (e.g., 0.1-5 mg/kg) bodyweight. For example, the inhibitor is administered at a dosage of 0.01, 0.02, 0.05, 0.1, 0.3, 0.5, 1, 3, 5, 10, 15, 20, 25, 30, 35, 40, 45, 50 mg/kg. In some embodiments, the inhibitor is administered every day, every other day, every 2 days, every 3 days, every 4 days, every 5 days, or every 6 days. In other embodiments, the inhibitor is administered every 1-10 weeks (e.g., every 1, 2, 3, 4, 5, 6, 7, 8, 9, or 10 weeks). For example, the inhibitor is administered for a total of 7 days to 3 years (e.g., 7 days, 14 days, 3 weeks, 4 weeks, 5 weeks, 6 weeks, 7 weeks, 8 weeks, 9 weeks, 10 weeks, 11 weeks, 12 weeks, 24 weeks, 36 weeks, 1 year, 1.5 years, 2 years, 2.5 years, or 3 years). For example, the inhibitor is administered indefinitely (e.g., at least 3 years). In some embodiments, the inhibitor is provided in an amount of 0.01-50 mg (e.g., 0.05-30 mg) per dose. For example, the inhibitor is administered in an amount of 0.01, 0.02, 0.05 mg, 0.1 mg, 0.2 mg, 0.4 mg, 0.8 mg, 2 mg, 5 mg, 10 mg, 15 mg, 20 mg, 25 mg, 30 mg, 40 mg, or 50 mg) per administration (e.g., per injection). In some cases, the inhibitor is administered biweekly. For example, the inhibitor is administered every other week for a total of 1-20 times (e.g., 1, 2, 4, 6, 8, 10, 15, or 20 times).

In some examples, the inhibitor (e.g., antibody described herein) is incorporated into or onto the vaccine device. In such cases, 0-100 mg (e.g., 5-100 mg, 10-100 mg, 20-100 mg, 30-100 mg, 40-100 mg, 50-100 mg, 60-100 mg, 70-100 mg, 80-100 mg, 90-100 mg, 1-95 mg, 1-90 mg, 5-95 mg, 5-90 mg, 5-80 mg, 5-70 mg, 5-60 mg, 5-50 mg, 5-40 mg, 5-30 mg, or 5-20 mg) of the inhibitor (e.g., antibody described herein) is present in the device. For example, the inhibitor (e.g., antibody described herein) is present in the device at a weight/weight concentration of at least 5% (e.g., at least 5%, 10%, 15%, 20%, 25%, 30%, 35%, 40%, 45%, 50%, 55%, 60%, 65%, 70%, 75%, 80%, 85%, 90%, 95%, 98%, 99%, or more).

For example, an inhibitor (e.g., anti-CTLA4 antibody or anti-PD1 antibody) is administered (e.g., systemically) at a dosage of 0.5-5 mg/kg (e.g., 3 mg/kg) body weight, e.g., 43 mg-435 mg per dose for a subject having a body weight of about 87 kg (e.g., 260 mg per dose on average). In some examples, the inhibitor (e.g., anti-CTLA4 antibody or anti-PD1 antibody) is administered (e.g., systemically) for 4 doses, e.g., at 0.5-5 mg/kg per dose (e.g., 3 mg/kg per dose), with a total dose of about 1000 mg after 4 doses. In other examples, the inhibitor (e.g., anti-CTLA4 antibody or anti-PD1 antibody) is administered in more than one dose (e.g., 1, 2, 3, 4, 5, 6, 7, 8, 9, 10, 11, 12, 13, 14, 15, 16, 17, 18, 19, 20, or more doses). In some embodiments, the time interval between doses is at least 1 day (e.g., 1, 2, 3, 4, 5, 6, 7 days or more, 1, 2, 3, 4, 5, 6, 7, 8, 9, 10, 11, or 12 weeks or more, 3, 4, 5, 6, 7, 8, 9, 10, 11, or 12 months or more, 1, 2, 3, 4, 5, 6, 7, 8, 9, 10, 11, 12, 13, 14, 15, 16, 17, 18, 19, or 20 years or more).

In some embodiments, ipilimumab is administered to a subject in need thereof at a dosage of 0.5-5 mg/kg (e.g., 3 mg/kg) body weight. For example, ipilimumab is administered every day, every other day, every 2 days, every 3 days, every 4 days, every 5 days, or every 6 days. For example, ipilimumab is administered once every 1-6 weeks (e.g., once every 3 weeks). For example, ipilimumab is administered to the subject for a total of 12 weeks or more. Ipilimumab is administered by routes such as injection or infusion. Ipilimumab is administered to a subject in need thereof for a total of 4 doses. For example, ipilimumab is administered at a dosage of 3 mg/kg body weight intravenously over 90 minutes every 3 weeks for a total of 4 doses. In some embodiments, ipilimumab is administered in combination (e.g., simultaneously or sequentially) with a vaccine device described herein.

In some cases, tremelimumab is administered to a subject in need thereof at a dosage of 1-20 mg/kg (e.g., 15 mg/kg) body weight. For example, tremelimumab is administered once every day, every other day, every 2 days, every 3 days, every 4 days, every 5 days, every 6 days, or every week. For example, tremelimumab is administered once every 10-100 days (e.g., 90 days).

In some instances, MDX-1106 is administered to a subject in need thereof at a dosage of 0.01-10 mg/kg (e.g., 0.1-10 mg/kg) body weight (e.g., 0.01-1 mg/kg, 0.5-8 mg/kg, 1-10 mg/kg, or 2-8 mg/kg). For example, MDX-1106 is administered at a dosage of 10 mg/kg. MDX-1106 is administered, e.g., intravenously. In some cases, MDX-1106 is administered once every day, every other day, every 2 days, every 3 days, every 4 days, every 5 days, every 6 days, or every week. In other cases, MDX-1106 is administered every 2 weeks, every 3 weeks, or every 4 weeks. For example, MDX-1106 is administered for a total period of at least 6 months (e.g., 6 months, 1 year, 2 years, 3 years or more).

The invention also contemplates administering MK3475 to a subject in need thereof at a dosage of 0.5 mg/kg, 1 mg/kg, 2 mg/kg 5 mg/kg, or 10 mg/kg bodyweight. MK3475 is administered once every day, every other day, every 2 days, every 3 days, every 4 days, every 5 days, every 6 days, or every week. In another embodiment, MK3475 is administered every other week, every 2 weeks, or every 3 weeks.

In some cases, CT-011 is administered to a subject in need thereof at a dosage of 0.05-6 mg/kg (e.g., 0.2-6.0 mg/kg) body weight.

In some embodiments, MDX-1105 is administered to a subject in need thereof at a dosage of 0.01-10 mg/kg (e.g., 0.1-10 mg/kg) body weight (e.g., 0.01, 0.05, 0.1, 0.3, 1, 3, or 10 mg/kg). For example, MDX-1105 is administered once every day, every other day, every 2 days, every 3 days, every 4 days, every 5 days, every 6 days, or every week. In other cases, MDX-1105 is administered every other week, every 2 weeks, or every 3 weeks. In a preferred embodiment, MDX-1105 is administered every 14 days for a total of at least 42 days.

The invention also provides for the administration of IMP321 to a subject in need thereof at a dosage of 0.01-30 mg (e.g., 0.050-30 mg, or 0.01, 0.05, 0.25, 1.25, 6.25, or 30 mg) per administration (e.g., per injection). For example, IMP321 is administered biweekly (e.g., for a total of at least 6 weeks, or at least 12 weeks). In other cases, IMP321 is administered once every day, every other day, every 2 days, every 3 days, every 4 days, every 5 days, every 6 days, or every week. In some cases, IMP321 is administered at a dosage of 5 mg/kg. IMP321 is administered by routes, such as subcutaneous injection.

In some embodiments, the inhibitor(s) described herein is administered in combination (e.g., simultaneously or sequentially) with a vaccine device described herein. For example, the inhibitor(s) is delivered systemically, while the vaccine is delivered locally. In some embodiments, the inhibitor(s) is included in or on the vaccine device. For example, the inhibitor(s) and the vaccine are delivered locally.

In other examples, the inhibitor is administered at least 6 hours (e.g., at least 6 hours, at least 12 hours, at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 6 months, at least 8 months, at least 1 year, at least 2 years, at least 3 years, at least 4 years, at least 6 years, at least 8 years, or more) prior to administration of the vaccine device. In other embodiments, the vaccine device is administered at least 6 hours (e.g., at least 6 hours, at least 12 hours, at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 6 months, at least 1 year, at least 2 years, at least 3 years, at least 4 years, at least 6 years, at least 8 years, or more) prior to administration of the inhibitor(s).

For example, an inhibitor (e.g., antibody described herein) is administered systemically prior to administration (e.g., implantation) of the vaccine device. In some cases, the inhibitor (e.g., antibody) causes debulking of a tumor (i.e., regression). For example, the debulking of the tumor occurs prior to, during, and/or after administration of the vaccine device.

As used herein, the term, "about", is plus or minus 1%, 2%, 3%, 4%, 5%, 6%, 7%, 8%, 9%, 10%, 12%, or 15%.

The invention will be further described in the following examples, which do not limit the scope of the invention described in the claims.

EXAMPLES

Example 1: Treatment of Tumor Bearing Mice with Anti-CTLA4 and Anti-PD1 Antibodies Mouse models of melanoma tumors were used to determine the effect of blockade antibodies (anti-CTLA4 or anti-PD1 antibodies) on tumor growth and survival. To establish melanoma tumors, mice were inoculated with $5 \times 10^5$ B16-F10 melanoma cells and allowed to develop for 9 days.

Mice bearing established melanoma tumors were treated with intraperitoneal (i.p.) injections of anti-CTLA4 or anti-PD1 antibodies. Antibody treatments were administered every 3 days and initiated on Day 3 of tumor challenge.

Tumor growth and survival of the mice were compared between untreated mice versus antibody-treated mice. Mice that were treated with either anti-CTLA4 antibody or anti-PD1 antibody had smaller tumor sizes (FIG. 1A) and longer survival times (FIG. 1B) than untreated mice.

The anti-CTLA4 antibody (9D9, catalog # BE0086) and anti-PD1 antibody (RMP1-14, catalog # BE0146**) were purchased from Bioxcell.

Example 2: Tumor Protection and T Cell Activity Induced by Therapeutic PLG Vaccination in Combination with Blockade Antibodies The effect of combining therapeutic PLG vaccination with an anti-PD1 or anti-CTLA4 antibody was determined using mouse models of melanoma tumors. To establish melanoma tumors, mice were inoculated with $5 \times 10^5$ B16-F10 melanoma cells and allowed to develop for 9 days.

Figure 2A:
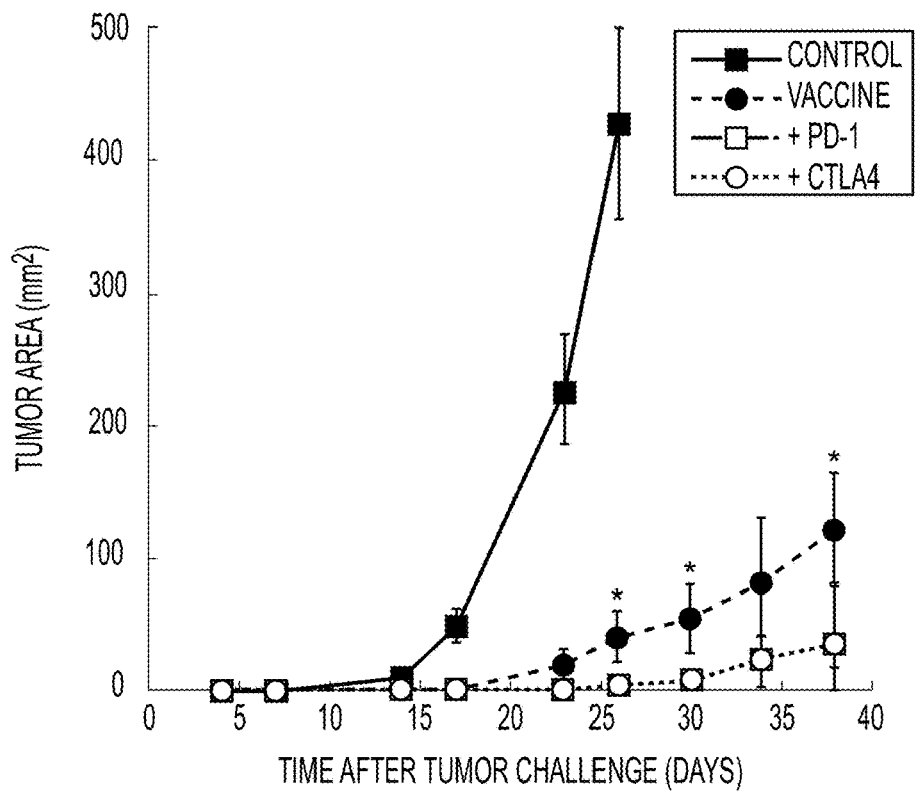
FIG. 2A is a graph of tumor area in melanoma tumor bearing mice after several days with or without vaccine and/or anti-PD1 or anti-CTLA4 antibodies. Values (n=10) represent mean and standard deviation. * P<0.05 as compared to all other experimental conditions unless otherwise noted.
Figure 2B:
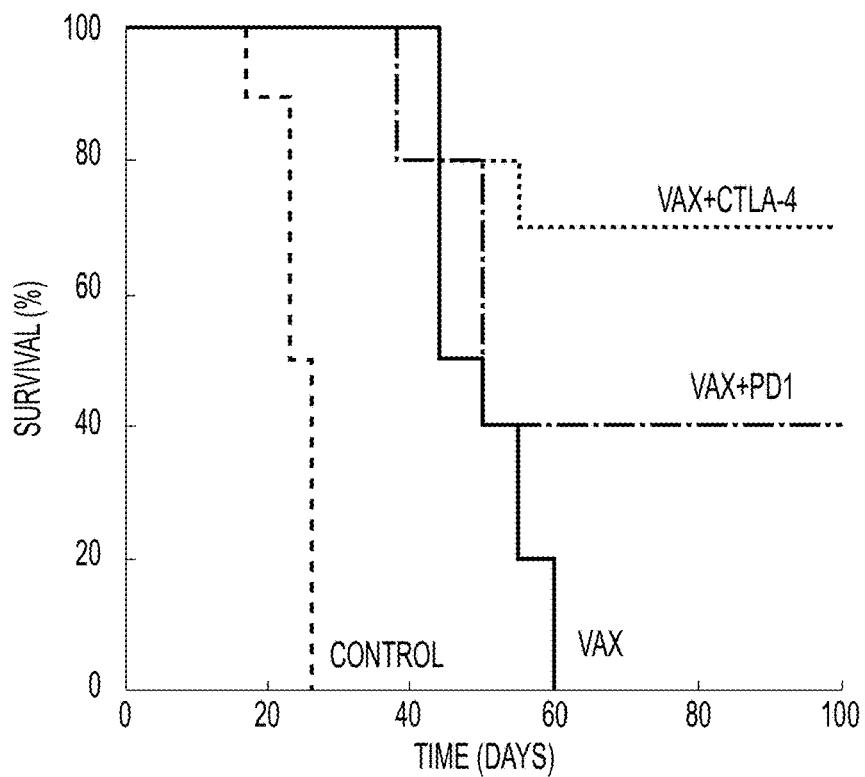
FIG. 2B is a Kaplar Meier survival curve showing the survival time of melanoma tumor bearing mice after treatment with or without vaccine and/or anti-PD1 or anti-CTLA4 antibodies. Values (n=10) represent mean and standard deviation.

The melanoma tumor bearing mice were either untreated, treated with PLG vaccines alone, or treated with PLG vaccines in combination with anti-PD1 or anti-CTLA4 antibodies. The antibody treatments were initiated on Day 3 after tumor challenge (with B16-F10 cells, as described above) and injected i.p. every 3 days for 24 days after tumor challenge. PLG vaccination was performed 9 days after tumor challenge. Tumor size (area in mm$^2$) and survival were determined for each treatment group. The tumor area is the product of the two longest diameters of the tumor. Tumor diameters were measured using standard methods (e.g., with calipers). Mice treated with vaccine alone survived longer and had tumors with smaller area than untreated mice (FIGS. 2A-B). Surprisingly, mice treated with vaccines in combination with either anti-PD1 or anti-CTLA4 antibodies survived longer and had tumors with smaller area than mice treated with vaccine alone (FIGS. 2A-B).

Example 3: Engineered Vaccines in Combination with Blockade Antibodies Enhances Intratumoral Effector T Cell Activity The total number of CD3$^+$CD8$^+$ tumor infiltrating T cells in each treatment group (i.e., untreated, vaccine alone, vaccine+anti-PD1 antibody, or vaccine+anti-CTLA4 antibody) was determined from B16 (a type of melanoma cell) tumors isolated from the mice. CD3, also called the T cell co-receptor, is a marker for T cells, as it is expressed on the surface of all mature T cells and is required for T cell activation. CD8 is a marker for cytotoxic T lymphocytes (CTLs). An increase in the number of CD3$^+$CD8$^+$ T cells that have infiltrated the tumor indicates an increased immune response against the tumor.

Also, the ratio of CD3$^+$CD8$^+$ T cells to CD3$^+$FoxP3$^+$ T regulatory (Treg) cells isolated from the B16 tumors of the mice was determined in each treatment group. FoxP3 is a marker for Treg cells, which modulate (e.g., suppress) the immune response. Thus, the ratio provides a measure of strength of the CTL versus Treg response. A higher ratio indicates an increased immune response against the tumor.

Figure 3A:
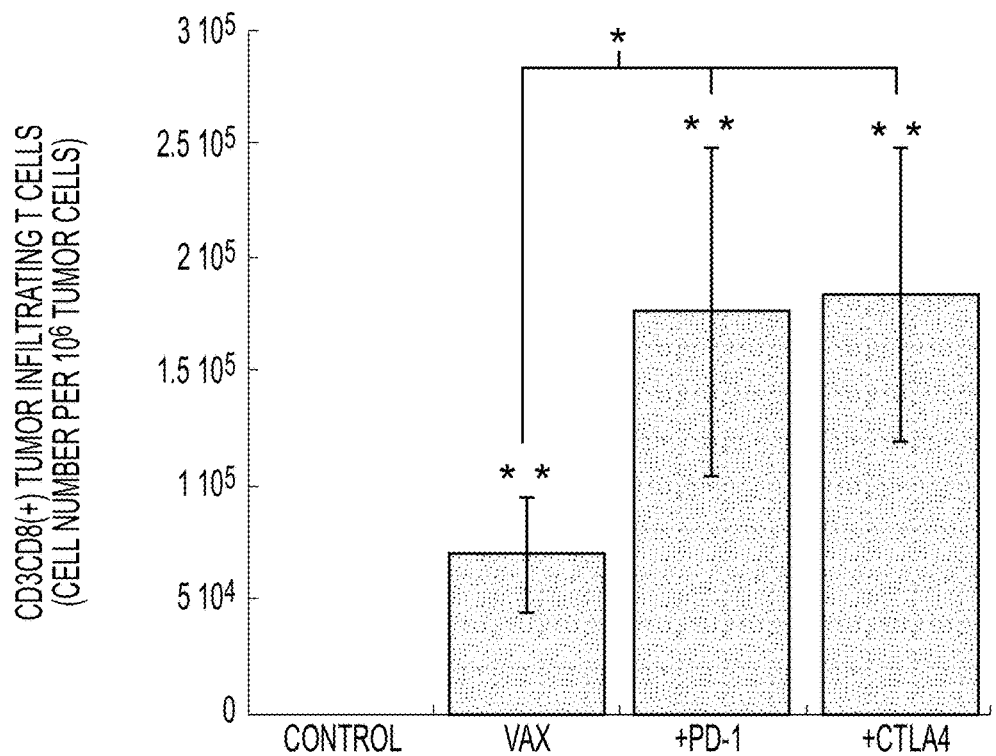
FIG. 3A is a bar graph of the number of $CD3^+CD8^+$ tumor infiltrating T cells present in B16 tumors extracted from melanoma tumor bearing mice after treatment with or without vaccine and/or anti-PD1 or anti-CTLA4 antibodies. Values (n=5) represent mean and standard deviation. * P<0.05 ** P<0.01 as compared to all other experimental conditions unless otherwise noted.
Figure 3B:
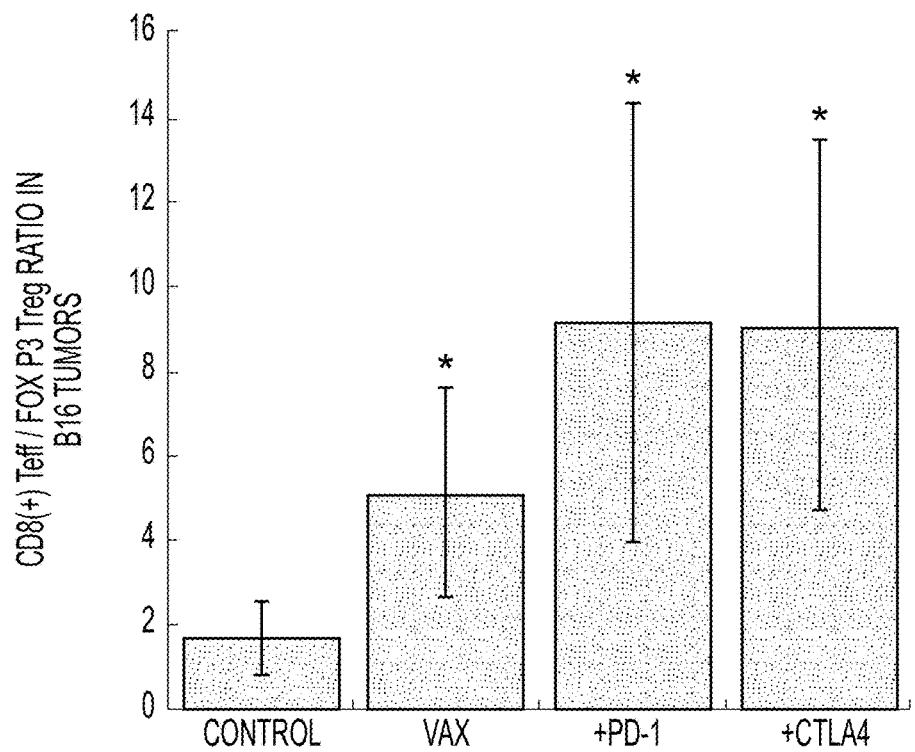
FIG. 3B is a bar graph of the ratio of $CD3^+CD8^+$ T effector cells to CD3+ $FoxP3^+$ T regulatory cells isolated from the B16 tumors of the mice with or without treatment with vaccine and/or anti-PD1 or anti-CTLA4 antibodies. Values (n=5) represent mean and standard deviation. * P<0.05 ** P<0.01 as compared to all other experimental conditions unless otherwise noted.

Antibodies were administered i.p. every 3 days starting on Day 3 after tumor challenge (with $5 \times 10^5$ B16-F10 cells) and vaccination was initiated 9 days after tumor challenge. The B16 tumors were extracted at day 20 to determine the types of T cells that have infiltrated the tumor. The number of tumor infiltrating CD3$^+$CD8$^+$ T cells was significantly higher in the vaccine treated mice than untreated mice (FIG. 3A). Also, the ratio of CD3$^+$CD8$^+$ T cells to CD3$^+$FoxP3$^+$ Treg cells was significantly higher in the vaccine treated mice than untreated mice (FIG. 3B). Surprisingly, the number of tumor infiltrating CD3$^+$CD8$^+$ T cells was significantly higher in the mice treated with a combination of vaccine+antibody compared to those treated with vaccine alone (FIG. 3A). Also, the ratio of CD3$^+$CD8$^+$ T cells to CD3$^+$FoxP3$^+$ Treg cells was significantly higher in the mice treated with a combination of vaccine+antibody compared to those treated with vaccine alone (FIG. 3B).

Taken together, these results indicate that the combination of PLG vaccines with anti-PD1 or anti-CTLA4 antibodies synergistically decreases tumor size, extends survival time, and enhances the T effector cell activity relative to Treg cell activity in the population of T cells isolated from tumors.

In addition, scaffold infiltrating leukocytes, specifically, the percentage of CTLs, were compared by flow cytometry among the treatment groups (i.e., blank matrices, PLG vaccines alone, or vaccines in combination with anti-PD1 or anti-CTLA4 antibodies) at 14 days post-implantation in mice. The antibody treatments were administered on days 0, 3, 6, 9 and 12 after vaccination. Single cell suspensions were prepared from scaffolds at Day 14 and stained for activated, CTL markers, CD8 and CD107a. The percentage of the cells in the scaffold that were positive for both markers was greater in the combination therapy than the vaccine alone treated mice (FIG. 5A).

Also, the fold increase (relative to blank controls) of CD8, scaffold-infiltrating T cells positive for both IFNγ and CD107a was compared in blank matrices, PLG vaccines alone, and vaccines in combination with anti-PD1 or anti-CTLA4 antibodies at 14 days post-implantation in mice. The antibody treatments were administered on days 0, 3, 6, 9 and 12 after vaccination. The vaccines were implanted 7 days after tumor challenge. CD107a is a marker for CTLs, and IFNγ is a cytokine involved in the immune response against tumors, and viral and bacterial infections. The fold increase in activated CD8+ T cells positive for IFNγ and CD107a was significantly greater in scaffolds from mice treated with the combination vaccine+antibody than vaccine alone (FIG. 5B).

Thus, the vaccine works synergistically with the blockade antibodies to enhance T effector cell activity locally, i.e., at the site of the implanted vaccine or within a vaccine. The vaccine plus blockade antibody combination also works synergistically to enhance the infiltration of tumors by activated CD8+ T cells (e.g., CTLs) and to enhance the T cell activity at tumor sites.

Example 4: Engineered PLG Vaccine in Combination with Blockade Antibodies Enhances Local T Effector Cell Activity The effect of the combination of a PLG vaccine with a blockade antibody on local T effector cell activity (i.e., at the site of vaccine scaffold implantation) was determined. Mice were treated with PLG vaccines alone or PLG vaccines in combination with an anti-CTLA4 antibody for 14 days. A subset of mice were treated with antibody and vaccine without tumor challenge to analyze the effects at the vaccine site. Another subset of mice were challenged with 500,000 B16 tumor cells. Vaccines were administered 7 days after tumor challenge. The antibody treatments were administered on days 0, 3, 6, 9 and 12 after vaccination.

Figure 4A:
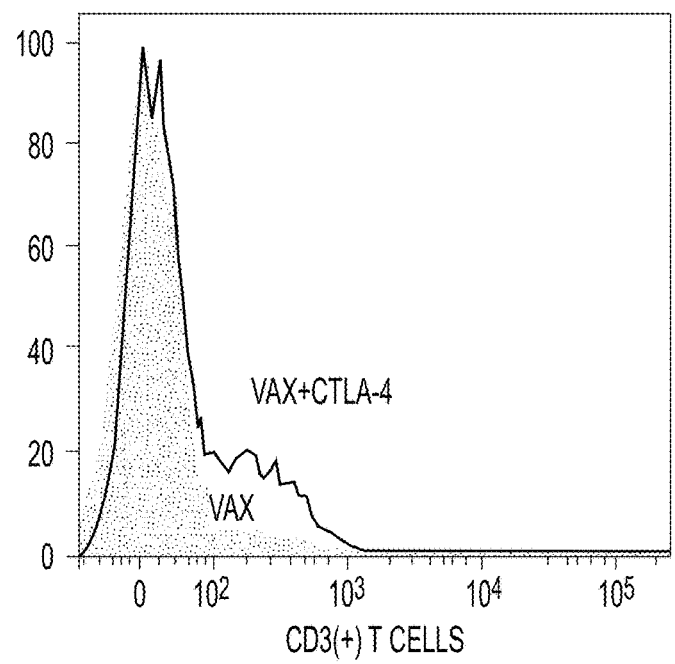
FIG. 4A is a flow cytometric histogram of CD3+ T cell infiltrates isolated from mice treated with PLG vaccines alone (VAX) or in combination with anti-CTLA4 antibody (VAX+CTLA-4) for 14 days.

Effects at the tumor site were examined, specifically the numbers of cytotoxic T cells, interferon gamma expression, CD107a expression, and Treg cell numbers. Flow cytometry was used to determine the number of CD3+ T cell infiltrates into the implanted vaccine scaffolds that were isolated from the two treatment groups. Mice treated with the combination (vaccine+anti-CTLA4 antibody) had more T cell infiltrates in the scaffolds than mice treated with vaccine alone (FIG. 4A).

Figure 4B:
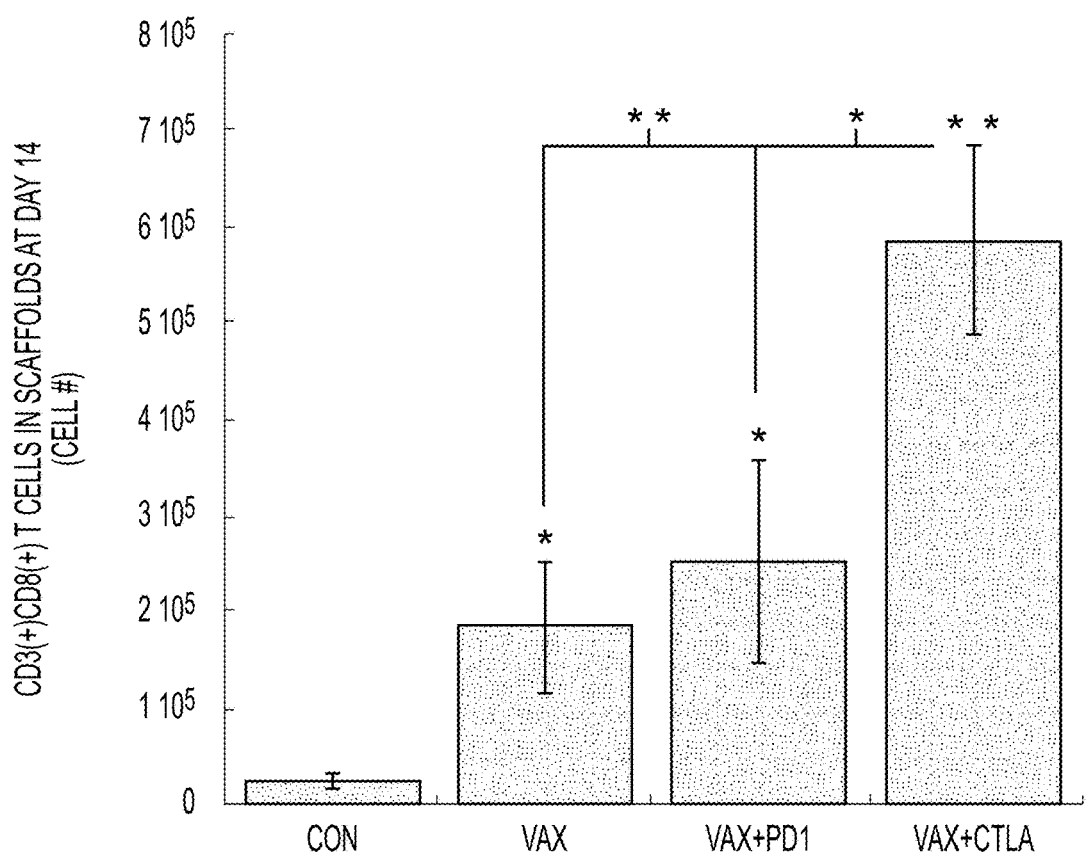
FIG. 4B is a bar graph showing the total number of $CD3^+CD8^+$ effector T cells isolated from mice implanted with blank matrices (Con), PLG vaccines alone (VAX), or vaccines in combination with anti-PD1 (VAX+PD1) or anti-CTLA4 (VAX+CTLA) antibodies for 14 days. Values (n=5) represent mean and standard deviation. * P<0.05 ** P<0.01 as compared to all other experimental conditions unless otherwise noted.

The total number of CD3$^+$CD8$^+$ T effector cells was also determined in mice implanted with blank matrices without vaccine, PLG vaccines alone, or vaccines in combination with anti-PD1 or anti-CTLA4 antibodies for 14 days. The antibody treatments were administered on days 0, 3, 6, 9 and 12 after vaccination. Surprisingly, the combination treatments led to a significantly higher number of CD3$^+$CD8$^+$ T effector cells infiltrated into the scaffolds than vaccine alone (FIG. 4B).

Example 5: Engineered PLG Vaccine in Combination with CTLA-4 Maintains Local T Cell Activity The amount of T cell infiltration into the PLG vaccines implanted in mice for 14 days was determined. Flow cytometry was used to determine the phenotypes (i.e., CD4$^+$CD8$^+$ versus CD4$^+$FoxP3$^+$) of T cell infiltrates isolated from PLG implants in mice treated with PLG vaccines alone (Vax) or in combination with anti-CTLA4 antibody (Vax+CTLA4) or with anti-PD1 antibody (Vax+PD1) (FIG. 6A). The proportion of CD4+ T cells that express CD8 was higher in the VAX+CTLA4 and VAX+PD1 mice than the VAX alone mice. Most of the CD4+ T cells in the VAX+CTLA mice had low expression levels of FoxP3 (FIG. 6A). Also, the ratio of CD3$^+$CD8$^+$ effector T cells to CD4$^+$FoxP3$^+$ Tcells was determined for cell isolated from PLG implants in mice treated with PLG vaccines alone (VAX) or in combination with anti-CTLA4 antibody (VAX+CTLA4) or with anti-PD1 antibody (VAX+PD1) for 30 days (FIG. 6B). The ratio of CD3$^+$CD8$^+$ effector T cells to CD4$^+$FoxP3$^+$ Tcells in the VAX+CTLA4 mice was significantly higher than VAX mice or VAX+PD1 mice (FIG. 6B). Thus, the combination of the PLG vaccine with an anti-CTLA4 antibody maintains local T cell activity and skews the T cell response toward cytotoxic T cell activity relative to suppressive Treg activity. These activities and responses are maintained for an extended period of time, e.g., for at least 30 days.

Example 6: Effector T Cell Activity is Greater than Regulatory T Cell Activity in Vaccine Draining Lymph Nodes Mice were treated with vaccine alone or in combination with anti-CTLA4 or anti-PD1 antibodies. The antibody treatments were administered on days 0, 3, 6, 9, and 12 after vaccination. The vaccine draining lymph nodes were then extracted at day 14 to measure the degree of T cell infiltration. Flow cytometry was used to quantify the percentage of CD8+ T cells and FoxP3$^+$ Treg cells in the vaccine draining lymph nodes. The ratio of CD3$^+$CD8$^+$ T cells to CD3$^+$ FoxP3$^+$ Treg cells was also determined.

Figure 7A:
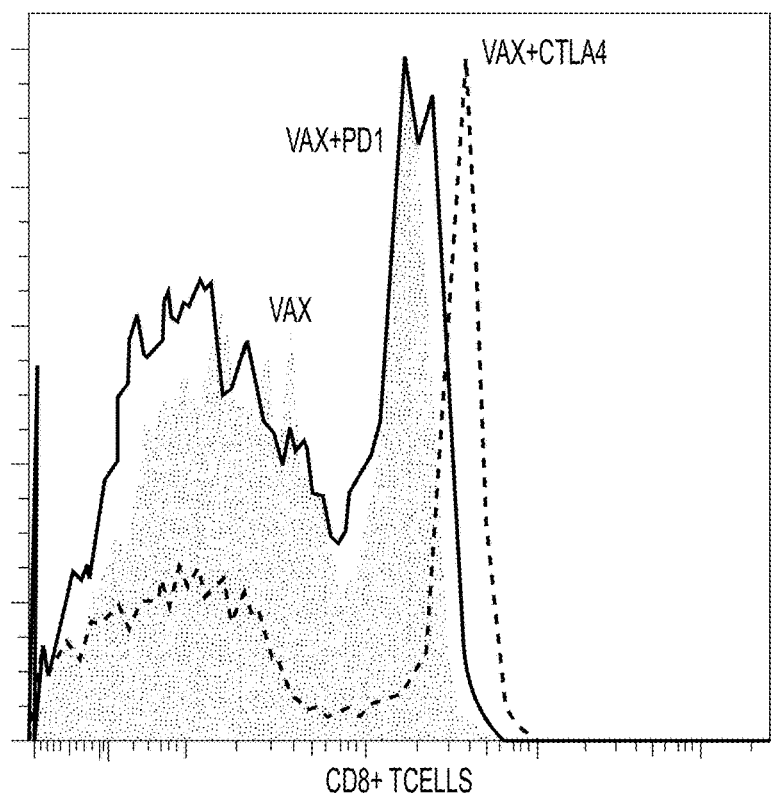
FIG. 7A is a set of flow cytometry histograms showing the number of CD8+ T effector cells in the vaccine draining lymph nodes of mice treated with vaccine alone (VAX) or in combination with anti-CTLA4 (Vax+CTLA4) or anti-PD1 (VAX+PD1) antibodies.
Figure 7B:
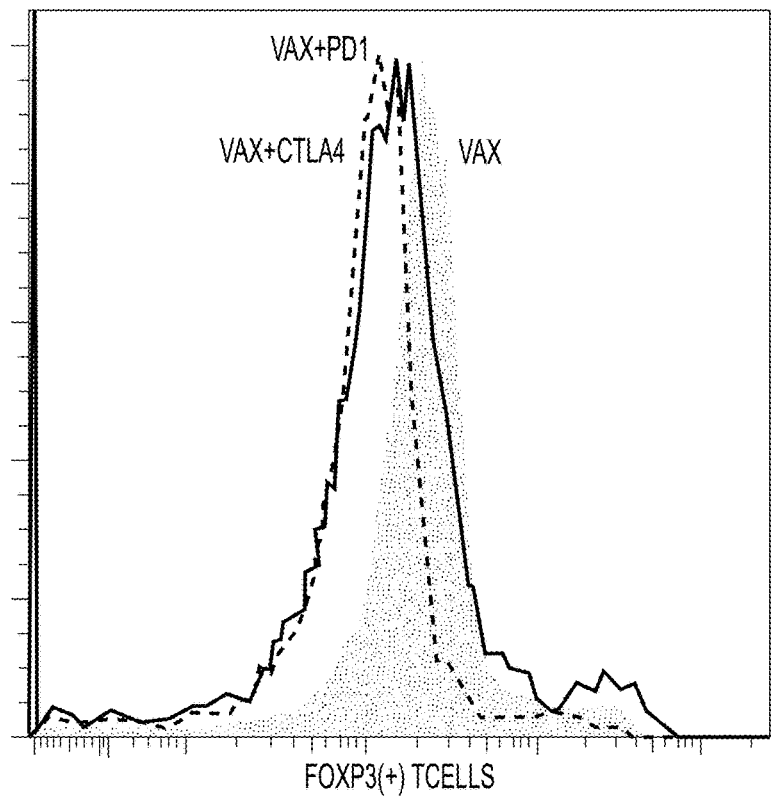
FIG. 7B is a set of flow cytometry histograms showing the number of $FoxP3^+$ Treg cells in the vaccine draining lymph nodes of mice treated with vaccine alone (VAX) or in combination with anti-CTLA4 (VAX+CTLA4) or anti-PD1 (VAX+PD1) antibodies.
Figure 8A:
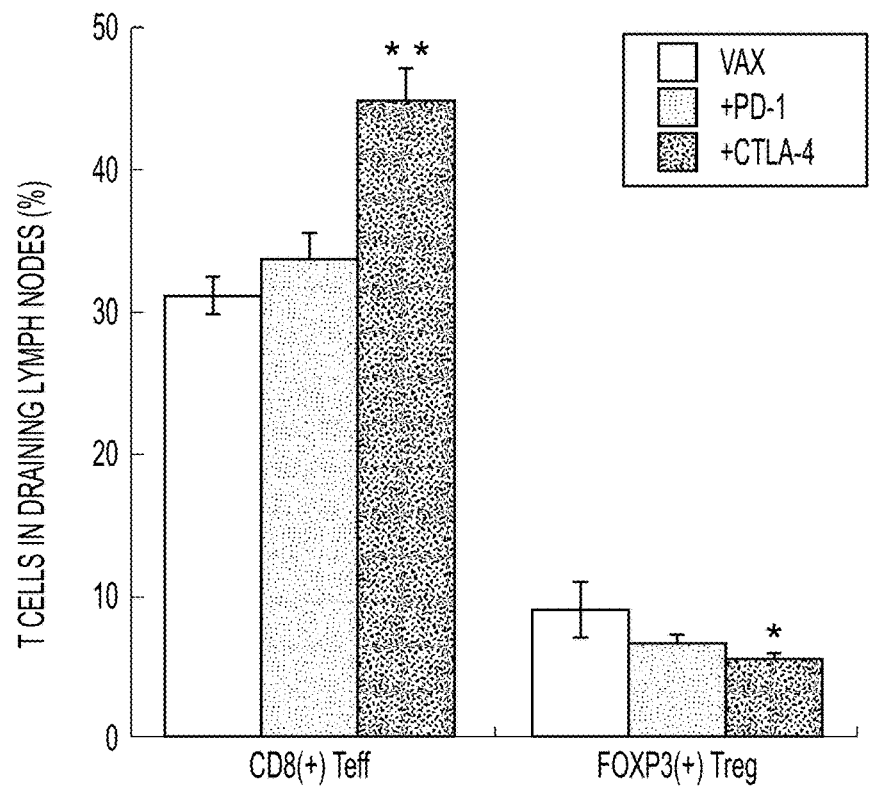
FIG. 8A is a bar graph showing the percentage of T cells in the draining lymph nodes that are $CD8^+$ or $FoxP3^+$ from mice treated with vaccine alone (VAX) or in combination with anti-CTLA4 (+CTLA-4) or anti-PD1 (+PD-1) antibodies. Values (n=5) represent mean and standard deviation (n=5). * P<0.05 ** P<0.01 as compared to all other experimental conditions unless otherwise noted.
Figure 8B:
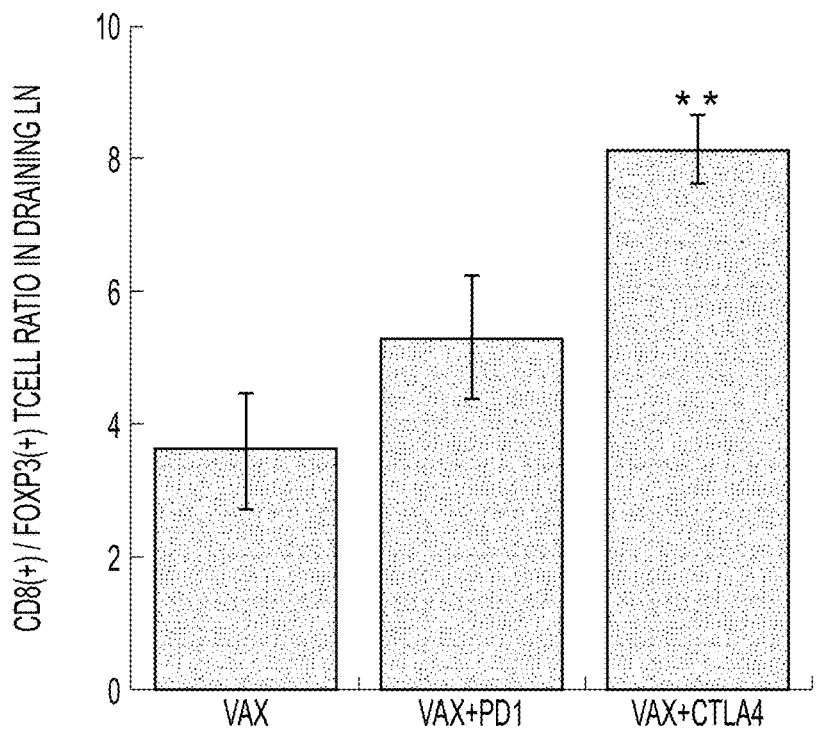
FIG. 8B is a bar graph showing the ratio of CD8+ T cells to $FoxP3^+$ T cells in the vaccine draining lymph nodes of mice treated with vaccine alone (VAX) or in combination with anti-CTLA4 (VAX+CTLA4) or anti-PD1 (VAX+PD1) antibodies. Values (n=5) represent mean and standard deviation (n=5). * P<0.05 ** P<0.01 as compared to all other experimental conditions unless otherwise noted.

By flow cytometry, the percentage of CD8+ T effector cells in the lymph nodes of mice treated with a combination of vaccine+antibody was greater than those from vaccine alone treated mice (FIGS. 7A and 8A). Also, the percentage of FoxP3$^+$ Treg cells in the lymph nodes of mice treated with the combination vaccine+antibody was lower than that of the vaccine alone treated mice (FIGS. 7B and 8A). The ratio of CD3$^+$CD8$^+$ T cells to CD3$^+$FoxP3$^+$ Treg cells in the lymph nodes of the combination vaccine+anti-CTLA4 antibody treated mice was significantly higher than that of the vaccine alone or the combination vaccine+anti-PD1 antibody treated mice (FIG. 8B).

Thus, the vaccine works synergistically with the blockade antibodies, in particular, the anti-CTLA4 antibody, to increase the proportion of T effector cells and decrease the proportion of Treg cells in the vaccine draining lymph nodes.

Figure 9B:
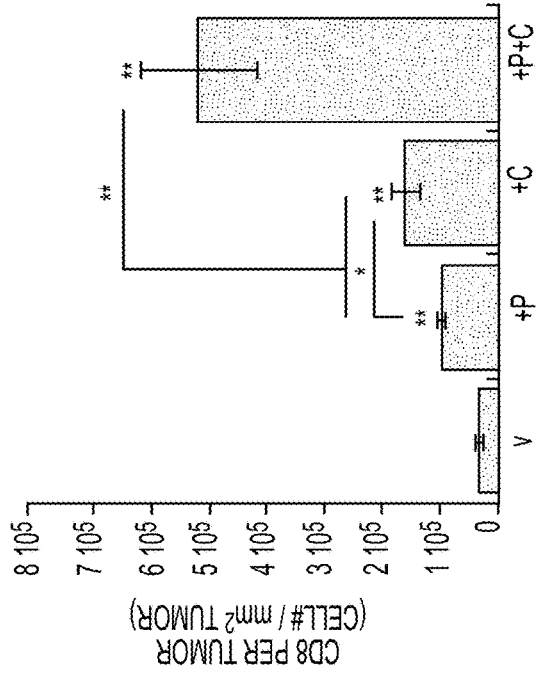
FIG. 9A-FIG. 9D is a series of bar graphs illustrating the combination of multiple checkpoint blockades with PLG cancer vaccines.
Figure 9D:
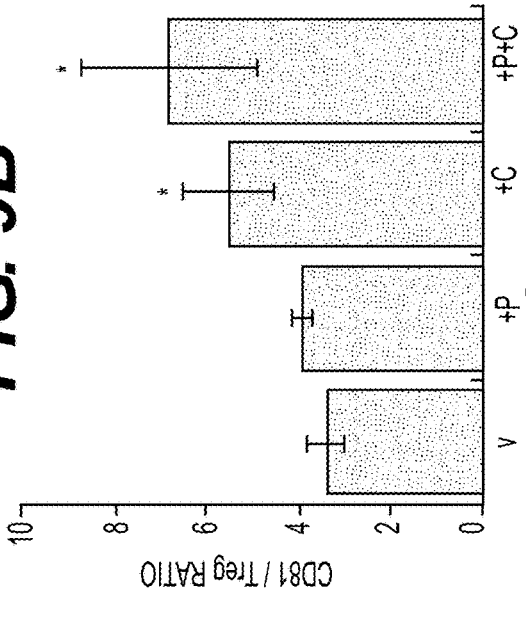
Figure 9A:
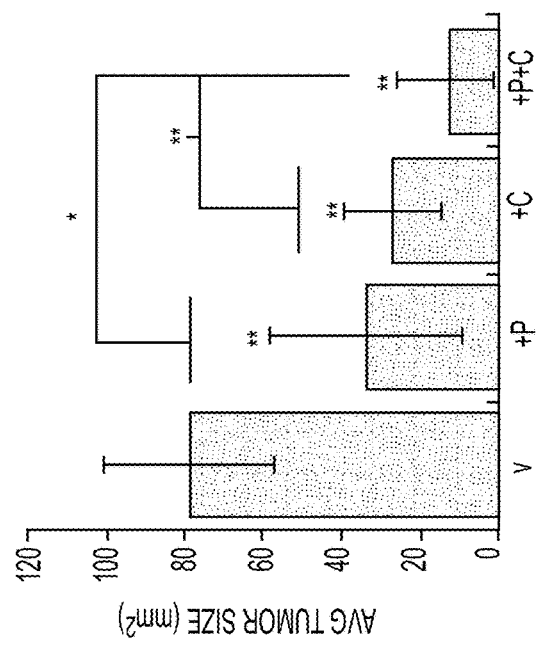
Figure 9C:
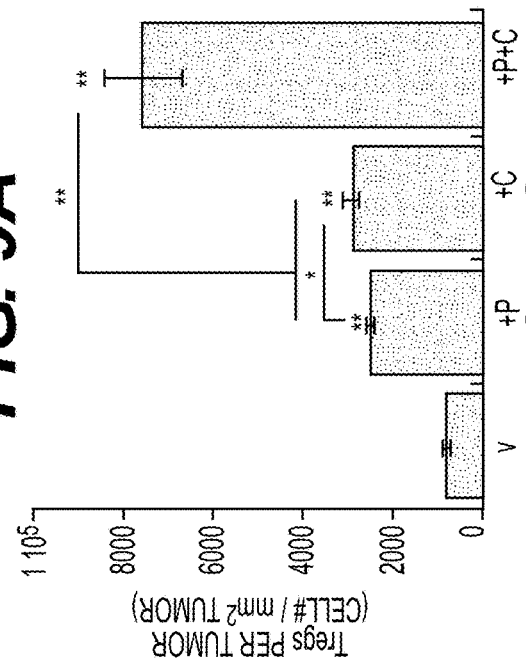

Example 7: Combining Anti-PD1 Antibody and Anti-CTLA4 Antibody with PLG Vaccination Enhances T Cell Activation and Tumor Inhibition in Melanoma Models Described herein is data related to structural vaccines in combination with checkpoint antibodies. Combining checkpoint blockade inhibitors, α-PD-1 and α-CTLA4, with PLG vaccination had a significant effect on tumor growth in comparison to vaccination with either antibody alone (FIG. 9A). The antibody treatments were administered i.p. as described for vaccination experiments until tumor excision at day 35 for Tcell infiltration analysis. Vaccination was initiated 9 days after tumor challenge. At day 35 after tumor challenge, mice treated with PLG vaccination in combination with either α-PD-1 or α-CTLA4 antibody alone had an approximately 2.2-2.6 fold inhibition in tumor progression relative to vaccination alone (FIG. 9A). Combining both antibodies with vaccination resulted in about a 5-fold decrease in B16 tumor growth at day 35 (FIG. 9A). The inhibition of tumor growth correlated with the magnitude of T cell infiltration into tumors. The combination of all three treatments (α-PD-1, α-CTLA4 and PLG vaccination) enhanced the numbers of C8(+) T cells in tumors, FoxP3(+) Tregs and the CD8 Tcell/Treg ratio relative to other treatments (FIG. 9B-FIG. 9D). These data suggest that the tumor inhibition induced by combining vaccination with blockade treatments is likely due to enhanced T cell activation and cytotoxicity as opposed to blocking the immune suppression mediated by Tregs as reported elsewhere.

Example 8: Combining Anti-PD1 Antibody and Anti-CTLA4 Antibody with PLG Vaccination Enhances Cytotoxic T Cell Response As described in detail below, combining blockade antibodies with PLG vaccination significantly skewed the tumor infiltrating leukocyte (TIL) response toward active, cytotoxic T cells, relative to suppressive Tregs (FIG. 10A-FIG. 10E and FIG. 11). This is consistent with the finding of tumor regression, as higher CD8/Treg ratios within tumors are indicative of effective vaccination (Curran et al., 2010 PNAS U.S.A., 107, 4275-4280). For FIGS. 10A-10E, the antibody treatments were administered i.p. as described for vaccination experiments until tumor excision at day 18 for Tcell infiltration analysis. Vaccination was initiated 9 days after tumor challenge. All cellular staining was performed on the total cell suspension extracted from tumors. Similarly, for FIG. 11, the antibody treatments were administered i.p. as described for vaccination experiments (every 3 days) until tumor excision at day 30 for Tcell infiltration analysis. Vaccination was initiated 9 days after tumor challenge.

Figure 11:
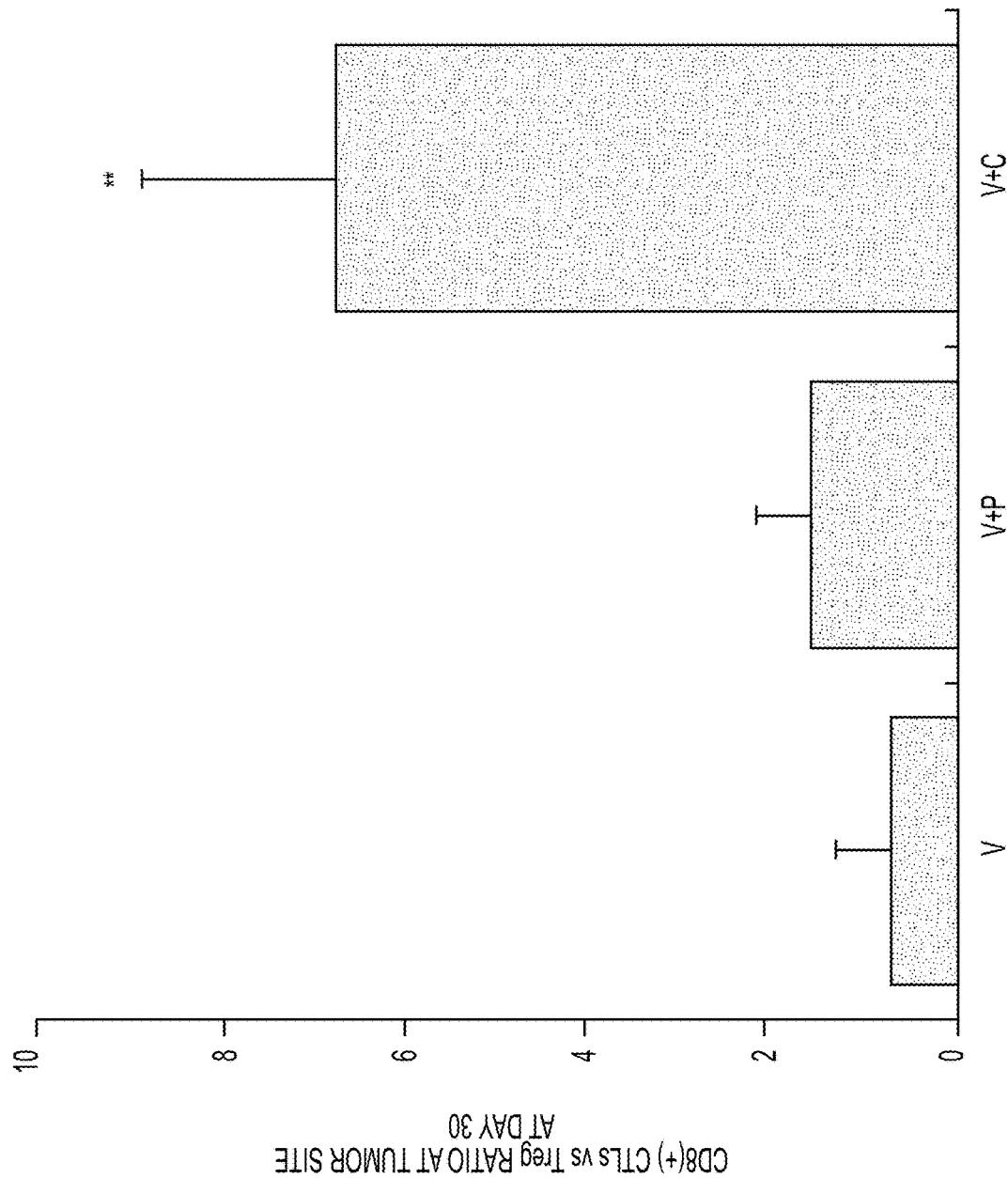
FIG. 11 is a bar chart showing the ratio of CD3(+)CD8(+) T cells to CD3(+)FoxP3(+) T regulatory cells isolated from the B16 tumors of untreated mice (Control) and mice treated with PLG vaccines alone (Vax) or in combination with anti-PD-1 (+PD-1) and anti-CTLA-4 (+CTLA-4) antibodies. Values represent mean and standard deviation (n=5). ** P<0.01 as calculated comparing V+C versus the other experimental conditions.

PLG Vaccination at day 9 after tumor challenge induced significant levels of CD3(+)CD8(+) T cell infiltration into 20-day-old B16 tumors, resulting in approximately 3,500 cytotoxic T cells per mm$^2$ of tumor (FIG. 10A). The addition of anti-PD-1 treatment to vaccination did not have a significant effect on the total numbers of tumor infiltrating CD3(+)CD8(+) T cells, whereas the addition of anti-CTLA-4 therapy produced cytotoxic T cell levels reaching over 17,000 CD3(+)CD8(+) T cells per mm$^2$ of tumor (FIG. 11). In contrast, these treatment groups had no effect on the numbers of tumor-resident CD4(+)FoxP3(+) Tregs (FIG. 10B). The intratumoral ratio of CD8(+) effectors to Tregs at Day 18 almost doubled with PD-1 antibody administration compared to vaccination alone (FIG. 10C). Strikingly, combining anti-CTLA-4 with vaccination resulted in a 9-fold increase in the Teff/Treg ratio compared to vaccination alone at Day 18 (25.3 to 2.8; FIG. 10C). The same analysis was conducted at Day 30 after tumor challenge, and only immunizations combined with anti-CTLA-4 were able to generate significant CD8/Treg ratios (approximately 6-fold increase; FIG. 11) consistent with the long-term survival data. In addition, supplementing vaccination with PD-1 or CTLA-4 antibody therapy resulted in 3-fold and 8-fold increases in intratumoral, cytotoxic T cell activation, as determined by CD107a and IFN-γ co-expression (FIG. 10D and FIG. 10E). The addition of checkpoint blockade enhanced not only the density of activated, CD8(+) TILs, but also the percentage of total CD8(+) T cells that were activated (FIG. 10D and FIG. 10E), indicating that these treatments promoted T cell cytotoxicity locally, within tumors.

Figure 12:
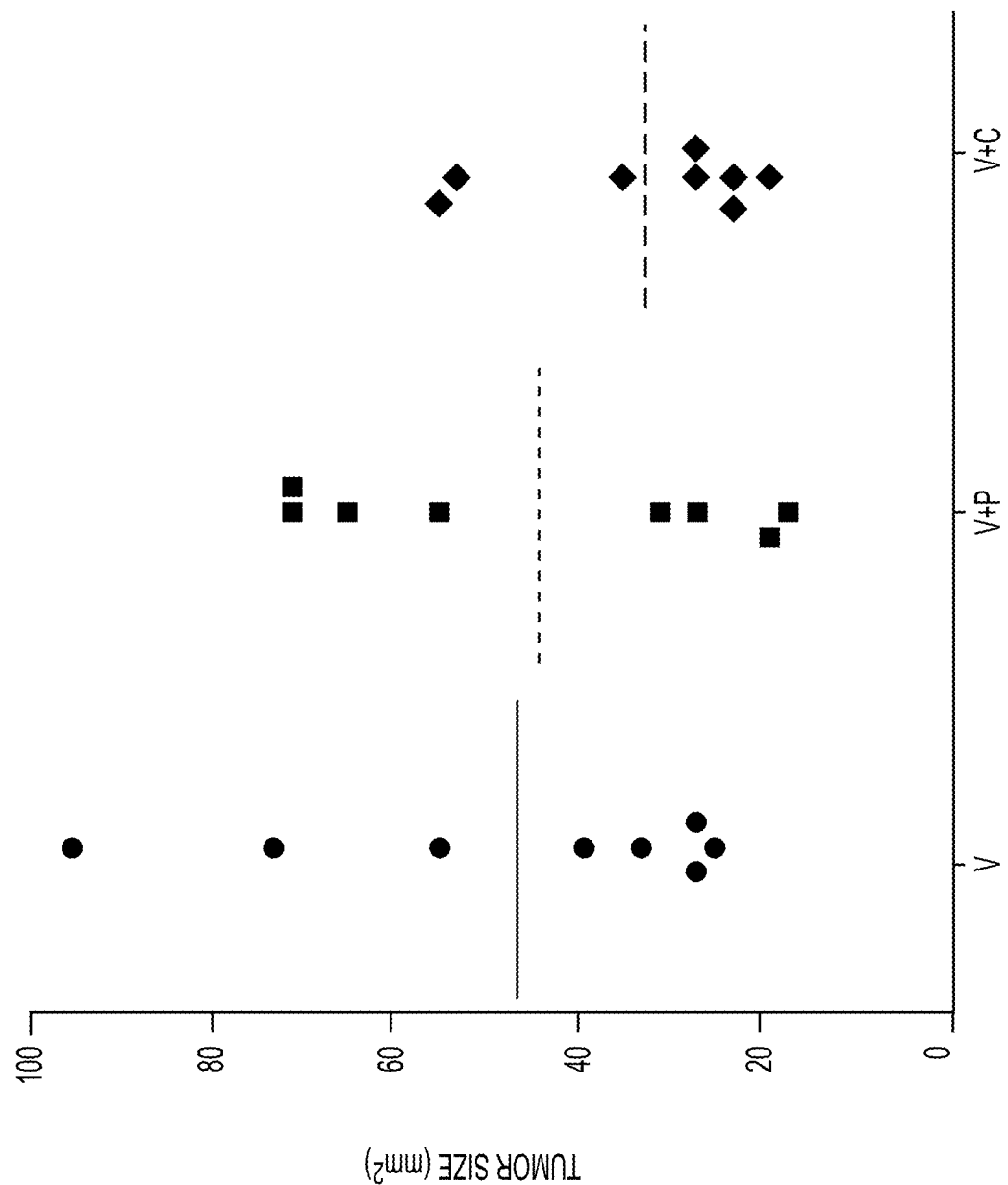
FIG. 12 is a dot plot showing the effects of stopping antibody treatment after PLG vaccination on tumor growth. A comparison of tumor area in mice bearing established melanoma tumors (inoculated with $5 \times 10^5$ B16-F10 cells) and treated with vaccines alone (V) or with vaccines in combination with i.p. injections of anti-PD1 (V+P) or anti-CTLA-4 (V+C) antibodies. Each data point represents one animal (n=8) and lines in the dot plot represent the average tumor area.

All tumors were pretreated with antibody blockade prior to vaccination because this sequence likely reflects the clinical setting where these antibodies are used to initially treat tumors as they become standards of care. However, if antibody administration is ceased after vaccination, the effects on tumor inhibition are lost (FIG. 12), suggesting that blockade treatment significantly augments the subsequent T cell responses induced by vaccination. In FIG. 12, four antibody treatments were administered on days 0, 3, 6, and 9. Mice were vaccinated on day 9 after tumor challenge and tumors size measurements were recorded at day 26 after tumor challenge.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

We claim:

1. A method of killing a cancer cell in a tumor in a subject in need thereof comprising administering to the subject:
   a) an inhibitor comprising an antibody, or an antigen binding fragment thereof, against an immune checkpoint protein; and
   b) a device comprising
      i) a macroporous scaffold composition comprising open, interconnected pores wherein the scaffold comprises a hydrogel or porous polymer;
      ii) a cell recruitment composition capable of recruiting an immune cell, wherein the cell recruitment composition is selected from the group consisting of a cytokine, a chemokine, a growth factor, and a combination thereof; and
      iii) a bioactive composition, wherein the bioactive composition is incorporated into or coated onto the scaffold composition, and wherein the bioactive composition comprises a cancer cell, a cancer antigen, or a cancer derived antigen,
      wherein the inhibitor is administered prior to and subsequent to the administration of the device, and wherein the method enhances the CD8 T cell:Treg cell ratio in the tumor, thereby killing a cancer cell in the tumor.

2. The method of claim 1, wherein migration of the immune cells to another site in the body is promoted by the open, interconnected macropores and by a deployment signal.

3. The method of claim 2, wherein the other site in the body is a nearby or remote tissue target.

4. The method of claim 1, wherein the inhibitor is also present in or on the device.

5. The method of claim 4, wherein the inhibitor is also coated in or on the scaffold composition.

6. The method of claim 1, wherein the inhibitor is not present in or on the device.

7. The method of claim 6, wherein the inhibitor is not coated in or on the scaffold composition.

8. The method of claim 1, wherein the inhibitor is also administered simultaneously with administration of the device.

9. The method of claim 1, wherein the device is implanted subcutaneously into the subject.

10. The method of claim 1, wherein the inhibitor is administered intravenously, intraperitoneally, subcutaneously, orally, intradermally, by inhalation, transmucosally, or rectally.

11. The method of claim 1, wherein the inhibitor is administered by injection, infusion, or inhalation.

12. The method of claim 1, wherein the inhibitor is administered at a dosage of 0.01-10 mg/kg body weight.

13. The method of claim 1, wherein the inhibitor is administered in an amount of 0.01-30 mg per dose.

14. The method of claim 1, wherein the cancer cell is resistant to cytotoxic T-lymphocyte (CTL)-mediated lysis.

15. The method of claim 1, wherein the cancer cell is resistant to natural killer (NK) cell mediated killing.

16. The method of claim 1, wherein the immune checkpoint protein is selected from the group consisting of a cytotoxic T-lymphocyte-associated antigen 4 (CTLA4), a programmed cell death protein 1 (PD1), a programmed cell death protein 1 ligand (PDL1), a lymphocyte activation gene 3 (LAG3), a B7-H3, a B7-H4, a T cell membrane protein 3 (TIM3), a 2B4 (CD244), a B and T lymphocyte attenuator (BTLA, CD272), an adenosine A2a receptor (A2aR), a killer cell immunoglobulin-like receptor (KIR), a C-type leptin receptor, and any combination thereof.

17. The method of claim 16, wherein the inhibitor is an antibody selected from the group consisting of an Ipilimumab, a Tremelimumab, an MDX-1106, an MK3475, a CT-011, an MGA271, a fragment thereof, and any combination thereof.

18. The method of claim 16, wherein the immune checkpoint protein is a PD-1.

19. The method of claim 16, wherein the immune checkpoint protein is a CTLA-4.

20. The method of claim 1, wherein the cell recruitment composition further comprises an Flt3L or a CCL20.

21. The method of claim 1, wherein the bioactive composition comprises a cancer antigen.

22. The method of claim 21, wherein the cancer antigen comprises a tumor cell lysate.

23. The method of claim 1, wherein the cancer cell is selected from the group consisting of a melanoma cell, a central nervous system (CNS) cancer cell, a CNS germ cell tumor cell, a lung cancer cell, leukemia cell, multiple myeloma cell, a renal cancer cell, a malignant glioma cell, a medulloblatoma cell, a breast cancer cell, an ovarian cancer cell, a prostate cancer cell, a bladder cancer cell, a fibrosarcoma cell, a pancreatic cancer cell, a gastric cancer cell, a head and neck cancer cell, a colorectal cancer cell, and any combination thereof.

24. The method of claim 1, wherein the cancer cell is a melanoma cell.

25. The method of claim 1, wherein the immune cell is a dendritic cell.

26. The method of claim 1, wherein the device firther comprises an adjuvant.

* * * * *